(12) United States Patent
Mirkin et al.

(10) Patent No.: US 6,777,186 B2
(45) Date of Patent: Aug. 17, 2004

(54) NANOPARTICLES HAVING OLIGONUCLEOTIDES ATTACHED THERETO AND USES THEREFOR

(75) Inventors: Chad A. Mirkin, Wilmette, IL (US); Robert L. Letsinger, Wilmette, IL (US); Robert C. Mucic, Glendale, CA (US); James J. Storhoff, Evanston, IL (US); Robert Elghanian, Skokie, IL (US); Thomas A. Taton, Little Canada, MN (US)

(73) Assignee: Nanosphere, Inc., Northbrook, IL (US)

( * ) Notice: Subject to any disclaimer, the term of this patent is extended or adjusted under 35 U.S.C. 154(b) by 28 days.

(21) Appl. No.: 09/981,344

(22) Filed: Oct. 15, 2001

(65) Prior Publication Data

US 2003/0044805 A1 Mar. 6, 2003

Related U.S. Application Data

(63) Continuation of application No. 09/603,830, filed on Jun. 26, 2000, now Pat. No. 6,506,564, which is a continuation-in-part of application No. 09/344,667, filed on Jun. 25, 1999, now Pat. No. 6,361,944, which is a continuation-in-part of application No. 09/240,755, filed on Jan. 29, 1999, now abandoned, which is a continuation-in-part of application No. PCT/US97/12783, filed on Jul. 21, 1997.

(60) Provisional application No. 60/031,809, filed on Jul. 29, 1996, and provisional application No. 60/200,161, filed on Apr. 26, 2000.

(51) Int. Cl.[7] .......................... C12Q 1/68; C07H 21/00; C07H 21/02; C07H 21/04

(52) U.S. Cl. ...................... 435/6; 536/23.1; 536/24.3; 536/24.33; 536/25.3; 536/26.6

(58) Field of Search ............. 435/6; 536/23.1, 536/24.3, 24.33, 25.3, 26.6

(56) References Cited

U.S. PATENT DOCUMENTS 4,193,983 A  3/1980  Ullman et al.
4,256,834 A  3/1981  Zuk et al.

(List continued on next page.)

FOREIGN PATENT DOCUMENTS

EP  0 630 974 A2  6/1994
EP  0 667 398 A2  8/1995

(List continued on next page.)

OTHER PUBLICATIONS

O.D. Velev, et al., "In Situ Assembly of Collordal Particles into Miniaturized Biosensors," *Langmuir*, vol. 15, No. 11, pp. 3693–3698, May 25, 1999.

(List continued on next page.)

*Primary Examiner*—Jezia Riley
(74) *Attorney, Agent, or Firm*—McDonnell Boehnen Hulbert & Berghoff

(57) ABSTRACT

The invention provides methods of detecting a nucleic acid. The methods comprise contacting the nucleic acid with one or more types of particles having oligonucleotides attached thereto. In one embodiment of the method, the oligonucleotides are attached to nanoparticles and have sequences complementary to portions of the sequence of the nucleic acid. A detectable change (preferably a color change) is brought about as a result of the hybridization of the oligonucleotides on the nanoparticles to the nucleic acid. The invention also provides compositions and kits comprising particles. The invention further provides methods of synthesizing unique nanoparticle-oligonucleotide conjugates, the conjugates produced by the methods, and methods of using the conjugates. In addition, the invention provides nanomaterials and nanostructures comprising nanoparticles and methods of nanofabrication utilizing nanoparticles. Finally, the invention provides a method of separating a selected nucleic acid from other nucleic acids.

34 Claims, 47 Drawing Sheets

[SEQ. ID NO: 3]
X-C-C-T-T-G-A-G-A-T-T-T-C-C-C-T-C
5'                                3'

G-G-A-A-C-T-C-T-A-A-A-G-G-G-A-G-X
3'                          [SEQ. ID NO: 4]  5'

X-C-C-T-T-G-A-G-A-T-T-T-C-C-C-T-C
G-G-A-A-C-T-C-T-A-A-A-G-G-G-A-G-X

U.S. PATENT DOCUMENTS

| | | | |
|---|---|---|---|
| 4,261,968 A | 4/1981 | Ullman et al. | |
| 4,313,734 A | 2/1982 | Leuvering | |
| 4,318,707 A | 3/1982 | Litman et al. | |
| 4,650,770 A | 3/1987 | Liu et al. | |
| 4,713,348 A | 12/1987 | Ullman | |
| 4,853,335 A | 8/1989 | Olsen et al. | |
| 4,868,104 A | 9/1989 | Kura et al. | |
| 4,996,143 A | 2/1991 | Heller et al. | 435/6 |
| 5,225,064 A | 7/1993 | Henkens et al. | |
| 5,284,748 A | 2/1994 | Mroczkowski et al. | |
| 5,288,609 A | 2/1994 | Engelhardt et al. | |
| 5,294,369 A | 3/1994 | Shigekawa et al. | |
| 5,360,895 A | 11/1994 | Hainfield et al. | |
| 5,384,073 A | 1/1995 | Shigekawa et al. | |
| 5,384,265 A | 1/1995 | Kidwell et al. | |
| 5,460,831 A | 10/1995 | Kossovsky et al. | |
| 5,472,881 A | 12/1995 | Beebe et al. | |
| 5,508,164 A | 4/1996 | Kausch et al. | 435/6 |
| 5,514,602 A | 5/1996 | Brooks, Jr. et al. | |
| 5,521,289 A | 5/1996 | Hainfeld et al. | |
| 5,543,158 A | 8/1996 | Gref et al. | |
| 5,571,726 A | 11/1996 | Brooks, Jr. et al. | |
| 5,599,668 A | 2/1997 | Stimpson et al. | |
| 5,609,907 A | 3/1997 | Natan | |
| 5,637,508 A | 6/1997 | Kidwell et al. | |
| 5,665,582 A | 9/1997 | Kaushch et al. | |
| 5,681,943 A | 10/1997 | Letsinger et al. | |
| 5,751,018 A | 5/1998 | Alivisatos et al. | |
| 5,830,986 A | 11/1998 | Merrill et al. | 528/332 |
| 5,900,481 A | 5/1999 | Lough et al. | 536/55.3 |
| 5,922,537 A | 7/1999 | Ewart et al. | 435/6 |
| 5,939,021 A | 8/1999 | Hansen et al. | |
| 5,972,615 A | 10/1999 | An et al. | 435/6 |
| 5,990,479 A | 11/1999 | Weiss et al. | |
| 6,025,202 A | 2/2000 | Natan | |
| 6,149,868 A | 11/2000 | Natan et al. | |
| 6,203,989 B1 | 3/2001 | Goldberg et al. | 435/6 |
| 6,214,560 B1 * | 4/2001 | Yguerabide et al. | 435/7.1 |
| 6,251,303 B1 | 6/2001 | Bawendi et al. | 252/301.4 R |
| 6,264,825 B1 | 7/2001 | Blackburn et al. | 205/777.5 |
| 6,277,489 B1 | 8/2001 | Abbott et al. | 428/403 |
| 6,306,610 B1 | 10/2001 | Bawendi et al. | 435/7.1 |
| 6,361,944 B1 | 3/2002 | Mirkin et al. | 435/6 |
| 6,365,418 B1 | 4/2002 | Wagner et al. | 436/518 |
| 6,417,340 B1 | 7/2002 | Mirkin et al. | 536/23.1 |

FOREIGN PATENT DOCUMENTS

| | | |
|---|---|---|
| WO | WO 89/06801 | 7/1989 |
| WO | WO 90/02205 | 3/1990 |
| WO | WO 92/04469 | 3/1992 |
| WO | WO 93/10564 | 5/1993 |
| WO | WO 93/25709 | 12/1993 |
| WO | WO 94/29484 | 12/1994 |
| WO | WO 97/40181 | 10/1997 |
| WO | WO 98/04740 | 2/1998 |
| WO | WO 98/10289 | 3/1998 |
| WO | WO 98/17317 | 4/1998 |
| WO | WO 99/23258 | 10/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 00/25136 | 5/2000 |
| WO | WO 01/00876 | 1/2001 |
| WO | WO 01/51665 | 7/2001 |
| WO | WO 01/73123 | 10/2001 |
| WO | WO 01/86301 | 11/2001 |
| WO | WO 02/04681 | 1/2002 |
| WO | WO 02/18643 | 3/2002 |
| WO | WO 02/36169 | 5/2002 |
| WO | WO 00/33079 | 6/2002 |
| WO | WO 02/46472 | 6/2002 |
| WO | WO 02/46483 | 6/2002 |

OTHER PUBLICATIONS

Stimpson, et al., "Real–time detection of DNA hybridization and melting on oligonucleotide arrays by using optical wave guides," *Proc. Natl. Acad. Sci.*, vol. 92, pp. 6379–6383, California Institute of Technology (1995) U.S.

Storhoff, et al., "Strategies for Organizing Nanoparticles into Aggregate Structures and Functional Materials," *Journal of Cluster Science*, vol. 8, No. 2, pp. 179–217, Plenum Publishing Corporation (1997) U.S.

Storhoff, et al., "One–Pot Colorimetric Differentiation of Polynucleotides with Single Base Imperfections Using Gold Nanoparticle Probes," *J. Am. Chem. Soc.*, vol. 20, pp. 1961–1964, American Chemical Society (1998) U.S.

Velev, et al., "In Situ Assembly of Colloidal Particles into Miniaturized Biosensors," *Langmuir*, vol. 15, No. 11, pp. 3693–3698, American Chemical Society (1999) U.S.

Zhu, et al., "The First Raman Spectrum of an Organic Monolayer on a High–Temperature Superconductor: Direct Spectroscopic Evidence for a Chemical Interaction between an Amine and $Yba_2Cu_3O_{7-\delta}$," *J. Am. Chem. Soc.*, vol. 119, pp. 235–236, American Chemical Society (1997) U.S.

Yguerabide, et al., "Light–Scattering Submicroscopic Particles as Highly Fluorescent Analogs and Their Use as Tracer Labels in Clinical and Biological Applications," I. Theory, *Analytical Biochemistry*, vol. 262, pp. 137–156 (1998) U.S.

Yguerabide, et al., "Light–Scattering Submicroscopic Particles as Highly Fluorescent Analogs and Their Use as Tracer Labels in Clinical and Biological Applications," II. Experimental Characterization, *Analytical Biochemistry*, vol. 262, pp. 157–176 (1998) U.S.

Brada, et al., "Golden Blot"—Detection of Polyclonal and Monoclonal Antibodies Bound to Antigens on Nitrocellulose by Protein A–Gold Complexes, *Analytical Biochemistry*, vol. 42, pp. 79–83 (1984) U.S.

Dunn, et al., A Novel Method to Map Transcripts: Evidence for homology between an Adenovirus mRNA and Discrete Multiple Regions of the Viral Genome, *Cell*, vol. 12, pp. 23–36, (1997) U.S.

Hacker, High performance Nanogold—Silver in situ hybridisation, *Eur. J. Histochem*, vol. 42, pp. 111–120 (1998) U.S.

Ranki, et al., "Sandwich hybridization as a convenient method for the detection of nucleic acids in crude samples," *Gene*, vol. 21, pp. 77–85 (1983) U.S.

Romano, et al., "An antiglobulin reagent labelled with colloidal gold for use in electron microscopy," *Immunochemistry*, vol. 11, pp. 521–522 (1974) Great Britain.

Alivasatos et al., "Organization of 'nanocrystal molecules' using DNA," *Nature*, vol. 382, pp. 609–611 (1996).

Bain, et al., "Modeling Organic Surfaces with Self–Assembled Monolayers," *Angew. Chem. Int. Ed. Engl.*, vol. 28, pp. 506–512 (1989).

Bradley, "The Chemistry of Transition Metal Colloids," *Clusters and Colloids: From Theory to Applications*, G. Schmid, Editor, BCH, Weinheim, New York, pp. 459–542 (1994).

Brust et al., "Novel Gold–Dithiol Nano–Networks with Non–Metallic Electronic Properties," *Adv. Mater.*, vol. 7, pp. 795–797 (1995).

Chen et al., "A Specific Quadrilateral Synthesized from DNA Branched Junctions," *J. Am. Chem. Soc.,* vol. 111, pp. 6402–6407 (1989).

Chen & Seeman, "Synthesis from DNA of a molecule with the connectivity of a cube," *Nature,* vol. 350, pp. 631–633 (1991).

Chen et al., Crystal Structure of a Four–Stranded Intercalated DNA: $d(C_4)^{\dagger\ddagger}$ *Biochem.,* vol. 33, pp. 13540–13546 (1994).

Dagani, "Supramolecular Assemblies DNA to organize gold nanoparticles," *Chemical & Engineering News,* p. 6–7, Aug. 19, 1996.

Dubois & Nuzzo, "Synthesis, Structure, and Properties of Model Organic Surfaces," *Annu. Rev. Phys. Chem.,* vol. 43, pp. 437–464 (1992).

Elghanian et al., "Selective Colorimetric Detection of Polynucleotides Based on the Distrance–Dependent Optical Properties of Gold Nanoparticles," *Science,* vol. 277, pp. 1078–1081 (1997).

Grabar et al., "Preparation and Characterization of Au Colloid Monolayers," *Anal. Chem.* vol. 67, pp. 735–743 (1995).

Hacia et al., "Detection of heterozygous mutations in BRCA1 using high density oligonucleotide arrays and two-–colour fluorescence analysis," *Nature Genet.,* vol. 14, pp. 441–447 (1996).

Jacoby, "Nanoparticles change color on binding to nucleotide target," *Chemical &Engineering News,* p. 10, Aug. 25, 1997.

Letsinger et al., Use of Hydrophobic Substituents in Controlling Self–Assembly of Oligonucleotides, *J. Am. Chem. Soc.,* vol. 115, pp. 7535–7536 (1993).

Letsinger et al., "Control of Excimer Emission and Photochemistry of Stilbene Units by Oligonucleotide Hybridization," *J. Am. Chem. Soc.,* vol. 116, pp. 811–812 (1994).

Marsh et al., "A new DNA nanostructure, the G–wire, imaged by scanning probe microscopy," *Nucleic Acids Res.,* vol. 23, pp. 696–700 (1995).

Mirkin, "H–DNA and Related Structures," *Annu. Review Biophys. Biomol. Struct.,* vol. 23, pp. 541–576 (1994).

Mirkin et al., "A DNA–based method for rationally assembling nanoparticles into macroscopic materials," *Nature,* vol. 382, pp. 607–609 (1996).

Mirkin et al., "DNA–Induced Assembly of Gold Nanoparticles: A Method for Rationally Organizing Colloidal Particles into Ordered Macroscopic Materials," *Abstract* 249, Abstracts of Papers Part 1, 212 ACS National Meeting 0–8412–3402–7, American Chemical Society, Orlando, FL, Aug. 25–29, 1996.

Mucic et al., "Synthesis and characterizations of DNA with ferrocenyl groups attached to their 5'–termini: electrochemical characterization of a redox–active nucleotide monolayer," *Chem. Commun.,* pp. 555–557 (1996).

Mulvaney, "Surface Plasmon Spectroscopy of Nanosized Metal Particles," *Langmuir,* vol. 12, pp. 788–800 (1996).

Rabke–Clemmer et al., "Analysis of Functionalized DNA Adsorption on Au(111) Using Electron Spectroscopy," *Langmuir,* vol. 10, pp. 1796–1800 (1994).

Roubi, "Molecular Machines—Nanodevice with rotating arms assembled from synthetic DNA," *Chemical & Engineering News,* p. 13, (Jan. 1999).

Seeman et al., "Synthetic DNA knots and catenanes," *New J. Chem.,* vol. 17, pp. 739–755 (1993).

Shaw & Wang, "Knotting of a DNA Chain During Ring Closure," *Science,* vol. 260, pp. 533–536 (1993).

Shekhtman et al., "Sterostructure of replicative DNA catenanes from eukaryotic cells," *New J. Chem.* vol. 17, pp. 757–763 (1993).

Smith and Feigon, "Quadruplex structure of Oxytricha telomeric DNA oligonucleotides," *Nature,* vol. 356, pp. 164–168 (1992).

Thein et al., "The use of synthetic oligonucleotides as specific hybridization probes in the diagnosis of genetic disorders," $2^{nd}$ Ed., K.E. Davies, Ed., Oxford University Press, Oxford, New York, Tokyo, p. 21–33 (1993).

Wang et al., "Assembly and Characterization of Five–Arm and Six–Arm DNA Brached Junctions," *Biochem.,* vol. 30, pp. 5667–5674 (1991).

Wang et al., "A DNA Aptamer Which Binds to and Inhibits Thrombin Exhibits a New Structural Motif for DNA," *Biochem.,* vol. 32, pp. 1899–1904 (1993).

Weisbecker et al., "Molecular Self–Assembly of Aliphatic Thiols on Gold Colloids," *Langmuir,* vol. 12, pp. 3763–3772 (1996).

Wells, "Unusual DNA Structures," *J. Biol. Chem.,* vol. 263, pp. 1095–1098 (1988).

Zhang et al., "Informational Liposomes: Complexes Derived from Cholesteryl–conjugated Oligonucleotides and Liposomes," *Tetrahedron Lett.,* vol. 37, pp. 6243–6246 (1996).

Borman, *Chem.Eng. News,* Dec. 9, 1996, pp. 42–43 (1996).

Tomlinson et al., *Anal. Biochem,* vol. 171, pp. 217–222 (1998).

Mohanty J., et al. "Pulsed laser excitation of phosphate stabilized silver nanoparticles," *Proc. Indian Acd. Sci.,* vol. 112, No. 1, p. 63–72.

Nicewarner–Peña S., et al., "Hybridization and Enzymatic Extension of Au Nanoparticle–Bound Oligonucleotides," *J. Am. Chem. Soc.,* vol. 124, p. 7314–7323 (2002).

Whitesides G.M., et al., "Soft Lithography in Biology and Biochemistry," *Annu. Rev. Biomed. Eng.,* p. 335–373 (2001).

Letsinger, R., et al., "Chemistry of Oligonucleotide–Gold Nanoparticle Conjugates," *Phosphorus, Sulfur and Silicon,* vol. 144, p. 359–362 (1999).

Letsinger, R., et al., "Use of a Steroid Cyclic Disulfide Anchor in Constructing Gold Nanoparticle—Oligonucleotide Conjugates," *Bioconjugate Chem,* p. 289–291 (2000).

Li Z., et al., "Multiple thiol–anchor capped DNA–gold nanoparticle conjugates," *Nucleic Acids Research,* vol. 30, p. 1558–1562 (2002).

Nuzzo R., et al., "Spontaneously Organized Molecular Assemblies. 3. Preparation and Properties of Solution Adsorbed Monolayers of Organic Disulfides on Gold Surfaces," *J. Am Chem. Soc.,* vol. 109, p. 2358–2368 (1987).

Otsuka, H., et al., "Quantitative and Reversible Lectin–Induced Association of Gold Nonoparticles Modified with □–Lactosyl–□–mercapto–poly(ethyleneglycol)," *J. Am Chem. Soc.,* vol. 123, p. 8226–8230 (2001).

Wuelfing, P., et al., "Nanometer Gold Clusters Protected by Surface–Bound Monolayers of Thiolated Poly(ethylene glycol) Polymer Electrolyte," *J. Am Chem. Soc.,* vol. 120, p. 12696–12697 (1998).

* cited by examiner

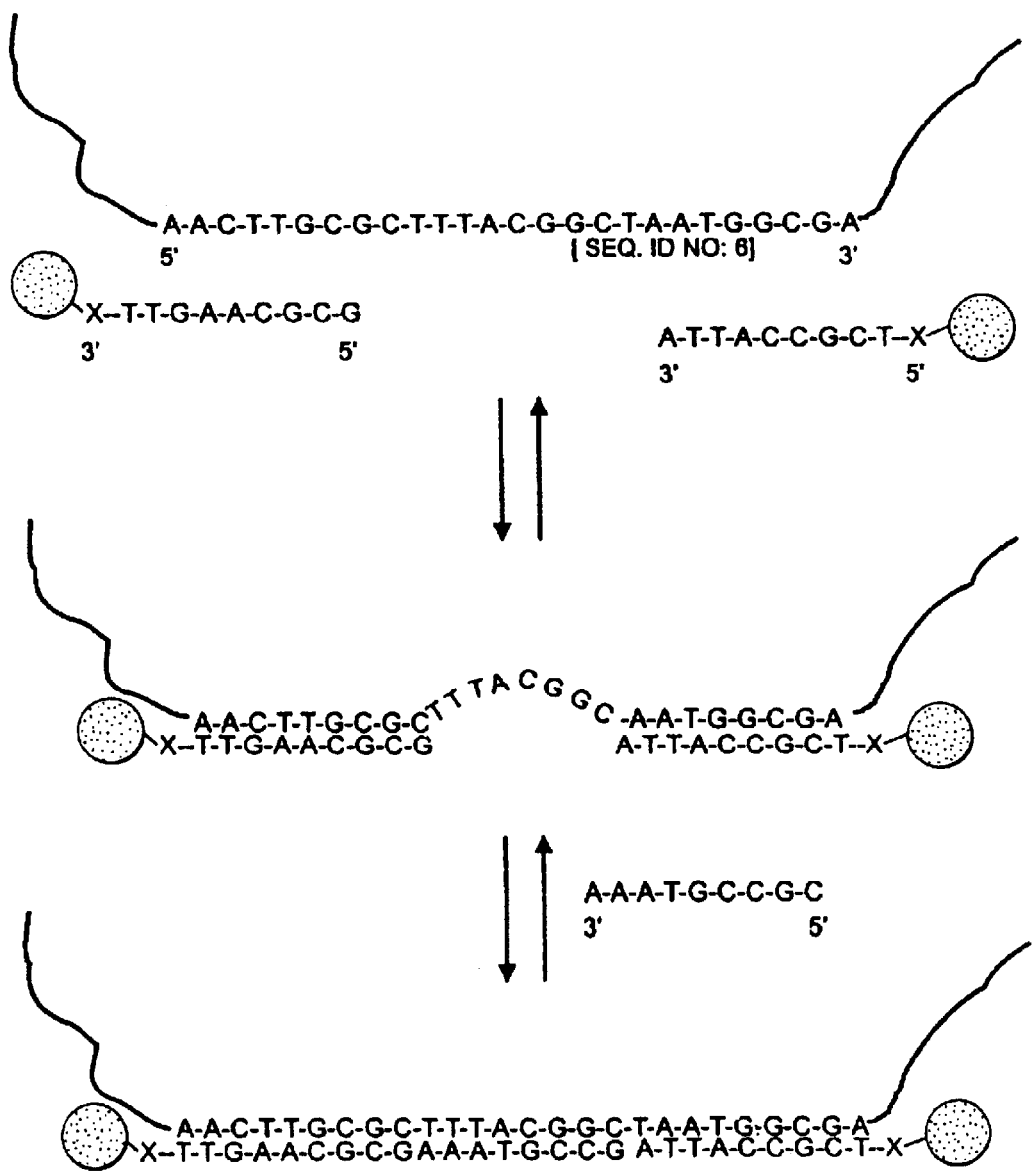

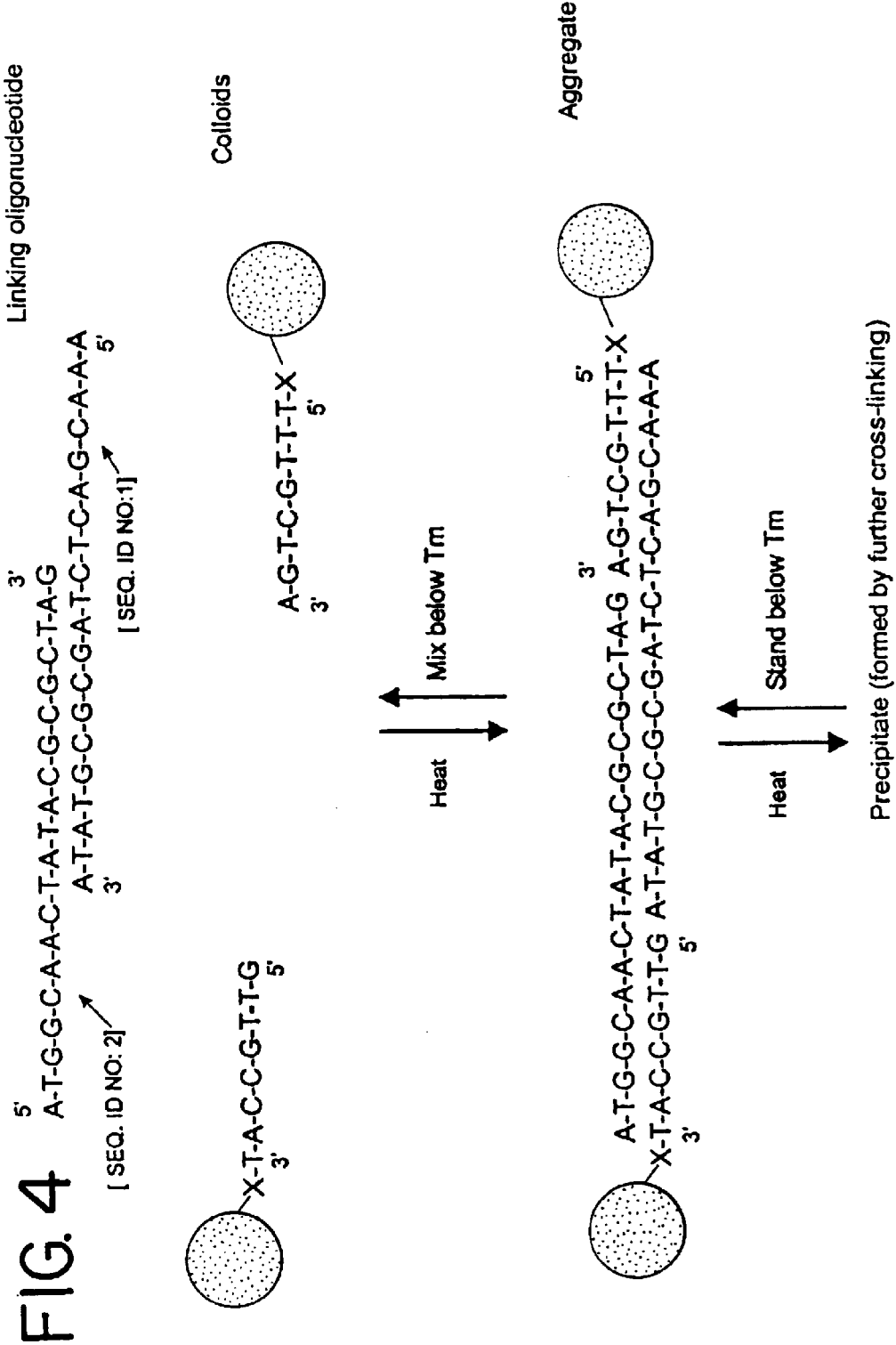

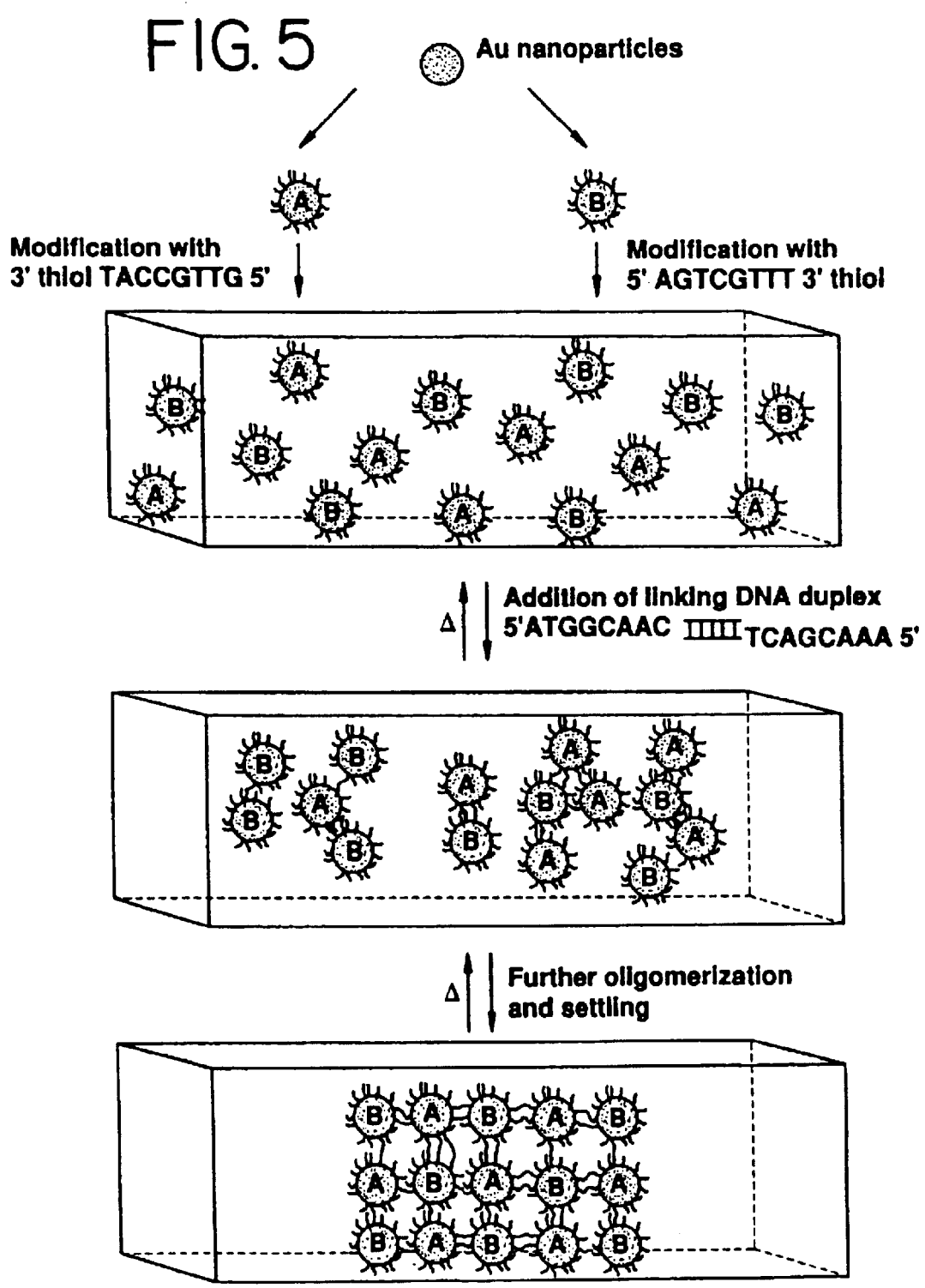

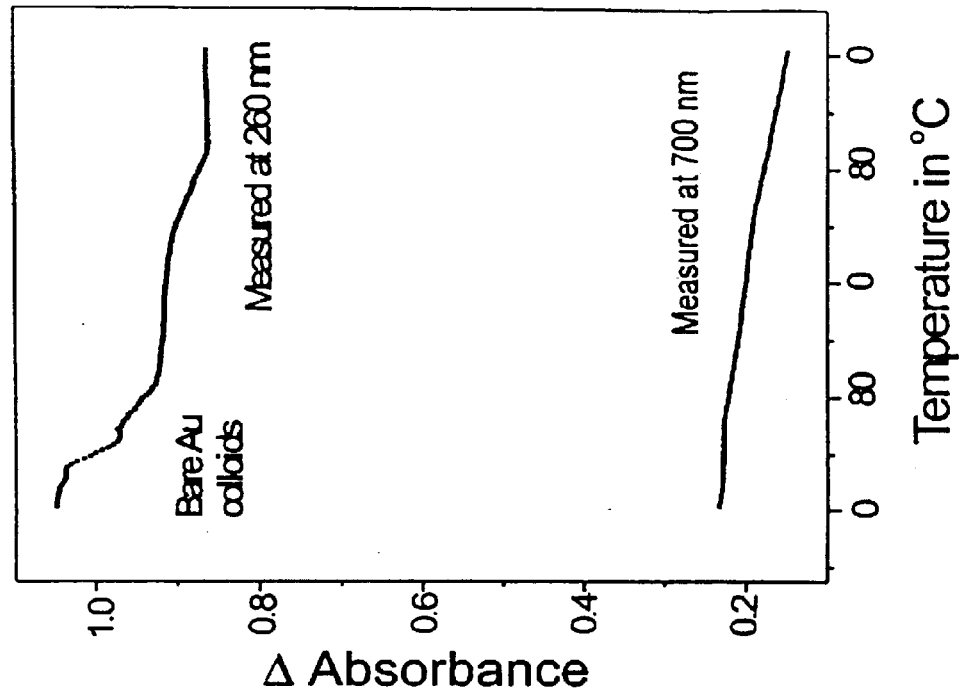
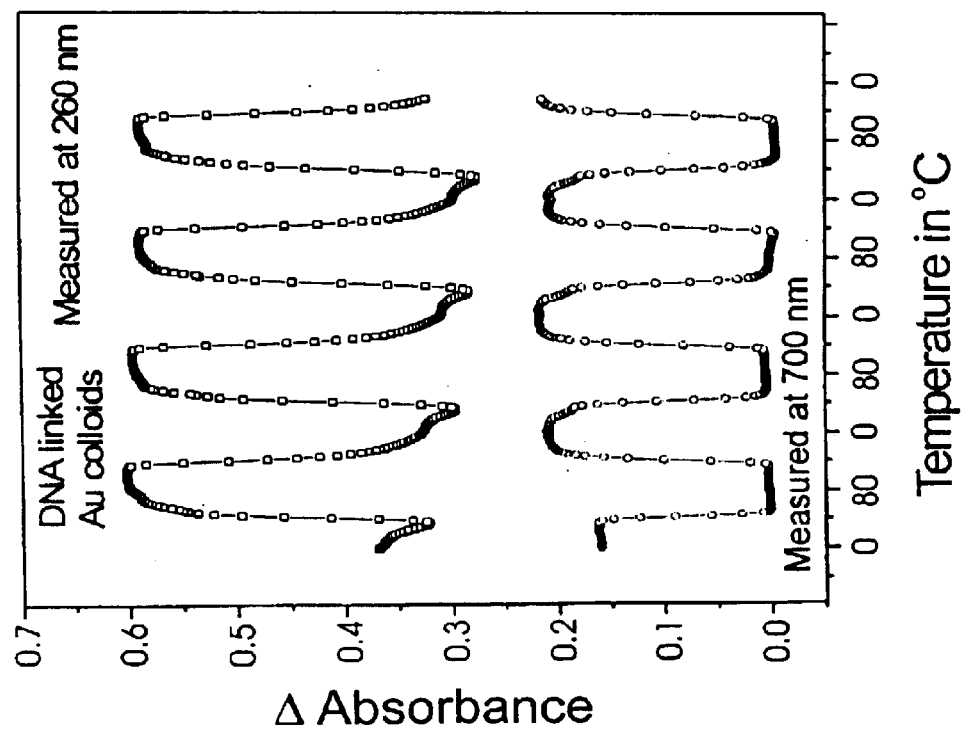

Complementary Target

Probes without Target

Half Complementary Target

Target - 6 bp

One bp Mismatch

Two bp Mismatch

FIG. 13A
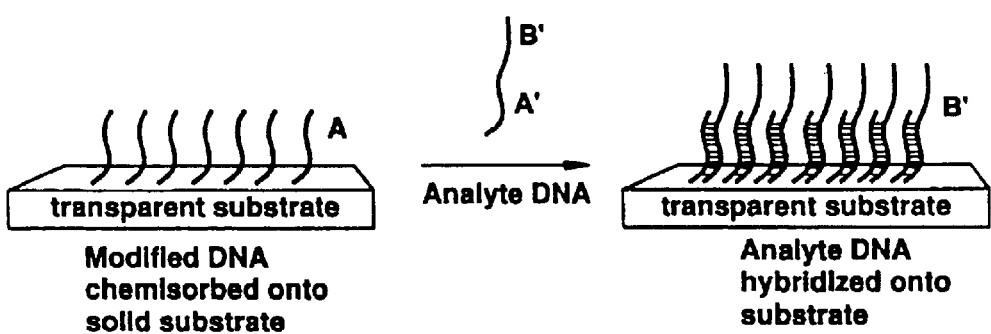
Modified DNA chemisorbed onto solid substrate
Analyte DNA hybridized onto substrate
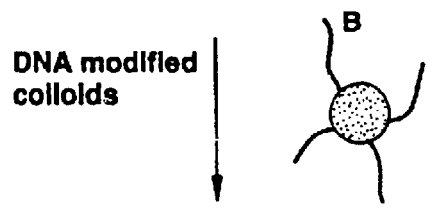
DNA modified colloids
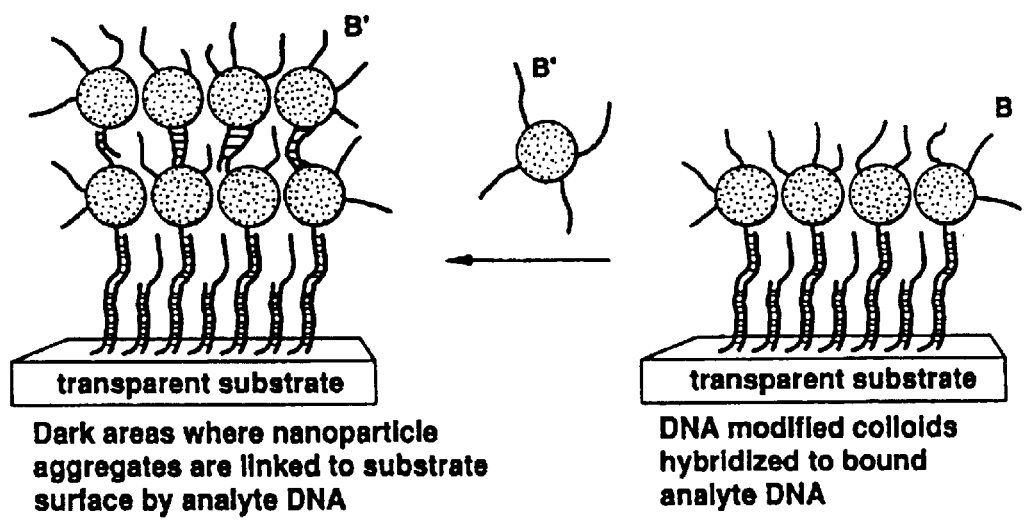
Dark areas where nanoparticle aggregates are linked to substrate surface by analyte DNA
DNA modified colloids hybridized to bound analyte DNA

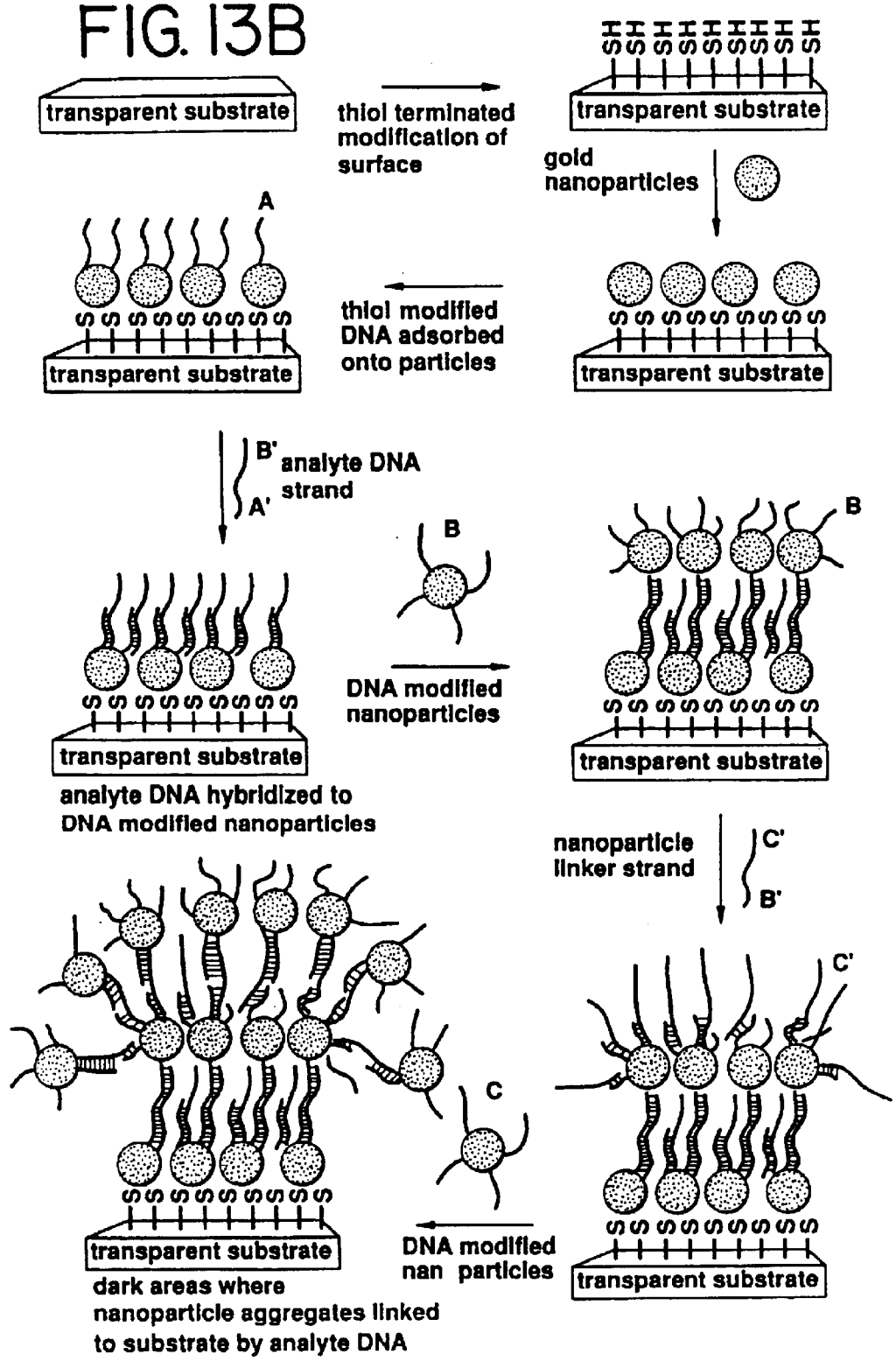

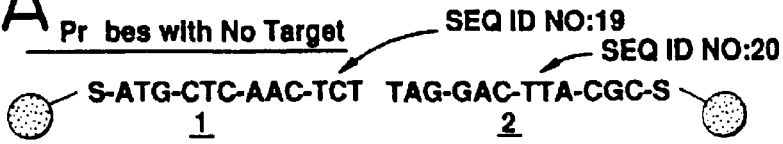
FIG. 15A Probes with No Target
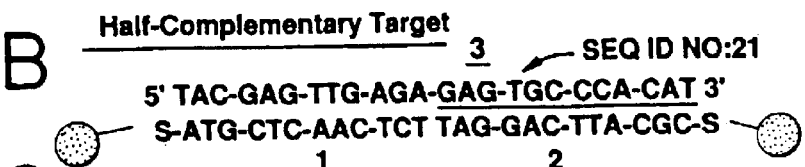
FIG. 15B Half-Complementary Target
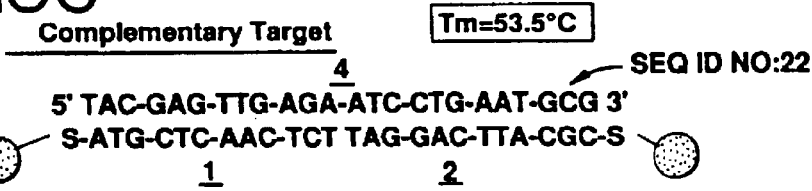
FIG. 15C Complementary Target
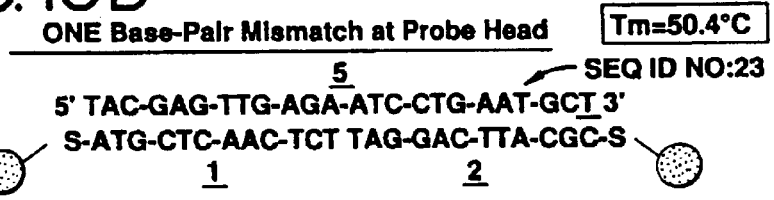
FIG. 15D ONE Base-Pair Mismatch at Probe Head
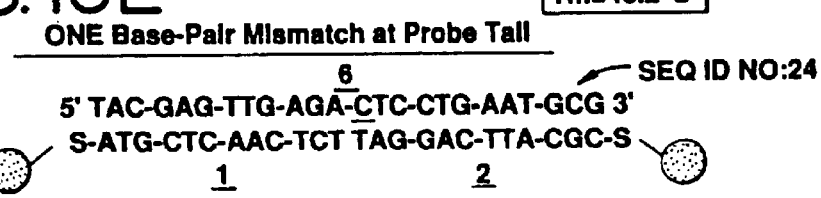
FIG. 15E ONE Base-Pair Mismatch at Probe Tail
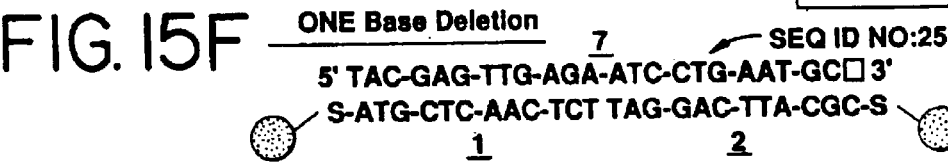
FIG. 15F ONE Base Deletion
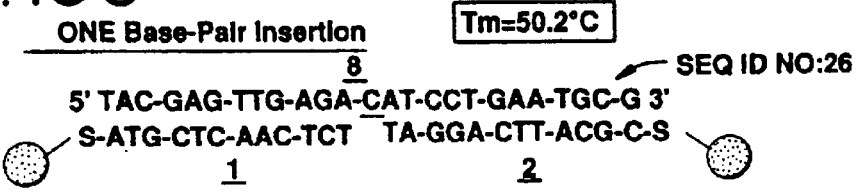
FIG. 15G ONE Base-Pair Insertion

FIG. 16A

24 Base Template

5' TAC-GAG-TTG-AGA-ATC-CTG-AAT-GCG 3'
∼S-ATG-CTC-AAC-TCT TAG-GAC-TTA-CGC-S /

48 Base Template with Complementary 24 Base Filler

5' TAC-GAG-TTG-AGA-CCG-TTA-AGA-CGA-GGC-AAT-CAT-GCA-ATC-CTG-AAT-GCG 3'
∼S-ATG-CTC-AAC-TCT GGC-AAT-TCT-GCT-CCG-TTA-GTA-CGT TAG-GAC-TTA-CGC-S /

72 Base Template with Complementary 48 Base Filler

5' TAC-GAG-TTG-AGA-CCG-TTA-AGA-CGA-GGC-AAT-CAT-GCA-TAT-ATT-GGA-CGC-TTT-ACG-GAC-AAC-ATC-CTG-AAT-GCG 3'
∼S-ATG-CTC-AAC-TCT GGC-AAT-TCT-GCT-CCG-TTA-GTA-CGT-ATA-TAA-CCT-GCG-AAA-TGC-CTG-TTG TAG-GAC-TTA-CGC-S /

1      2

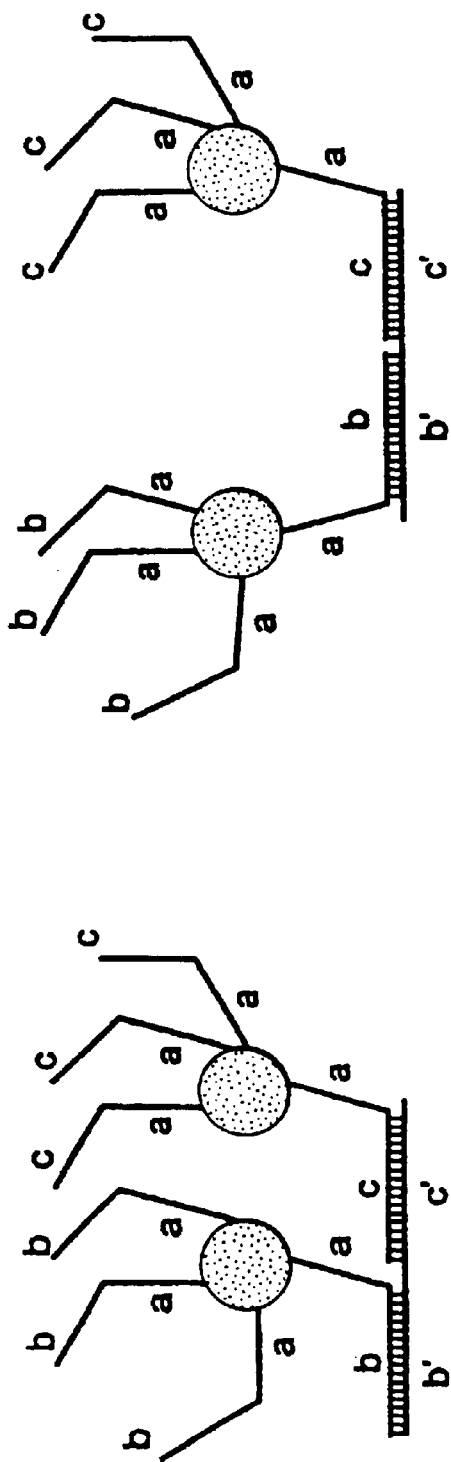
FIG. 17A
FIG. 17B
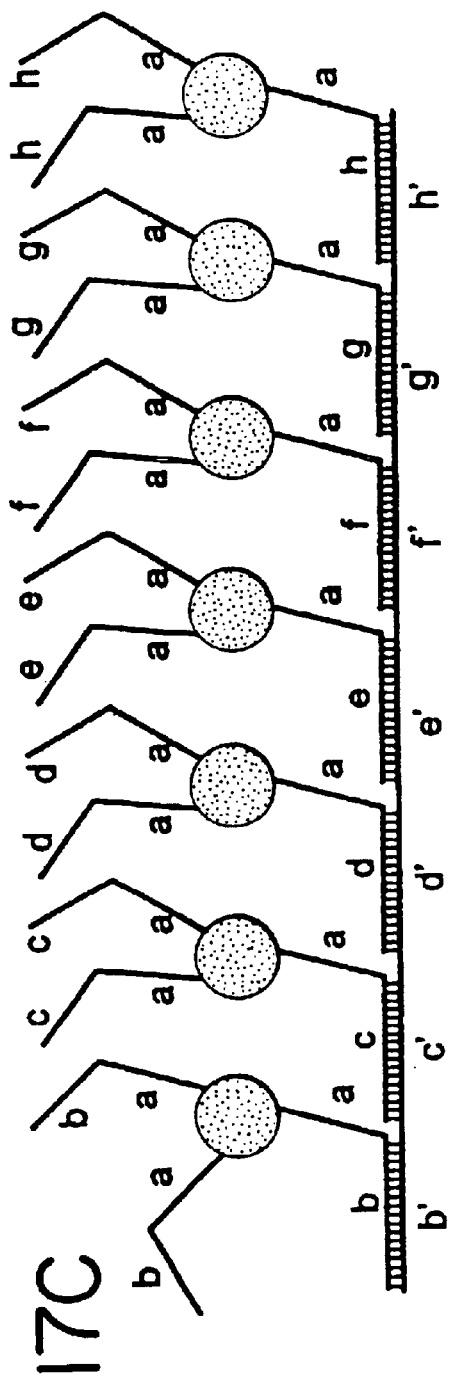
FIG. 17C

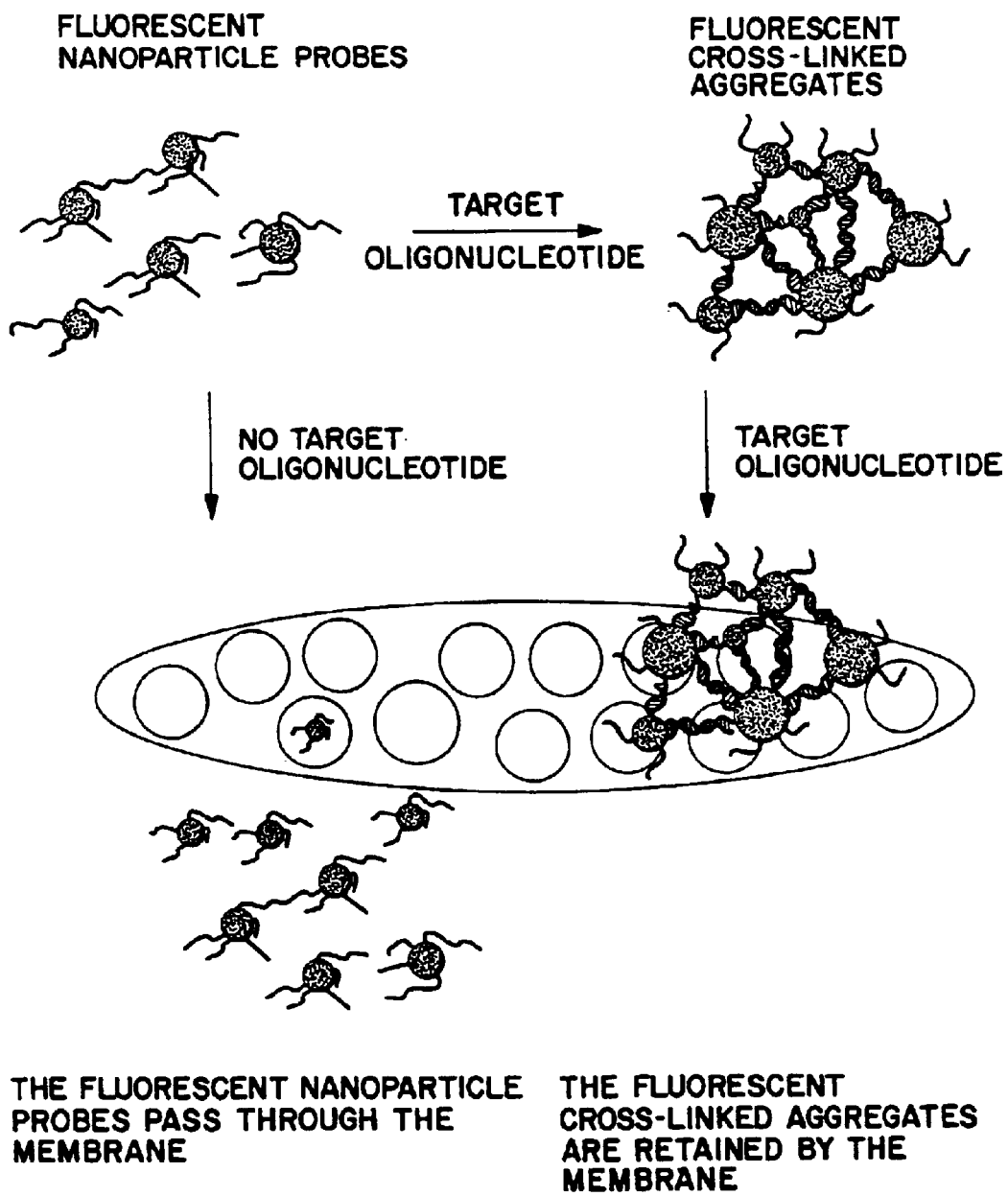

FIG. 23

Anthrax PCR Product

5'G GCG GAT GAG TCA GTA GTT AAG GAG GCT CAT AGA GAA GTA ATT AAT
3'C CGC CTA CTC AGT CAT CAA TTC CTC CGA GTA TCT CTT CAT TAA TTA

TCG TCA ACA <u>GAG GGA TTA TTG TTA AAT ATT GAT AAG GAT</u> ATA AGA AAA
AGC AGT TGT CTC CCT AAT AAC AAT TTA TAA CTA TTC CTA TAT TCT TTT

ATA TTA TCC AGG GTT ATA TTG TAG AAA TTG AAG ATA CTG AAG GGC TT 3'
TAT AAT AGG TCC CAA TAT AAC ATC TTT AAC TTC TAT GAC TTC CCG AA 5'

141 mer Anthrax PCR product   [SEQ ID NO:36]

3' CTC CCT AAT AAC AAT ─◯           3' TTA TAA CTA TTC CTA ─◯

[SEQ ID NO:37]                      [SEQ ID NO:38]

Oligonucleotide-Nanoparticle Probes

Blocker Oligonucleotides

3' C CGC CTA CTC AGT CAT CAA TTC CTC CGA GT        [SEQ ID NO:39]
3' A TCT CTT CAT TAA TTA AGC AGT TGT              [SEQ ID NO:40]
3' TAT TCT TTT TAT AAT AGG TCC CAA TAT            [SEQ ID NO:41]
3' AAC ATC TTT AAC TTC TAT GAC TTC CCG AA         [SEQ ID NO:42]

FIG. 24
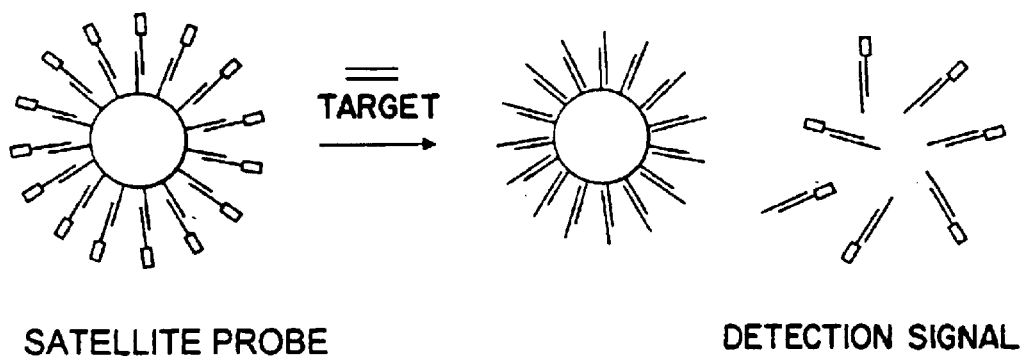
SATELLITE PROBE    DETECTION SIGNAL
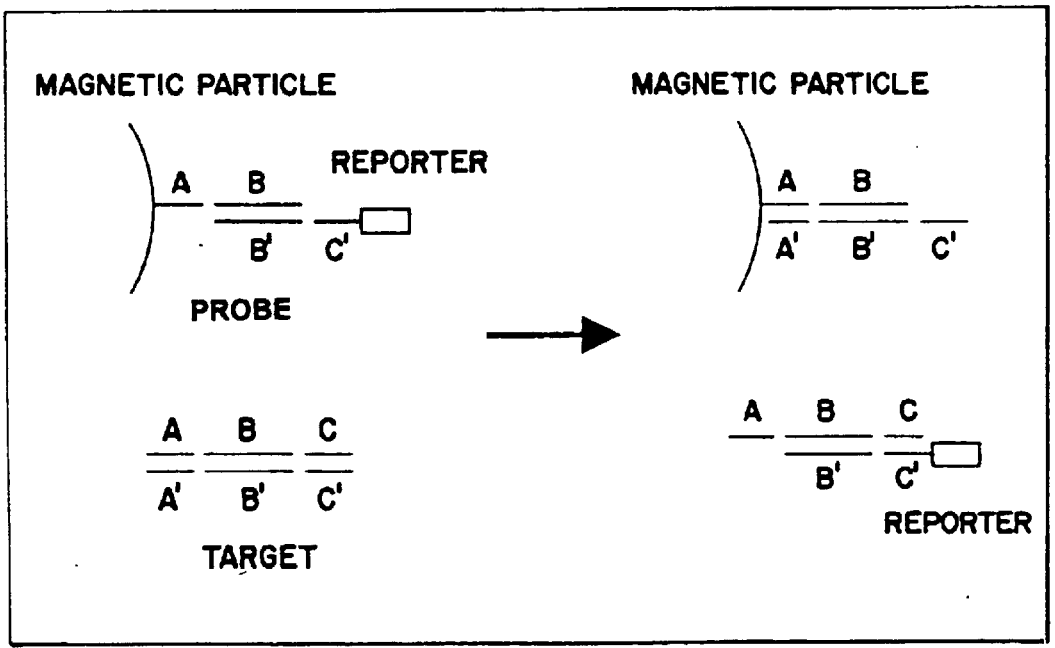

FIG. 32
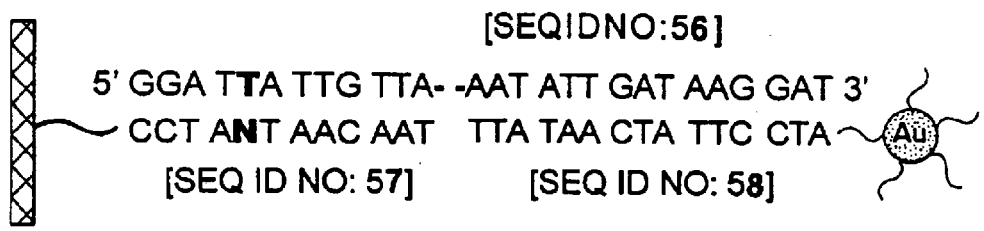
N = A (complementary),
G,C,T (mismatched)
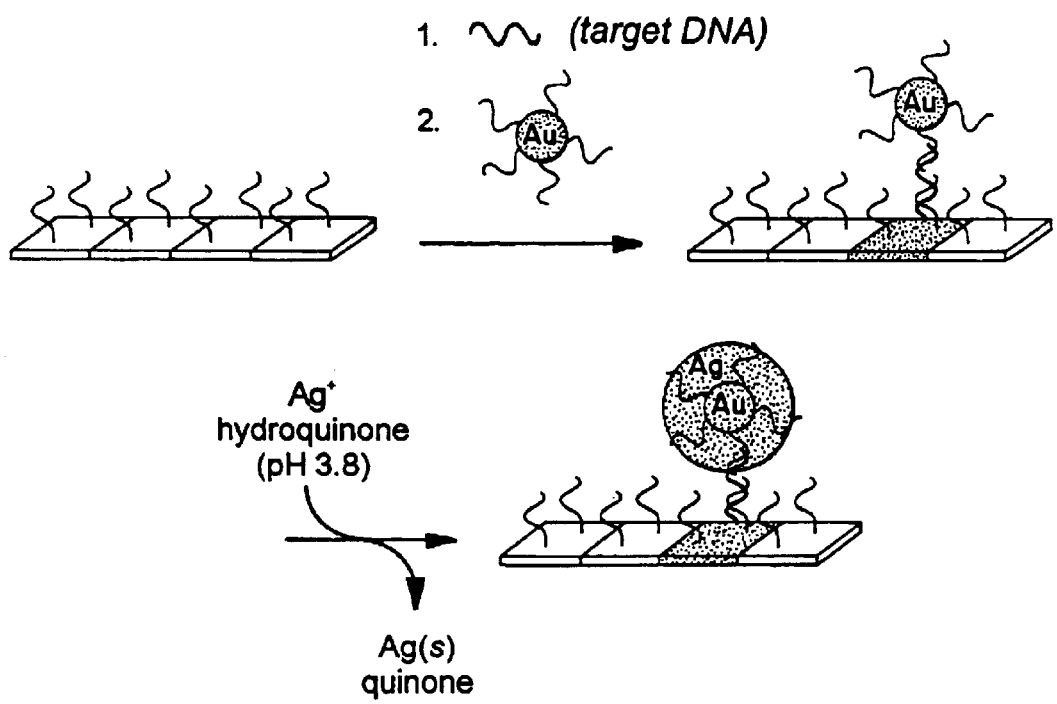

FIG. 33
  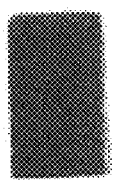
A B C
  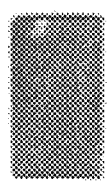 
D E F G

C  A  T  G

FIG.37A
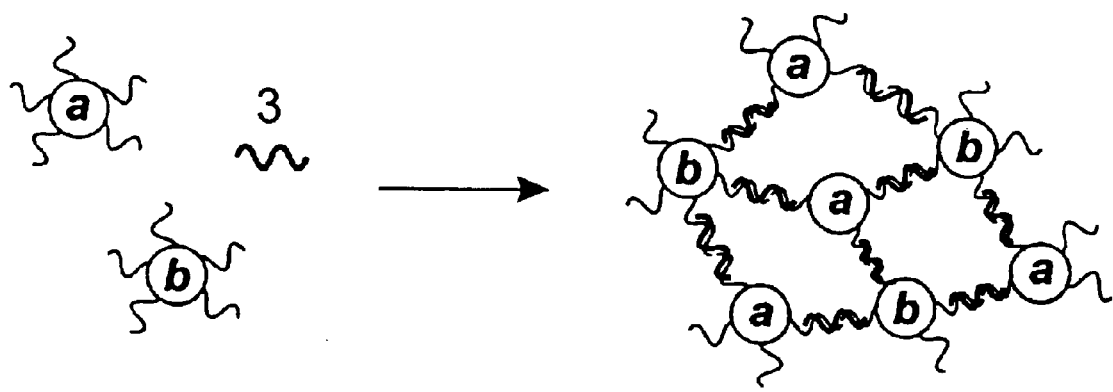
FIG.37B
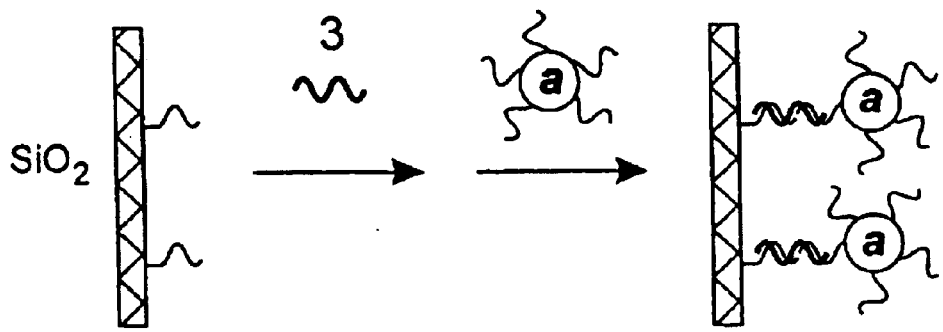
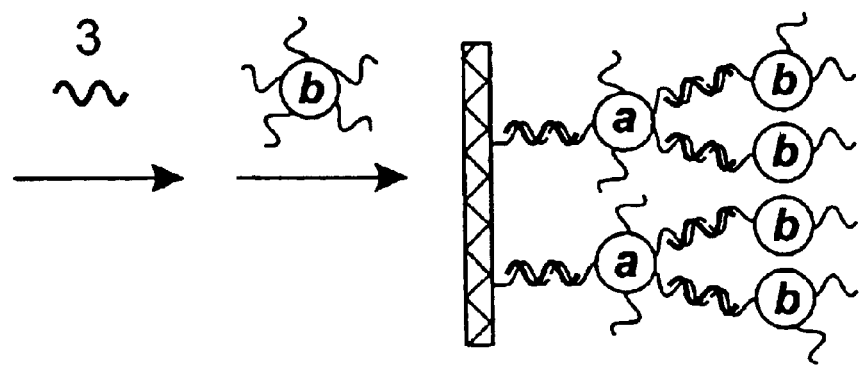

```
                        SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 1
aaacgactct agcgcgtata                                           20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 2
atggcaacta tacgcgctag                                           20

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 3
ccttgagatt tccctc                                               16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 4
gagggaaatc tcaagg                                               16

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 5
aacttgcgct aatggcga                                             18

<210> SEQ ID NO 6
<211> LENGTH: 26
<212> TYPE: DNA
<213> ORGANISM: Artificial Sequence
<220> FEATURE:
```

```
<223> OTHER INFORMATION: Description of Artificial Sequence:random
      synthetic sequence

<400> SEQUENCE: 6
aagttgcgct ttacggctaa tggcga                                             26

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 7
tctccttccc ttttc                                                         15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 8
gaaaagggaa ggaga                                                         15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 9
cttttccctt cctct                                                         15

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 10
aaacgactct agcgcgtata gttgccat                                           28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 11
atggcaacta tacgcgctag agtcgttt                                           28

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence:random
``` synthetic sequence

<400> SEQUENCE: 12
cctatcgacc atgct                                                15

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 13
agcatggtcg ataggaaacg actctagcgc                                30

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 14
gcgctagagt cgttt                                                15

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 15
agcatggtcg ataggatggc aactatacgc                                30

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 16
gtcgatagga aacgactcta gcgc                                      24

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 17
agcatggttg ataggaaacg actctagcgc                                30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:random
      synthetic sequence

```
<400> SEQUENCE: 18
agcatgtttg ataggaaacg actctagcgc                                    30

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 19
tctcaactcg ta                                                       12

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 20
cgcattcagg at                                                       12

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 21
tacgagttga gagagtgccc acat                                          24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 22
tacgagttga gaatcctgaa tgcg                                          24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 23
tacgagttga gaatcctgaa tgct                                          24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence
```

```
<400> SEQUENCE: 24
tacgagttga gactcctgaa tgcg                                          24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 25
tacgagttga gaatcctgaa tgc                                           23

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 26
tacgagttga gacatcctga atgcg                                         25

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 27
tacgagttga gaatcctgaa tgcg                                          24

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 28
taggacttac gc                                                       12

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 29
tacgagttga gaccgttaag acgaggcaat catgcaatcc tgaatgcg                48

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 30
```

```
tgcatgattg cctcgtctta acgg                                             24

<210> SEQ ID NO 31
<211> LENGTH: 72
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 31
tacgagttga gaccgttaag acgaggcaat catgcatata ttggacgctt tacggacaac     60
atcctgaatg cg                                                          72

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 32
gttgtccgta aagcgtccaa tatatgcatg attgcctcgt cttaacgg                   48

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 33
tctcaactcg ta                                                          12

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 34
tacgagttga gaatcctgaa tgcg                                             24

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 35
cgcattcagg at                                                          12

<210> SEQ ID NO 36
<211> LENGTH: 141
<212> TYPE: DNA
<213> ORGANISM: anthrax

<400> SEQUENCE: 36
ggcggatgag tcagtagtta aggaggctca tagagaagta attaattcgt caacagaggg     60
```

-continued

```
attattgtta aatattgata aggatataag aaaaatatta tccagggtta tattgtagaa      120
attgaagata ctgaagggct t                                                141
```

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 37

```
taacaataat ccctc                                                        15
```

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 38

```
atccttatca atatt                                                        15
```

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 39

```
tgagcctcct taactactga ctcatccgcc                                        30
```

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 40

```
tgttgacgaa ttaattactt ctcta                                             25
```

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 41

```
tataaccctg gataatattt ttcttat                                           27
```

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence:random
      synthetic sequence

```
<400> SEQUENCE: 42
aagcccttca gtatcttcaa tttctacaa                                29

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 43
tctcaactcg taaaaaaaaa aa                                       22

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 44
tacgagttga gaatcctgaa tgcg                                     24

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 45
aaaaaaaaaa cgcattcagg at                                       22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 46
tctcaactcg taaaaaaaaa aa                                       22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 47
aaaaaaaaaa cgcattcagg at                                       22

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 48
```
tacgagttga gaatcctgaa tgcg 24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 49
ctacttagat ccgagtgccc acat 24

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 50
cgcattcagg at 12

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 51
aaaaaaaaaa aaaaaaaaaa cgcattcagg at 32

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 52
cgcattcagg atwwwwwwww wwwwwwwwww ww 32

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 53
atcctgaatg cg 12

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 54
atcctgaatg cg                                                          12

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 55
aaaaaaaaaa aaaaaaaaaa                                                  20

<210> SEQ ID NO 56
<211> LENGTH: 27
<212> TYPE: DNA
<213> ORGANISM: Anthrax

<400> SEQUENCE: 56
ggattattgt taattattga taaggat                                          27

<210> SEQ ID NO 57
<211> LENGTH: 12
<212> TYPE: DNA
<213> ORGANISM: Anthrax
<220> FEATURE:
<221> NAME/KEY: misc_feature
<222> LOCATION: (9)..(9)
<223> OTHER INFORMATION: n stands for a, g, c, or t

<400> SEQUENCE: 57
taacaatnat cc                                                          12

<210> SEQ ID NO 58
<211> LENGTH: 15
<212> TYPE: DNA
<213> ORGANISM: Anthrax

<400> SEQUENCE: 58
atccttatca atatt                                                       15

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 59
tctcaactcg ta                                                          12

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 60
tacgagttga gaatcctgaa tgcg                                             24

<210> SEQ ID NO 61
<211> LENGTH: 48
<212> TYPE: DNA

-continued

```
<213> ORGANISM: Artificial Sequence
<220> FEATURE:
<223> OTHER INFORMATION: Description of Artificial Sequence:random
      synthetic sequence

<400> SEQUENCE: 61
gcgtaagtcc taacgtacta acggagcaga attgccagag ttgagcat                    48

<210> SEQ ID NO 62
<211> LENGTH: 72
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 62
gcgtaagtcc tacaacaggc atttcgcagg ttatatacgt actaacggag cagaattgcc       60
agagttgagc at                                                           72

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 63
tgcatgattg cctcgtctta acgg                                              24

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence:random
      synthetic sequence

<400> SEQUENCE: 64
gttgtccgta aagcgtccaa tatatgcatg attgcctcgt cttaacgg                    48
```

NANOPARTICLES HAVING OLIGONUCLEOTIDES ATTACHED THERETO AND USES THEREFOR

This application is a continuation of U.S. application Ser. No. 09/603,830, filed Jun. 26, 2000 now U.S. Pat. No. 6,506,564, issued Jan. 14, 2003, which is a continuation-inpart of application Ser. No. 09/344,667, filed Jun. 25, 1999, now U.S. Pat. No. 6,361,944, issued Mar. 26, 2002, which was a continuation-in-part of application Ser. No. 09/240,755, filed Jan. 29, 1999 (abandoned), which was a continuation-in-part of pending PCT application PCT/US97/12783, which was filed Jul. 21, 1997. Benefit of provisional applications No. 60/031,809, filed Jul. 29, 1996, and 60/200,161, filed Apr. 26, 2000 is also hereby claimed.

This invention was made with government support under National Institutes Of Health (NIH) grant GM10265 and Army Research Office (ARO) grant DAAG55-0967-1-0133. The government has certain rights in the invention.

FIELD OF THE INVENTION

The invention relates to methods of detecting nucleic acids, whether natural or synthetic, and whether modified or unmodified. The invention also relates to materials for detecting nucleic acids and methods of making those materials. The invention further relates to methods of nanofabrication. Finally, the invention relates to methods of separating a selected nucleic acid from other nucleic acids.

BACKGROUND OF THE INVENTION

The development of methods for detecting and sequencing nucleic acids is critical to the diagnosis of genetic, bacterial, and viral diseases. See Mansfield, E. S. et al. *Molecular and Cellular Probes*, 9, 145–156 (1995). At present, there are a variety of methods used for detecting specific nucleic acid sequences. Id. However, these methods are complicated, time-consuming and/or require the use of specialized and expensive equipment. A simple, fast method of detecting nucleic acids which does not require the use of such equipment would clearly be desirable.

A variety of methods have been developed for assembling metal and semiconductor colloids into nanomaterials. These methods have focused on the use of covalent linker molecules that possess functionalities at opposing ends with chemical affinities for the colloids of interest. One of the most successful approaches to date, Brust et al., *Adv. Mater.*, 7, 795–797 (1995), involves the use of gold colloids and well-established thiol adsorption chemistry, Bain & Whitesides, *Angew. Chem. Int. Ed. Engl.*, 28, 506–512 (1989) and Dubois & Nuzzo, *Annu. Rev. Phys. Chem.*, 43, 437–464 (1992). In this approach, linear alkanedithiols are used as the particle linker molecules. The thiol groups at each end of the linker molecule covalently attach themselves to the colloidal particles to form aggregate structures. The drawbacks of this method are that the process is difficult to control and the assemblies are formed irreversibly. Methods for systematically controlling the assembly process are needed if the materials properties of these structures are to be exploited fully.

The potential utility of DNA for the preparation of biomaterials and in nanofabrication methods has been recognized. In this work, researchers have focused on using the sequence-specific molecular recognition properties of oligonucleotides to design impressive structures with well-defined geometric shapes and sizes. Shekhtman et al., *New J. Chem.*, 17, 757–763 (1993); Shaw & Wang, *Science*, 260, 533–536 (1993); Chen et al., *J. Am Chem. Soc.*, 111, 6402–6407 (1989); Chen & Seeman, *Nature*, 350, 631–633 (1991); Smith and Feigon, *Nature*, 356, 164–168 (1992); Wang et al., *Biochem.*, 32, 1899–1904 (1993); Chen et al., *Biochem.*, 33, 13540–13546 (1994); Marsh et al., *Nucleic Acids Res.*, 23, 696–700 (1995); Mirkin, *Annu. Review Biophys. Biomol. Struct.*, 23, 541–576 (1994); Wells, *J. Biol. Chem.*, 263, 1095–1098 (1988); Wang et al., *Biochem.*, 30, 5667–5674 (1991). However, the theory of producing DNA structures is well ahead of experimental confirmation. Seeman et al., *New J. Chem.*, 17, 739–755 (1993).

SUMMARY OF THE INVENTION

The invention provides methods of detecting nucleic acids. In one embodiment, the method comprises contacting a nucleic acid with a type of nanoparticles having oligonucleotides attached thereto (nanoparticle-oligonucleotide conjugates). The nucleic acid has at least two portions, and the oligonucleotides on each nanoparticle have a sequence complementary to the sequences of at least two portions of the nucleic acid. The contacting takes place under conditions effective to allow hybridization of the oligonucleotides on the nanoparticles with the nucleic acid. The hybridization of the oligonucleotides on the nanoparticles with the nucleic acid results in a detectable change.

In another embodiment, the method comprises contacting a nucleic acid with at least two types of nanoparticles having oligonucleotides attached thereto. The oligonucleotides on the first type of nanoparticles have a sequence complementary to a first portion of the sequence of the nucleic acid. The oligonucleotides on the second type of nanoparticles have a sequence complementary to a second portion of the sequence of the nucleic acid. The contacting takes place under conditions effective to allow hybridization of the oligonucleotides on the nanoparticles with the nucleic acid, and a detectable change brought about by this hybridization is observed.

In a further embodiment, the method comprises providing a substrate having a first type of nanoparticles attached thereto. The first type of nanoparticles has oligonucleotides attached thereto, and the oligonucleotides have a sequence complementary to a first portion of the sequence of a nucleic acid. The substrate is contacted with the nucleic acid under conditions effective to allow hybridization of the oligonucleotides on the nanoparticles with the nucleic acid. Then, a second type of nanoparticles having oligonucleotides attached thereto is provided. The oligonucleotides have a sequence complementary to one or more other portions of the sequence of the nucleic acid, and the nucleic acid bound to the substrate is contacted with the second type of nanoparticle-oligonucleotide conjugates under conditions effective to allow hybridization of the oligonucleotides on the second type of nanoparticles with the nucleic acid. A detectable change may be observable at this point. The method may further comprise providing a binding oligonucleotide having a selected sequence having at least two portions, the first portion being complementary to at least a portion of the sequence of the oligonucleotides on the second type of nanoparticles. The binding oligonucleotide is contacted with the second type of nanoparticle-oligonucleotide conjugates bound to the substrate under conditions effective to allow hybridization of the binding oligonucleotide to the oligonucleotides on the nanoparticles. Then, a third type of nanoparticles having oligonucleotides attached thereto, the oligonucleotides having a sequence complementary to the sequence of a second portion of the binding oligonucleotide, is contacted with the binding oligonucleotide bound to the substrate under conditions effective to allow hybridization of the binding oligonucleotide to the oligonucleotides on the nanoparticles. Finally, the detectable change produced by these hybridizations is observed.

In yet another embodiment, the method comprises contacting a nucleic acid with a substrate having oligonucleotides attached thereto, the oligonucleotides having a sequence complementary to a first portion of the sequence of the nucleic acid. The contacting takes place under conditions effective to allow hybridization of the oligonucleotides on the substrate with the nucleic acid. Then, the nucleic acid bound to the substrate is contacted with a first type of nanoparticles having oligonucleotides attached thereto, the oligonucleotides having a sequence complementary to a second portion of the sequence of the nucleic acid. The contacting takes place under conditions effective to allow hybridization of the oligonucleotides on the nanoparticles with the nucleic acid. Next, the first type of nanoparticle-oligonucleotide conjugates bound to the substrate is contacted with a second type of nanoparticles having oligonucleotides attached thereto, the oligonucleotides on the second type of nanoparticles having a sequence complementary to at least a portion of the sequence of the oligonucleotides on the first type of nanoparticles, the contacting taking place under conditions effective to allow hybridization of the oligonucleotides on the first and second types of nanoparticles. Finally, a detectable change produced by these hybridizations is observed.

In another embodiment, the method comprises contacting a nucleic acid with a substrate having oligonucleotides attached thereto, the oligonucleotides having a sequence complementary to a first portion of the sequence of the nucleic acid. The contacting takes place under conditions effective to allow hybridization of the oligonucleotides on the substrate with the nucleic acid. Then, the nucleic acid bound to the substrate is contacted with liposomes having oligonucleotides attached thereto, the oligonucleotides having a sequence complementary to a portion of the sequence of the nucleic acid. This contacting takes place under conditions effective to allow hybridization of the oligonucleotides on the liposomes with the nucleic acid. Next, the liposome-oligonucleotide conjugates bound to the substrate are contacted with a first type of nanoparticles having at least a first type of oligonucleotides attached thereto. The first type of oligonucleotides have a hydrophobic group attached to the end not attached to the nanoparticles, and the contacting takes place under conditions effective to allow attachment of the oligonucleotides on the nanoparticles to the liposomes as a result of hydrophobic interactions. A detectable change may be observable at this point. The method may further comprise contacting the first type of nanoparticle-oligonucleotide conjugates bound to the liposomes with a second type of nanoparticles having oligonucleotides attached thereto. The first type of nanoparticles have a second type of oligonucleotides attached thereto which have a sequence complementary to at least a portion of the sequence of the oligonucleotides on the second type of nanoparticles, and the oligonucleotides on the second type of nanoparticles having a sequence complementary to at least a portion of the sequence of the second type of oligonucleotides on the first type of nanoparticles. The contacting takes place under conditions effective to allow hybridization of the oligonucleotides on the first and second types of nanoparticles. Then, a detectable change is observed.

In another embodiment, the method comprises contacting a nucleic acid to be detected with a substrate having oligonucleotides attached thereto. The oligonucleotides have a sequence complementary to a first portion of the sequence of said nucleic acid, the contacting takes place under conditions effective to allow hybridization of the oligonucleotides on the substrate with said nucleic acid. Next, said nucleic acid bound to the substrate is contacted with a type of nanoparticles having oligonucleotides attached thereto. The oligonucleotides have a sequence complementary to a second portion of the sequence of said nucleic acid. The contacting takes place under conditions effective to allow hybridization of the oligonucleotides on the nanoparticles with said nucleic acid. Then, the substrate is contacted with silver stain to produce a detectable change, and the detectable change is observed.

In yet another embodiment, the method comprises providing a substrate having a first type of nanoparticles attached thereto. The nanoparticles have oligonucleotides attached thereto, the oligonucleotides having a sequence complementary to a first portion of the sequence of a nucleic acid to be detected. Then, the nucleic acid is contacted with the nanoparticles attached to the substrate under conditions effective to allow hybridization of the oligonucleotides on the nanoparticles with said nucleic acid. Next, an aggregate probe comprising at least two types of nanoparticles having oligonucleotides attached thereto is provided. The nanoparticles of the aggregate probe are bound to each other as a result of the hybridization of some of the oligonucleotides attached to them. At least one of the types of nanoparticles of the aggregate probe have oligonucleotides attached thereto which have a sequence complementary to a second portion of the sequence of said nucleic acid. Finally, said nucleic acid bound to the substrate is contacted with the aggregate probe under conditions effective to allow hybridization of the oligonucleotides on the aggregate probe with said nucleic acid, and a detectable change is observed.

In a further embodiment, the method comprises providing a substrate having oligonucleotides attached thereto. The oligonucleotides have a sequence complementary to a first portion of the sequence of a nucleic acid to be detected. An aggregate probe comprising at least two types of nanoparticles having oligonucleotides attached thereto is provided. The nanoparticles of the aggregate probe are bound to each other as a result of the hybridization of some of the oligonucleotides attached to them. At least one of the types of nanoparticles of the aggregate probe have oligonucleotides attached thereto which have a sequence complementary to a second portion of the sequence of said nucleic acid. The nucleic acid, the substrate and the aggregate probe are contacted under conditions effective to allow hybridization of said nucleic acid with the oligonucleotides on the aggregate probe and with the oligonucleotides on the substrate, and a detectable change is observed.

In a further embodiment, the method comprises providing a substrate having oligonucleotides attached thereto. An aggregate probe comprising at least two types of nanoparticles having oligonucleotides attached thereto is provided. The nanoparticles of the aggregate probe are bound to each other as a result of the hybridization of some of the oligonucleotides attached to them. At least one of the types of nanoparticles of the aggregate probe have oligonucleotides attached thereto which have a sequence complementary to a first portion of the sequence of a nucleic acid to be detected. A type of nanoparticles having at least two types of oligonucleotides attached thereto is provided. The first type of oligonucleotides has a sequence complementary to a second portion of the sequence of said nucleic acid, and the second type of oligonucleotides has a sequence complementary to at least a portion of the sequence of the oligonucleotides attached to the substrate. The nucleic acid, the aggregate probe, the nanoparticles and the substrate are contacted under conditions effective to allow hybridization of said nucleic acid with the oligonucleotides on the aggregate probe and on the nanoparticles and hybridization of the oligonucleotides on the nanoparticles with the oligonucleotides on the substrate, and a detectable change is observed.

In another embodiment, the method comprises contacting a nucleic acid to be detected with a substrate having oligonucleotides attached thereto. The oligonucleotides have a sequence complementary to a first portion of the sequence of said nucleic acid. The contacting takes place under conditions effective to allow hybridization of the oligonucleotides on the substrate with said nucleic acid. The nucleic acid bound to the substrate is contacted with liposomes having oligonucleotides attached thereto, the oligonucleotides having a sequence complementary to a portion of the sequence of said nucleic acid. The contacting takes place under conditions effective to allow hybridization of the oligonucleotides on the liposomes with said nucleic acid. An aggregate probe comprising at least two types of nanoparticles having oligonucleotides attached thereto is provided. The nanoparticles of the aggregate probe are bound to each other as a result of the hybridization of some of the oligonucleotides attached to them, at least one of the types of nanoparticles of the aggregate probe having oligonucleotides attached thereto which have a hydrophobic group attached to the end not attached to the nanoparticles. The liposomes bound to the substrate are contacted with the aggregate probe under conditions effective to allow attachment of the oligonucleotides on the aggregate probe to the liposomes as a result of hydrophobic interactions, and a detectable change is observed.

In yet another embodiment, the method comprises providing a substrate having oligonucleotides attached thereto. The oligonucleotides having a sequence complementary to a first portion of the sequence of a nucleic acid to be detected. A core probe comprising at least two types of nanoparticles is provided. Each type of nanoparticles has oligonucleotides attached thereto which are complementary to the oligonucleotides on at least one of the other types of nanoparticles. The nanoparticles of the aggregate probe are bound to each other as a result of the hybridization of the oligonucleotides attached to them. Next, a type of nanoparticles having two types of oligonucleotides attached thereto is provided. The first type of oligonucleotides has a sequence complementary to a second portion of the sequence of said nucleic acid, and the second type of oligonucleotides has a sequence complementary to a portion of the sequence of the oligonucleotides attached to at least one of the types of nanoparticles of the core probe. The nucleic acid, the nanoparticles, the substrate and the core probe are contacted under conditions effective to allow hybridization of said nucleic acid with the oligonucleotides on the nanoparticles and with the oligonucleotides on the substrate and to allow hybridization of the oligonucleotides on the nanoparticles with the oligonucleotides on the core probe, and a detectable change is observed.

Another embodiment of the method comprises providing a substrate having oligonucleotides attached thereto, the oligonucleotides having a sequence complementary to a first portion of the sequence of a nucleic acid to be detected. A core probe comprising at least two types of nanoparticles is provided. Each type of nanoparticles has oligonucleotides attached thereto which are complementary to the oligonucleotides on at least one other type of nanoparticles. The nanoparticles of the aggregate probe are bound to each other as a result of the hybridization of the oligonucleotides attached to them. A type of linking oligonucleotides comprising a sequence complementary to a second portion of the sequence of said nucleic acid and a sequence complementary to a portion of the sequence of the oligonucleotides attached to at least one of the types of nanoparticles of the core probe is provided. The nucleic acid, the linking oligonucleotides, the substrate and the core probe are contacted under conditions effective to allow hybridization of said nucleic acid with the linking oligonucleotides and with the oligonucleotides on the substrate and to allow hybridization of the oligonucleotides on the linking oligonucleotides with the oligonucleotides on the core probe, and a detectable change is observed.

In yet another embodiment, the method comprises providing nanoparticles having oligonucleotides attached thereto and providing one or more types of binding oligonucleotides. Each of the binding oligonucleotides has two portions. The sequence of one portion is complementary to the sequence of one of the portions of the nucleic acid, and the sequence of the other portion is complementary to the sequence of the oligonucleotides on the nanoparticles. The nanoparticle-oligonucleotide conjugates and the binding oligonucleotides are contacted under conditions effective to allow hybridization of the oligonucleotides on the nanoparticles with the binding oligonucleotides. The nucleic acid and the binding oligonucleotides are contacted under conditions effective to allow hybridization of the binding oligonucleotides with the nucleic acid. Then, a detectable change is observed. The nanoparticle-oligonucleotide conjugates may be contacted with the binding oligonucleotides prior to being contacted with the nucleic acid, or all three may be contacted simultaneously.

In another embodiment, the method comprises contacting a nucleic acid with at least two types of particles having oligonucleotides attached thereto. The oligonucleotides on the first type of particles have a sequence complementary to a first portion of the sequence of the nucleic acid and have energy donor molecules on the ends not attached to the particles. The oligonucleotides on the second type of particles have a sequence complementary to a second portion of the sequence of the nucleic acid and have energy acceptor molecules on the ends not attached to the particles. The contacting takes place under conditions effective to allow hybridization of the oligonucleotides on the particles with the nucleic acid, and a detectable change brought about by this hybridization is observed. The energy donor and acceptor molecules may be fluorescent molecules.

In a further embodiment, the method comprises providing a type of microspheres having oligonucleotides attached thereto. The oligonucleotides have a sequence complementary to a first portion of the sequence of the nucleic acid and are labeled with a fluorescent molecule. A type of nanoparticles having oligonucleotides attached thereto and which produce a detectable change is also provided. These oligonucleotides have a sequence complementary to a second portion of the sequence of the nucleic acid. The nucleic acid is contacted with the microspheres and the nanoparticles under conditions effective to allow hybridization of the oligonucleotides on the latex microspheres and on the nanoparticles with the nucleic acid. Then, changes in fluorescence, another detectable change, or both are observed.

In another embodiment, the method comprises providing a first type of metallic or semiconductor nanoparticles having oligonucleotides attached thereto. The oligonucleotides have a sequence complementary to a first portion of the sequence of the nucleic acid and are labeled with a fluorescent molecule. A second type of metallic or semiconductor nanoparticles having oligonucleotides attached thereto is also provided. These oligonucleotides have a sequence complementary to a second portion of the sequence of the nucleic acid and are also labeled with a fluorescent molecule. The nucleic acid is contacted with the two types of nanoparticles under conditions effective to allow hybridization of the oligonucleotides on the two types of nanoparticles with the nucleic acid. Then, changes in fluorescence are observed.

In a further embodiment, the method comprises providing a type of particle having oligonucleotides attached thereto. The oligonucleotides have a first portion and a second portion, both portions being complementary to portions of the sequence of the nucleic acid. A type of probe oligonucleotides comprising a first portion and a second portion is also provided. The first portion has a sequence complementary to the first portion of the oligonucleotides attached to the particles, and both portions are complementary to portions of the sequence of the nucleic acid. The probe oligonucleotides are also labeled with a reporter molecule at one end. Then, the particles and the probe oligonucleotides are contacted under conditions effective to allow for hybridization of the oligonucleotides on the particles with the probe oligonucleotides to produce a satellite probe. Then, the satellite probe is contacted with the nucleic acid under conditions effective to provide for hybridization of the nucleic acid with the probe oligonucleotides. The particles are removed and the reporter molecule detected.

In yet another embodiment of the method of the invention, a nucleic acid is detected by contacting the nucleic acid with a substrate having oligonucleotides attached thereto. The oligonucleotides have a sequence complementary to a first portion of the sequence of the nucleic acid. The oligonucleotides are located between a pair of electrodes located on the substrate. The contacting takes place under conditions effective to allow hybridization of the oligonucleotides on the substrate with the nucleic acid. Then, the nucleic acid bound to the substrate, is contacted with a type of nanoparticles. The nanoparticles are made of a material which can conduct electricity. The nanoparticles will have one or more types of oligonucleotides attached to them, at least one of the types of oligonucleotides having a sequence complementary to a second portion of the sequence of the nucleic acid. The contacting takes place under conditions effective to allow hybridization of the oligonucleotides on the nanoparticles with the nucleic acid. If the nucleic acid is present, a change in conductivity can be detected. In a preferred embodiment, the substrate will have a plurality of pairs of electrodes located on it in an array to allow for the detection of multiple portions of a single nucleic acid, the detection of multiple different nucleic acids, or both. Each of the pairs of electrodes in the array will have a type of oligonucleotides attached to the substrate between the two electrodes.

The invention further provides a method of detecting a nucleic acid wherein the method is performed on a substrate. The method comprises detecting the presence, quantity or both, of the nucleic acid with an optical scanner.

The invention further provides kits for detecting nucleic acids. In one embodiment, the kit comprises at least one container, the container holding at least two types of nanoparticles having oligonucleotides attached thereto. The oligonucleotides on the first type of nanoparticles have a sequence complementary to the sequence of a first portion of a nucleic acid. The oligonucleotides on the second type of nanoparticles have a sequence complementary to the sequence of a second portion of the nucleic acid.

Alternatively, the kit may comprise at least two containers. The first container holds nanoparticles having oligonucleotides attached thereto which have a sequence complementary to the sequence of a first portion of a nucleic acid. The second container holds nanoparticles having oligonucleotides attached thereto which have a sequence complementary to the sequence of a second portion of the nucleic acid.

In a further embodiment, the kit comprises at least one container. The container holds metallic or semiconductor nanoparticles having oligonucleotides attached thereto. The oligonucleotides have a sequence complementary to portion of a nucleic acid and have fluorescent molecules attached to the ends of the oligonucleotides not attached to the nanoparticles.

In yet another embodiment, the kit comprises a substrate, the substrate having attached thereto nanoparticles, the nanoparticles having oligonucleotides attached thereto which have a sequence complementary to the sequence of a first portion of a nucleic acid. The kit also includes a first container holding nanoparticles having oligonucleotides attached thereto which have a sequence complementary to the sequence of a second portion of the nucleic acid. The kit further includes a second container holding a binding oligonucleotide having a selected sequence having at least two portions, the first portion being complementary to at least a portion of the sequence of the oligonucleotides on the nanoparticles in the first container. The kit also includes a third container holding nanoparticles having oligonucleotides attached thereto, the oligonucleotides having a sequence complementary to the sequence of a second portion of the binding oligonucleotide.

In another embodiment, the kit comprises a substrate having oligonucleotides attached thereto which have a sequence complementary to the sequence of a first portion of a nucleic acid, a first container holding nanoparticles having oligonucleotides attached thereto which have a sequence complementary to the sequence of a second portion of the nucleic acid, and a second container holding nanoparticles having oligonucleotides attached thereto which have a sequence complementary to at least a portion of the oligonucleotides attached to the nanoparticles in the first container.

In yet another embodiment, the kit comprises a substrate, a first container holding nanoparticles, a second container holding a first type of oligonucleotides having a sequence complementary to the sequence of a first portion of a nucleic acid, a third container holding a second type of oligonucleotides having a sequence complementary to the sequence of a second portion of the nucleic acid, and a fourth container holding a third type of oligonucleotides having a sequence complementary to at least a portion of the sequence of the second type of oligonucleotides.

In a further embodiment, the kit comprises a substrate having oligonucleotides attached thereto which have a sequence complementary to the sequence of a first portion of a nucleic acid. The kit also includes a first container holding liposomes having oligonucleotides attached thereto which have a sequence complementary to the sequence of a second portion of the nucleic acid and a second container holding nanoparticles having at least a first type of oligonucleotides attached thereto, the first type of oligonucleotides having a hydrophobic group attached to the end not attached to the nanoparticles so that the nanoparticles can be attached to the liposomes by hydrophobic interactions. The kit may further comprise a third container holding a second type of nanoparticles having oligonucleotides attached thereto, the oligonucleotides having a sequence complementary to at least a portion of the sequence of a second type of oligonucleotides attached to the first type of nanoparticles. The second type of oligonucleotides attached to the first type of nanoparticles have a sequence complementary to the sequence of the oligonucleotides on the second type of nanoparticles.

In another embodiment, the kit comprises a substrate having nanoparticles attached to it. The nanoparticles have oligonucleotides attached to them which have a sequence complementary to the sequence of a first portion of a nucleic acid. The kit also includes a first container holding an aggregate probe. The aggregated probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a sequence complementary to a second portion of the sequence of the nucleic acid.

In yet another embodiment, the kit comprises a substrate having oligonucleotides attached to it. The oligonucleotides have a sequence complementary to the sequence of a first portion of a nucleic acid. The kit further includes a first container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached thereto which have a sequence complementary to a second portion of the sequence of the nucleic acid.

In an additional embodiment, the kit comprises a substrate having oligonucleotides attached to it and a first container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a sequence complementary to a first portion of the sequence of the nucleic acid. The kit also includes a second container holding nanoparticles. The nanoparticles have at least two types of oligonucleotides attached to them. The first type of oligonucleotides has a sequence complementary to a second portion of the sequence of the nucleic acid. The second type of oligonucleotides has a sequence complementary to at least a portion of the sequence of the oligonucleotides attached to the substrate.

In another embodiment, the kit comprises a substrate which has oligonucleotides attached to it. The oligonucleotides have a sequence complementary to the sequence of a first portion of a nucleic acid. The kit also comprises a first container holding liposomes having oligonucleotides attached to them. The oligonucleotides have a sequence complementary to the sequence of a second portion of the nucleic acid. The kit further includes a second container holding an aggregate probe comprising at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a hydrophobic groups attached to the ends not attached to the nanoparticles.

In a further embodiment, the kit may comprise a first container holding nanoparticles having oligonucleotides attached thereto. The kit also includes one or more additional containers, each container holding a binding oligonucleotide. Each binding oligonucleotide has a first portion which has a sequence complementary to at least a portion of the sequence of oligonucleotides on the nanoparticles and a second portion which has a sequence complementary to the sequence of a portion of a nucleic acid to be detected. The sequences of the second portions of the binding oligonucleotides may be different as long as each sequence is complementary to a portion of the sequence of the nucleic acid to be detected.

In another embodiment, the kit comprises a container holding one type of nanoparticles having oligonucleotides attached thereto and one or more types of binding oligonucleotides. Each of the types of binding oligonucleotides has a sequence comprising at least two portions. The first portion is complementary to the sequence of the oligonucleotides on the nanoparticles, whereby the binding oligonucleotides are hybridized to the oligonucleotides on the nanoparticles in the container(s). The second portion is complementary to the sequence of a portion of the nucleic acid.

In another embodiment, kits may comprise one or two containers holding two types of particles. The first type of particles having oligonucleotides attached thereto which have a sequence complementary to the sequence of a first portion of a nucleic acid. The oligonucleotides are labeled with an energy donor on the ends not attached to the particles. The second type of particles having oligonucleotides attached thereto which have a sequence complementary to the sequence of a second portion of a nucleic acid. The oligonucleotides are labeled with an energy acceptor on the ends not attached to the particles. The energy donors and acceptors may be fluorescent molecules.

In a further embodiment, the kit comprises a first container holding nanoparticles having oligonucleotides attached thereto. The kit also includes one or more additional containers, each container holding binding oligonucleotides. Each binding oligonucleotide has a first portion which has a sequence complementary to at least a portion of the sequence of oligonucleotides on the nanoparticles and a second portion which has a sequence complementary to the sequence of a portion of a nucleic acid to be detected. The sequences of the second portions of the binding oligonucleotides may be different as long as each sequence is complementary to a portion of the sequence of the nucleic acid to be detected.

In yet another embodiment, the kit comprises a container holding one type of nanoparticles having oligonucleotides attached thereto and one or more types of binding oligonucleotides. Each of the types of binding oligonucleotides has a sequence comprising at least two portions. The first portion is complementary to the sequence of the oligonucleotides on the nanoparticles, whereby the binding oligonucleotides are hybridized to the oligonucleotides on the nanoparticles in the container(s). The second portion is complementary to the sequence of a portion of the nucleic acid.

In another alternative embodiment, the kit comprises at least three containers. The first container holds nanoparticles. The second container holds a first oligonucleotide having a sequence complementary to the sequence of a first portion of a nucleic acid. The third container holds a second oligonucleotide having a sequence complementary to the sequence of a second portion of the nucleic acid. The kit may further comprise a fourth container holding a binding oligonucleotide having a selected sequence having at least two portions, the first portion being complementary to at least a portion of the sequence of the second oligonucleotide, and a fifth container holding an oligonucleotide having a sequence complementary to the sequence of a second portion of the binding oligonucleotide.

In another embodiment, the kit comprises one or two containers, the container(s) holding two types of particles. The first type of particles having oligonucleotides attached thereto that have a sequence complementary to a first portion of the sequence of a nucleic acid and have energy donor molecules attached to the ends not attached to the nanoparticles. The second type of particles having oligonucleotides attached thereto that have a sequence complementary to a second portion of the sequence of a nucleic acid and have energy acceptor molecules attached to the ends not attached to the nanoparticles. The energy donors and acceptors may be fluorescent molecules.

In a further embodiment, the kit comprises a first container holding a type of microspheres having oligonucleotides attached thereto. The oligonucleotides have a sequence complementary to a first portion of the sequence of a nucleic acid and are labeled with a fluorescent molecule. The kit also comprises a second container holding a type of nanoparticles having oligonucleotides attached thereto. The oligonucleotides have a sequence complementary to a second portion of the sequence of the nucleic acid.

In another embodiment, the kit comprises a first container holding a first type of metallic or semiconductor nanoparticles having oligonucleotides attached thereto. The oligonucleotides have a sequence complementary to a first portion of the sequence of a nucleic acid and are labeled with a fluorescent molecule. The kit also comprises a second container holding a second type of metallic or semiconductor nanoparticles having oligonucleotides attached thereto. These oligonucleotides have a sequence complementary to a second portion of the sequence of a nucleic acid and are labeled with a fluorescent molecule.

In another embodiment, the kit comprises a container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a sequence complementary to a portion of the sequence of a nucleic acid.

In an additional embodiment, the kit comprises a container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a hydrophobic group attached to the end not attached to the nanoparticles.

In a further embodiment, the kit comprises a container holding a satellite probe. The satellite probe comprises a particle having attached thereto oligonucleotides. The oligonucleotides have a first portion and a second portion, both portions having sequences complementary to portions of the sequence of a nucleic acid. The satellite probe also comprises probe oligonucleotides hybridized to the oligonucleotides attached to the nanoparticles. The probe oligonucleotides have a first portion and a second portion. The first portion has a sequence complementary to the sequence of the first portion of the oligonucleotides attached to the particles, and both portions have sequences complementary to portions of the sequence of the nucleic acid. The probe oligonucleotides also have a reporter molecule attached to one end.

In another embodiment, the kit comprising a container holding a core probe, the core probe comprising at least two types of nanoparticles having oligonucleotides attached thereto, the nanoparticles of the core probe being bound to each other as a result of the hybridization of some of the oligonucleotides attached to them.

In yet another embodiment, the kit comprises a substrate having attached to it at least one pair of electrodes with oligonucleotides attached to the substrate between the electrodes. The oligonucleotides have a sequence complementary to a first portion of the sequence of a nucleic acid to be detected.

The invention also provides the satellite probe, an aggregate probe and a core probe.

The invention further provides a substrate having nanoparticles attached thereto. The nanoparticles may have oligonucleotides attached thereto which have a sequence complementary to the sequence of a first portion of a nucleic acid.

The invention also provides a metallic or semiconductor nanoparticle having oligonucleotides attached thereto. The oligonucleotides are labeled with fluorescent molecules at the ends not attached to the nanoparticle.

The invention further provides a method of nanofabrication. The method comprises providing at least one type of linking oligonucleotide having a selected sequence, the sequence of each type of linking oligonucleotide having at least two portions. The method further comprises providing one or more types of nanoparticles having oligonucleotides attached thereto, the oligonucleotides on each type of nanoparticles having a sequence complementary to a portion of the sequence of a linking oligonucleotide. The linking oligonucleotides and nanoparticles are contacted under conditions effective to allow hybridization of the oligonucleotides on the nanoparticles to the linking oligonucleotides so that a desired nanomaterials or nanostructure is formed.

The invention provides another method of nanofabrication. This method comprises providing at least two types of nanoparticles having oligonucleotides attached thereto. The oligonucleotides on the first type of nanoparticles have a sequence complementary to that of the oligonucleotides on the second type of nanoparticles. The oligonucleotides on the second type of nanoparticles have a sequence complementary to that of the oligonucleotides on the first type of nanoparticle-oligonucleotide conjugates. The first and second types of nanoparticles are contacted under conditions effective to allow hybridization of the oligonucleotides on the nanoparticles to each other so that a desired nanomaterials or nanostructure is formed.

The invention further provides nanomaterials or nanostructures composed of nanoparticles having oligonucleotides attached thereto, the nanoparticles being held together by oligonucleotide connectors.

The invention also provides a composition comprising at least two types of nanoparticles having oligonucleotides attached thereto. The oligonucleotides on the first type of nanoparticles have a sequence complementary to the sequence of a first portion of a nucleic acid or a linking oligonucleotide. The oligonucleotides on the second type of nanoparticles have a sequence complementary to the sequence of a second portion of the nucleic acid or linking oligonucleotide.

The invention further provides an assembly of containers comprising a first container holding nanoparticles having oligonucleotides attached thereto, and a second container holding nanoparticles having oligonucleotides attached thereto. The oligonucleotides attached to the nanoparticles in the first container have a sequence complementary to that of the oligonucleotides attached to the nanoparticles in the second container. The oligonucleotides attached to the nanoparticles in the second container have a sequence complementary to that of the oligonucleotides attached to the nanoparticles in the first container.

The invention also provides a nanoparticle having a plurality of different oligonucleotides attached to it.

The invention further provides a method of separating a selected nucleic acid having at least two portions from other nucleic acids. The method comprises providing one or more types of nanoparticles having oligonucleotides attached thereto, the oligonucleotides on each of the types of nanoparticles having a sequence complementary to the sequence of one of the portions of the selected nucleic acid. The selected nucleic acid and other nucleic acids are contacted with the nanoparticles under conditions effective to allow hybridization of the oligonucleotides on the nanoparticles with the selected nucleic acid so that the nanoparticles hybridized to the selected nucleic acid aggregate and precipitate.

In addition, the invention provides methods of making unique nanoparticle-oligonucleotide conjugates. The first such method comprises binding oligonucleotides to charged nanoparticles to produce stable nanoparticle-oligonucleotide conjugates. To do so, oligonucleotides having covalently bound thereto a moiety comprising a functional group which can bind to the nanoparticles are contacted with the nanoparticles in water for a time sufficient to allow at least some of the oligonucleotides to bind to the nanoparticles by means of the functional groups. Next, at least one salt is added to the water to form a salt solution. The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. After adding the salt, the oligonucleotides and nanoparticles are incubated in the salt solution for an additional period of time sufficient to allow sufficient additional oligonucleotides to bind to the nanoparticles to produce the stable nanoparticle-oligonucleotide conjugates. The invention also includes the stable nanoparticle-oligonucleotide conjugates, methods of using the conjugates to detect and separate nucleic acids, kits comprising the conjugates, methods of nanofabrication using the conjugates, and nanomaterials and nanostructures comprising the conjugates.

The invention provides another method of binding oligonucleotides to nanoparticles to produce nanoparticle-oligonucleotide conjugates. The method comprises providing oligonucleotides, the oligonucleotides comprising a type of recognition oligonucleotides and a type of diluent oligonucleotides. The oligonucleotides and the nanoparticles are contacted under conditions effective to allow at least some of each of the types of oligonucleotides to bind to the nanoparticles to produce the conjugates. The invention also includes the nanoparticle-oligonucleotide conjugates produced by this method, methods of using the conjugates to detect and separate nucleic acids, kits comprising the conjugates, methods of nanofabrication using the conjugates, and nanomaterials and nanostructures comprising the conjugates. "Recognition oligonucleotides" are oligonucleotides which comprise a sequence complementary to at least a portion of the sequence of a nucleic acid or oligonucleotide target. "Diluent oligonucleotides" may have any sequence which does not interfere with the ability of the recognition oligonucleotides to be bound to the nanoparticles or to bind to their targets.

The invention provides yet another method of binding oligonucleotides to nanoparticles to produce nanoparticle-oligonucleotide conjugates. The method comprises providing oligonucleotides, the oligonucleotides comprising at least one type of recognition oligonucleotides. The recognition oligonucleotides comprise a recognition portion and a spacer portion. The recognition portion of the recognition oligonucleotides has a sequence complementary to at least one portion of the sequence of a nucleic acid or oligonucleotide target. The spacer portion of the recognition oligonucleotide is designed so that it can bind to the nanoparticles. As a result of the binding of the spacer portion of the recognition oligonucleotide to the nanoparticles, the recognition portion is spaced away from the surface of the nanoparticles and is more accessible for hybridization with its target. To make the conjugates, the oligonucleotides, including the recognition oligonucleotides, and the nanoparticles are contacted under conditions effective allow at least some of the recognition oligonucleotides to bind to the nanoparticles. The invention also includes the nanoparticle-oligonucleotide conjugates produced by this method, methods of using the conjugates to detect and separate nucleic acids, kits comprising the conjugates, methods of nanofabrication using the conjugates, and nanomaterials and nanostructures comprising the conjugates.

As used herein, a "type of oligonucleotides" refers to a plurality of oligonucleotide molecules having the same sequence. A "type of" nanoparticles, conjugates, particles, latex microspheres, etc. having oligonucleotides attached thereto refers to a plurality of that item having the same type(s) of oligonucleotides attached to them. "Nanoparticles having oligonucleotides attached thereto" are also sometimes referred to as "nanoparticle-oligonucleotide conjugates" or, in the case of the detection methods of the invention, "nanoparticle-oligonucleotide probes," "nanoparticle probes," or just "probes."

BRIEF DESCRIPTION OF THE DRAWINGS

FIG. 3: Schematic diagram of a variation of the system shown in FIG. 2. The oligonucleotides on the two nanoparticles have sequences complementary to two different portions of the single-stranded DNA shown which are separated by a third portion which is not complementary to the oligonucleotides on the nanoparticles. Also shown is an optional filler oligonucleotide which can be used to hybridize with the noncomplementary portion of the single-stranded DNA. When the DNA, nanoparticles and filler oligonucleotides are combined, the nanoparticles aggregate, with the formation of nicked, double-stranded oligonucleotide connectors.

FIG. 4: Schematic diagram illustrating reversible aggregation of nanoparticles having oligonucleotides attached thereto as a result of hybridization and de-hybridization with a linking oligonucleotide. The illustrated linking oligonucleotide is a double-stranded DNA having overhanging termini (sticky ends) which are complementary to the oligonucleotides attached to the nanoparticles.

FIG. 5: Schematic diagram illustrating the formation of nanoparticle aggregates by combining nanoparticles having oligonucleotides attached thereto with linking oligonucleotides having sequences complementary to the oligonucleotides attached to the nanoparticles.

FIGS. 8A–B: FIG. 8A is a graph of change in absorbance versus temperature/time for the system illustrated in FIG. 4. At low temperatures, gold nanoparticles having oligonucleotides attached thereto aggregate due to hybridization with linking oligonucleotides (see FIG. 4). At high temperature (80° C.), the nanoparticles are de-hybridized. Changing the temperature over time shows that this is a reversible process. FIG. 8B is a graph of change in absorbance versus temperature/time performed in the same manner using an aqueous solution of unmodified gold nanoparticles. The reversible changes seen in FIG. 8A are not observed.

FIG. 9A is a TEM image of aggregated gold nanoparticles held together by hybridization of the oligonucleotides on the gold nanoparticles with linking oligonucleotides. FIG. 9B is a TEM image of a two-dimensional aggregate showing the ordering of the linked nanoparticles.

In FIG. 10, one nanoparticle has an oligonucleotide attached to it which is composed of all purines, and the other nanoparticle has an oligonucleotide attached to it which is composed of all pyrimidines. The third oligonucleotide for forming the triple-stranded connector (not attached to a nanoparticle) is composed of pyrimidines.

In FIG. 11, the circles represent the nanoparticles, the formulas are oligonucleotide sequences, and s is the thio-alkyl linker. The multiple oligonucleotides on the two types of nanoparticles can hybridize to each other, leading to the formation of an aggregate structure.

FIGS. 13A–B: Schematic diagrams illustrating systems for detecting DNA (analyte DNA) using nanoparticles and a transparent substrate.

FIG. 14A is a graph of absorbance versus wavelength in nm showing changes in absorbance when gold nanoparticles having oligonucleotides attached thereto (one population of which is in solution and one population of which is attached to a transparent substrate as illustrated in FIG. 13B) aggregate due to hybridization with linking oligonucleotides. FIG. 14B a graph of change in absorbance for the hybridized system referred to in FIG. 14A as the temperature is increased (melted).

FIGS. 15A–G: Schematic diagrams illustrating systems for detecting nucleic acid using nanoparticles having oligonucleotides attached thereto. Oligonucleotide-nanoparticle conjugates 1 and 2 and single-stranded oligonucleotide targets 3, 4, 5, 6, 7 and 8 are illustrated. The circles represent the nanoparticles, the formulas are oligonucleotide sequences, and S represents the thio-alkyl linker.

FIGS. 16A–C: Schematic diagrams illustrating systems for detecting nucleic acid using nanoparticles having oligonucleotides attached thereto. Oligonucleotide-nanoparticle conjugates 1 and 2, single-stranded oligonucleotide targets of different lengths, and filler oligonucleotides of different lengths are illustrated. The circles represent the nanoparticles, the formulas are oligonucleotide sequences, and S represents the thio-alkyl linker.

FIGS. 17A–E: Schematic diagrams illustrating nanoparticle-oligonucleotide conjugates and systems for detecting nucleic acid using nanoparticles having oligonucleotides attached thereto. The circles represent the nanoparticles, the straight lines represent oligonucleotide chains (bases not shown), two closely-spaced parallel lines represent duplex segments, and the small letters indicate specific nucleotide sequences (a is complementary to a', b is complementary to b', etc.).

FIG. 19A is a graph of absorbance versus wavelength in nm showing changes in absorbance when gold nanoparticle-oligonucleotide conjugates assemble in multiple layers on a transparent substrate as illustrated in FIG. 13A. FIG. 19B is a graph of change in absorbance for the hybridized system referred to in FIG. 19A as the temperature is increased (melted).

FIG. 22: Schematic diagram illustrating a system for detecting target nucleic acid using two types of fluorescently-labeled oligonucleotide-nanoparticle conjugates. The closed circles represent the nanoparticles, and the large oval represents a microporous membrane.

FIG. 23: Sequences of materials utilized in an assay for Anthrax Protective Antigen (see Example 12).

FIG. 24: Schematic diagram illustrating a system for detecting target nucleic acid using a "satellite probe" which comprises magnetic nanoparticles (dark spheres) having oligonucleotides (straight lines) attached to them, probe oligonucleotides (straight lines) hybridized to the oligonucleotides attached to the nanoparticles, the probe oligonucleotides being labeled with a reporter group (open rectangular box). A, B, C, A', B', and C' represent specific nucleotide sequences, with A, B and C being complementary to A', B' and C', respectively.

FIG. 27A shows fluorescence spectra comparing dispersed and aggregated QDs, with an excitation at 400 nm. The samples were prepared identically, except for the addition of complementary "linker" DNA to one and an equal volume and concentration of non-complementary DNA to the other. FIG. 27B shows UV-Visible spectra of QD/QD assemblies at different temperatures before, during and after "melting". FIG. 27C shows high resolution TEM image of a portion of a hybrid gold/QD assembly. The lattice fringes of the QDs, which resemble fingerprints, appear near each gold nanoparticle. FIG. 27D shows UV-Visible spectra of hybrid gold/QD assemblies at different temperatures before, during and after "melting". The insets in FIGS. 27B and 27D display temperature versus extinction profiles for the thermal denaturation of the assemblies. Denaturation experiments were conducted in 0.3 M NaCl, 10 mM phosphate buffer (pH 7), 0.01% sodium azide with 13 nm gold nanoparticles and/or ~4 nm CdSe/ZnS core/shell QDs.

FIG. 32: Schematic diagram illustrating system for detecting a target DNA in a four-element array on a substrate using nanoparticle-oligonucleotide conjugates and amplification with silver staining.

FIG. 33: Images obtained with a flatbed scanner of 7 mm×13 mm oligonucleotide-functionalized float glass slides. (A) Slide before hybridization of DNA target and gold nanoparticle-oligonucleotide indicator conjugate. (B) Slide A after hybridization of 10 nM target DNA and 5 nM nanoparticle-oligonucleotide indicator conjugate. A pink color was imparted by attached, red 13 nm diameter gold nanoparticles. (C) Slide B after exposure to silver amplification solution for 5 minutes. (D) Same as (A). (E) Slide D after hybridization of 100 pM target and 5 nM nanoparticle-oligonucleotide indicator conjugate. The absorbance of the nanoparticle layer was too low to be observed with the naked eye or flatbed scanner. (F) Slide E after exposure to silver amplification solution for 5 minutes. Note that slide F is much lighter than slide C, indicating lower target concentration. (G) Control slide, exposed to 5 nM nanoparticle-oligonucleotide indicator conjugate and exposed to silver amplification solution for 5 minutes. No darkening of the slide was observed.

FIG. 37: Schematic diagram illustrating system for forming aggregates (A) or layers (B) of nanoparticles (a and b) linked by a linking nucleic acid (3).

FIG. 39A: FE-SEM of one layer of oligonucleotide-functionalized gold nanoparticles cohybridized with DNA linker to an oligonucleotide-functionalized, conductive indium-tin-oxide (ITO) slide (prepared in the same way as oligonucleotide-functionalized glass slide). The visible absorbance spectrum of this slide was identical to FIG. 38A, indicating that functionalization and nanoparticle coverage on ITO is similar to that on glass. The average density of counted nanoparticles from 10 such images was approximately 800 nanoparticles/$\mu m^2$. FIG. 39B: FE-SEM image of two layers of nanoparticles on the ITO slide. The average density of counted nanoparticles from 10 such images was approximately 2800 particles/$\mu m^2$. FIG. 39C: Absorbance at 260 nm ($A_{260}$) showing dissociation of a 0.5 $\mu$M solution of the oligonucleotide duplex (1+2+3; see FIG. 37, A) to single strands in 0.3 M NaCl, 10 mM phosphate buffer solution (pH 7). FIGS. 39D–F: Absorbance at 260 nm ($A_{260}$) showing dissociation of 1 layer (FIG. 39D), 4 layers (FIG. 39E) and 10 layers (FIG. 39F) of oligonucleotide-functionalized gold nanoparticles from glass slides immersed in 0.3 M NaCl, 10 mM phosphate buffer solution. Melting profiles were obtained by measuring the decreasing absorption at 520 nm ($A_{520}$) through the slides with increasing temperature. In each of FIGS. 39D–F, the insets show the first derivatives of the measured dissociation curves. FWHM of these curves were (FIG. 39C inset) 13.2° C., (FIG. 39D inset) 5.6° C., (FIG. 39E inset) 3.2° C., and (FIG. 39F inset) 2.9° C.

DETAILED DESCRIPTION OF THE PRESENTLY PREFERRED EMBODIMENTS

Figure 1:
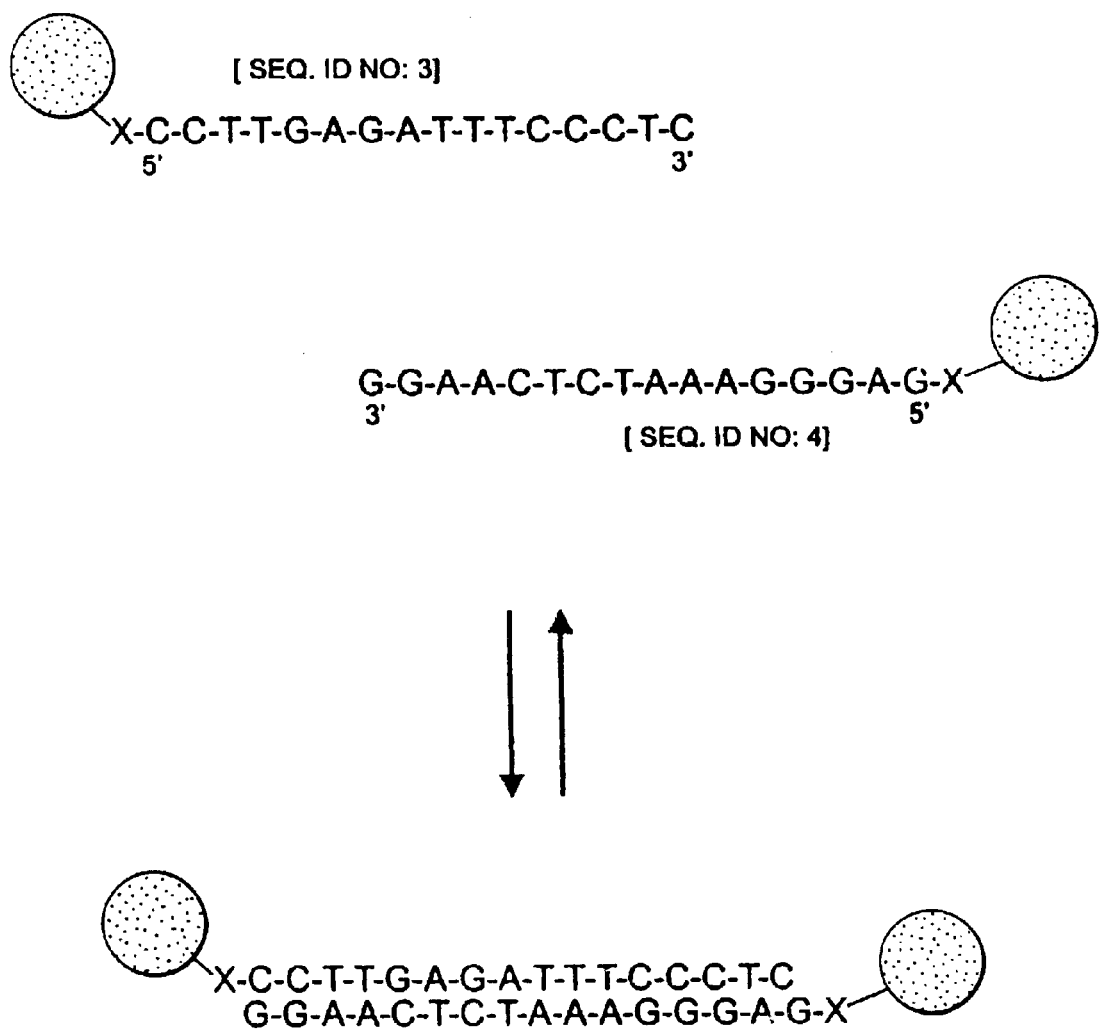
FIG. 1: Schematic diagram illustrating the formation of nanoparticle aggregates by combining nanoparticles having complementary oligonucleotides attached to them, the nanoparticles being held together in the aggregates as a result of the hybridization of the complementary oligonucleotides. X represents any covalent anchor (such as —S($CH_2$)$_3$OP(O) (O$^-$)—, where S is joined to a gold nanoparticle). For the sake of simplicity in FIG. 1 and some subsequent figures, only one oligonucleotide is shown to be attached to each particle but, in fact, each particle has several oligonucleotides attached to it. Also, it is important to note that in FIG. 1 and subsequent figures, the relative sizes of the gold nanoparticles and the oligonucleotides are not drawn to scale.

Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm. The nanoparticles may also be rods.

Methods of making metal, semiconductor and magnetic nanoparticles are well-known in the art. See, e.g., Schmid, G. (ed.) *Clusters and Colloids* (V C H, Weinheim, 1994); Hayat, M. A. (ed.) *Colloidal Gold: Principles, Methods, and Applications* (Academic Press, San Diego, 1991); Massart, R., *IEEE Transactions On Magnetics,* 17, 1247 (1981); Ahmadi, T. S. et al., *Science,* 272, 1924 (1996); Henglein, A. et al., *J. Phys. Chem.,* 99, 14129 (1995); Curtis, A. C., et al., *Angew. Chem. Int. Ed. Engl.,* 27, 1530 (1988).

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.,* 32, 41 (1993); Henglein, *Top. Curr. Chem.,* 143, 113 (1988); Henglein, *Chem. Rev.,* 89, 1861 (1989); Brus, *Appl. Phys. A.,* 53, 465 (1991); Bahncmann, in *Photochemical Conversion and Storage of Solar Energy* (eds. Pelizetti and Schiavello 1991), page 251; Wang and Herron, *J. Phys. Chem.,* 95, 525 (1991); Olshavsky et al., *J. Am. Chem. Soc.,* 112, 9438 (1990); Ushida et al., *J. Phys. Chem.,* 95, 5382 (1992).

Suitable nanoparticles are also commercially available from, e.g., Ted Pella, Inc. (gold), Amersham Corporation (gold) and Nanoprobes, Inc. (gold).

Presently preferred for use in detecting nucleic acids are gold nanoparticles. Gold colloidal particles have high extinction coefficients for the bands that give rise to their beautiful colors. These intense colors change with particle size, concentration, interparticle distance, and extent of aggregation and shape (geometry) of the aggregates, making these materials particularly attractive for colorimetric assays. For instance, hybridization of oligonucleotides attached to gold nanoparticles with oligonucleotides and nucleic acids results in an immediate color change visible to the naked eye (see, e.g., the Examples).

Gold nanoparticles are also presently preferred for use in nanofabrication for the same reasons given above and because of their stability, ease of imaging by electron microscopy, and well-characterized modification with thiol functionalities (see below). Also preferred for use in nanofabrication are semiconductor nanoparticles because of their unique electronic and luminescent properties.

The nanoparticles, the oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry,* Houston, Tex., pages 109–121 (1995). See also, Mucic et al. *Chem. Commun.* 555–557 (1996) (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370–377 (1974) and Matteucci and Caruthers, *J. Am. Chem. Soc.*, 103, 3185–3191 (1981) for binding of oligonucleotides to silica and glass surfaces, and Grabaretal., *Anal. Chem.*, 67, 735–743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410–421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984–990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec et al., *J. Phys. Chem.*, 92, 2597 (1988) (rigid phosphates on metals).

Each nanoparticle will have a plurality of oligonucleotides attached to it. As a result, each nanoparticle-oligonucleotide conjugate can bind to a plurality of oligonucleotides or nucleic acids having the complementary sequence.

Oligonucleotides of defined sequences are used for a variety of purposes in the practice of the invention. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

The invention provides methods of detecting nucleic acids. Any type of nucleic acid may be detected, and the methods may be used, e.g., for the diagnosis of disease and in sequencing of nucleic acids. Examples of nucleic acids that can be detected by the methods of the invention include genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, etc. Thus, examples of the uses of the methods of detecting nucleic acids include: the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori*, *Escherichia coli* infections, Legionella infections, Mycoplasma infections, Salmonella infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

The methods of detecting nucleic acids based on observing a color change with the naked eye are cheap, fast, simple, robust (the reagents are stable), do not require specialized or expensive equipment, and little or no instrumentation is required. This makes them particularly suitable for use in, e.g., research and analytical laboratories in DNA sequencing, in the field to detect the presence of specific pathogens, in the doctor's office for quick identification of an infection to assist in prescribing a drug for treatment, and in homes and health centers for inexpensive first-line screening.

The nucleic acid to be detected may be isolated by known methods, or may be detected directly in cells, tissue samples, biological fluids (e.g., saliva, urine, blood, serum), solutions containing PCR components, solutions containing large excesses of oligonucleotides or high molecular weight DNA, and other samples, as also known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Methods of preparing nucleic acids for detection with hybridizing probes are well known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995).

If a nucleic acid is present in small amounts, it may be applied by methods known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Preferred is polymerase chain reaction (PCR) amplification.

One method according to the invention for detecting nucleic acid comprises contacting a nucleic acid with one or more types of nanoparticles having oligonucleotides attached thereto. The nucleic acid to be detected has at least two portions. The lengths of these portions and the distance (s), if any, between them are chosen so that when the oligonucleotides on the nanoparticles hybridize to the nucleic acid, a detectable change occurs. These lengths and distances can be determined empirically and will depend on the type of particle used and its size and the type of electrolyte which will be present in solutions used in the assay (as is known in the art, certain electrolytes affect the conformation of nucleic acids).

Also, when a nucleic acid is to be detected in the presence of other nucleic acids, the portions of the nucleic acid to which the oligonucleotides on the nanoparticles are to bind must be chosen so that they contain sufficient unique sequence so that detection of the nucleic acid will be specific. Guidelines for doing so are well known in the art.

Figure 2:
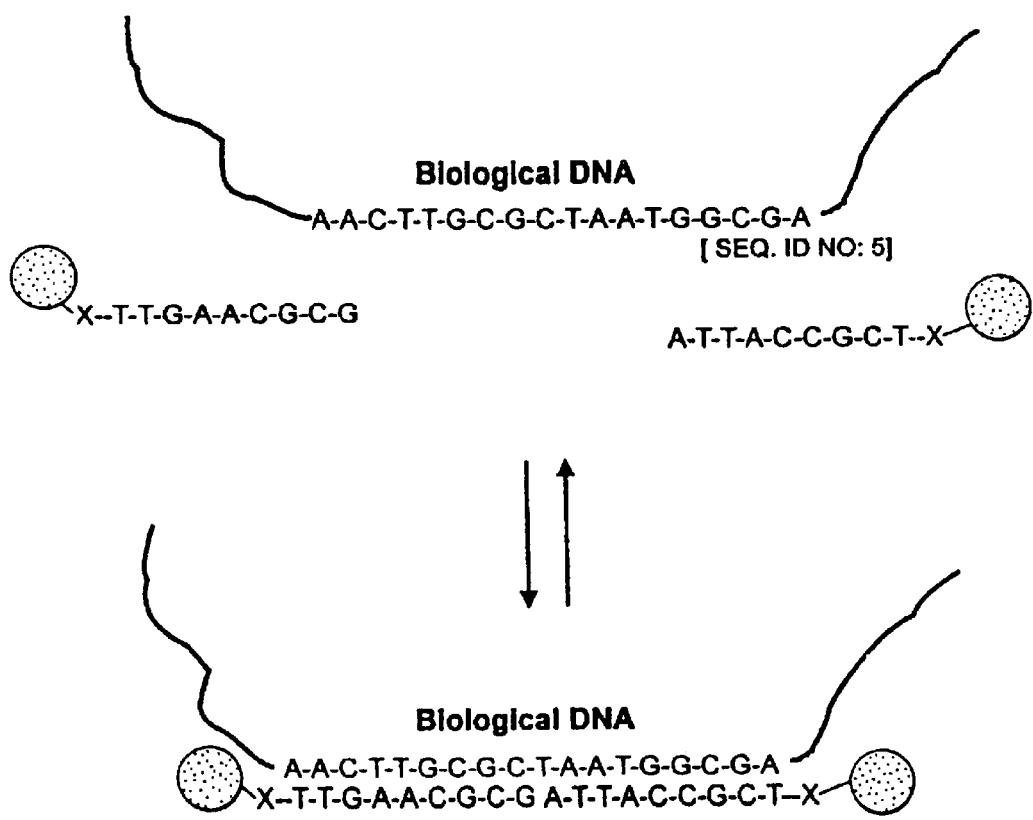
FIG. 2: Schematic diagram illustrating a system for detecting nucleic acid using nanoparticles having oligonucleotides attached thereto. The oligonucleotides on the two nanoparticles have sequences complementary to two different portions of the single-stranded DNA shown. As a consequence, they hybridize to the DNA producing detectable changes (forming aggregates and producing a color change).

Although nucleic acids may contain repeating sequences close enough to each other so that only one type of oligonucleotide-nanoparticle conjugate need be used, this will be a rare occurrence. In general, the chosen portions of the nucleic acid will have different sequences and will be contacted with nanoparticles carrying two or more different oligonucleotides, preferably attached to different nanoparticles. An example of a system for the detection of nucleic acid is illustrated in FIG. 2. As can be seen, a first oligonucleotide attached to a first nanoparticle has a sequence complementary to a first portion of the target sequence in the single-stranded DNA. A second oligonucleotide attached to a second nanoparticle has a sequence complementary to a second portion of the target sequence in the DNA. Additional portions of the DNA could be targeted with corresponding nanoparticles. See FIG. 17. Targeting several portions of a nucleic acid increases the magnitude of the detectable change.

The contacting of the nanoparticle-oligonucleotide conjugates with the nucleic acid takes place under conditions effective for hybridization of the oligonucleotides on the nanoparticles with the target sequence(s) of the nucleic acid. These hybridization conditions are well known in the art and can readily be optimized for the particular system employed. See, e.g., Sambrook et al., *Molecular Cloning: A Laboratory Manual* (2nd ed. 1989). Preferably stringent hybridization conditions are employed.

Faster hybridization can be obtained by freezing and thawing a solution containing the nucleic acid to be detected and the nanoparticle-oligonucleotide conjugates. The solution may be frozen in any convenient manner, such as placing it in a dry ice-alcohol bath for a sufficient time for the solution to freeze (generally about 1 minute for 100 µL of solution). The solution must be thawed at a temperature below the thermal denaturation temperature, which can conveniently be room temperature for most combinations of nanoparticle-oligonucleotide conjugates and nucleic acids. The hybridization is complete, and the detectable change may be observed, after thawing the solution.

The rate of hybridization can also be increased by warming the solution containing the nucleic acid to be detected and the nanoparticle-oligonucleotide conjugates to a temperature below the dissociation temperature (Tm) for the complex formed between the oligonucleotides on the nanoparticles and the target nucleic acid. Alternatively, rapid hybridization can be achieved by heating above the dissociation temperature (Tm) and allowing the solution to cool.

The rate of hybridization can also be increased by increasing the salt concentration (e.g., from 0.1 M to 0.3 M NaCl).

The detectable change that occurs upon hybridization of the oligonucleotides on the nanoparticles to the nucleic acid may be a color change, the formation of aggregates of the nanoparticles, or the precipitation of the aggregated nanoparticles. The color changes can be observed with the naked eye or spectroscopically. The formation of aggregates of the nanoparticles can be observed by electron microscopy or by nephelometry. The precipitation of the aggregated nanoparticles can be observed with the naked eye or microscopically. Preferred are changes observable with the naked eye. Particularly preferred is a color change observable with the naked eye.

The observation of a color change with the naked eye can be made more readily against a background of a contrasting color. For instance, when gold nanoparticles are used, the observation of a color change is facilitated by spotting a sample of the hybridization solution on a solid white surface (such as silica or alumina TLC plates, filter paper, cellulose nitrate membranes, and nylon membranes, preferably a C-18 silica TLC plate) and allowing the spot to dry. Initially, the spot retains the color of the hybridization solution (which ranges from pink/red, in the absence of hybridization, to purplish-red/purple, if there has been hybridization). On drying at room temperature or 80° C. (temperature is not critical), a blue spot develops if the nanoparticle-oligonucleotide conjugates had been linked by hybridization with the target nucleic acid prior to spotting. In the absence of hybridization (e.g., because no target nucleic acid is present), the spot is pink. The blue and the pink spots are stable and do not change on subsequent cooling or heating or over time. They provide a convenient permanent record of the test. No other steps (such as a separation of hybridized and unhybridized nanoparticle-oligonucleotide conjugates) are necessary to observe the color change.

An alternate method for easily visualizing the assay results is to spot a sample of nanoparticle probes hybridized to a target nucleic acid on a glass fiber filter (e.g., Borosilicate Microfiber Filter, 0.7 micron pore size, grade FG75, for use with gold nanoparticles 13 nm in size), while drawing the liquid through the filter. Subsequent rinsing with water washes the excess, non-hybridized probes through the filter, leaving behind an observable spot comprising the aggregates generated by hybridization of the nanoparticle probes with the target nucleic acid (retained because these aggregates are larger than the pores of the filter). This technique may provide for greater sensitivity, since an excess of nanoparticle probes can be used. Unfortunately, the nanoparticle probes stick to many other solid surfaces that have been tried (silica slides, reverse-phase plates, and nylon, nitrocellulose, cellulose and other membranes), and these surfaces cannot be used.

An important aspect of the detection system illustrated in FIG. 2 is that obtaining a detectable change depends on cooperative hybridization of two different oligonucleotides to a given target sequence in the nucleic acid. Mismatches in either of the two oligonucleotides will destabilize the interparticle connection. It is well known that a mismatch in base pairing has a much greater destabilizing effect on the binding of a short oligonucleotide probe than on the binding of a long oligonucleotide probe. The advantage of the system illustrated in FIG. 2 is that it utilizes the base discrimination associated with a long target sequence and probe (eighteen base-pairs in the example illustrated in FIG. 2), yet has the sensitivity characteristic of a short oligonucleotide probe (nine base-pairs in the example illustrated in FIG. 2).

The target sequence of the nucleic acid may be contiguous, as in FIG. 2, or the two portions of the target sequence may be separated by a third portion which is not complementary to the oligonucleotides on the nanoparticles, as illustrated in FIG. 3. In the latter case, one has the option of using a filler oligonucleotide which is free in solution and which has a sequence complementary to that of this third portion (see FIG. 3). When the filler oligonucleotide hybridizes with the third portion of the nucleic acid, a double-stranded segment is created, thereby altering the average distance between the nanoparticles and, consequently, the color. The system illustrated in FIG. 3 may increase the sensitivity of the detection method.

Some embodiments of the method of detecting nucleic acid utilize a substrate. By employing a substrate, the detectable change (the signal) can be amplified and the sensitivity of the assay increased.

Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates).

In one embodiment, oligonucleotides are attached to the substrate. The oligonucleotides can be attached to the substrates as described in, e.g., Chrisey et al., *Nucleic Acids Res.*, 24, 3031–3039 (1996); Chrisey et al., *Nucleic Acids Res.*, 24, 3040–3047 (1996); Mucic et al., *Chem. Commun.*, 555 (1996); Zimmermann and Cox, *Nucleic Acids Res.*, 22, 492 (1994); Bottomley et al., *J. Vac. Sci. Technol. A*, 10, 591 (1992); and Hegner et al., *FEBS Lett.*, 336, 452 (1993).

The oligonucleotides attached to the substrate have a sequence complementary to a first portion of the sequence of a nucleic acid to be detected. The nucleic acid is contacted with the substrate under conditions effective to allow hybridization of the oligonucleotides on the substrate with the nucleic acid. In this manner the nucleic acid becomes bound to the substrate. Any unbound nucleic acid is preferably washed from the substrate before adding nanoparticle-oligonucleotide conjugates.

Next, the nucleic acid bound to the substrate is contacted with a first type of nanoparticles having oligonucleotides attached thereto. The oligonucleotides have a sequence complementary to a second portion of the sequence of the nucleic acid, and the contacting takes place under conditions effective to allow hybridization of the oligonucleotides on the nanoparticles with the nucleic acid. In this manner the first type of nanoparticles become bound to the substrate. After the nanoparticle-oligonucleotide conjugates are bound to the substrate, the substrate is washed to remove any unbound nanoparticle-oligonucleotide conjugates and nucleic acid.

The oligonucleotides on the first type of nanoparticles may all have the same sequence or may have different sequences that hybridize with different portions of the nucleic acid to be detected. When oligonucleotides having different sequences are used, each nanoparticle may have all of the different oligonucleotides attached to it or, preferably, the different oligonucleotides are attached to different nanoparticles. FIG. 17 illustrates the use of nanoparticle-oligonucleotide conjugates designed to hybridize to multiple portions of a nucleic acid. Alternatively, the oligonucleotides on each of the first type of nanoparticles may have a plurality of different sequences, at least one of which must hybridize with a portion of the nucleic acid to be detected (see FIG. 25B).

Finally, the first type of nanoparticle-oligonucleotide conjugates bound to the substrate is contacted with a second type of nanoparticles having oligonucleotides attached thereto. These oligonucleotides have a sequence complementary to at least a portion of the sequence(s) of the oligonucleotides attached to the first type of nanoparticles, and the contacting takes place under conditions effective to allow hybridization of the oligonucleotides on the first type of nanoparticles with those on the second type of nanoparticles. After the nanoparticles are bound, the substrate is preferably washed to remove any unbound nanoparticle-oligonucleotide conjugates.

The combination of hybridizations produces a detectable change. The detectable changes are the same as those described above, except that the multiple hybridizations result in an amplification of the detectable change. In particular, since each of the first type of nanoparticles has multiple oligonucleotides (having the same or different sequences) attached to it, each of the first type of nanoparticle-oligonucleotide conjugates can hybridize to a plurality of the second type of nanoparticle-oligonucleotide conjugates. Also, the first type of nanoparticle-oligonucleotide conjugates may be hybridized to more than one portion of the nucleic acid to be detected. The amplification provided by the multiple hybridizations may make the change detectable for the first time or may increase the magnitude of the detectable change. This amplification increases the sensitivity of the assay, allowing for detection of small amounts of nucleic acid.

If desired, additional layers of nanoparticles can be built up by successive additions of the first and second types of nanoparticle-oligonucleotide conjugates. In this way, the number of nanoparticles immobilized per molecule of target nucleic acid can be further increased with a corresponding increase in intensity of the signal.

Also, instead of using first and second types of nanoparticle-oligonucleotide conjugates designed to hybridize to each other directly, nanoparticles bearing oligonucleotides that would serve to bind the nanoparticles together as a consequence of hybridization with binding oligonucleotides could be used.

Methods of making the nanoparticles and the oligonucleotides and of attaching the oligonucleotides to the nanoparticles are described above. The hybridization conditions are well known in the art and can be readily optimized for the particular system employed (see above).

An example of this method of detecting nucleic acid (analyte DNA) is illustrated in FIG. 13A. As shown in that Figure, the combination of hybridizations produces dark areas where nanoparticle aggregates are linked to the substrate by analyte DNA. These dark areas may be readily observed with the naked eye using ambient light, preferably viewing the substrate against a white background. As can be readily seen from FIG. 13A, this method provides a means of amplifying a detectable change.

Figure 25A:
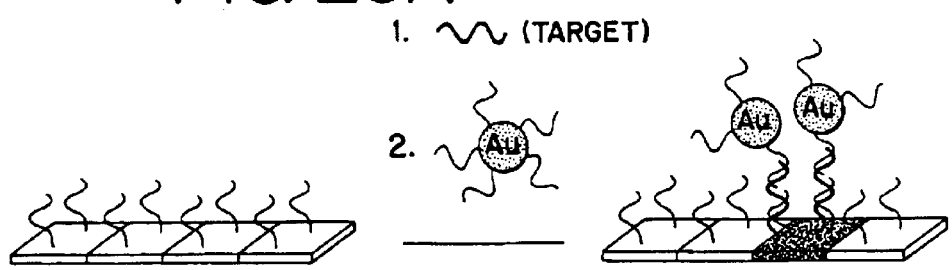
FIGS. 25A–B: Schematic diagrams illustrating systems for detecting DNA using nanoparticles and a transparent substrate. In these figures, a, b and c refer to different oligonucleotide sequences, and a', b' and c' refer to oligonucleotide sequences complementary to a, b and c, respectively.
Figure 25B:
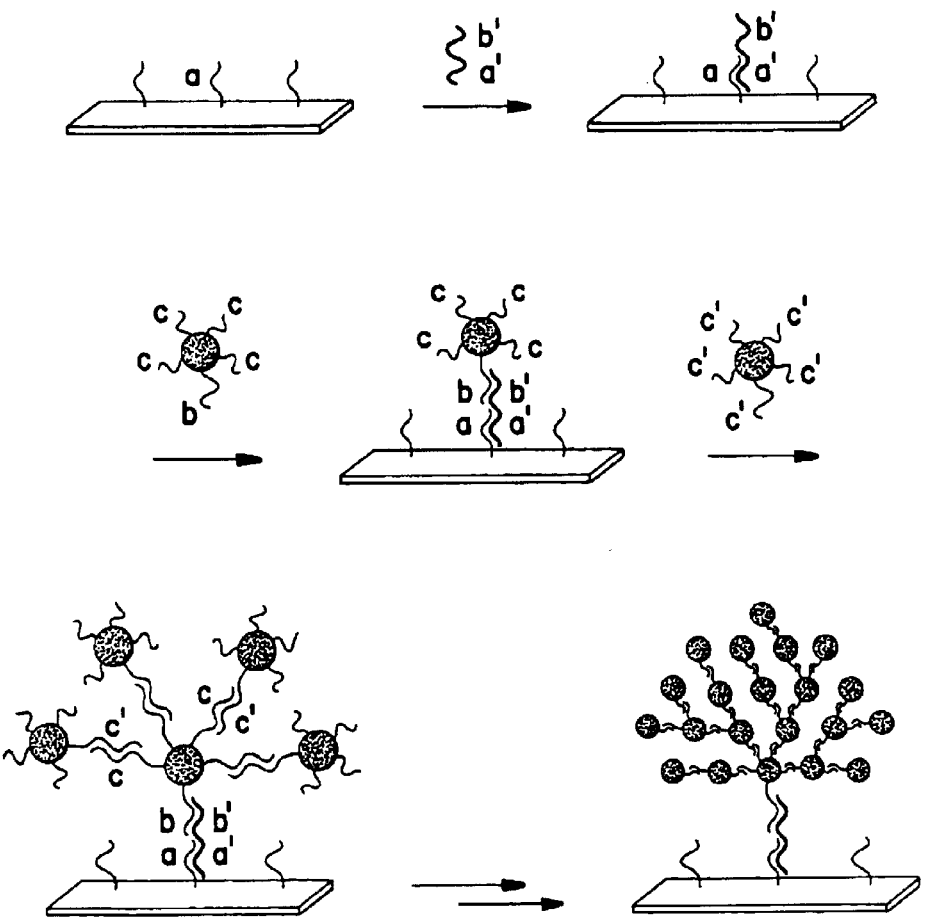

Another example of this method of detecting nucleic acid is illustrated in FIG. 25B. As in the example illustrated in FIG. 13A, the combination of hybridizations produces dark areas where nanoparticle aggregates are linked to the substrate by analyte DNA which can be observed with the naked eye.

In another embodiment, nanoparticles are attached to the substrate. Nanoparticles can be attached to substrates as described in, e.g., Grabar et al., *Analyt. Chem.*, 67, 73–743 (1995); Bethell et al., *J. Electroanal. Chem.*, 409, 137 (1996); Bar et al., *Langmuir*, 12, 1172 (1996); Colvin et al., *J. Am. Chem. Soc.*, 114, 5221 (1992).

After the nanoparticles are attached to the substrate, oligonucleotides are attached to the nanoparticles. This may be accomplished in the same manner described above for the attachment of oligonucleotides to nanoparticles in solution. The oligonucleotides attached to the nanoparticles have a sequence complementary to a first portion of the sequence of a nucleic acid.

The substrate is contacted with the nucleic acid under conditions effective to allow hybridization of the oligonucleotides on the nanoparticles with the nucleic acid. In this manner the nucleic acid becomes bound to the substrate. Unbound nucleic acid is preferably washed from the substrate prior to adding further nanoparticle-oligonucleotide conjugates.

Then, a second type of nanoparticles having oligonucleotides attached thereto is provided. These oligonucleotides have a sequence complementary to a second portion of the sequence of the nucleic acid, and the nucleic acid bound to the substrate is contacted with the second type of nanoparticle-oligonucleotide conjugates under conditions effective to allow hybridization of the oligonucleotides on the second type of nanoparticle-oligonucleotide conjugates with the nucleic acid. In this manner, the second type of nanoparticle-oligonucleotide conjugates becomes bound to the substrate. After the nanoparticles are bound, any unbound nanoparticle-oligonucleotide conjugates and nucleic acid are washed from the substrate. A change (e.g., color change) may be detectable at this point.

The oligonucleotides on the second type of nanoparticles may all have the same sequence or may have different sequences that hybridize with different portions of the nucleic acid to be detected. When oligonucleotides having different sequences are used, each nanoparticle may have all of the different oligonucleotides attached to it or, preferably, the different oligonucleotides may be attached to different nanoparticles. See FIG. 17.

Next, a binding oligonucleotide having a selected sequence having at least two portions, the first portion being complementary to at least a portion of the sequence of the oligonucleotides on the second type of nanoparticles, is contacted with the second type of nanoparticle-oligonucleotide conjugates bound to the substrate under conditions effective to allow hybridization of the binding oligonucleotide to the oligonucleotides on the nanoparticles. In this manner, the binding oligonucleotide becomes bound to the substrate. After the binding oligonucleotides are bound, unbound binding oligonucleotides are washed from the substrate.

Finally, a third type of nanoparticles having oligonucleotides attached thereto is provided. The oligonucleotides have a sequence complementary to the sequence of a second portion of the binding oligonucleotide. The nanoparticle-oligonucleotide conjugates are contacted with the binding oligonucleotide bound to the substrate under conditions effective to allow hybridization of the binding oligonucleotide to the oligonucleotides on the nanoparticles. After the nanoparticles are bound, unbound nanoparticle-oligonucleotide conjugates are washed from the substrate.

The combination of hybridizations produces a detectable change. The detectable changes are the same as those described above, except that the multiple hybridizations result in an amplification of the detectable change. In particular, since each of the second type of nanoparticles has multiple oligonucleotides (having the same or different sequences) attached to it, each of the second type of nanoparticle-oligonucleotide conjugates can hybridize to a plurality of the third type of nanoparticle-oligonucleotide conjugates (through the binding oligonucleotide). Also, the second type of nanoparticle-oligonucleotide conjugates may be hybridized to more than one portion of the nucleic acid to be detected. The amplification provided by the multiple hybridizations may make the change detectable for the first time or may increase the magnitude of the detectable change. The amplification increases the sensitivity of the assay, allowing for detection of small amounts of nucleic acid.

If desired, additional layers of nanoparticles can be built up by successive additions of the binding oligonucleotides and second and third types of nanoparticle-oligonucleotide conjugates. In this way, the nanoparticles immobilized per molecule of target nucleic acid can be further increased with a corresponding increase in intensity of the signal.

Also, the use of the binding oligonucleotide can be eliminated, and the second and third types of nanoparticle-oligonucleotide conjugates can be designed so that they hybridize directly to each other.

Methods of making the nanoparticles and the oligonucleotides and of attaching the oligonucleotides to the nanoparticles are described above. The hybridization conditions are well known in the art and can be readily optimized for the particular system employed (see above).

An example of this method of detecting nucleic acid (analyte DNA) is illustrated in FIG. 13B. As shown in that Figure, the combination of hybridizations produces dark areas where nanoparticle aggregates are linked to the substrate by analyte DNA. These dark areas may be readily observed with the naked eye as described above. As can be seen from FIG. 13B, this embodiment of the method of the invention provides another means of amplifying the detectable change.

Another amplification scheme employs liposomes. In this scheme, oligonucleotides are attached to a substrate. Suitable substrates are those described above, and the oligonucleotides can be attached to the substrates as described above. For instance, where the substrate is glass, this can be accomplished by condensing the oligonucleotides through phosphoryl or carboxylic acid groups to aminoalkyl groups on the substrate surface (for related chemistry see Grabar et al., *Anal. Chem.*, 67, 735–743 (1995)).

The oligonucleotides attached to the substrate have a sequence complementary to a first portion of the sequence of the nucleic acid to be detected. The nucleic acid is contacted with the substrate under conditions effective to allow hybridization of the oligonucleotides on the substrate with the nucleic acid. In this manner the nucleic acid becomes bound to the substrate. Any unbound nucleic acid is preferably washed from the substrate before adding additional components of the system.

Next, the nucleic acid bound to the substrate is contacted with liposomes having oligonucleotides attached thereto. The oligonucleotides have a sequence complementary to a second portion of the sequence of the nucleic acid, and the contacting takes place under conditions effective to allow hybridization of the oligonucleotides on the liposomes with the nucleic acid. In this manner the liposomes become bound to the substrate. After the liposomes are bound to the substrate, the substrate is washed to remove any unbound liposomes and nucleic acid.

The oligonucleotides on the liposomes may all have the same sequence or may have different sequences that hybridize with different portions of the nucleic acid to be detected. When oligonucleotides having different sequences are used, each liposome may have all of the different oligonucleotides attached to it or the different oligonucleotides may be attached to different liposomes.

To prepare oligonucleotide-liposome conjugates, the oligonucleotides are linked to a hydrophobic group, such as cholesteryl (see Letsinger et al., *J. Am. Chem. Soc.*, 115, 7535–7536 (1993)), and the hydrophobic-oligonucleotide conjugates are mixed with a solution of liposomes to form liposomes with hydrophobic-oligonucleotide conjugates anchored in the membrane (see Zhang et al., *Tetrahedron Lett.*, 37, 6243–6246 (1996)). The loading of hydrophobic-oligonucleotide conjugates on the surface of the liposomes can be controlled by controlling the ratio of hydrophobic-oligonucleotide conjugates to liposomes in the mixture. It has been observed that liposomes bearing oligonucleotides attached by hydrophobic interaction of pendent cholesteryl groups are effective in targeting polynucleotides immobilized on a nitrocellulose membrane (Id.). Fluorescein groups anchored in the membrane of the liposome were used as the reporter group. They served effectively, but sensitivity was limited by the fact that the signal from fluorescein in regions of high local concentration (e.g., on the liposome surface) is weakened by self quenching.

The liposomes are made by methods well known in the art. See Zhang et al., *Tetrahedron Lett.*, 37, 6243 (1996). The liposomes will generally be about 5–50 times larger in size (diameter) than the nanoparticles used in subsequent steps. For instance, for nanoparticles about 13 nm in diameter, liposomes about 100 nm in diameter are preferably used.

The liposomes bound to the substrate are contacted with a first type of nanoparticles having at least a first type of oligonucleotides attached thereto. The first type of oligonucleotides have a hydrophobic group attached to the end not attached to the nanoparticles, and the contacting takes place under conditions effective to allow attachment of the oligonucleotides on the nanoparticles to the liposomes as a result of hydrophobic interactions. A detectable change may be observable at this point.

The method may further comprise contacting the first type of nanoparticle-oligonucleotide conjugates bound to the liposomes with a second type of nanoparticles having oligonucleotides attached thereto. The first type of nanoparticles have a second type of oligonucleotides attached thereto which have a sequence complementary to at least a portion of the sequence of the oligonucleotides on the second type of nanoparticles, and the oligonucleotides on the second type of nanoparticles have a sequence complementary to at least a portion of the sequence of the second type of oligonucleotides on the first type of nanoparticles. The contacting takes place under conditions effective to allow hybridization of the oligonucleotides on the first and second types of nanoparticles. This hybridization will generally be performed at mild temperatures (e.g., 5° C. to 60° C.), so conditions (e.g., 0.3–1.0 M NaCl) conducive to hybridization at room temperature are employed. Following hybridization, unbound nanoparticle-oligonucleotide conjugates are washed from the substrate.

The combination of hybridizations produces a detectable change. The detectable changes are the same as those described above, except that the multiple hybridizations result in an amplification of the detectable change. In particular, since each of the liposomes has multiple oligonucleotides (having the same or different sequences) attached to it, each of the liposomes can hybridize to a plurality of the first type of nanoparticle-oligonucleotide conjugates. Similarly, since each of the first type of nanoparticles has multiple oligonucleotides attached to it, each of the first type of nanoparticle-oligonucleotide conjugates can hybridize to a plurality of the second type of nanoparticle-oligonucleotide conjugates. Also, the liposomes may be hybridized to more than one portion of the nucleic acid to be detected. The amplification provided by the multiple hybridizations may make the change detectable for the first time or may increase the magnitude of the detectable change. This amplification increases the sensitivity of the assay, allowing for detection of small amounts of nucleic acid.

If desired, additional layers of nanoparticles can be built up by successive additions of the first and second types of nanoparticle-oligonucleotide conjugates. In this way, the number of nanoparticles immobilized per molecule of target nucleic acid can be further increased with a corresponding increase in the intensity of the signal.

Also, instead of using second and third types of nanoparticle-oligonucleotide conjugates designed to hybridize to each other directly, nanoparticles bearing oligonucleotides that would serve to bring the nanoparticles together as a consequence of hybridization with binding oligonucleotides could be used.

Methods of making the nanoparticles and the oligonucleotides and of attaching the oligonucleotides to the nanoparticles are described above. A mixture of oligonucleotides functionalized at one end for binding to the nanoparticles and with or without a hydrophobic group at the other end can be used on the first type of nanoparticles. The relative ratio of these oligonucleotides bound to the average nanoparticle will be controlled by the ratio of the concentrations of the two oligonucleotides in the mixture. The hybridization conditions are well known in the art and can be readily optimized for the particular system employed (see above).

Figure 18:
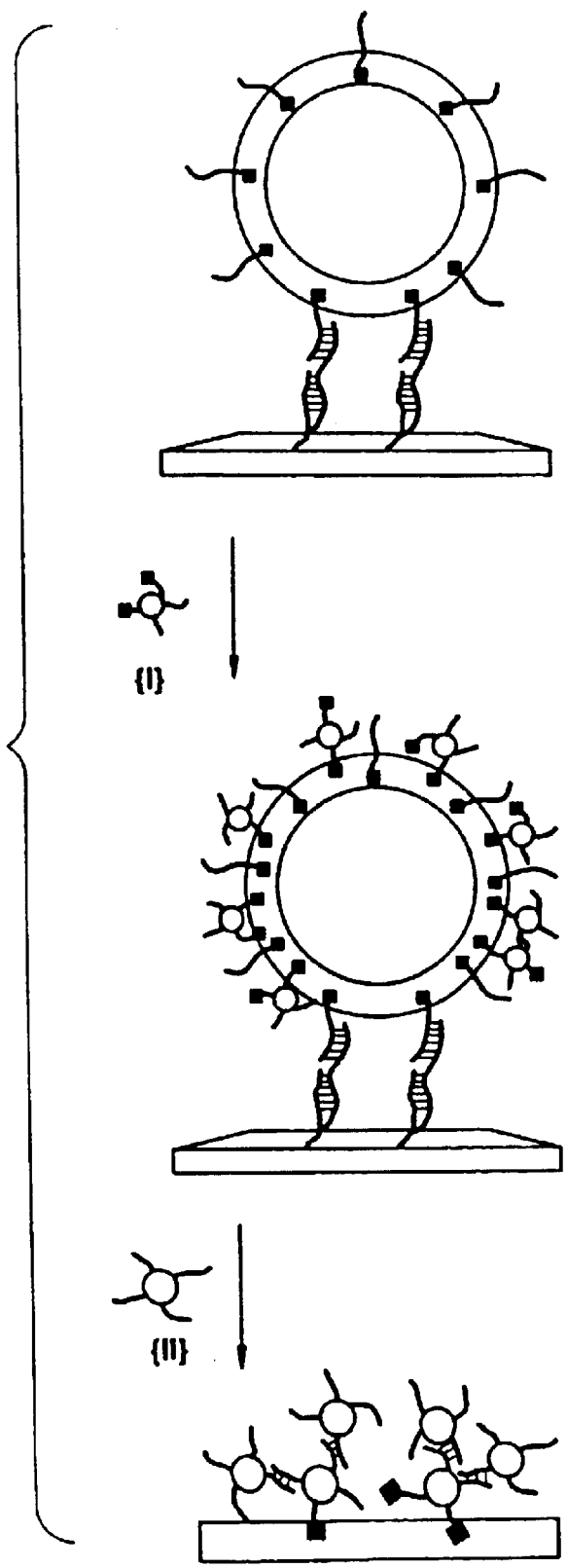
FIG. 18: Schematic diagram illustrating a system for detecting nucleic acid using liposomes (large double circle), nanoparticles (small open circles) and a transparent substrate. The filled-in squares represent cholesteryl groups, the squiggles represent oligonucleotides, and the ladders represent double-stranded (hybridized) oligonucleotides.

An example of this method of detecting nucleic acid is illustrated in FIG. 18. The hybridization of the first type of nanoparticle-oligonucleotide conjugates to the liposomes may produce a detectable change. In the case of gold nanoparticles, a pink/red color may be observed or a purple/blue color may be observed if the nanoparticles are close enough together. The hybridization of the second type of nanoparticle-oligonucleotide conjugates to the first type of nanoparticle-oligonucleotide conjugates will produce a detectable change. In the case of gold nanoparticles, a purple/blue color will be observed. All of these color changes may be observed with the naked eye.

Figure 28A:
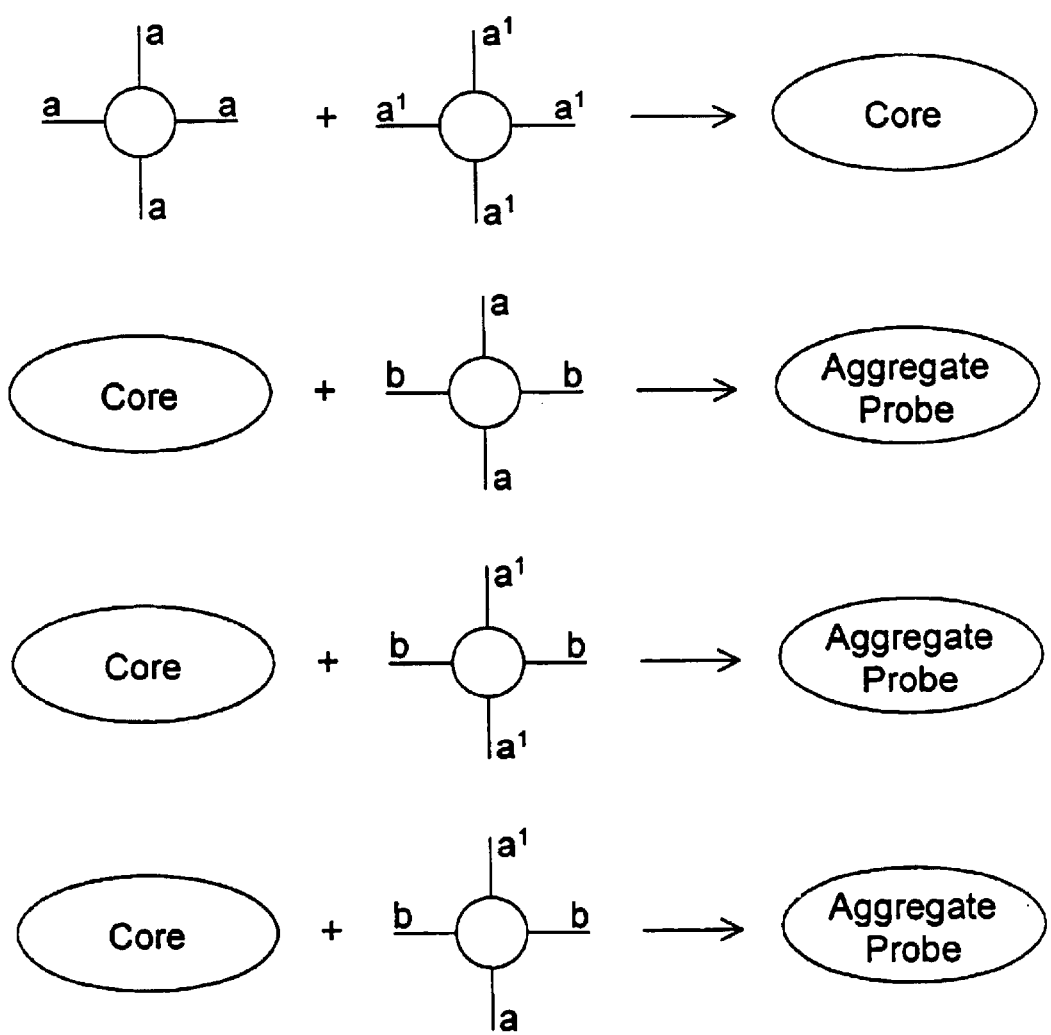
FIGS. 28A–E: Schematic diagrams illustrating the preparation of core probes, aggregate probes and systems for detecting DNA using these probes. In these figures, a, b, c and d refer to different oligonucleotide sequences, and a', b', c' and d' refer to oligonucleotide sequences complementary to a, b, c and d, respectively.

In yet other embodiments utilizing a substrate, an "aggregate probe" can be used. The aggregate probe can be prepared by allowing two types of nanoparticles having complementary oligonucleotides (a and a') attached to them to hybridize to form a core (illustrated in FIG. 28A). Since each type of nanoparticle has a plurality of oligonucleotides attached to it, each type of nanoparticles will hybridize to a plurality of the other type of nanoparticles. Thus, the core is an aggregate containing numerous nanoparticles of both types. The core is then capped with a third type of nanoparticles having at least two types of oligonucleotides attached to them. The first type of oligonucleotides has a sequence b which is complementary to the sequence b' of a portion of a nucleic acid to be detected. The second type of oligonucleotides has sequence a or a' so that the third type of nanoparticles will hybridize to nanoparticles on the exterior of the core. The aggregate probe can also be prepared by utilizing two types of nanoparticles (see FIG. 28B). Each type of nanoparticles has at least two types of oligonucleotides attached to them. The first type of oligonucleotides present on each of the two types of nanoparticles has sequence b which is complementary to the sequence b' of a portion of the nucleic acid to be detected. The second type of oligonucleotides on the first type of nanoparticles has a sequence a which is complementary to the sequence a' of the second type of oligonucleotides on the second type of nanoparticles (see FIG. 28B) so that the two types of nanoparticles hybridize to each other to form the aggregate probe. Since each type of nanoparticles has a plurality of oligonucleotides attached to it, each type of nanoparticles will hybridize to a plurality of the other type of nanoparticles to form an aggregate containing numerous nanoparticles of both types.

Figure 28B:
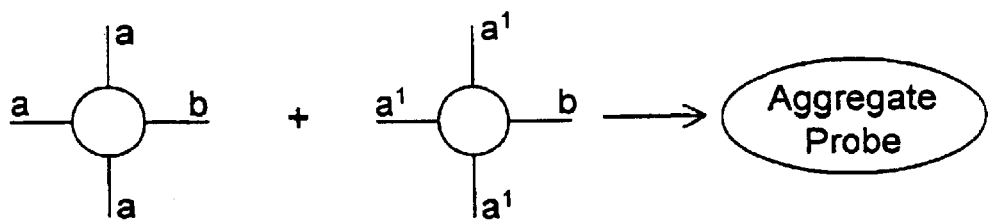
Figure 28C:
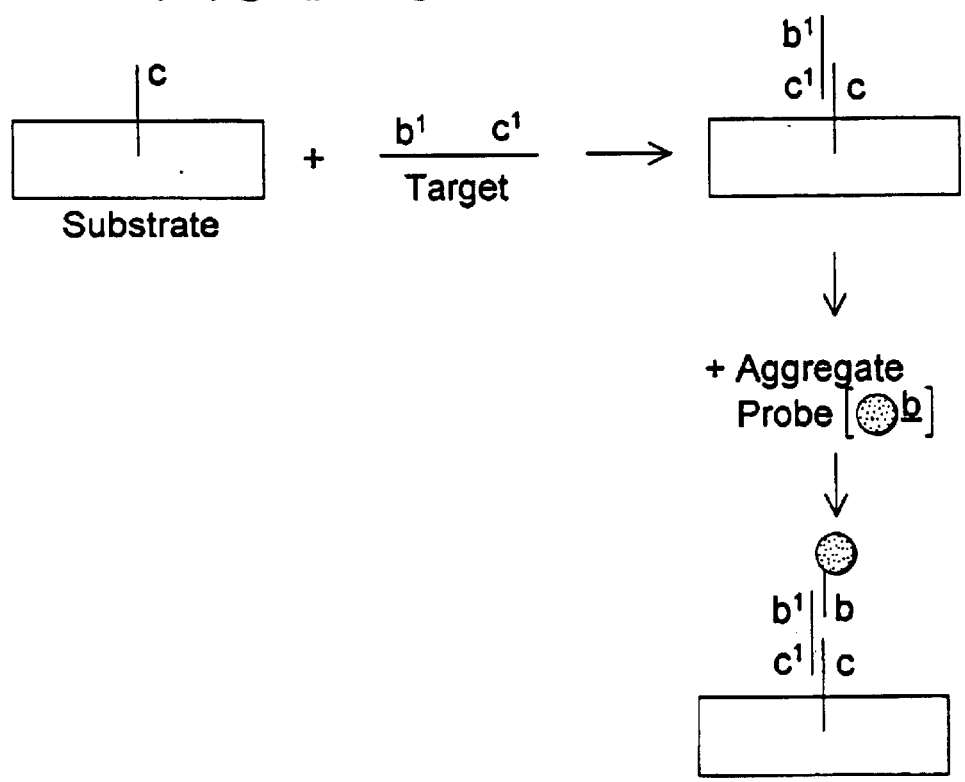
Figure 28D:
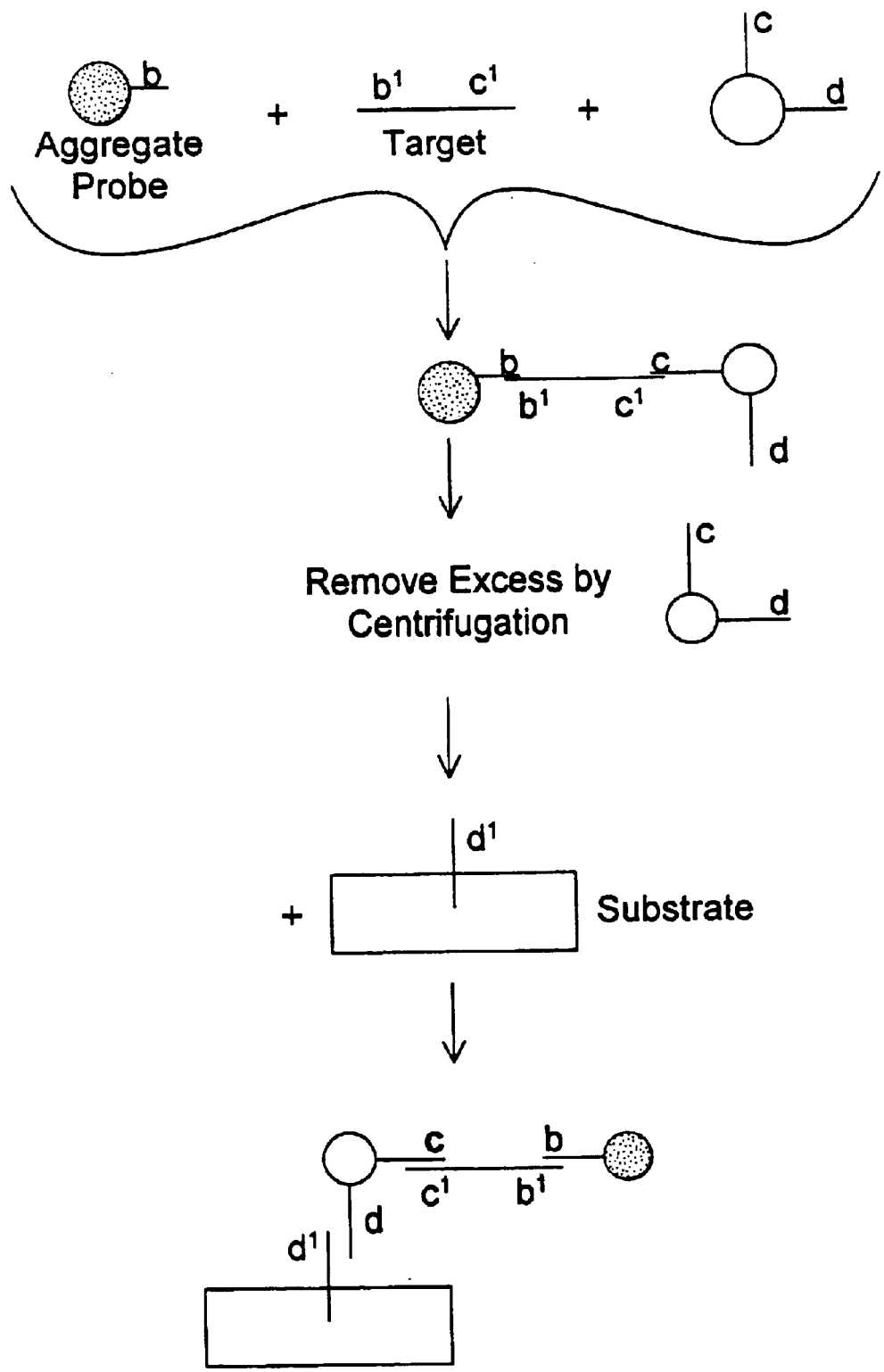

The aggregate probe can be utilized to detect nucleic acid in any of the above assay formats performed on a substrate, eliminating the need to build up layers of individual nanoparticles in order to obtain or enhance a detectable change. To even further enhance the detectable change, layers of aggregate probes can be built up by using two types of aggregate probes, the first type of aggregate probe having oligonucleotides attached to it that are complementary to oligonucleotides on the other type of aggregate probe. In particular, when the aggregate probe is prepared as illustrated in FIG. 28B, the aggregate probes can hybridize to each other to form the multiple layers. Some of the possible assay formats utilizing aggregate probes are illustrated in FIGS. 28C–D. For instance, a type of oligonucleotides comprising sequence c is attached to a substrate (see FIG. 28C). Sequence c is complementary to the sequence c' of a portion of a nucleic acid to be detected. The target nucleic acid is added and allowed to hybridize to the oligonucleotides attached to the substrate, after which the aggregate probe is added and allowed to hybridize to the portion of the target nucleic acid having sequence b', thereby producing a detectable change. Alternatively, the target nucleic acid can first be hybridized to the aggregate probe in solution and subsequently hybridized to the oligonucleotides on the substrate, or the target nucleic acid can simultaneously be hybridized to the aggregate probe and the oligonucleotides on the substrate. In another embodiment, the target nucleic acid is allowed to react with the aggregate probe and another type of nanoparticles in solution (see FIG. 28D). Some of the oligonucleotides attached to this additional type of nanoparticles comprise sequence c so that they hybridize to sequence c' of the target nucleic acid and some of the oligonucleotides attached to this additional type of nanoparticles comprise sequence d so that they can subsequently hybridize to oligonucleotides comprising sequence d' which are attached to the substrate.

Figure 28E:
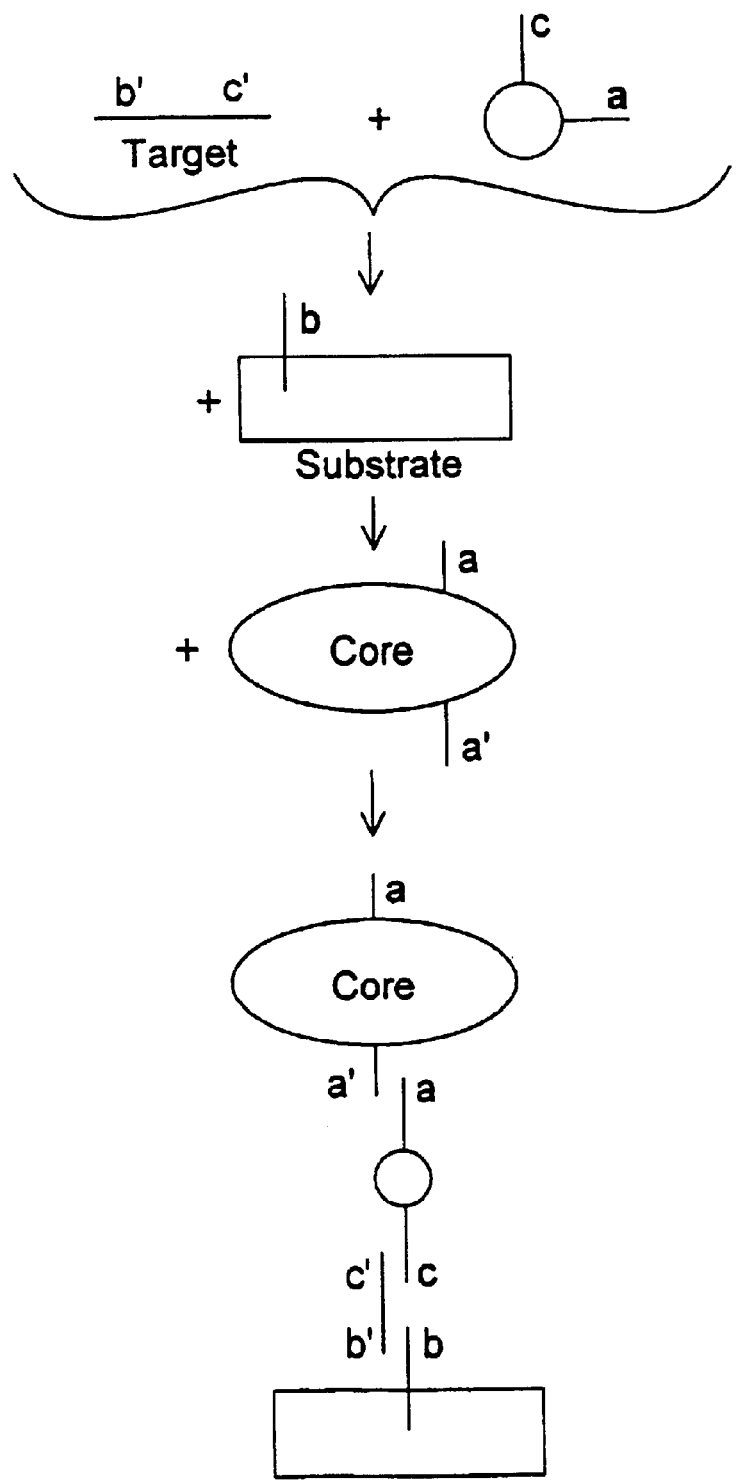

The core itself can also be used as a probe to detect nucleic acids. One possible assay format is illustrated in FIG. 28E. As illustrated there, a type of oligonucleotides comprising sequence b is attached to a substrate. Sequence b is complementary to the sequence b' of a portion of a nucleic acid to be detected. The target nucleic acid is contacted with the substrate and allowed to hybridize to the oligonucleotides attached to the substrate. Then, another type of nanoparticles is added. Some of the oligonucleotides attached to this additional type of nanoparticles comprise sequence c so which is complementary to sequence c' of the target nucleic acid so that the nanoparticles hybridize to the target nucleic acid bound to the substrate. Some of the oligonucleotides attached to the additional type of nanoparticles comprise sequence a or a' complementary to sequences a and a' on the core probe, and the core probe is added and allowed to hybridize to the oligonucleotides on the nanoparticles. Since each core probe has sequences a and a' attached to the nanoparticles which comprise the core, the core probes can hybridize to each other to form multiple layers attached to the substrate, providing a greatly enhanced detectable change. In alternative embodiments, the target nucleic acid could be contacted with the additional type of nanoparticles in solution prior to being contacted with the substrate, or the target nucleic acid, the nanoparticles and the substrate could all be contacted simultaneously. In yet another alternative embodiment, the additional type of nanoparticles could be replaced by a linking oligonucleotide comprising both sequences c and a or a'.

When a substrate is employed, a plurality of the initial types of nanoparticle-oligonucleotide conjugates or oligonucleotides can be attached to the substrate in an array for detecting multiple portions of a target nucleic acid, for detecting multiple different nucleic acids, or both. For instance, a substrate may be provided with rows of spots, each spot containing a different type of oligonucleotide or oligonucleotide-nanoparticle conjugate designed to bind to a portion of a target nucleic acid. A sample containing one or more nucleic acids is applied to each spot, and the rest of the assay is performed in one of the ways described above using appropriate oligonucleotide-nanoparticle conjugates, oligonucleotide-liposome conjugates, aggregate probes, core probes, and binding oligonucleotides.

Finally, when a substrate is employed, a detectable change can be produced or further enhanced by silver staining. Silver staining can be employed with any type of nanoparticles that catalyze the reduction of silver. Preferred are nanoparticles made of noble metals (e.g., gold and silver). See Bassell, et al., *J. Cell Biol.*, 126, 863–876 (1994); Braun-Howland et al., *Biotechniques*, 13, 928–931 (1992). If the nanoparticles being employed for the detection of a nucleic acid do not catalyze the reduction of silver, then silver ions can be complexed to the nucleic acid to catalyze the reduction. See Braun et al., *Nature*, 391, 775 (1998). Also, silver stains are known which can react with the phosphate groups on nucleic acids.

Silver staining can be used to produce or enhance a detectable change in any assay performed on a substrate, including those described above. In particular, silver staining has been found to provide a huge increase in sensitivity for assays employing a single type of nanoparticle, such as the one illustrated in FIG. 25A, so that the use of layers of nanoparticles, aggregate probes and core probes can often be eliminated.

In assays for detecting nucleic acids performed on a substrate, the detectable change can be observed with an optical scanner. Suitable scanners include those used to scan documents into a computer which are capable of operating in the reflective mode (e.g., a flatbed scanner), other devices capable of performing this function or which utilize the same type of optics, any type of greyscale-sensitive measurement device, and standard scanners which have been modified to scan substrates according to the invention (e.g., a flatbed scanner modified to include a holder for the substrate) (to date, it has not been found possible to use scanners operating in the transmissive mode). The resolution of the scanner must be sufficient so that the reaction area on the substrate is larger than a single pixel of the scanner. The scanner can be used with any substrate, provided that the detectable change produced by the assay can be observed against the substrate (e.g., a grey spot, such as that produced by silver staining, can be observed against a white background, but cannot be observed against a grey background). The scanner can be a black-and-white scanner or, preferably, a color scanner. Most preferably, the scanner is a standard color scanner of the type used to scan documents into computers. Such scanners are inexpensive and readily available commercially. For instance, an Epson Expression 636 (600×600 dpi), a UMAX Astra 1200 (300× 300 dpi), or a Microtec 1600 (1600×1600 dpi) can be used. The scanner is linked to a computer loaded with software for processing the images obtained by scanning the substrate. The software can be standard software which is readily available commercially, such as Adobe Photoshop 5.2 and Corel Photopaint 8.0. Using the software to calculate greyscale measurements provides a means of quantitating the results of the assays. The software can also provide a color number for colored spots and can generate images (e.g., printouts) of the scans which can be reviewed to provide a qualitative determination of the presence of a nucleic acid, the quantity of a nucleic acid, or both. In addition, it has been found that the sensitivity of assays such as that described in Example 5 can be increased by subtracting the color that represents a negative result (red in Example 5) from the color that represents a positive result (blue in Example 5). The computer can be a standard personal computer which is readily available commercially. Thus, the use of a standard scanner linked to a standard computer loaded with standard software can provide a convenient, easy, inexpensive means of detecting and quantitating nucleic acids when the assays are performed on substrates. The scans can also be stored in the computer to maintain a record of the results for further reference or use. Of course, more sophisticated instruments and software can be used, if desired.

Figure 17D:
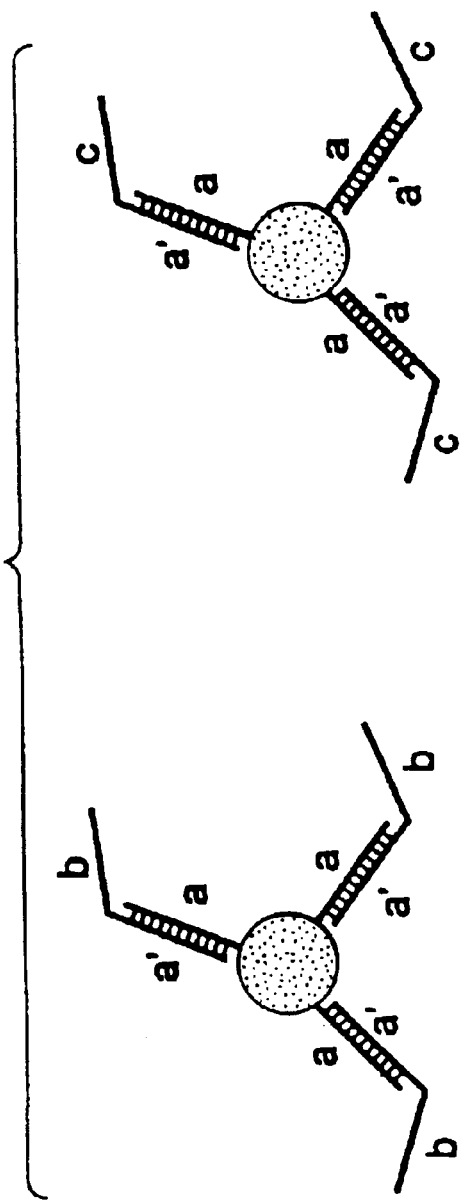
Figure 17E:
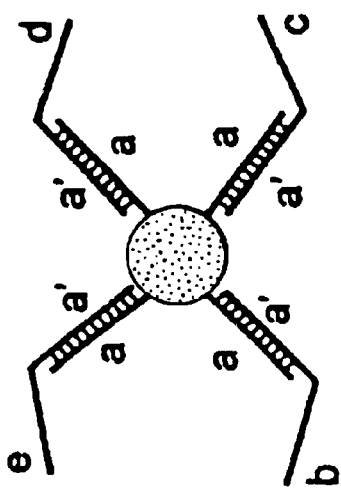

A nanoparticle-oligonucleotide conjugate which may be used in an assay for any nucleic acid is illustrated in FIGS. 17D–E. This "universal probe" has oligonucleotides of a single sequence attached to it. These oligonucleotides can hybridize with a binding oligonucleotide which has a sequence comprising at least two portions. The first portion is complementary to at least a portion of the sequence of the oligonucleotides on the nanoparticles. The second portion is complementary to a portion of the sequence of the nucleic acid to be detected. A plurality of binding oligonucleotides having the same first portion and different second portions can be used, in which case the "universal probe", after hybridization to the binding oligonucleotides, can bind to multiple portions of the nucleic acid to be detected or to different nucleic acid targets.

Figure 20A:
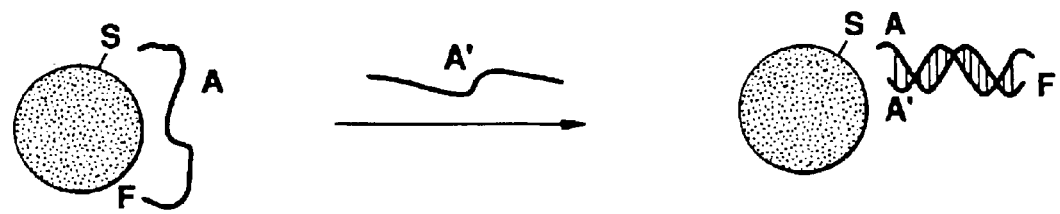
FIGS. 20A–B: Illustrations of schemes using fluorescent-labeled oligonucleotides attached to metallic or semiconductor quenching nanoparticles (FIG. 20A) or to non-metallic, non-semiconductor particles (FIG. 20B).

In a number of other embodiments of the invention, the detectable change is created by labeling the oligonucleotides, the nanoparticles, or both with molecules (e.g., fluorescent molecules and dyes) that produce detectable changes upon hybridization of the oligonucleotides on the nanoparticles with the target nucleic acid. For instance, oligonucleotides attached to metal and semiconductor nanoparticles can have a fluorescent molecule attached to the end not attached to the nanoparticles. Metal and semiconductor nanoparticles are known fluorescence quenchers, with the magnitude of the quenching effect depending on the distance between the nanoparticles and the fluorescent molecule. In the unhybridized state, the oligonucleotides attached to the nanoparticles interact with the nanoparticles, so that significant quenching will be observed. See FIG. 20A. Upon hybridization to a target nucleic acid, the fluorescent molecule will become spaced away from the nanoparticles, diminishing quenching of the fluorescence. See FIG. 20A. Longer oligonucleotides should give rise to larger changes in fluorescence, at least until the fluorescent groups are moved far enough away from the nanoparticle surfaces so that an increase in the change is no longer observed. Useful lengths of the oligonucleotides can be determined empirically. Metallic and semiconductor nanoparticles having fluorescent-labeled oligonucleotides attached thereto can be used in any of the assay formats described above, including those performed in solution or on substrates.

Methods of labeling oligonucleotides with fluorescent molecules and measuring fluorescence are well known in the art. Suitable fluorescent molecules are also well known in the art and include the fluoresceins, rhodamines and Texas Red. The oligonucleotides will be attached to the nanoparticles as described above.

In yet another embodiment, two types of fluorescent-labeled oligonucleotides attached to two different particles can be used. Suitable particles include polymeric particles (such as polystyrene particles, polyvinyl particles, acrylate and methacrylate particles), glass particles, latex particles, Sepharose beads and others like particles well known in the art. Methods of attaching oligonucleotides to such particles are well known in the art. See Chrisey et al., *Nucleic Acids Research*, 24, 3031–3039 (1996) (glass) and Charreyre et al., *Langmuir*, 13, 3103–3110 (1997), Fahy et al., *Nucleic Acids Research*, 21, 1819–1826 (1993), Elaissari et al., *J. Colloid Interface Sci.*, 202, 251–260(1998), Kolarova et al., *Biotechniques*, 20, 196–198 (1996) and Wolf et al., *Nucleic Acids Research*, 15, 2911–2926 (1987) (polymer/latex). In particular, a wide variety of functional groups are available on the particles or can be incorporated into such particles. Functional groups include carboxylic acids, aldehydes, amino groups, cyano groups, ethylene groups, hydroxyl groups, mercapto groups, and the like. Nanoparticles, including metallic and semiconductor nanoparticles, can also be used.

Figure 20B:
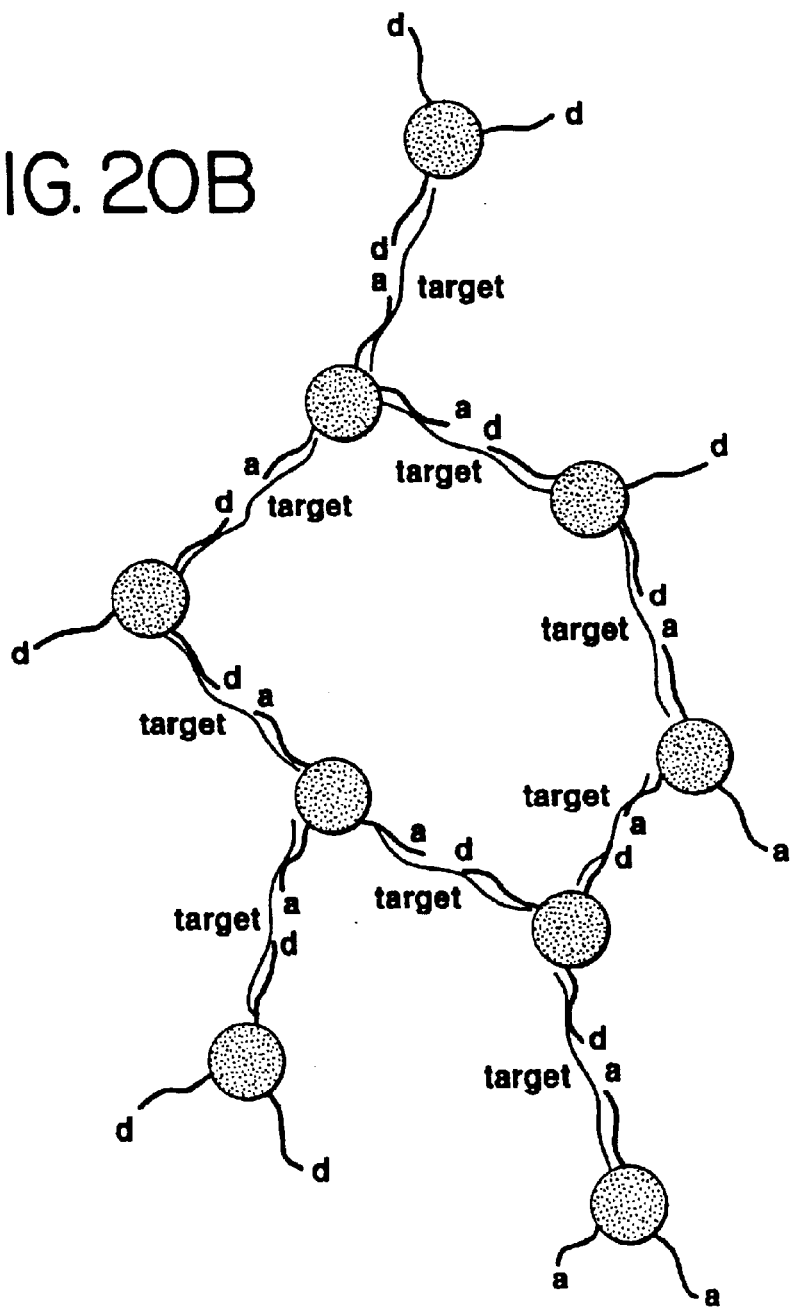

The two fluorophores are designated d and a for donor and acceptor. A variety of fluorescent molecules useful in such combinations are well known in the art and are available from, e.g., Molecular Probes. An attractive combination is fluorescein as the donor and Texas Red as acceptor. The two types of nanoparticle-oligonucleotide conjugates with d and a attached are mixed with the target nucleic acid, and fluorescence measured in a fluorimeter. The mixture will be excited with light of the wavelength that excites d, and the mixture will be monitored for fluorescence from a. Upon hybridization, d and a will be brought in proximity (see FIG. 20B). In the case of non-metallic, non-semiconductor particles, hybridization will be shown by a shift in fluorescence from that for d to that for a or by the appearance of fluorescence for a in addition to that for d. In the absence of hybridization, the flurophores will be too far apart for energy transfer to be significant, and only the fluorescence of d will be observed. In the case of metallic and semiconductor nanoparticles, lack of hybridization will be shown by a lack of fluorescence due to d or a because of quenching (see above). Hybridization will be shown by an increase in fluorescence due to a.

As will be appreciated, the above described particles and nanoparticles having oligonucleotides labeled with acceptor and donor fluorescent molecules attached can be used in the assay formats described above, including those performed in solution and on substrates. For solution formats, the oligonucleotide sequences are preferably chosen so that they bind to the target nucleic acid as illustrated in FIGS. 15A–G. In the formats shown in FIGS. 13A–B and 18, the binding oligonucleotides may be used to bring the acceptor and donor fluorescent molecules on the two nanoparticles in proximity. Also, in the format illustrated in FIG. 13A, the oligonucleotides attached the substrate may be labeled with d. Further, other labels besides fluorescent molecules can be used, such as chemiluminescent molecules, which will give a detectable signal or a change in detectable signal upon hybridization.

Figure 21:
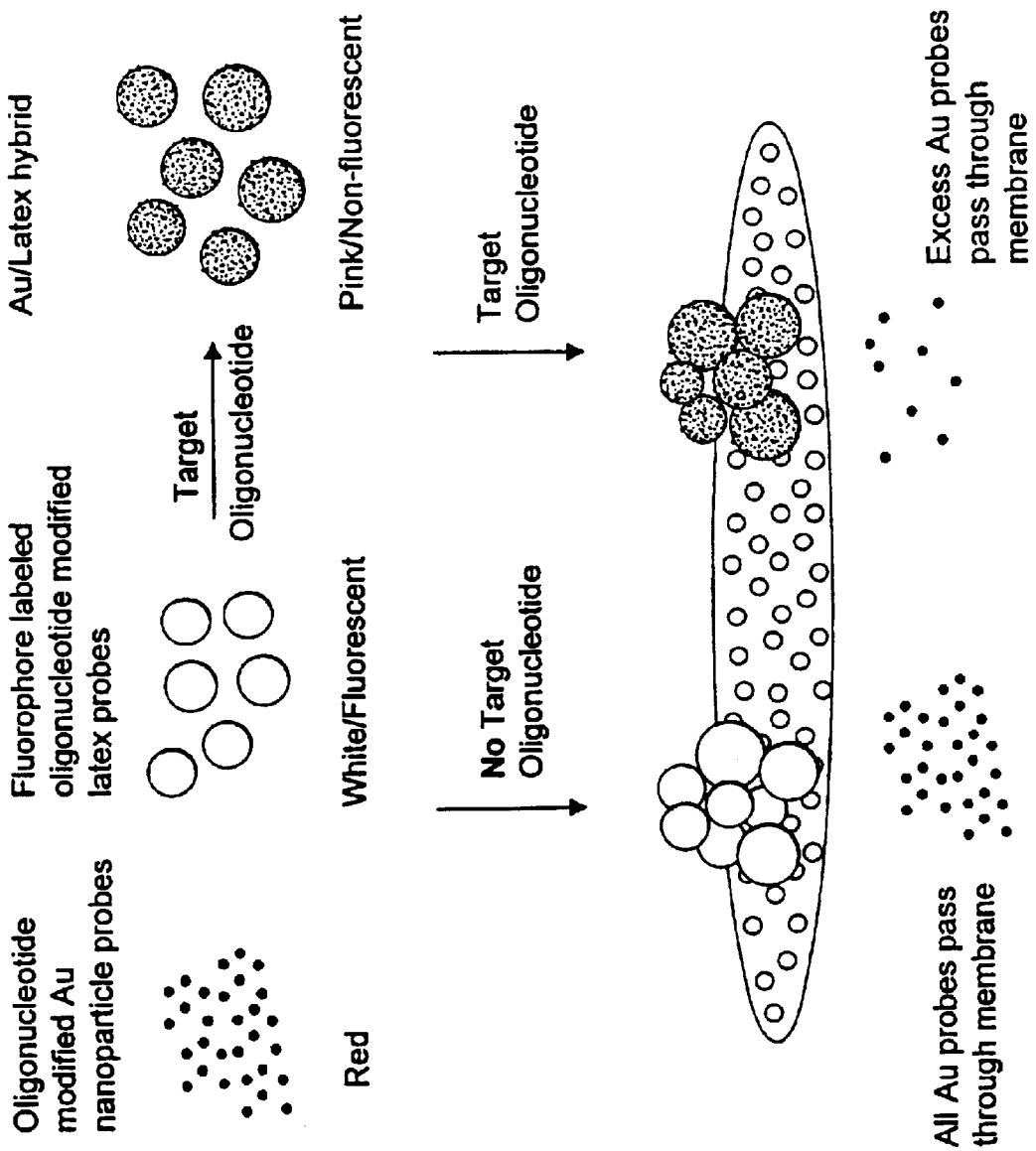
FIG. 21: Schematic diagram illustrating a system for detecting target nucleic acid using gold nanoparticles having oligonucleotides attached thereto and latex microspheres having fluorescently-labeled oligonucleotides attached thereto. The small, closed, dark circles represent the nanoparticles, the large, open circles represent the latex microspheres, and the large oval represents a microporous membrane.

Another embodiment of the detection method of the invention is a very sensitive system that utilizes detection of changes in fluorescence and color (illustrated in FIG. 21). This system employs latex microspheres to which are attached oligonucleotides labeled with a fluorescent molecule and gold nanoparticles to which are attached oligonucleotides. The oligonucleotide-nanoparticle conjugates can be prepared as described above. Methods of attaching oligonucleotides to latex microspheres are well known (see, e.g., Charreyre et al., *Langmuir*, 13:3103–3110 (1997); Elaissari et al., *J. Colloid Interface Sci.*, 202:251–260 (1998)), as are methods of labeling oligonucleotides with fluorescent molecules (see above). The oligonucleotides on the latex microspheres and the oligonucleotides on the gold nanoparticles have sequences capable of hybridizing with different portions of the sequence of a target nucleic acid, but not with each other. When a target nucleic acid comprising sequences complementary to the sequences of the oligonucleotides on the latex microspheres and gold nanoparticles is contacted with the two probes, a network structure is formed (see FIG. 21). Due to the quenching properties of the gold nanoparticles, the fluorescence of the oligonucleotides attached to the latex microspheres is quenched while part of this network. Indeed, one gold nanoparticle can quench many fluorophore molecules since gold nanoparticles have very large absorption coefficients. Thus, the fluorescence of a solution containing nucleic acid and the two particles can be monitored to detect the results, with a reduction in, or elimination of, fluorescence indicating a positive result. Preferably, however, the results of the assay are detected by placing a droplet of the solution onto a microporous material (see FIG. 21). The microporous material should be transparent or a color (e.g., white) which allows for detection of the pink/red color of the gold nanoparticles. The microporous material should also have a pore size sufficiently large to allow the gold nanoparticles to pass through the pores and sufficiently small to retain the latex microspheres on the surface of the microporous material when the microporous material is washed. Thus, when using such a microporous material, the size (diameter) of the latex microspheres must be larger than the size (diameter) of the gold nanoparticles. The microporous material must also be inert to biological media. Many suitable microporous materials are known in the art and include various filters and membranes, such as modified polyvinylidene fluoride (PVDF, such as Durapore™ membrane filters purchased from Millipore Corp.) and pure cellulose acetate (such as AcetatePlus™ membrane filters purchased from Micron Separations Inc.). Such a microporous material retains the network composed of target nucleic acid and the two probes, and a positive result (presence of the target nucleic acid) is evidenced by a red/pink color (due to the presence of the gold nanoparticles) and a lack of fluorescence (due to quenching of fluorescence by the gold nanoparticles) (see FIG. 21). A negative result (no target nucleic acid present) is evidenced by a white color and fluorescence, because the gold nanoparticles would pass through the pores of the microporous material when it is washed (so no quenching of the fluorescence would occur), and the white latex microspheres would be trapped on top of it (see FIG. 21). In addition, in the case of a positive result, changes in fluorescence and color can be observed as a function of temperature. For instance, as the temperature is raised, fluorescence will be observed once the dehybridization temperature has been reached. Therefore, by looking at color or fluorescence as a function of temperature, information can be obtained about the degree of complementarity between the oligonucleotide probes and the target nucleic acid. As noted above, this detection method exhibits high sensitivity. As little as 3 femtomoles of single-stranded target nucleic acid 24 bases in length and 20 femtomoles of double-stranded target nucleic acid 24 bases in length have been detected with the naked eye. The method is also very simple to use. Fluorescence can be generated by simply illuminating the solution or microporous material with a UV lamp, and the fluorescent and colorimetric signals can be monitored by the naked eye. Alternatively, for a more quantitative result, a fluorimeter can be employed in front-face mode to measure the fluorescence of the solution with a short pathlength.

The above embodiment has been described with particular reference to latex microspheres and gold nanoparticles. Any other microsphere or nanoparticle, having the other properties described above and to which oligonucleotides can be attached, can be used in place of these particles. Many suitable particles and nanoparticles are described above, along with techniques for attaching oligonucleotides to them. In addition, microspheres and nanoparticles having other measurable properties may be used. For instance, polymer-modified particles and nanoparticles, where the polymer can be modified to have any desirable property, such as fluorescence, color, or electrochemical activity, can be used. See, Watson et al., *J. Am. Chem. Soc.*, 121, 462–463 (1999) (polymer-modified gold nanoparticles). Also, magnetic, polymer-coated magnetic, and semiconducting particles can be used. See Chan et al., *Science*, 281, 2016 (1998); Bruchez et al., *Science*, 281, 2013 (1998); Kolarova et al., *Biotechniques*, 20, 196–198 (1996).

In yet another embodiment, two probes comprising metallic or semiconductor nanoparticles having oligonucleotides labeled with fluorescent molecules attached to them are employed (illustrated in FIG. 22). The oligonucleotide-nanoparticle conjugates can be prepared and labeled with fluorescent molecules as described above. The oligonucleotides on the two types of oligonucleotide-nanoparticle conjugates have sequences capable of hybridizing with different portions of the sequence of a target nucleic acid, but not with each other. When a target nucleic acid comprising sequences complementary to the sequences of the oligonucleotides on the nanoparticles is contacted with the two probes, a network structure is formed (see FIG. 22). Due to the quenching properties of the metallic or semiconductor nanoparticles, the fluorescence of the oligonucleotides attached to the nanoparticles is quenched while part of this network. Thus, the fluorescence of a solution containing nucleic acid and the two probes can be monitored to detect the results, with a reduction in, or elimination of, fluorescence indicating a positive result. Preferably, however, the results of the assay are detected by placing a droplet of the solution onto a microporous material (see FIG. 22). The microporous material should have a pore size sufficiently large to allow the nanoparticles to pass through the pores and sufficiently small to retain the network on the surface of the microporous material when the microporous material is washed (see FIG. 22). Many suitable microporous materials are known in the art and include those described above. Such a microporous material retains the network composed of target nucleic acid and the two probes, and a positive result (presence of the target nucleic acid) is evidenced by a lack of fluorescence (due to quenching of fluorescence by the metallic or semiconductor nanoparticles) (see FIG. 22). A negative result (no target nucleic acid present) is evidenced by fluorescence because the nanoparticles would pass through the pores of the microporous material when it is washed (so no quenching of the fluorescence would occur) (see FIG. 22). There is low background fluorescence because unbound probes are washed away from the detection area. In addition, in the case of a positive result, changes in fluorescence can be observed as a function of temperature. For instance, as the temperature is raised, fluorescence will be observed once the dehybridization temperature has been reached. Therefore, by looking at fluorescence as a function of temperature, information can be obtained about the degree of complementarity between the oligonucleotide probes and the target nucleic acid. Fluorescence can be generated by simply illuminating the solution or microporous material with a UV lamp, and the fluorescent signal can be monitored by the naked eye. Alternatively, for a more quantitative result, a fluorimeter can be employed in front-face mode to measure the fluorescence of the solution with a short path length.

In yet other embodiments, a "satellite probe" is used (see FIG. 24). The satellite probe comprises a central particle with one or several physical properties that can be exploited for detection in an assay for nucleic acids (e.g., intense color, fluorescence quenching ability, magnetism). Suitable particles include the nanoparticles and other particles described above. The particle has oligonucleotides (all having the same sequence) attached to it (see FIG. 24). Methods of attaching oligonucleotides to the particles are described above. These oligonucleotides comprise at least a first portion and a second portion, both of which are complementary to portions of the sequence of a target nucleic acid (see FIG. 24). The satellite probe also comprises probe oligonucleotides. Each probe oligonucleotide has at least a first portion and a second portion (see FIG. 24). The sequence of the first portion of the probe oligonucleotides is complementary to the first portion of the sequence of the oligonucleotides immobilized on the central particle (see FIG. 24). Consequently, when the central particle and the probe oligonucleotides are brought into contact, the oligonucleotides on the particle hybridize with the probe oligonucleotides to form the satellite probe (see FIG. 24). Both the first and second portions of the probe oligonucleotides are complementary to portions of the sequence of the target nucleic acid (see FIG. 24). Each probe oligonucleotide is labeled with a reporter molecule (see FIG. 24), as further described below. The amount of hybridization overlap between the probe oligonucleotides and the target (length of the portion hybridized) is as large as, or greater than, the hybridization overlap between the probe oligonucleotides and the oligonucleotides attached to the particle (see FIG. 24). Therefore, temperature cycling resulting in dehybridization and rehybridization would favor moving the probe oligonucleotides from the central particle to the target. Then, the particles are separated from the probe oligonucleotides hybridized to the target, and the reporter molecule is detected.

The satellite probe can be used in a variety of detection strategies. For example, if the central particle has a magnetic core and is covered with a material capable of quenching the fluorescence of fluorophores attached to the probe oligonucleotides that surround it, this system can be used in an in situ fluorometric detection scheme for nucleic acids. Functionalized polymer-coated magnetic particles ($Fe_3O_4$) are available from several commercial sources including Dynal (Dynabeads™) and Bangs Laboratories (Estapor™), and silica-coated magnetic $Fe_3O_4$ nanoparticles could be modified (Liu et al., *Chem. Mater.*, 10, 3936–3940 (1998))using well-developed silica surface chemistry (Chrisey et al., *Nucleic Acids Research*, 24, 3031–3039 (1996)) and employed as magnetic probes as well. Further, the dye molecule, 4-((4-(dimethylamino)phenyl)-azo)benzoic acid (DABCYL) has been shown to be an efficient quencher of fluorescence for a wide variety of fluorphores attached to oligonucleotides (Tyagi et al., *Nature Biotech.*, 16, 49–53 (1998). The commercially-available succinimidyl ester of DABCYL (Molecular Probes) forms extremely stable amide bonds upon reaction with primary alkylamino groups. Thus, any magnetic particle or polymer-coated magnetic particle with primary alkyl amino groups could be modified with both oligonucleotides, as well as these quencher molecules. Alternatively, the DABCYL quencher could be attached directly to the surface-bound oligonucleotide, instead of the alkyl amino-modified surface. The satellite probe comprising the probe oligonucleotides is brought into contact with the target. The temperature is cycled so as to cause dehybridization and rehybridization, which causes the probe oligonucleotides to move from the central particle to the target. Detection is accomplished by applying a magnetic field and removing the particles from solution and measuring the fluorescence of the probe oligonucleotides remaining in solution hybridized to the target.

This approach can be extended to a colorimetric assay by using magnetic particles with a dye coating in conjunction with probe oligonucleotides labeled with a dye which has optical properties that are distinct from the dye on the magnetic nanoparticles or perturb those of the dye on the magnetic nanoparticles. When the particles and the probe oligonucleotides are in solution together, the solution will exhibit one color which derives from a combination of the two dyes. However, in the presence of a target nucleic acid and with temperature cycling, the probe oligonucleotides will move from the satellite probe to the target. Once this has happened, application of a magnetic field will remove the magnetic, dye-coated particles from solution leaving behind probe oligonucleotides labeled with a single dye hybridized to the target. The system can be followed with a colorimeter or the naked eye, depending upon target levels and color intensities.

This approach also can be further extended to an electrochemical assay by using an oligonucleotide-magnetic particle conjugate in conjunction with a probe oligonucleotide having attached a redox-active molecule. Any modifiable redox-active species can be used, such as the well-studied redox-active ferrocene derivative. A ferrocene derivatized phosphoramidite can be attached to oligonucleotides directly using standard phosphoramidite chemistry. Mucic et al., *Chem. Commun.*, 555 (1996); Eckstein, ed., in *Oligonucleotides and Analogues*, 1st ed., Oxford University, New York, N.Y. (1991). The ferrocenylphosphoramidite is prepared in a two-step synthesis from 6-bromohexylferrocene. In a typical preparation, 6-bromohexylferrocene is stirred in an aqueous HMPA solution at 120° C. for 6 hours to from 6-hydroxyhexylferrocene. After purification, the 6-hydroxyhexylferrocene is added to a THF solution of N,N-diisopropylethylamine and beta-cyanoethyl-N,N-diisopropylchlorophosphoramide to form the ferrocenylphosphoramidite. Oligonucleotide-modified polymer-coated gold nanoparticles, where the polymer contains electrochemically-active ferrocene molecules, could also be utilized. Watson et al., *J. Am. Chem. Soc.*, 121, 462–463 (1999). A copolymer of amino reactive sites (e.g., anhydrides) could be incorporated into the polymer for reaction with amino-modified oligonucleotides. Moller et al., *Bioconjugate Chem.*, 6, 174–178 (1995). In the presence of target and with temperature cycling, the redox-active probe oligonucleotides will move from the satellite probe to the target. Once this has happened, application of the magnetic field will remove is the magnetic particles from solution leaving behind the redox-active probe oligonucleotides hybridized with the target nucleic acid. The amount of target then can be determined by cyclic voltammetry or any electrochemical technique that can interrogate the redox-active molecule.

In yet another embodiment of the invention, a nucleic acid is detected by contacting the nucleic acid with a substrate having oligonucleotides attached thereto. The oligonucleotides have a sequence complementary to a first portion of the sequence of the nucleic acid. The oligonucleotides are located between a pair of electrodes located on the substrate. The substrate must be made of a material which is not a conductor of electricity (e.g., glass, quartz, polymers, plastics). The electrodes may be made of any standard material (e.g., metals, such as gold, platinum, tin oxide). The electrodes can be fabricated by conventional microfabrication techniques. See, e.g., *Introduction To Microlithography* (L. F. Thompson et al., eds., American Chemical Society, Washington, D.C. 1983). The substrate may have a plurality of pairs of electrodes located on it in an array to allow for the detection of multiple portions of a single nucleic acid, the detection of multiple different nucleic acids, or both. Arrays of electrodes can be purchased (e.g., from AbbtechScientific, Inc., Richmond, Va.) or can be made by conventional microfabrication techniques. See, e.g., *Introduction To Microlithography* (L. F. Thompson et al., eds., American Chemical Society, Washington, D.C. 1983). Suitable photomasks for making the arrays can be purchased (e.g., from Photronics, Milpitas, Calif.). Each of the pairs of electrodes in the array will have a type of oligonucleotides attached to the substrate between the two electrodes. The contacting takes place under conditions effective to allow hybridization of the oligonucleotides on the substrate with the nucleic acid. Then, the nucleic acid bound to the substrate, is contacted with a type of nanoparticles. The nanoparticles must be made of a material which can conduct electricity. Such nanoparticles include those made of metal, such as gold nanoparticles, and semiconductor materials. The nanoparticles will have one or more types of oligonucleotides attached to them, at least one of the types of oligonucleotides having a sequence complementary to a second portion of the sequence of the nucleic acid. The contacting takes place under conditions effective to allow hybridization of the oligonucleotides on the nanoparticles with the nucleic acid. If the nucleic acid is present, the circuit between the electrodes should be closed because of the attachment of the nanoparticles to the substrate between the electrodes, and a change in conductivity will be detected. If the binding of a single type of nanoparticles does not result in closure of the circuit, this situation can be remedied by using a closer spacing between the electrodes, using larger nanoparticles, or employing another material that will close the circuit (but only if the nanoparticles have been bound to the substrate between the electrodes). For instance, when gold nanoparticles are used, the substrate can be contacted with silver stain (as described above) to deposit silver between the electrodes to close the circuit and produce the detectable change in conductivity. Another way to close the circuit in the case where the addition of a single type of nanoparticles is not sufficient, is to contact the first type of nanoparticles bound to the substrate with a second type of nanoparticles having oligonucleotides attached to them that have a sequence complementary to the oligonucleotides on the first type of nanoparticles. The contacting will take place under conditions effective so that the oligonucleotides on the second type of nanoparticle hybridize to those on the first type of oligonucleotides. If needed, or desired, additional layers of nanoparticles can be built up by alternately adding the first and second types of nanoparticles until a sufficient number of nanoparticles are attached to the substrate to close the circuit. Another alternative to building up individual layers of nanoparticles would be the use of an aggregate probe (see above).

The invention also provides kits for detecting nucleic acids. In one embodiment, the kit comprises at least one container, the container holding at least two types of nanoparticles having oligonucleotides attached thereto. The oligonucleotides on the first type of nanoparticles have a sequence complementary to the sequence of a first portion of a nucleic acid. The oligonucleotides on the second type of nanoparticles have a sequence complementary to the sequence of a second portion of the nucleic acid. The container may further comprise filler oligonucleotides having a sequence complementary to a third portion of the nucleic acid, the third portion being located between the first and second portions. The filler oligonucleotide may also be provided in a separate container.

In a second embodiment, the kit comprises at least two containers. The first container holds nanoparticles having oligonucleotides attached thereto which have a sequence complementary to the sequence of a first portion of a nucleic acid. The second container holds nanoparticles having oligonucleotides attached thereto which have a sequence no complementary to the sequence of a second portion of the nucleic acid. The kit may further comprise a third container holding a filler oligonucleotide having a sequence complementary to a third portion of the nucleic acid, the third portion being located between the first and second portions.

In another alternative embodiment, the kits can have the oligonucleotides and nanoparticles in separate containers, and the oligonucleotides would have to be attached to the nanoparticles prior to performing an assay to detect a nucleic acid. The oligonucleotides and/or the nanoparticles may be functionalized so that the oligonucleotides can be attached to the nanoparticles. Alternatively, the oligonucleotides and/or nanoparticles may be provided in the kit without functional groups, in which case they must be functionalized prior to performing the assay.

In another embodiment, the kit comprises at least one container. The container holds metallic or semiconductor nanoparticles having oligonucleotides attached thereto. The oligonucleotides have a sequence complementary to a portion of a nucleic acid and have fluorescent molecules attached to the ends of the oligonucleotides not attached to the nanoparticles.

In yet another embodiment, the kit comprises a substrate, the substrate having attached thereto nanoparticles. The nanoparticles have oligonucleotides attached thereto which have a sequence complementary to the sequence of a first portion of a nucleic acid. The kit also includes a first container holding nanoparticles having oligonucleotides attached thereto which have a sequence complementary to the sequence of a second portion of the nucleic acid. The oligonucleotides may have the same or different sequences, but each of the oligonucleotides has a sequence complementary to a portion of the nucleic acid. The kit further includes a second container holding a binding oligonucleotide having a selected sequence having at least two portions, the first portion being complementary to at least a portion of the sequence of the oligonucleotides on the nanoparticles in the first container. The kit also includes a third container holding nanoparticles having oligonucleotides attached thereto, the oligonucleotides having a sequence complementary to the sequence of a second portion of the binding oligonucleotide.

In another embodiment, the kit comprises a substrate having oligonucleotides attached thereto which have a sequence complementary to the sequence of a first portion of a nucleic acid. The kit also includes a first container holding nanoparticles having oligonucleotides attached thereto which have a sequence complementary to the sequence of a second portion of the nucleic acid. The oligonucleotides may have the same or different sequences, but each of the oligonucleotides has a sequence complementary to a portion of the nucleic acid. The kit further includes a second container holding nanoparticles having oligonucleotides attached thereto which have a sequence complementary to at least a portion of the oligonucleotides attached to the nanoparticles in the first container.

In yet another embodiment, the kits can have the substrate, oligonucleotides and nanoparticles in separate containers. The substrate, oligonucleotides, and nanoparticles would have to be appropriately attached to each other prior to performing an assay to detect a nucleic acid. The substrate, oligonucleotides and/or the nanoparticles may be functionalized to expedite this attachment. Alternatively, the substrate, oligonucleotides and/or nanoparticles may be provided in the kit without functional groups, in which case they must be functionalized prior to performing the assay.

In a further embodiment, the kit comprises a substrate having oligonucleotides attached thereto which have a sequence complementary to the sequence of a first portion of a nucleic acid. The kit also includes a first container holding liposomes having oligonucleotides attached thereto which have a sequence complementary to the sequence of a second portion of the nucleic acid and a second container holding nanoparticles having at least a first type of oligonucleotides attached thereto, the first type of oligonucleotides having a cholesteryl group attached to the end not attached to the nanoparticles so that the nanoparticles can attach to the liposomes by hydrophobic interactions. The kit may further comprise a third container holding a second type of nanoparticles having oligonucleotides attached thereto, the oligonucleotides having a sequence complementary to at least a portion of the sequence of a second type of oligonucleotides attached to the first type of nanoparticles. The second type of oligonucleotides attached to the first type of nanoparticles having a sequence complementary to the sequence of the oligonucleotides on the second type of nanoparticles.

In another embodiment, the kit may comprise a substrate having nanoparticles attached to it. The nanoparticles have oligonucleotides attached to them which have a sequence complementary to the sequence of a first portion of a nucleic acid. The kit also includes a first container holding an aggregate probe. The aggregated probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a sequence complementary to a second portion of the sequence of the nucleic acid.

In yet another embodiment, the kit may comprise a substrate having oligonucleotides attached to it. The oligonucleotides have a sequence complementary to the sequence of a first portion of a nucleic acid. The kit further includes a first container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached thereto which have a sequence complementary to a second portion of the sequence of the nucleic acid.

In an additional embodiment, the kit may comprise a substrate having oligonucleotides attached to it and a first container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a sequence complementary to a first portion of the sequence of the nucleic acid. The kit also includes a second container holding nanoparticles. The nanoparticles have at least two types of oligonucleotides attached to them. The first type of oligonucleotides has a sequence complementary to a second portion of the sequence of the nucleic acid. The second type of oligonucleotides has a sequence complementary to at least a portion of the sequence of the oligonucleotides attached to the substrate.

In another embodiment, the kit may comprise a substrate which has oligonucleotides attached to it. The oligonucleotides have a sequence complementary to the sequence of a first portion of a nucleic acid. The kit also comprises a first container holding liposomes having oligonucleotides attached to them. The oligonucleotides have a sequence complementary to the sequence of a second portion of the nucleic acid. The kit further includes a second container holding an aggregate probe comprising at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a hydrophobic groups attached to the ends not attached to the nanoparticles.

In a further embodiment, the kit may comprise a first container holding nanoparticles having oligonucleotides attached thereto. The kit also includes one or more additional containers, each container holding a binding oligonucleotide. Each binding oligonucleotide has a first portion which has a sequence complementary to at least a portion of the sequence of oligonucleotides on the nanoparticles and a second portion which has a sequence complementary to the sequence of a portion of a nucleic acid to be detected. The sequences of the second portions of the binding oligonucleotides may be different as long as each sequence is complementary to a portion of the sequence of the nucleic acid to be detected.

In another embodiment, the kit comprises a container holding one type of nanoparticles having oligonucleotides attached thereto and one or more types of binding oligonucleotides. Each of the types of binding oligonucleotides has a sequence comprising at least two portions. The first portion is complementary to the sequence of the oligonucleotides on the nanoparticles, whereby the binding oligonucleotides are hybridized to the oligonucleotides on the nanoparticles in the container(s). The second portion is complementary to the sequence of a portion of the nucleic acid.

In another embodiment, kits may comprise one or two containers holding two types of particles. The first type of particles having oligonucleotides attached thereto which have a sequence complementary to the sequence of a first portion of a nucleic acid. The oligonucleotides are labeled with an energy donor on the ends not attached to the particles. The second type of particles having oligonucleotides attached thereto which have a sequence complementary to the sequence of a second portion of a nucleic acid. The oligonucleotides are labeled with an energy acceptor on the ends not attached to the particles. The energy donors and acceptors may be fluorescent molecules In a further embodiment, the kit comprises a first container holding a type of latex microspheres having oligonucleotides attached thereto. The oligonucleotides have a sequence complementary to a first portion of the sequence of a nucleic acid and are labeled with a fluorescent molecule. The kit also comprises a second container holding a type of gold nanoparticles having oligonucleotides attached thereto. These oligonucleotides have a sequence complementary to a second portion of the sequence of the nucleic acid.

In another embodiment, the kit comprises a first container holding a first type of metallic or semiconductor nanoparticles having oligonucleotides attached thereto. The oligonucleotides have a sequence complementary to a first portion of the sequence of a nucleic acid and are labeled with a fluorescent molecule. The kit also comprises a second container holding a second type of metallic or semiconductor nanoparticles having oligonucleotides attached thereto. These oligonucleotides have a sequence complementary to a second portion of the sequence of a nucleic acid and are labeled with a fluorescent molecule.

In a further embodiment, the kit comprises a container holding a satellite probe. The satellite probe comprises a particle having attached thereto oligonucleotides. The oligonucleotides have a first portion and a second portion, both portions having sequences complementary to portions of the sequence of a nucleic acid. The satellite probe also comprises probe oligonucleotides hybridized to the oligonucleotides attached to the nanoparticles. The probe oligonucleotides have a first portion and a second portion. The first portion has a sequence complementary to the sequence of the first portion of the oligonucleotides attached to the particles, and both portions have sequences complementary to portions of the sequence of the nucleic acid. The probe oligonucleotides also have a reporter molecule attached to one end.

In another embodiment, the kit may comprise a container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a sequence complementary to a portion of the sequence of a nucleic acid.

In an additional embodiment, the kit may comprise a container holding an aggregate probe. The aggregate probe comprises at least two types of nanoparticles having oligonucleotides attached to them. The nanoparticles of the aggregate probe are bound to each other as a result of the hybridization of some of the oligonucleotides attached to each of them. At least one of the types of nanoparticles of the aggregate probe has oligonucleotides attached to it which have a hydrophobic group attached to the end not attached to the nanoparticles.

In yet another embodiment, the invention provides a kit comprising a substrate having located thereon at least one pair of electrodes with oligonucleotides attached to the substrate between the electrodes. In a preferred embodiment, the substrate has a plurality of pairs of electrodes attached to it in an array to allow for the detection of multiple portions of a single nucleic acid, the detection of multiple different nucleic acids, or both.

The kits may also contain other reagents and items useful for detecting nucleic acid. The reagents may include PCR reagents, reagents for silver staining, hybridization reagents, buffers, etc. Other items which may be provided as part of the kit include a solid surface (for visualizing hybridization) such as a TLC silica plate, microporous materials, syringes, pipettes, cuvettes, containers, and a thermocycler (for controlling hybridization and de-hybridization temperatures). Reagents for functionalizing the nucleotides or nanoparticles may also be included in the kit.

The precipitation of aggregated nanoparticles provides a means of separating a selected nucleic acid from other nucleic acids. This separation may be used as a step in the purification of the nucleic acid. Hybridization conditions are those described above for detecting a nucleic acid. If the temperature is below the Tm (the temperature at which one-half of an oligonucleotide is bound to its complementary strand) for the binding of the oligonucleotides on the nanoparticles to the nucleic acid, then sufficient time is needed for the aggregate to settle. The temperature of hybridization (e.g., as measured by Tm) varies with the type of salt (NaCl or $MgCl_2$) and its concentration. Salt compositions and concentrations are selected to promote hybridization of the oligonucleotides on the nanoparticles to the nucleic acid at convenient working temperatures without inducing aggregation of the colloids in the absence of the nucleic acid.

The invention also provides a method of nanofabrication. The method comprises providing at least one type of linking oligonucleotide having a selected sequence. A linking oligonucleotide used for nanofabrication may have any desired sequence and may be single-stranded or double-stranded. It may also contain chemical modifications in the base, sugar, or backbone sections. The sequences chosen for the linking oligonucleotides and their lengths and strandedness will contribute to the rigidity or flexibility of the resulting nanomaterial or nanostructure, or a portion of the nanomaterial or nanostructure. The use of a single type of linking oligonucleotide, as well as mixtures of two or more different types of linking oligonucleotides, is contemplated. The number of different linking oligonucleotides used and their lengths will contribute to the shapes, pore sizes and other structural features of the resulting nanomaterials and nanostructures.

The sequence of a linking oligonucleotide will have at least a first portion and a second portion for binding to oligonucleotides on nanoparticles. The first, second or more binding portions of the linking oligonucleotide may have the same or different sequences.

If all of the binding portions of a linking oligonucleotide have the same sequence, only a single type of nanoparticle with oligonucleotides having a complementary sequence attached thereto need be used to form a nanomaterial or nanostructure. If the two or more binding portions of a linking oligonucleotide have different sequences, then two or more nanoparticle-oligonucleotide conjugates must be used. See, e.g., FIG. 17. The oligonucleotides on each of the nanoparticles will have a sequence complementary to one of the two or more binding portions of the sequence of the linking oligonucleotide. The number, sequence(s) and length (s) of the binding portions and the distance(s), if any, between them will contribute to the structural and physical properties of the resulting nanomaterials and nanostructures. Of course, if the linking oligonucleotide comprises two or more portions, the sequences of the binding portions must be chosen so that they are not complementary to each other to avoid having one portion of the linking nucleotide bind to another portion.

The linking oligonucleotides and nanoparticle-oligonucleotide conjugates are contacted under conditions effective for hybridization of the oligonucleotides attached to the nanoparticles with the linking oligonucleotides so that a desired nanomaterial or nanostructure is formed wherein the nanoparticles are held together by oligonucleotide connectors. These hybridization conditions are well known in the art and can be optimized for a particular nanofabrication scheme (see above). Stringent hybridization conditions are preferred.

The invention also provides another method of nanofabrication. This method comprises providing at least two types of nanoparticle-oligonucleotide conjugates. The oligonucleotides on the first type of nanoparticles have a sequence complementary to that of the oligonucleotides on the second type of nanoparticles. The oligonucleotides on the second type of nanoparticles have a sequence complementary to that of the oligonucleotides on the first type of nanoparticles. The nanoparticle-oligonucleotide conjugates are contacted under conditions effective to allow hybridization of the oligonucleotides on the nanoparticles to each other so that a desired nanomaterial or nanostructure is formed wherein the nanoparticles are held together by oligonucleotide connectors. Again, these hybridization conditions are well-known in the art and can be optimized for a particular nanofabrication scheme.

In both nanofabrication methods of the invention, the use of nanoparticles having one or more different types of oligonucleotides attached thereto is contemplated. The number of different oligonucleotides attached to a nanoparticle and the lengths and sequences of the one or more oligonucleotides will contribute to the rigidity and structural features of the resulting nanomaterials and nanostructures.

Also, the size, shape and chemical composition of the nanoparticles will contribute to the properties of the resulting nanomaterials and nanostructures. These properties include optical properties, optoelectronic properties, electrochemical properties, electronic properties, stability in various solutions, pore and channel size variation, ability to separate bioactive molecules while acting as a filter, etc. The use of mixtures of nanoparticles having different sizes, shapes and/or chemical compositions, as well as the use of nanoparticles having uniform sizes, shapes and chemical composition, are contemplated.

In either fabrication method, the nanoparticles in the resulting nanomaterial or nanostructure are held together by oligonucleotide connectors. The sequences, lengths, and strandedness of the oligonucleotide connectors, and the number of different oligonucleotide connectors present will contribute to the rigidity and structural properties of the nanomaterial or nanostructure. If an oligonucleotide connector is partially double-stranded, its rigidity can be increased by the use of a filler oligonucleotide as described above in connection with the method of detecting nucleic acid. The rigidity of a completely double-stranded oligonucleotide connector can be increased by the use of one or more reinforcing oligonucleotides having complementary sequences so that they bind to the double-stranded oligonucleotide connector to form triple-stranded oligonucleotide connectors. The use of quadruple-stranded oligonucleotide connectors based on deoxyguanosine or deoxycytidine quartets is also contemplated.

Several of a variety of systems for organizing nanoparticles based on oligonucleotide hybridization are illustrated in the figures. In a simple system (FIG. 1) one set of nanoparticles bears oligonucleotides with a defined sequence and another set of nanoparticles bears oligonucleotides with a complementary sequence. On mixing the two sets of nanoparticle-oligonucleotide conjugates under hybridization conditions, the two types of particles are linked by double stranded oligonucleotide connectors which serve as spacers to position the nanoparticles at selected distances.

An attractive system for spacing nanoparticles involves the addition of one free linking oligonucleotide as illustrated in FIG. 2. The sequence of the linking oligonucleotide will have at least a first portion and a second portion for binding to oligonucleotides on nanoparticles. This system is basically the same as utilized in the nucleic acid detection method, except that the length of the added linking oligonucleotide can be selected to be equal to the combined lengths of oligonucleotides attached to the nanoparticles. The related system illustrated in FIG. 3 provides a convenient means to tailor the distance between nanoparticles without having to change the sets of nanoparticle-oligonucleotide conjugates employed.

A further elaboration of the scheme for creating defined spaces between nanoparticles is illustrated in FIG. 4. In this case a double stranded segment of DNA or RNA containing overhanging ends is employed as the linking oligonucleotide. Hybridization of the single-stranded, overhanging segments of the linking oligonucleotide with the oligonucleotides attached to the nanoparticles affords multiple double-stranded oligonucleotide cross-links between the nanoparticles.

Figure 10:
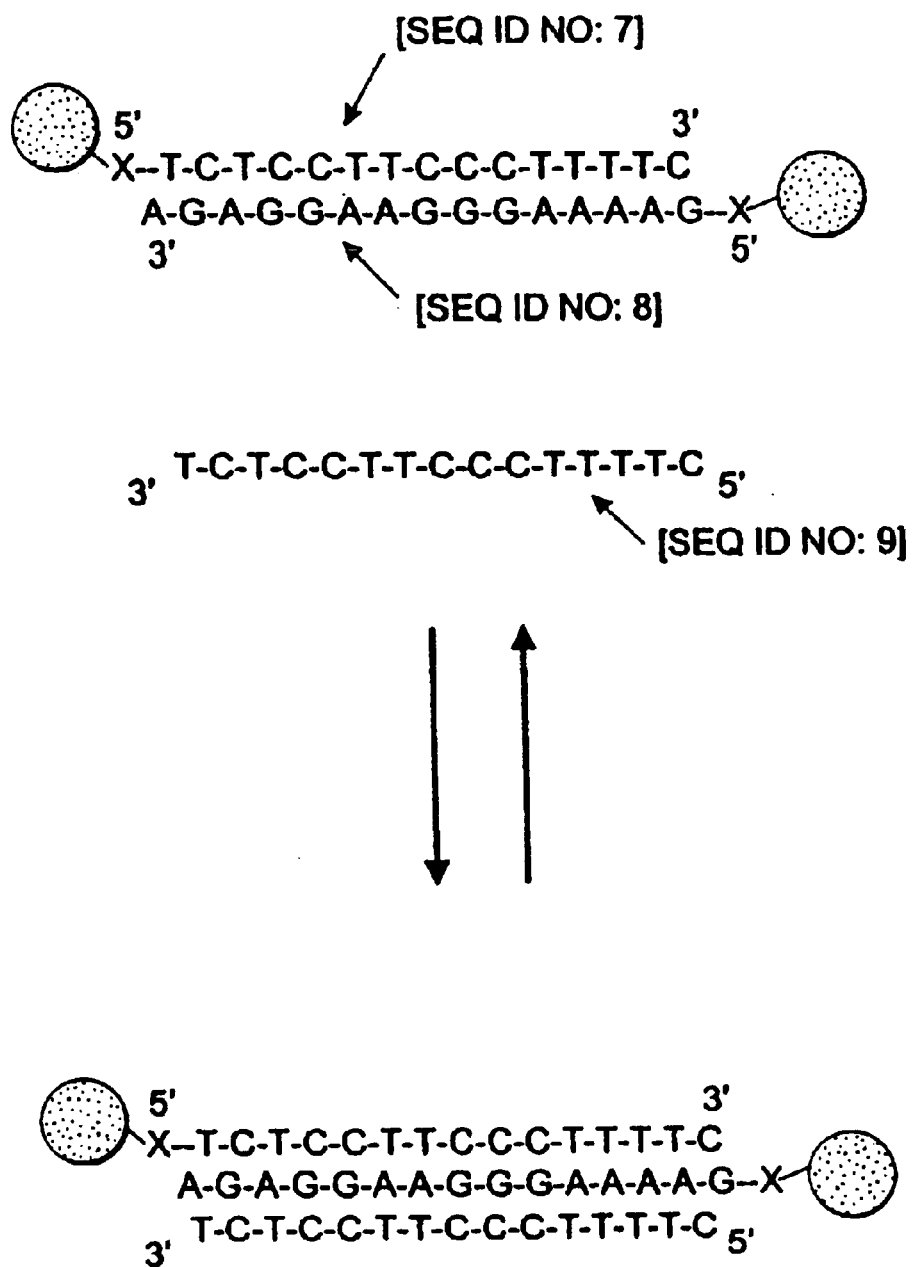
FIG. 10: Schematic diagram illustrating the formation of thermally-stable triple-stranded oligonucleotide connectors between nanoparticles having the pyrimidine:purine:pyrimidine motif. Such triple-stranded connectors are stiffer than double-stranded connectors.

Stiffer nanomaterials and nanostructures, or portions thereof, can be generated by employing triple-stranded oligonucleotide connectors between nanoparticles. In forming the triple strand, one may exploit either the pyrimidine:purine:pyrimidine motif (Moser, H. E. and Dervan, P. B. *Science*, 238, 645–650 (1987) or the purine:purine:pyrimidine motif(Pilch, D. S. et al. *Biochemistry*, 30, 6081–6087 (1991). An example of the organization of nanoparticles by generating triple-stranded connectors by the pyrimidine:purine:pyrimidine motif are illustrated in FIG. 10. In the system shown in FIG. 10, one set of nanoparticles is conjugated with a defined strand containing pyrimidine nucleotides and the other set is conjugated with a complementary oligonucleotide containing purine nucleotides. Attachment of the oligonucleotides is designed such that the nanoparticles are separated by the double-stranded oligonucleotide formed on hybridization. Then, a free pyrimidine oligonucleotide with an orientation opposite that for the pyrimidine strand linked to the nanoparticle is added to the system prior to, simultaneously with, or just subsequent to mixing the nanoparticles. Since the third strand in this system is held by Hoogsteen base pairing, the triple strand is relatively unstable thermally. Covalent bridges spanning the breadth of the duplex are known to stabilize triple-stranded complexes (Salunke, M., Wu, T., Letsinger, R. L., *J. Am, Chem. Soc.* 114, 8768–8772, (1992). Letsinger, R. L. and Wu, T. *J. Am Chem. Soc.*, 117, 7323–7328 (1995). Prakash, G. and Kool, *J. Am. Chem. Soc.*, 114, 3523–3527 (1992).

For construction of nanomaterials and nanostructures, it may be desirable in some cases to "lock" the assembly in place by covalent cross-links after formation of the nanomaterial or nanostructure by hybridization of the oligonucleotide components. This can be accomplished by incorporating functional groups that undergo a triggered irreversible reaction into the oligonucleotides. An example of a functional group for this purpose is a stilbenedicarboxamide group. It has been demonstrated that two stilbenedicarboxamide groups aligned within hybridized oligonucleotides readily undergo cross-linking on irradiation with ultraviolet light (340 nm) (Lewis, F. D. et al. (1995) *J. Am. Chem. Soc.* 117, 8785–8792).

Alternatively, one could employ the displacement of a 5'-O-tosyl group from an oligonucleotide, held at the 3'-position to a nanoparticle by a mercaptoalkly group, with a thiophosphoryl group at the 3'-end of an oligonucleotide held to an nanoparticle by a mercaptoalkyl group. In the presence of an oligonucleotide that hybridizes to both oligonucleotides and, thereby, brings the thiophosphoryl group into proximity of the tosyl group, the tosyl group will be displaced by the thiophosphoryl group, generating an oligonucleotide linked at the ends to two different nanoparticles. For displacement reactions of this type, see Herrlein et al.,*J. Am. Chem. Soc.*, 177, 10151–10152 (1995). The fact that thiophosphoryl oligonucleotides do not react with gold nanoparticles under the conditions employed in attaching mercaptoalkyl-oligonucleotides to gold nanoparticles enables one to prepare gold nanoparticle-oligonucleotide conjugates anchored through the mercapto group to the nanoparticles and containing a terminal thiophosphoryl group free for the coupling reaction.

A related coupling reaction to lock the assembled nanoparticle system in place utilizes displacement of bromide from a terminal bromoacetylaminonucleoside by a terminal thiophosphoryl-oligonucleotide as described in Gryaznov and Letsinger, J. Am. Chem. Soc., 115, 3808. This reaction proceeds much like the displacement of tosylate described above, except that the reaction is faster. Nanoparticles bearing oligonucleotides terminated with thiophosphoryl groups are prepared as described above. For preparation of nanoparticles bearing oligonucleotides terminated with bromoacetylamino groups, one first prepares an oligonucleotide terminated at one end by an aminonucleoside (e.g., either 5'-amino-5'-deoxythymidine or 3'-amino-3'-deoxythymidine) and at the other end by a mercaptoalkyl group. Molecules of this oligonucleotide are then anchored to the nanoparticles through the mercapto groups, and the nanoparticle-oligonucleotide conjugate is then converted the N-bromoacetylamino derivative by reaction with a bromoacetyl acylating agent.

A fourth coupling scheme to lock the assemblies in place utilizes oxidation of nanoparticles bearing oligonucleotides terminated by thiophosphoryl groups. Mild oxidizing agents, such as potassium triiodide, potassium ferricyanide (see Gryaznov and Letsinger, Nucleic Acids Research, 21, 1403) or oxygen, are preferred.

In addition, the properties of the nanomaterials and nanostructures can be altered by incorporating into the interconnecting oligonucleotide chains organic and inorganic functions that are held in place by covalent attachment to the oligonucleotide chains. A wide variety of backbone, base and sugar modifications are well known (see for example Uhlmann, E., and Peyman, A. Chemical Reviews, 90, 544–584 (1990). Also, the oligonucleotide chains could be replaced by "Peptide Nucleic Acid" chains (PNA), in which the nucleotide bases are held by a polypeptide backbone (see Wittung, P. et al., Nature, 368, 561–563 (1994).

As can be seen from the foregoing, the nanofabrication method of the invention is extremely versatile. By varying the length, sequence and strandedness of the linking oligonucleotides, the number, length, and sequence of the binding portions of the linking oligonucleotides, the length, sequence and number of the oligonucleotides attached to the nanoparticles, the size, shape and chemical composition of the nanoparticles, the number and types of different linking oligonucleotides and nanoparticles used, and the strandedness of the oligonucleotide connectors, nanomaterials and nanostructures having a wide range of structures and properties can be prepared. These structures and properties can be varied further by cross-linking of the oligonucleotide connectors, by functionalizing the oligonucleotides, by backbone, base or sugar modifications of the oligonucleotides, or by the use of peptide-nucleic acids.

The nanomaterials and nanostructures that can be made by the nanofabrication method of the invention include nanoscale mechanical devices, separation membranes, biofilters, and biochips. It is contemplated that the nanomaterials and nanostructures of the invention can be used as chemical sensors, in computers, for drug delivery, for protein engineering, and as templates for biosynthesis/nanostructure fabrication/directed assembly of other structures. See generally Seeman et al., New J. Chem., 17, 739 (1993) for other possible applications. The nanomaterials and nanostructures that can be made by the nanofabrication method of the invention also can include electronic devices. Whether nucleic acids could transport electrons has been the subject of substantial controversy. As shown in Example 21 below, nanoparticles assembled by DNA conduct electricity (the DNA connectors function as semiconductors).

Finally, the invention provides methods of making unique nanoparticle-oligonucleotide conjugates. In the first such method, oligonucleotides are bound to charged nanoparticles to produce stable nanoparticle-oligonucleotide conjugates. Charged nanoparticles include nanoparticles made of metal, such as gold nanoparticles.

The method comprises providing oligonucleotides having covalently bound thereto a moiety comprising a functional group which can bind to the nanoparticles. The moieties and functional groups are those described above for binding (i.e., by chemisorption or covalent bonding) oligonucleotides to nanoparticles. For instance, oligonucleotides having an alkanethiol or an alkanedisulfide covalently bound to their 5' or 3' ends can be used to bind the oligonucleotides to a variety of nanoparticles, including gold nanoparticles.

The oligonucleotides are contacted with the nanoparticles in water for a time sufficient to allow at least some of the oligonucleotides to bind to the nanoparticles by means of the functional groups. Such times can be determined empirically. For instance, it has been found that a time of about 12–24 hours gives good results. Other suitable conditions for binding of the oligonucleotides can also be determined empirically. For instance, a concentration of about 10–20 nM nanoparticles and incubation at room temperature gives good results.

Next, at least one salt is added to the water to form a salt solution. The salt can be any water-soluble salt. For instance, the salt may be sodium chloride, magnesium chloride, potassium chloride, ammonium chloride, sodium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of is time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time has been found to give the highest surface density of oligonucleotides on the nanoparticles. Suitable ionic strengths can be determined empirically for each salt or combination of salts. A final concentration of sodium chloride of from about 0.1 M to about 1.0 M in phosphate buffer, preferably with the concentration of sodium chloride being increased gradually over time, has been found to give good results.

After adding the salt, the oligonucleotides and nanoparticles are incubated in the salt solution for an additional period of time sufficient to allow sufficient additional oligonucleotides to bind to the nanoparticles to produce the stable nanoparticle-oligonucleotide conjugates. As will be described in detail below, an increased surface density of the oligonucleotides on the nanoparticles has been found to stabilize the conjugates. The time of this incubation can be determined empirically. A total incubation time of about 24–48, preferably 40 hours, has been found to give good results (this is the total time of incubation; as noted above, the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results.

The conjugates produced by use of the "aging" step have been found to be considerably more stable than those produced without the "aging" step. As noted above, this increased stability is due to the increased density of the oligonucleotides on the surfaces of the nanoparticles which is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. Preferably, the surface density is at least 15 picomoles/cm$^2$. Since the ability of the oligonucleotides of the conjugates to hybridize with nucleic acid and oligonucleotide targets can be diminished if the surface density is too great, the surface density is preferably no greater than about 35–40 picomoles/cm$^2$.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

Aside from their stability, the nanoparticle-oligonucleotide conjugates made by this method exhibit other remarkable properties. See, e.g., Examples 5, 7, and 19 of the present application. In particular, due to the high surface density of the conjugates, they will assemble into large aggregates in the presence of a target nucleic acid or oligonucleotide. The temperature over which the aggregates form and dissociate has unexpectedly been found to be quite narrow, and this unique feature has important practical consequences. In particular, it increases the selectivity and sensitivity of the methods of detection of the present invention. A single base mismatch and as little as 20 femtomoles of target can be detected using the conjugates. Although these features were originally discovered in assays performed in solution, the advantages of the use of these conjugates have been found to extend to assays performed on substrates, including those in which only a single type of conjugate is used.

It has been found that the hybridization efficiency of nanoparticle-oligonucleotide conjugates can be increased dramatically by the use of recognition oligonucleotides which comprise a recognition portion and a spacer portion. "Recognition oligonucleotides" are oligonucleotides which comprise a sequence complementary to at least a portion of the sequence of a nucleic acid or oligonucleotide target. In this embodiment, the recognition oligonucleotides comprise a recognition portion and a spacer portion, and it is the recognition portion which hybridizes to the nucleic acid or oligonucleotide target. The spacer portion of the recognition oligonucleotide is designed so that it can bind to the nanoparticles. For instance, the spacer portion could have a moiety covalently bound to it, the moiety comprising a functional group which can bind to the nanoparticles. These are the same moieties and functional groups as described above. As a result of the binding of the spacer portion of the recognition oligonucleotide to the nanoparticles, the recognition portion is spaced away from the surface of the nanoparticles and is more accessible for hybridization with its target. The length and sequence of the spacer portion providing good spacing of the recognition portion away from the nanoparticles can be determined empirically. It has been found that a spacer portion comprising at least about 10 nucleotides, preferably 10–30 nucleotides, gives good results. The spacer portion may have any sequence which does not interfere with the ability of the recognition oligonucleotides to become bound to the nanoparticles or to a nucleic acid or oligonucleotide target. For instance, the spacer portions should not sequences complementary to each other, to that of the recognition olignucleotides, or to that of the nucleic acid or oligonucleotide target of the recognition oligonucleotides. Preferably, the bases of the nucleotides of the spacer portion are all adenines, all thymines, all cytidines, or all guanines, unless this would cause one of the problems just mentioned. More preferably, the bases are all adenines or all thymines. Most preferably the bases are all thymines.

It has further been found that the use of diluent oligonucleotides in addition to recognition oligonucleotides provides a means of tailoring the conjugates to give a desired level of hybridization. The diluent and recognition oligonucleotides have been found to attach to the nanoparticles in about the same proportion as their ratio in the solution contacted with the nanoparticles to prepare the conjugates. Thus, the ratio of the diluent to recognition oligonucleotides bound to the nanoparticles can be controlled so that the conjugates will participate in a desired number of hybridization events. The diluent oligonucleotides may have any sequence which does not interfere with the ability of the recognition oligonucleotides to be bound to the nanoparticles or to bind to a nucleic acid or oligonucleotide target. For instance, the diluent oligonulceotides should not have a sequence complementary to that of the recognition oligonucleotides or to that of the nucleic acid or oligonucleotide target of the recognition oligonucleotides. The diluent oligonucleotides are also preferably of a length shorter than that of the recognition oligonucleotides so that the recognition oligonucleotides can bind to their nucleic acid or oligonucleotide targets. If the recognition oligonucleotides comprise spacer portions, the diluent oligonulceotides are, most preferably, about the same length as the spacer portions. In this manner, the diluent oligonucleotides do not interfere with the ability of the recognition portions of the recognition oligonucleotides to hybridize with nucleic acid or oligonucleotide targets. Even more preferably, the diluent oligonucleotides have the same sequence as the sequence of the spacer portions of the recognition oligonucleotides.

As can be readily appreciated, highly desirable nanoparticle-oligonucleotide conjugates can be prepared by employing all of the methods described above. By doing so, stable conjugates with tailored hybridization abilities can be produced.

Any of the above conjugates can be, and are preferably, used in any of the methods of detecting nucleic acids described above, and the invention also provides a kit comprising a container holding any of the above conjugates.

In addition, the conjugates can be, and are preferably, used in any of the methods of nanofabrication of the invention and the method of separating nucleic acids.

It is to be noted that the term "a" or "an" entity refers to one or more of that entity. For example, "a characteristic" refers to one or more characteristics or at least one characteristic. As such, the terms "a" (or "an"), "one or more" and "at least one" are used interchangeably herein. It is also to be noted that the terms "comprising", "including", and "having" have been used interchangeably.

EXAMPLES

Example 1

Preparation of Oligonucleotide-Modified Gold Nanoparticles

A. Preparation of Gold Nanoparticles

Gold colloids (13 nm diameter) were prepared by reduction of $HAuCl_4$ with citrate as described in Frens, Nature Phys. Sci., 241, 20 (1973) and Grabar, Anal. Chem., 67, 735 (1995). Briefly, all glassware was cleaned in aqua regia (3 parts HCl, 1 part $HNO_3$), rinsed with Nanopure $H_2O$, then oven dried prior to use. $HAuCl_4$ and sodium citrate were purchased from Aldrich Chemical Company. Aqueous $HAuCl_4$ (1 mM, 500 mL) was brought to reflux while stirring. Then, 38.8 mM sodium citrate (50 mL) was added quickly. The solution color changed from pale yellow to burgundy, and refluxing was continued for 15 min. After cooling to room temperature, the red solution was filtered through a Micron Separations Inc. 1 micron filter. Au colloids were characterized by UV-vis spectroscopy using a Hewlett Packard 8452A diode array spectrophotometer and by Transmission Electron Microscopy (TEM) using a Hitachi 8100 transmission electron microscope. Gold particles with diameters of 13 nm will produce a visible color change when aggregated with target and probe oligonucleotide sequences in the 10–35 nucleotide range.

B. Synthesis of Oligonucleotides

Oligonucleotides were synthesized on a 1 micromole scale using a Milligene Expedite DNA synthesizer in single column mode using phosphoramidite chemistry. Eckstein, F. (ed.) *Oligonucleotides and Analogues: A Practical Approach* (IRL Press, Oxford, 1991). All solutions were purchased from Milligene (DNA synthesis grade). Average coupling efficiency varied from 98 to 99.8%, and the final dimethoxytrityl (DMT) protecting group was not cleaved from the oligonucleotides to aid in purification.

For 3'-thiol-oligonucleotides, Thiol-Modifier C3 S—S CPG support was purchased from Glen Research and used in the automated synthesizer. During normal cleavage from the solid support (16 hr at 55° C.), 0.05 M dithiothreitol (DTT) was added to the $NH_4OH$ solution to reduce the 3' disulfide to the thiol. Before purification by reverse phase high pressure liquid chromatography (HPLC), excess DTT was removed by extraction with ethyl acetate.

For 5'-thiol oligonucleotides, 5'-Thiol-Modifier $C_6$-phosphoramidite reagent was purchased from Glen Research, 44901 Falcon Place, Sterling, Va. 20166. The oligonucleotides were synthesized, and the final DMT protecting group removed. Then, 1 ml of dry acetonitrile was added to 100 µmole of the 5' Thiol Modifier $C_6$-phosphoramidite. 200 µL of the amidite solution and 200 µL of activator (fresh from synthesizer) were mixed and introduced onto the column containing the synthesized oligonucleotides still on the solid support by syringe and pumped back and forth through the column for 10 minutes. The support was then washed (2×1 mL) with dry acetonitrile for 30 seconds. 700 µL of a 0.016 $MI_2/H_2O$/pyridine mixture (oxidizer solution) was introduced into the column, and was then pumped back and forth through the column with two syringes for 30 second. The support was then washed with a 1:1 mixture of $CH_3CN$/pyridine (2×1 mL) for 1 minute, followed by a final wash with dry acetonitrile (2×1 mL) with subsequent drying of the column with a stream of nitrogen. The trityl protecting group was not removed, which aids in purification.

Reverse phase HPLC was performed with a Dionex DX500 system equipped with a Hewlett Packard ODS hypersil column (4.6×200 mm, 5 mm particle size) using 0.03 M $Et_3NH^+$ $OAc^-$ buffer (TEAA), pH 7, with a 1%/min. gradient of 95% $CH_3CN$/5% TEAA. The flow rate was 1 mL/min. with UV detection at 260 nm. Preparative HPLC was used to purify the DMT-protected unmodified oligonucleotides (elution at 27 min). After collection and evaporation of the buffer, the DMT was cleaved from the oligonucleotides by treatment with 80% acetic acid for 30 min at room temperature. The solution was then evaporated to near dryness, water was added, and the cleaved DMT was extracted from the aqueous oligonucleotide solution using ethyl acetate. The amount of oligonucleotide was determined by absorbance at 260 nm, and final purity assessed by reverse phase HPLC (elution time 14.5 minutes).

The same protocol was used for purification of the 3'-thiol-oligonucleotides, except that DTT was added after extraction of DMT to reduce the amount of disulfide formed. After six hours at 40° C., the DTT was extracted using ethyl acetate, and the oligonucleotides repurified by HPLC (elution time 15 minutes).

For purification of the 5' thiol modified oligonucleotides, preparatory HPLC was performed under the same conditions as for unmodified oligonucleotides. After purification, the trityl protecting group was removed by adding 150 µL of a 50 mM $AgNO_3$ solution to the dry oligonucleotide sample. The sample turned a milky white color as the cleavage occurred. After 20 minutes, 200 µL of a 10 mg/ml solution of DTT was added to complex the Ag (five minute reaction time), and the sample was centrifuged to precipitate the yellow complex. The oligonucleotide solution (<50 OD) was then transferred onto a desalting NAP-5 column (Pharmacia Biotech, Uppsala, Sweden) for purification (contains DNA Grade Sephadex G-25 Medium for desalting and buffer exchange of oligonucleotides greater than 10 bases). The amount of 5' thiol modified oligonucleotide was determined by UV-vis spectroscopy by measuring the magnitude of the absorbance at 260 nm. The final purity was assessed by performing ion-exchange HPLC with a Dionex Nucleopac PA-100 (4×250) column using a 10 mM NaOH solution (pH 12) with a 2%/min gradient of 10 mM NaOH, 1M NaCl solution. Typically, two peaks resulted with elution times of approximately 19 minutes and 25 minutes (elution times are dependent on the length of the oligonucleotide strand). These peaks corresponded to the thiol and the disulfide oligonucleotides respectively.

C. Attachment of Olizonucleotides to Gold Nanoparticles

An aqueous solution of 17 nM (150 µL) Au colloids, prepared as described in part A above, was mixed with 3.75 µM (46 µL) 3'-thiol-TTTGCTGA, prepared as described in part B and allowed to stand for 24 hours at room temperature in 1 ml Eppendorf capped vials. A second solution of colloids was reacted with 3.75 μM (46 μL) 3'-thiol-TACCGTTG. Note that these oligonucleotides are non-complementary. Shortly before use, equal amounts of each of the two nanoparticle solutions were combined. Since the oligonucleotides are noncomplementary, no reaction took place.

The oligonucleotide-modified nanoparticles are stable at elevated temperatures (80° C.) and high salt concentrations (1M NaCl) for days and have not been observed to undergo particle growth. Stability in high salt concentrations is important, since such conditions are required for the hybridization reactions that form the basis of the methods of detection and nanofabrication of the invention.

Example 2

Formation of Nanoparticle Aggregates

A. Preparation of Linking Oligonucleotide

Two (nonthiolated) oligonucleotides were synthesized as described in part B of Example 1. They had the following sequences:

```
3' ATATGCGCGA TCTCAGCAAA [SEQ ID NO:1]; and

3' GATCGCGCAT ATCAACGGTA [SEQ ID NO:2].
```

Mixing of these two oligonucleotides in a 1 M NaCl, 10 mM phosphate buffered (pH 7.0) solution, resulted in hybridization to form a duplex having a 12-base-pair overlap and two 8-base-pair sticky ends. Each of the sticky ends had a sequence which was complementary to that of one of the oligonucleotides attached to the Au colloids prepared in part C of Example 1.

B. Formation of Nanoparticle Aggregates

Figure 6A:
FIG. 6: Cuvettes containing two types of gold colloids, each having a different oligonucleotide attached thereto and a linking double-stranded oligonucleotide with sticky ends complementary to the oligonucleotides attached to the nanoparticles (see FIG. 4). Cuvette A—at 80° C., which is above the Tm of the linking DNA; de-hybridized (thermally denatured). The color is dark red. Cuvette B—after cooling to room temperature, which is below the Tm of the linking DNA; hybridization has taken place, and the nanoparticles have aggregated, but the aggregates have not precipitated. The color is purple. Cuvette C—after several hours at room temperature, the aggregated nanoparticles have settled to the bottom of the cuvette. The solution is clear, and the precipitate is pinkish gray. Heating B or C will result in A.
Figure 6B:
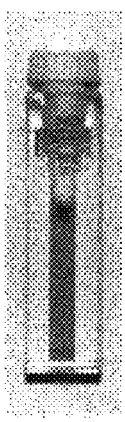
Figure 6C:

The linking oligonucleotides prepared in part A of this example (0.17 μM final concentration after dilution with NaCl) were added to the nanoparticle-oligonucleotide conjugates prepared in part C of Example 1 (5.1 nM final concentration after dilution with NaCl) at room temperature. The solution was then diluted with aqueous NaCl (to a final concentration of 1 M) and buffered at pH 7 with 10 mM phosphate, conditions which are suitable for hybridization of the oligonucleotides. An immediate color change from red to purple was observed, and a precipitation reaction ensued. See FIG. 6. Over the course of several hours, the solution became clear and a pinkish-gray precipitate settled to the bottom of the reaction vessel. See FIG. 6.

Figure 7:
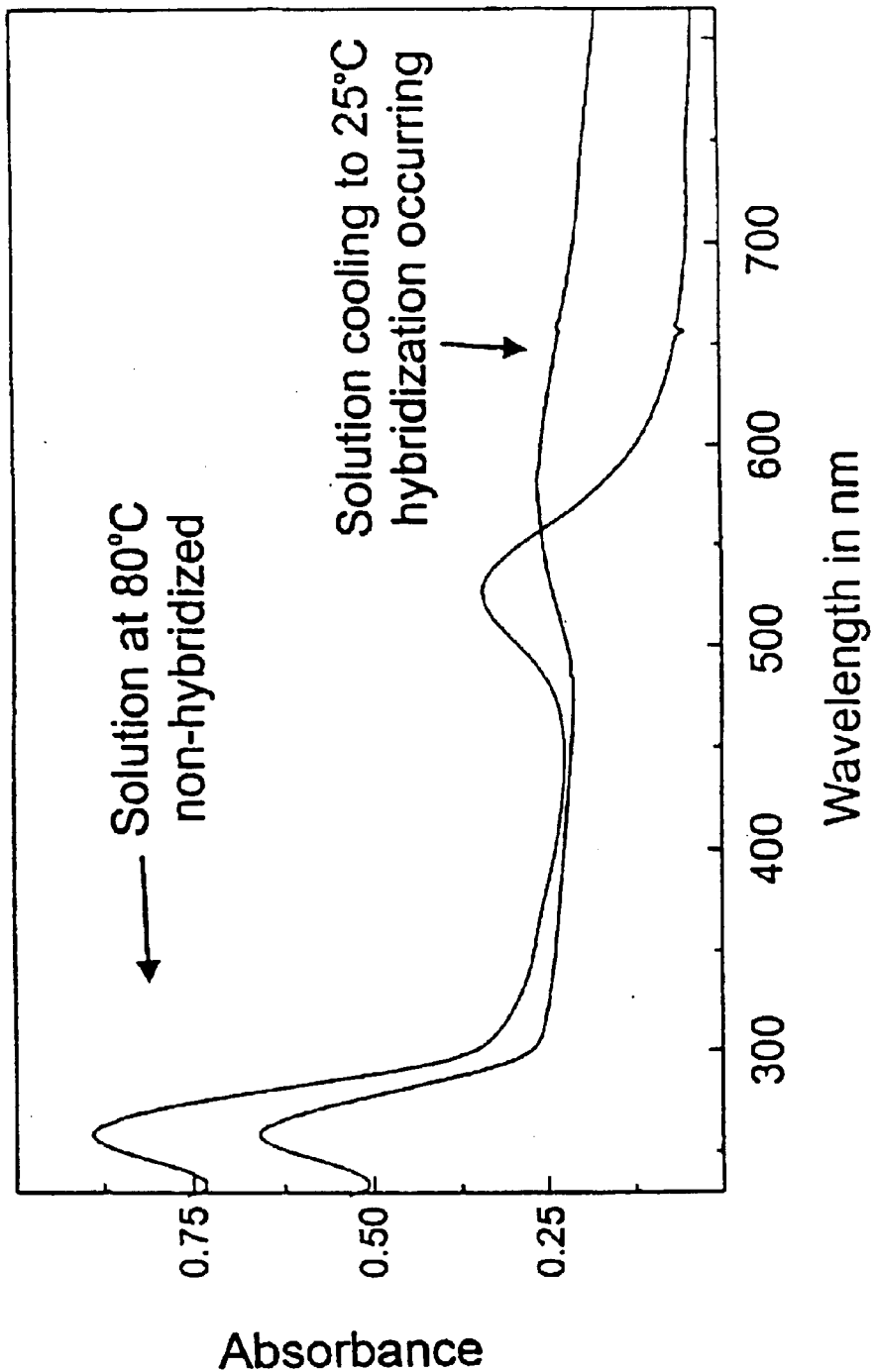
FIG. 7: A graph of absorbance versus wavelength in nm showing changes in absorbance when gold nanoparticles having oligonucleotides attached thereto aggregate due to hybridization with linking oligonucleotides upon lowering of the temperature, as illustrated in FIG. 4.

To verify that this process involved both the oligonucleotides and colloids, the precipitate was collected and resuspended (by shaking) in 1 M aqueous NaCl buffered at pH 7. Any of the oligonucleotides not hybridized to the nanoparticles are removed in this manner. Then, a temperature/time dissociation experiment was performed by monitoring the characteristic absorbance for the hybridized oligodeoxyribonucleotides (260 nm) and for the aggregated colloids which is reflective of the gold interparticle distance (700 nm). See FIG. 7.

Changes in absorbance at 260 and 700 nm were recorded on a Perkin-Elmer Lambda 2 UV-vis Spectrophotometer using a Peltier PTP-1 Temperature Controlled Cell Holder while cycling the temperature at a rate of 1° C./minute between 0° C. and 80° C. DNA solutions were approximately 1 absorbance unit(s) (OD), buffered at pH 7 using 10 mM phosphate buffer and at 1M NaCl concentration.

The results are shown in FIG. 8A. As the temperature was cycled between 0° C. and 80° C. (which is 38° C. above the dissociation temperature ($T_m$) for the duplex ($T_m$=42° C.)), there was an excellent correlation between the optical signatures for both the colloids and oligonucleotides. The UV-vis spectrum for naked Au colloids was much less temperature dependent, FIG. 8B.

There was a substantial visible optical change when the polymeric oligonucleotide-colloid precipitate was heated above its melting point. The clear solution turned dark red as the polymeric biomaterial de-hybridized to generate the unlinked colloids which are soluble in the aqueous solution. The process was reversible, as evidenced by the temperature traces in FIG. 8A.

In a control experiment, a 14-T:14-A duplex was shown to be ineffective at inducing reversible Au colloid particle aggregation. In another control experiment, a linking oligonucleotide duplex with four base pair mismatches in the sticky ends was found not to induce reversible particle aggregation of oligonucleotide-modified nanoparticles (prepared as described in part C of Example 1 and reacted as described above). In a third control experiment, non-thiolated oligonucleotides having sequences complementary to the sticky ends of the linking oligonucleotide and reacted with nanoparticles did not produce reversible aggregation when the nanoparticles were combined with the linking oligonucleotide.

Figure 9A:
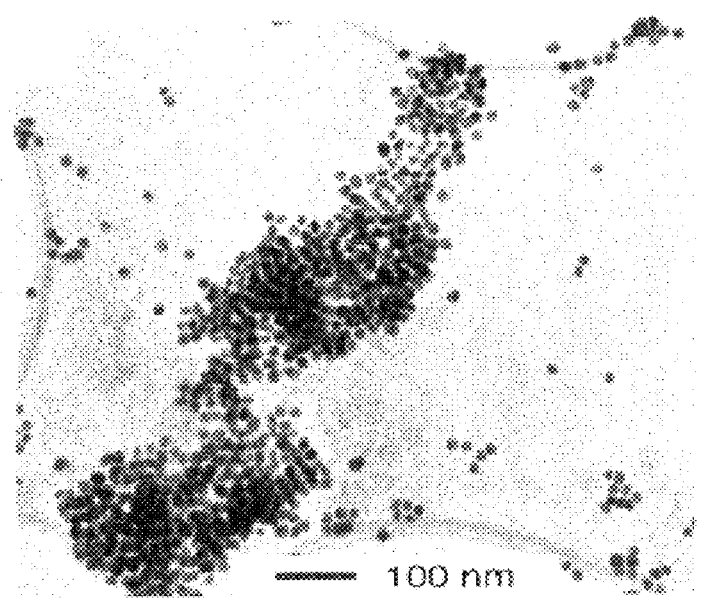
FIGS. 9A–B: Transmission Electron Microscope (TEM) images.

Further evidence of the polymerization/assembly process came from Transmission Electron Microscopy (TEM) studies of the precipitate. TEM was performed on a Hitachi 8100 Transmission Electron Microscope. A typical sample was prepared by dropping 100 μL of colloid solution onto a holey carbon grid. The grid, then, was dried under vacuum and imaged. TEM images of Au colloids linked by hybridized oligonucleotides showed large assembled networks of the Au colloids, FIG. 9A. Naked Au colloids do not aggregate under comparable conditions but rather disperse or undergo particle growth reactions. Hayat, *Colloidal Gold: Principles, Methods, and Applications* (Academic Press, San Diego, 1991). Note that there is no evidence of colloid particle growth in the experiments performed to date; the hybridized colloids seem to be remarkably regular in size with an average diameter of 13 nm.

Figure 9B:
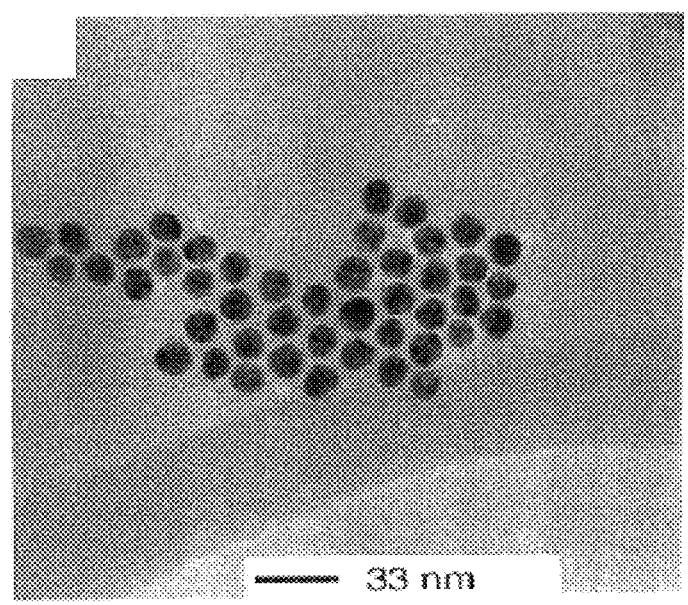

With TEM, a superposition of layers is obtained, making it difficult to assess the degree of order for three-dimensional aggregates. However, smaller scale images of single layer, two-dimensional aggregates provided more evidence for the self-assembly process, FIG. 9B. Close-packed assemblies of the aggregates with uniform particle separations of approximately 60 Å can be seen. This distance is somewhat shorter than the estimated 95 Å spacing expected for colloids connected by rigid oligonucleotide hybrids with the sequences that were used. However, because of the nicks in the duplex obtained after hybridization of the oligonucleotides on the nanoparticles to the linking oligonucleotides, these were not rigid hybrids and were quite flexible. It should be noted that this is a variable that can be controlled by reducing the system from four overlapping strands to three (thereby reducing the number of nicks) or by using triplexes instead of duplexes.

Example 3

Preparation of Oligonucleotide-Modified Gold Nanoparticles

Gold colloids (13 nm diameter) were prepared as described in Example 1. Thiol-oligonucleotides [HS(CH$_2$)

₆OP(O)(O⁻)-oligonucleotide] were also prepared as described in Example 1.

The method of attaching thiol-oligonucleotides to gold nanoparticles described in Example 1 was found not to produce satisfactory results in some cases. In particular, when long oligonucleotides were used, the oligonucleotide-colloid conjugates were not stable in the presence of a large excess of high molecular weight salmon sperm DNA used as model for the background DNA that would normally be present in a diagnostic system. Longer exposure of the colloids to the thiol-oligonucleotides produced oligonucleotide-colloid conjugates that were stable to salmon sperm DNA, but the resulting conjugates failed to hybridize satisfactorily. Further experimentation led to the following procedure for attaching thiol-oligonucleotides of any length to gold colloids so that the conjugates are stable to high molecular weight DNA and hybridize satisfactorily.

A 1 mL solution of the gold colloids (17 nM) in water was mixed with excess (3.68 μM) thiol-oligonucleotide (28 bases in length) in water, and the mixture was allowed to stand for 12–24 hours at room temperature. Then, 100 μL of a 0.1 M sodium hydrogen phosphate buffer, pH 7.0, and 100 μL of 1.0 M NaCl were premixed and added. After 10 minutes, 10 μL of 1% aqueous NaN$_3$ were added, and the mixture was allowed to stand for an additional 40 hours. This "aging" step was designed to increase the surface coverage by the thiol-oligonucleotides and to displace oligonucleotide bases from the gold surface. Somewhat cleaner, better defined red spots in subsequent assays were obtained if the solution was frozen in a dry-ice bath after the 40-hour incubation and then thawed at room temperature. Either way, the solution was next centrifuged at 14,000 rpm in an Eppendorf Centrifuge 5414 for about 15 minutes to give a very pale pink supernatant containing most of the oligonucleotide (as indicated by the absorbance at 260 nm) along with 7–10% of the colloidal gold (as indicated by the absorbance at 520 nm), and a compact, dark, gelatinous residue at the bottom of the tube. The supernatant was removed, and the residue was resuspended in about 200 μL of buffer (10 mM phosphate, 0.1 M NaCl) and recentrifuged. After removal of the supernatant solution, the residue was taken up in 1.0 mL of buffer (10 mM phosphate, 0.1 M NaCl) and 10 μL of a 1% aqueous solution of NaN$_3$. Dissolution was assisted by drawing the solution into, and expelling it from, a pipette several times. The resulting red master solution was stable (i.e., remained red and did not aggregate) on standing for months at room temperature, on spotting on silica thin-layer chromatography (TLC) plates (see Example 4), and on addition to 2 M NaCl, 10 mM MgCl$_2$, or solutions containing high concentrations of salmon sperm DNA.

Example 4

Acceleration of Hybridization of Nanoparticle-Oligonucleotide Conjugates

Figure 11:
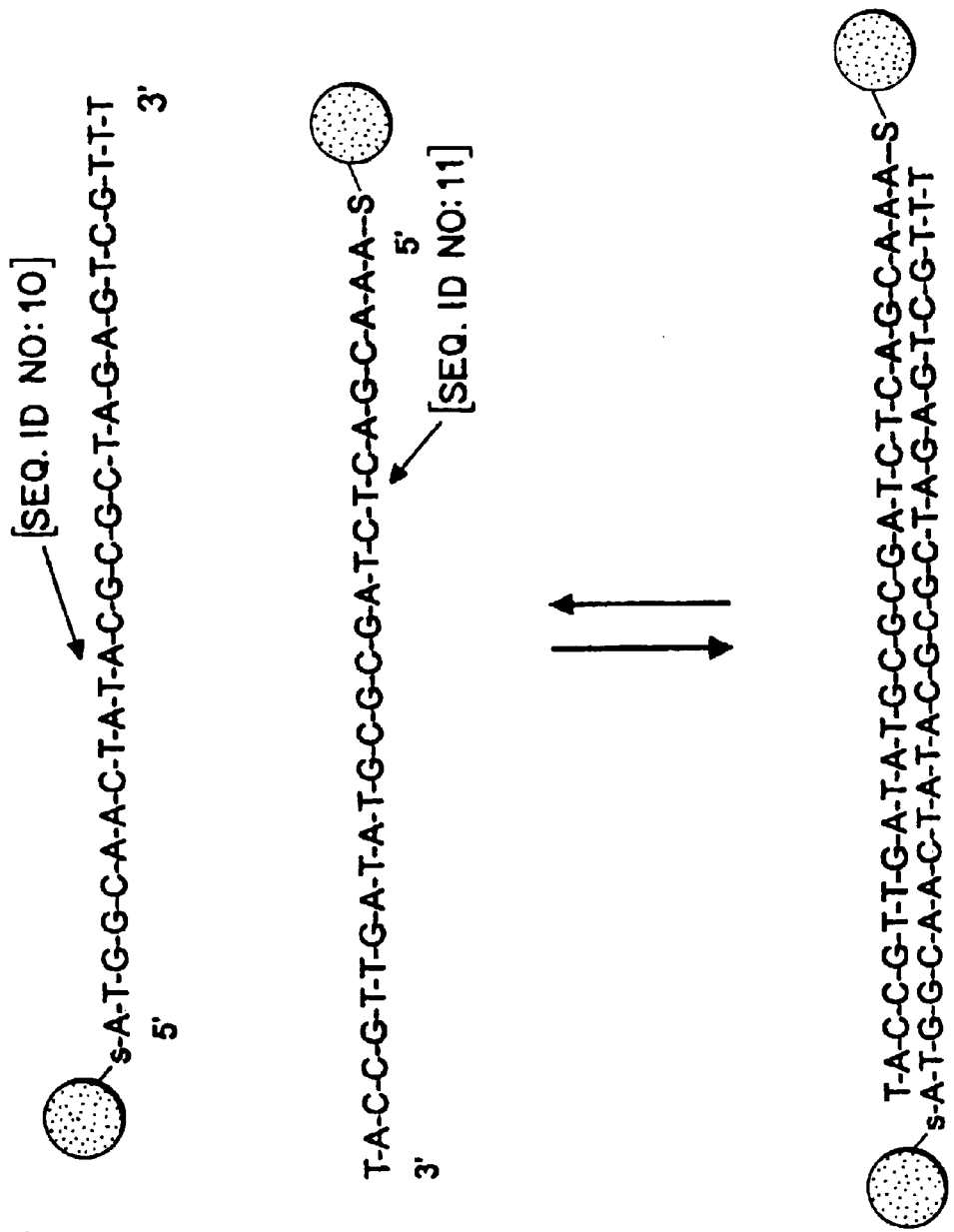
FIG. 11: Schematic diagram illustrating the formation of nanoparticle aggregates by combining nanoparticles having complementary oligonucleotides attached to them, the nanoparticles being held together in the aggregates as a result of the hybridization of the complementary oligonucleotides.

The oligonucleotide-gold colloid conjugates I and II illustrated in FIG. 11 were prepared as described in Example 3. The hybridization of these two conjugates was extremely slow. In particular, mixing samples of conjugates I and II in aqueous 0.1 M NaCl or in 10 mM MgCl$_2$ plus 0.1 M NaCl and allowing the mixture to stand at room temperature for a day produced little or no color change.

Two ways were found to improve hybridization. First, faster results were obtained by freezing the mixture of conjugates I and II (each 15 nM contained in a solution of 0.1 M NaCl) in a dry ice-isopropyl alcohol bath for 5 minutes and then thawing the mixture at room temperature. The thawed solution exhibited a bluish color. When 1 μL of the solution was spotted on a standard C-18 TLC silica plate (Alltech Associates), a strong blue color was seen immediately. The hybridization and consequent color change caused by the freeze-thawing procedure were reversible. On heating the hybridized solution to 80° C., the solution turned red and produced a pink spot on a TLC plate. Subsequent freezing and thawing returned the system to the (blue) hybridized state (both solution and spot on a C-18 TLC plate). In a similar experiment in which the solution was not refrozen, the spot obtained on the C-18 TLC plate was pink.

A second way to obtain faster results is to warm the conjugates and target. For instance, in another experiment, oligonucleotide-gold colloid conjugates and an oligonucleotide target sequence in a 0.1 M NaCl solution were warmed rapidly to 65° C. and allowed to cool to room temperature over a period of 20 minutes. On spotting on a C-18 silica plate and drying, a blue spot indicative of hybridization was obtained. In contrast, incubation of the conjugates and target at room temperature for an hour in 0.1 M NaCl solution did not produce a blue color indicative of hybridization. Hybridization is more rapid in 0.3 M NaCl.

Example 5

Assays Using Nanoparticle-Oligonucleotide Conjugates

Figure 12A:
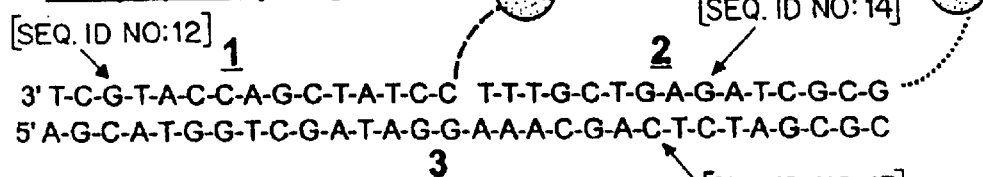
FIGS. 12A–F: Schematic diagrams illustrating systems for detecting nucleic acid using nanoparticles having oligonucleotides attached thereto. Oligonucleotide-nanoparticle conjugates 1 and 2 and single-stranded oligonucleotide targets 3, 4, 5, 6 and 7 are illustrated. The circles represent the nanoparticles, the formulas are oligonucleotide sequences, and the dotted and dashed lines represent connecting links of nucleotide.
Figure 12B:
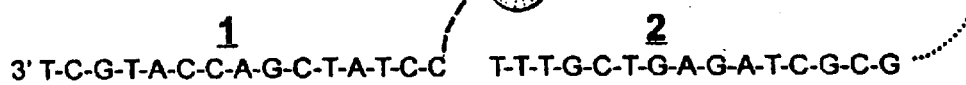
Figure 12C:
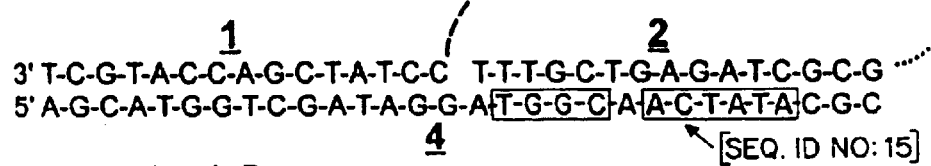
Figure 12D:
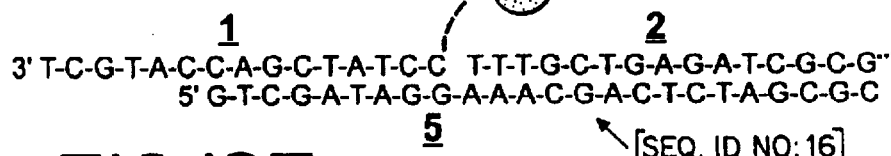
Figure 12E:
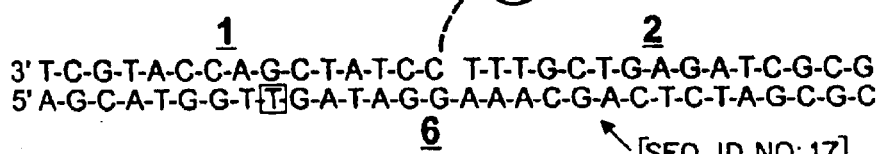
Figure 12F:
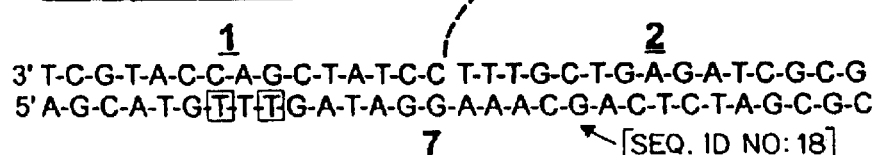

The oligonucleotide-gold colloid conjugates 1 and 2 illustrated in FIGS. 12A–F were prepared as described in Example 3, and the oligonucleotide target 3 illustrated in FIG. 12A was prepared as described in Example 2. Mismatched and deletion targets 4, 5, 6, and 7 were purchased from the Northwestern University Biotechnology Facility, Chicago, Ill. These oligonucleotides were synthesized on a 40 nmol scale and purified on an reverse phase C18 cartridge (OPC). Their purity was determined by performing ion exchange HPLC.

Selective hybridization was achieved by heating rapidly and then cooling rapidly to the stringent temperature. For example, hybridization was carried out in 100 μL of 0.1 M NaCl plus 5 mM MgCl$_2$ containing 15 nM of each oligonucleotide-colloid conjugate 1 and 2, and 3 nanomoles of target oligonucleotide 3, 4, 5, 6, or 7, heating to 74° C., cooling to the temperatures indicated in Table 1 below, and incubating the mixture at this temperature for 10 minutes. A 3 μL sample of each reaction mixture was then spotted on a C-18 TLC silica plate. On drying (5 minutes), a strong blue color appeared if hybridization had taken place.

The results are presented in Table 1 below. Pink spots signify a negative test (i.e., that the nanoparticles were not brought together by hybridization), and blue spots signify a positive test (i.e., that the nanoparticles were brought into proximity due to hybridization involving both of the oligonucleotide-colloid conjugates).

TABLE 1

| Reactants | Results (Color) | | | |
| --- | --- | --- | --- | --- |
|  | 45° C. | 50° C. | 60° C. | 74° C. |
| 1 + 2 | Pink | Pink | Pink | Pink |
| 1 + 2 + 3 (match) | Blue | Blue | Blue | Blue |
| 1 + 2 + 4 (half complement mismatch) | Pink | Pink | Pink | Pink |
| 1 + 2 + 5 (−6 bp) | Blue | Pink | Pink | Pink |

TABLE 1-continued

| Reactants | Results (Color) | | | |
|---|---|---|---|---|
| | 45° C. | 50° C. | 60° C. | 74° C. |
| 1 + 2 + 6 (1 bp mismatch) | Blue | Blue | Pink | Pink |
| 1 + 2 + 7 (2 bp mismatch) | Pink | Pink | Pink | Pink |

As can be seen in Table 1, hybridization at 60° C. gave a blue spot only for the fully-matched target 3. Hybridization at 50° C. yielded blue spots with both targets 3 and 6. Hybridization at 45° C. gave blue spots with targets 3, 5 and 6.

In a related series, a target containing a single mismatch T nucleotide was found to give a positive test at 58° C. (blue color) and a negative test (red color) at 64° C. with conjugates 1 and 2. Under the same conditions, the fully-matched target (3) gave a positive test at both temperatures, showing that the test can discriminate between a target that is fully matched and one containing a single mismatched base.

Similar results were achieved using a different hybridization method. In particular, selective hybridization was achieved by freezing, thawing and then warming rapidly to the stringent temperature. For example, hybridization was carried out in 100 μL of 0.1 M NaCl containing 15 nM of each oligonucleotide-colloid conjugate 1 and 2, and 10 picomoles of target oligonucleotide 3, 4, 5, 6, or 7, freezing in a dry ice-isopropyl alcohol bath for 5 minutes, thawing at room temperature, then warming rapidly to the temperatures indicated in Table 2 below, and incubating the mixture at this temperature for 10 minutes. A 3 μL sample of each reaction mixture was then spotted on a C-18 TLC silica plate. The results are presented in Table 2.

TABLE 2

| Reactants (probes) + target | Results (color) | | | | |
|---|---|---|---|---|---|
| | RT | 35° C. | 40° C. | 54° C. | 64° C. |
| (1 + 2) + 3 | blue | blue | blue | blue | pink |
| (1 + 2) | pink | pink | pink | pink | pink |
| (1 + 2) + 4 | pink | pink | pink | pink | pink |
| (1 + 2) + 5 | blue | blue | pink | pink | pink |
| (1 + 2) + 6 | blue | blue | blue | pink | pink |
| (1 + 2) + 7 | blue | pink | pink | pink | pink |

An important feature of these systems was that the color change associated with the temperature change was very sharp, occurring over a temperature range of about 1° C. This indicates high cooperativity in the melting and association processes involving the colloid conjugates and enables one to easily discriminate between oligonucleotide targets containing a fully-matched sequence and a single basepair mismatch.

The high degree of discrimination may be attributed to two features. The first is the alignment of two relatively short probe oligonucleotide segments (15 nucleotides) on the target is required for a positive signal. A mismatch in either segment is more destabilizing than a mismatch in a longer probe (e.g., an oligonucleotide 30 bases long) in a comparable two-component detection system. Second, the signal at 260 nm, obtained on hybridization of the target oligonucleotides with the nanoparticle conjugates in solution, is nanoparticle-based, not DNA-based. It depends on dissociation of an assembly of nanoparticles organized in a polymeric network by multiple oligonucleotide duplexes. This results in a narrowing of the temperature range that is observed for aggregate dissociation, as compared with standard DNA thermal denaturation. In short, some duplexes in the crosslinked aggregates can dissociate without dispersing the nanoparticles into solution. Therefore, the temperature range for aggregate melting is very narrow (4° C.) as compared with the temperature range associated with melting the comparable system without nanoparticles (12° C.). Even more striking and advantageous for this detection approach is the temperature range for the colorimetric response (<1° C.) observe on the C18 silica plates. In principle, this three-component nanoparticle based strategy will be more selective than any two-component detection system based on a single-strand probe hybridizing with target nucleic acid.

A master solution containing 1 nmol of target 3 was prepared in 100 μl of hybridization buffer (0.3 M NaCl, 10 mM phosphate, pH 7). One μl of this solution corresponds to 10 picomole of target oligonucleotide. Serial dilutions were performed by taking an aliquot of the master solution and diluting it to the desired concentration with hybridization buffer. Table 3 shows the sensitivity obtained using 3 μl of a mixture of probes 1 and 2 with different amounts of target 3. After performing the hybridization using freeze-thaw conditions, 3 μl aliquots of these solutions were spotted onto C-18 TLC plates to determine color. In Table 3 below, pink signifies a negative test, and blue signifies a positive test.

TABLE 3

| Amount of Target | Results |
|---|---|
| 1 picomole | blue (positive) |
| 200 femtomole | blue (positive) |
| 100 femtomole | blue (positive) |
| 20 femtomole | blue (positive) |
| 10 femtomoie | purplish (ambiguous) |

This experiment indicates that 10 femtomoles is the lower limit of detection for this particular system.

Example 6

Assays Using Nanoparticle-Oligonucleotide Conjugates

DNA modified nanoparticles were adsorbed onto modified transparent substrates as shown in FIG. 13B. This method involved the linking of DNA modified nanoparticles to nanoparticles that were attached to a glass substrate, using DNA hybridization interactions.

Glass microscope slides were purchased from Fisher scientific. Slides were cut into approximately 5×15 mm pieces, using a diamond tipped scribing pen. Slides were cleaned by soaking for 20 minutes in a solution of 4:1 $H_2SO_4:H_2O_2$ at 50° C. Slides were then rinsed with copious amounts of water, then ethanol, and dried under a stream of dry nitrogen. To functionalize the slide surface with a thiol terminated silane, the slides were soaked in a degassed ethanolic 1% (by volume) mercaptopropyl-trimethoxysilane solution for 12 hours. The slides were removed from the ethanol solutions and rinsed with ethanol, then water. Nanoparticles were adsorbed onto the thiol terminated surface of the slides by soaking in solutions containing the 13 nm diameter gold nanoparticles (preparation described in Example 1). After 12 hours in the colloidal solutions, the slides were removed and rinsed with water. The resulting slides have a pink appearance due to the adsorbed nanoparticles and exhibit similar UV-vis absorbance profiles (surface plasmon absorbance peak at 520 nm) as the aqueous gold nanoparticle colloidal solutions. See FIG. 14A.

DNA was attached to the nanoparticle modified surface by soaking the glass slides in 0.2 OD (1.7 µM) solution containing freshly purified 3' thiol oligonucleotide (3' thiol ATGCTCAACTCT [SEQ ID NO:33]) (synthesized as described in Examples 1 and 3). After 12 hours of soaking time, the slides were removed and rinsed with water.

Figure 14A:
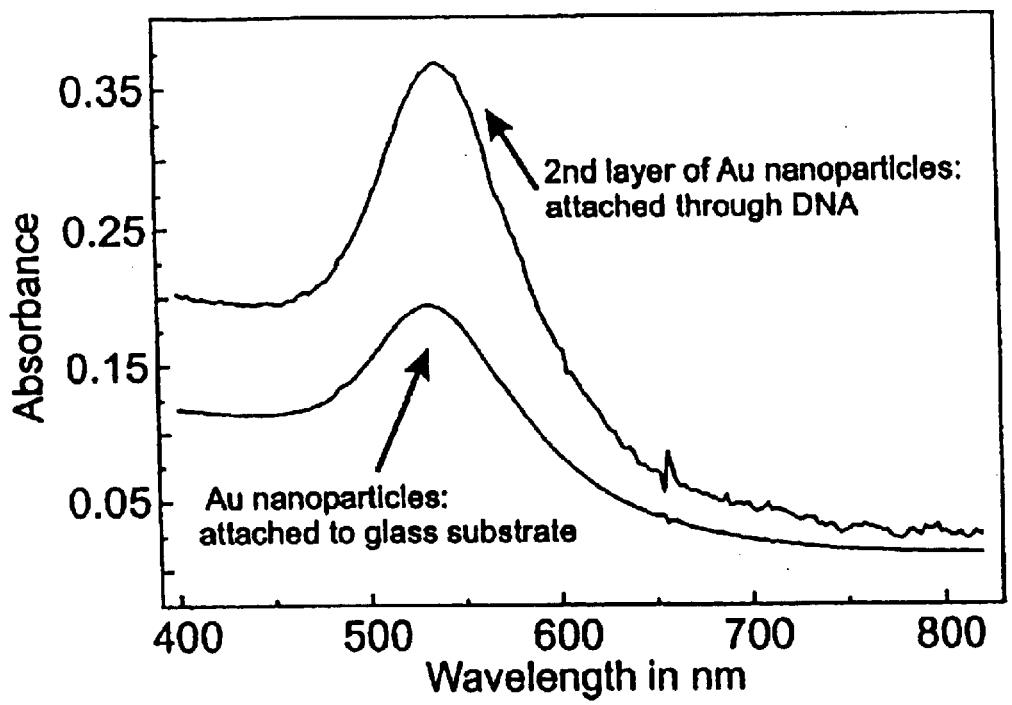
FIGS. 14A–B.

To demonstrate the ability of an analyte DNA strand to bind nanoparticles to the modified substrate, a linking oligonucleotide was prepared. The linking oligonucleotide (prepared as described in Example 2) was 24 bp long (5' TACGAGTTGAGAATCCTGAATGCG [SEQ ID NO:34]) with a sequence containing a 12 bp end that was complementary to the DNA already adsorbed onto the substrate surface (SEQ ID NO:33). The substrate was then soaked in a hybridization buffer (0.5 M NaCl, 10 mM phosphate buffer pH 7) solution containing the linking oligonucleotide (0.4 OD, 1.7 µM) for 12 hours. After removal and rinsing with similar buffer, the substrate was soaked in a solution containing 13 nm diameter gold nanoparticles which had been modified with an oligonucleotide (TAGGACTTACGC 5' thiol [SEQ ID NO:35]) (prepared as described in Example 3) that is complementary to the unhybridized portion of the linking oligonucleotide attached to the substrate. After 12 hours of soaking, the substrate was removed and rinsed with the hybridization buffer. The substrate color had darkened to a purple color and the UV-vis absorbance at 520 nm approximately doubled (FIG. 14A).

Figure 14B:
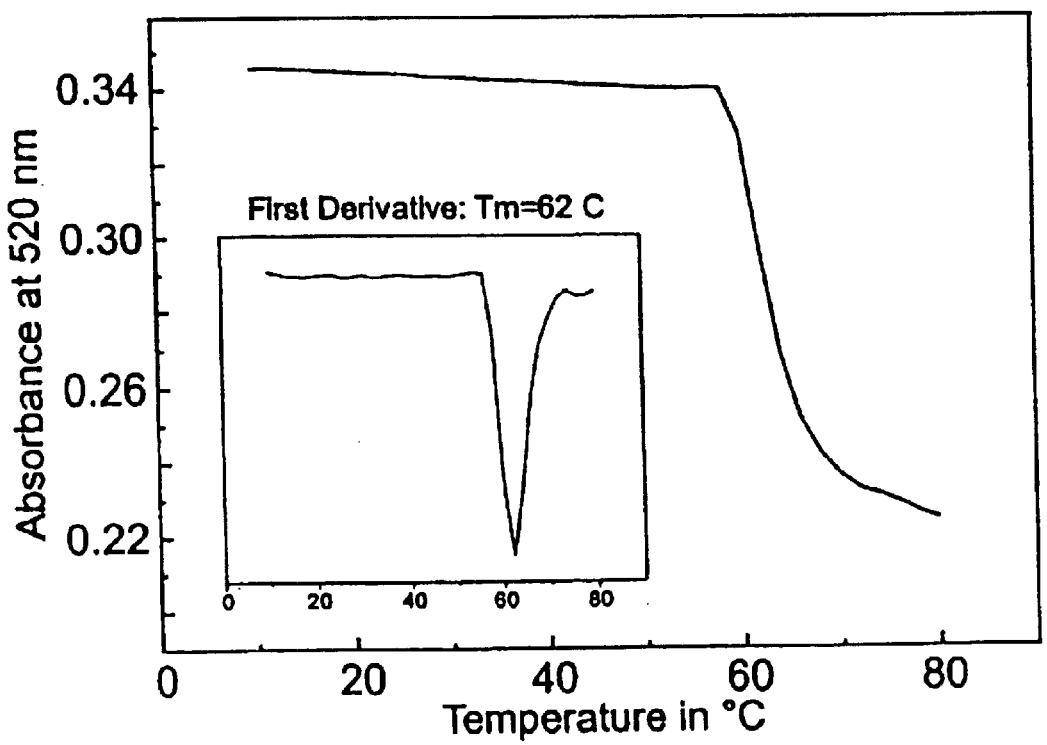

To verify that the oligonucleotide modified gold nanoparticles were attached to the oligonucleotide/nanoparticle modified surface through DNA hybridization interactions with the linking oligonucleotide, a melting curve was performed. For the melting experiment, the substrate was placed in a cuvette containing 1 mL of hybridization buffer and the same apparatus used in Example 2, part B, was used. The absorbance signal due to the nanoparticles (520 nm) was monitored as the temperature of the substrate was increased at a rate of 0.5° C. per minute. The nanoparticle signal dramatically dropped when the temperature passed 60° C. See FIG. 14B. A first derivative of the signal showed a melting temperature of 62° C., which corresponds with the temperature seen for the three DNA sequences hybridized in solution without nanoparticles. See FIG. 14B.

Example 7

Assays Using Nanoparticle-Oligonucleotide Conjugates

The detection system illustrated in FIGS. 15A–G was designed so that the two probes 1 and 2 align in a tail-to-tail fashion onto a complementary target 4 (see FIGS. 15A–G). This differs from the system described in Example 5 where the two probes align contiguously on the target strand (see FIGS. 12A–F).

The oligonucleotide-gold nanoparticle conjugates 1 and 2 illustrated in FIGS. 15A–G were prepared as described in Example 3, except that the nanoparticles were redispersed in hybridization buffer (0.3 M NaCl, 10 mM phosphate, pH 7). The final nanoparticle-oligonucleotide conjugate concentration was estimated to be 13 nM by measuring the reduction in intensity of the surface plasmon band at 522 nm which gives rise to the red color of the nanoparticles. The oligonucleotide targets illustrated in FIGS. 15A–G were purchased from the Northwestern University Biotechnology Facility, Evanston, Ill.

When 150 µL of hybridization buffer containing 13 nM oligonucleotide-nanoparticle conjugates 1 and 2 was mixed with 60 picomoles (6 µL) of target 4, the solution color immediately changed from red to purple. This color change occurs as a result of the formation of large oligonucleotide-linked polymeric networks of gold nanoparticles, which leads to a red shift in the surface plasmon resonance of the nanoparticles. When the solution was allowed to stand for over 2 hours, precipitation of large macroscopic aggregates was observed. A 'melting analysis' of the solution with the suspended aggregates was performed. To perform the 'melting analysis', the solution was diluted to 1 ml with hybridization buffer, and the optical signature of the aggregates at 260 nm was recorded at one minute intervals as the temperature was increased from 25° C. to 75° C., with a holding time of 1 minute/degree. Consistent with characterization of the aggregate as an oligonucleotide-nanoparticle polymer, a characteristic sharp transition (full width at half maximum, $FW_{1/2}$ of the first derivative=3.5° C.) was observed with a "melting temperature" ($T_m$) of 53.5° C. This compares well with the $T_m$ associated with the broader transition observed for oligonucleotides without nanoparticles ($T_m$=54° C., $FW_{1/2}$=~13.5° C.). The 'melting analysis' of the oligonucleotide solution without nanoparticles was performed under similar conditions as the analysis with nanoparticles, except that the temperature was increased from 10–80° C. Also, the solution was 1.04 µM in each oligonucleotide component.

To test the selectivity of the system, the $T_m$ for the aggregate formed from the perfect complement 4 of probes 1 and 2 was compared with the $T_m$'s for aggregates formed from targets that contained one base mismatches, deletions, or insertions (FIGS. 15A–G). Significantly, all of the gold nanoparticle-oligonucleotide aggregates that contained imperfect targets exhibited significant, measurable destabilization when compared to the aggregates formed from the perfect complement, as evidenced by $T_m$ values for the various aggregates (see FIGS. 15A–G). The solutions containing the imperfect targets could easily be distinguished from the solution containing the perfect complement by their color when placed in a water bath held at 52.5° C. This temperature is above the $T_m$ of the mismatched polynucleotides, so only the solution with the perfect target exhibited a purple color at this temperature. A 'melting analysis' was also performed on the probe solution which contained the half-complementary target. Only a minute increase in absorbance at 260 nm was observed.

Next, 2 µL (20 picomoles) of each of the oligonucleotide targets (FIGS. 15A–G) were added to a solution containing 50 µL of each probe (13 nM) in hybridization buffer. After standing for 15 minutes at room temperature, the solutions were transferred to a temperature-controlled water bath and incubated at the temperatures indicated in Table 4 below for five minutes. A 3 µl sample of each reaction mixture was then spotted on a C-18 silica plate. Two control experiments were performed to demonstrate that the alignment of both probes onto the target is necessary to trigger aggregation and, therefore, a color change. The first control experiment consisted of both probes 1 and 2 without target present. The second control experiment consisted of both probes 1 and 2 with a target 3 that is complementary to only one of the probe sequences (FIG. 15B). The results are presented in Table 4 below. Pink spots signify a negative test, and blue spots signify a positive test.

Notably, the colorimetric transition that can be detected by the naked eye occurs over less than 1° C., thereby allowing one to easily distinguish the perfect target 4 from the targets with mismatches (5 and 6), an end deletion (7), and a one base insertion at the point in the target where the two oligonucleotide probes meet (8) (see Table 4). Note that the colorimetric transition $T_c$ is close in temperature, but not identical, to $T_m$. In both controls, there were no signs of particle aggregation or instability in the solutions, as evidenced by the pinkish red color which was observed at all temperatures, and they showed negative spots (pink) in the plate test at all temperatures (Table 4).

The observation that the one base insertion target 8 can be differentiated from the fully complementary target 4 is truly remarkable given the complete complementarity of the insertion strand with the two probe sequences. The destabilization of the aggregate formed from 8 and the nanoparticle probes appears to be due to the use of two short probes and the loss of base stacking between the two thymidine bases where the probe tails meet when hybridized to the fully complementary target. A similar effect was observed when a target containing a three base pair insertion (CCC) was hybridized to the probes under comparable conditions, ($T_m$=51° C.). In the system described above in Example 5, targets with base insertions could not be distinguished from the fully complementary target. Therefore, the system described in this example is very favorable in terms of selectivity. This system also exhibited the same sensitivity as the system described in Example 5, which is approximately femtomoles without amplification techniques.

The results indicate that any one base mismatch along the target strand can be detected, along with any insertions into the target strand. Importantly, the temperature range over which a color change can be detected is extremely sharp, and the change occurs over a very narrow temperature range. This sharp transition indicates that there is a large degree of cooperativity in the melting process involving the large network of colloids which are linked by the target oligonucleotide strands. This leads to the remarkable selectivity as shown by the data.

TABLE 4

| Reactants | Results (color) | | | | | |
|---|---|---|---|---|---|---|
| (probes) + target | RT | 47.6° C. | 50.5° C. | 51.4° C. | 52.7° C. | 54.5° C. |
| (1 + 2) | pink | pink | pink | pink | pink | pink |
| (1 + 2) + 3 | pink | pink | pink | pink | pink | pink |
| (1 + 2) + 4 | blue | blue | blue | blue | blue | pink |
| (1 + 2) + 5 | blue | blue | blue | pink | pink | pink |
| (1 + 2) + 6 | blue | pink | pink | pink | pink | pink |
| (1 + 2) + 7 | blue | blue | blue | blue | pink | pink |
| (1 + 2) + 8 | blue | blue | pink | pink | pink | pink |

Example 8

Assays Using Nanoparticle-Oligonucleotide Conjugates

A set of experiments were performed involving hybridization with 'filler' duplex oligonucleotides. Nanoparticle-oligonucleotide conjugates 1 and 2 illustrated in FIG. 16A were incubated with targets of different lengths (24, 48 and 72 bases in length) and complementary filler oligonucleotides, as illustrated in FIGS. 16A–C. Otherwise, the conditions were as described in Example 7. Also, the oligonucleotides and nanoparticle-oligonucleotide conjugates were prepared as described in Example 7.

As expected, the different reaction solutions had markedly different optical properties after hybridization due to the distance-dependent optical properties of the gold nanoparticles. See Table 5 below. However, when these solutions were spotted onto a C-18 TLC plate, a blue color developed upon drying at room temperature or 80° C., regardless of the length of the target oligonucleotide and the distance between the gold nanoparticles. See Table 5. This probably occurs because the solid support enhances aggregation of the hybridized oligonucleotide-nanoparticle conjugates. This demonstrates that by spotting solutions onto the TLC plate, the distance between the gold nanoparticles can be substantial (at least 72 bases), and calorimetric detection is still possible.

TABLE 5

| | Results (Color) | |
|---|---|---|
| Target Length | Solution | TLC Plate |
| 24 bases | Blue | Blue |
| 48 bases | Pink | Blue |
| 72 bases | Pink | Blue |
| Probes 1 + 2 only | Pink | Pink |

The color changes observed in this and other examples occur when the distance between the gold nanoparticles (the interparticle distance) is approximately the same or less than the diameter of the nanoparticle. Thus, the size of the nanoparticles, the size of the oligonucleotides attached to them, and the spacing of the nanoparticles when they are hybridized to the target nucleic acid affect whether a color change will be observable when the oligonucleotide-nanoparticle conjugates hybridize with the nucleic acid targets to form aggregates. For instance, gold nanoparticles with diameters of 13 nm will produce a color change when aggregated using oligonucleotides attached to the nanoparticles designed to hybridize with target sequences 10–35 nucleotides in length. The spacing of the nanoparticles when they are hybridized to the target nucleic acid adequate to give a color change will vary with the extent of aggregation, as the results demonstrate. The results also indicate that the solid surface enhances further aggregation of already-aggregated samples, bringing the gold nanoparticles closer together.

The color change observed with gold nanoparticles is attributable to a shift and broadening of the surface plasmon resonance of the gold. This color change is unlikely for gold nanoparticles less than about 4 nm in diameter because the lengths of the oligonucleotides necessary for specific detection of nucleic acid would exceed the nanoparticle diameter.

Example 9

Assays Using Nanoparticle-Oligonucleotide Conjugates

Five microliters of each probe 1 and 2 (FIG. 12A) were combined to a final concentration of 0.1 M NaCl with buffer (10 mM phosphate, pH 7), and 1 microliter of human urine was added to the solution. When this solution was frozen, thawed, and then spotted on a C-18 TLC plate, a blue color did not develop. To a similar solution containing 12.5 microliters of each probe and 2.5 microliters of human urine, 0.25 microliters (10 picomoles) of target 3 (FIG. 12A) was added. The solution was frozen, thawed and then spotted onto a C-18 TLC plate, and a blue spot was obtained.

Similar experiments were performed in the presence of human saliva. A solution containing 12.5 microliters of each probe 1 and 2 and 0.25 microliters of target 3 was heated to 70° C. After cooling to room temperature, 2.5 microliters of a saliva solution (human saliva diluted 1:10 with water) was added. After the resultant solution was frozen, thawed and then spotted onto a C-18 TLC plate, a blue spot was obtained, indicating hybridization of the probes with the target. In control experiments with no target added, blue spots were not observed.

Example 10

Assays Using Nanoparticle-Oligonucleotide Conjugates

An assay was performed as illustrated in FIG. 13A. First, glass microscope slides, purchased from Fisher scientific, were cut into approximately 5×15 mm pieces, using a diamond tipped scribing pen. Slides were cleaned by soaking for 20 minutes in a solution of 4:1 $H_2SO_4:H_2O_2$ at 50° C. Slides were then rinsed with copious amounts of water, then ethanol, and dried under a stream of dry nitrogen. Thiol-modified DNA was adsorbed onto the slides using a modified procedure reported in the literature (Chrisey et al., Nucleic Acids Res., 24, 3031–3039 (1996) and Chrisey et al., Nucleic Acids Res., 24, 3040–3047 (1996)). First, the slides were soaked in a 1% solution of trimethoxysilylpropyldiethyltriamine (DETA, purchased from United Chemical Technologies, Bristol, Pa.) in 1 mM acetic acid in Nanopure water for 20 minutes at room temperature. The slides were rinsed with water, then ethanol. After drying with a dry nitrogen stream, the slides were baked at 120° C. for 5 minutes using a temperature-controlled heating block. The slides were allowed to cool, then were soaked in a 1 mM succinimidyl 4-(malemidophenyl)-butyrate (SMPB, purchased from Sigma Chemicals) solution in 80:20 methanol:dimethoxysulfoxide for 2 hours at room temperature. After removal from the SMPB solution and rinsing with ethanol, amine sites that were not coupled to the SMPB crosslinker were capped as follows. First, the slides were soaked for 5 minutes in a 8:1 THF:pyridine solution containing 10% 1-methyl imidazole. Then the slides were soaked in 9:1 THF:acetic anhydride solution for five minutes. These capping solutions were purchased from Glen Research, Sterling, Va. The slides were rinsed with THF, then ethanol, and finally water.

DNA was attached to the surfaces by soaking the modified glass slides in a 0.2 OD (1.7 μM) solution containing freshly purified oligonucleotide (3' thiol ATGCTCAACTCT [SEQ ID NO:33]). After 12 hours of soaking time, the slides were removed and rinsed with water.

Figure 19A:
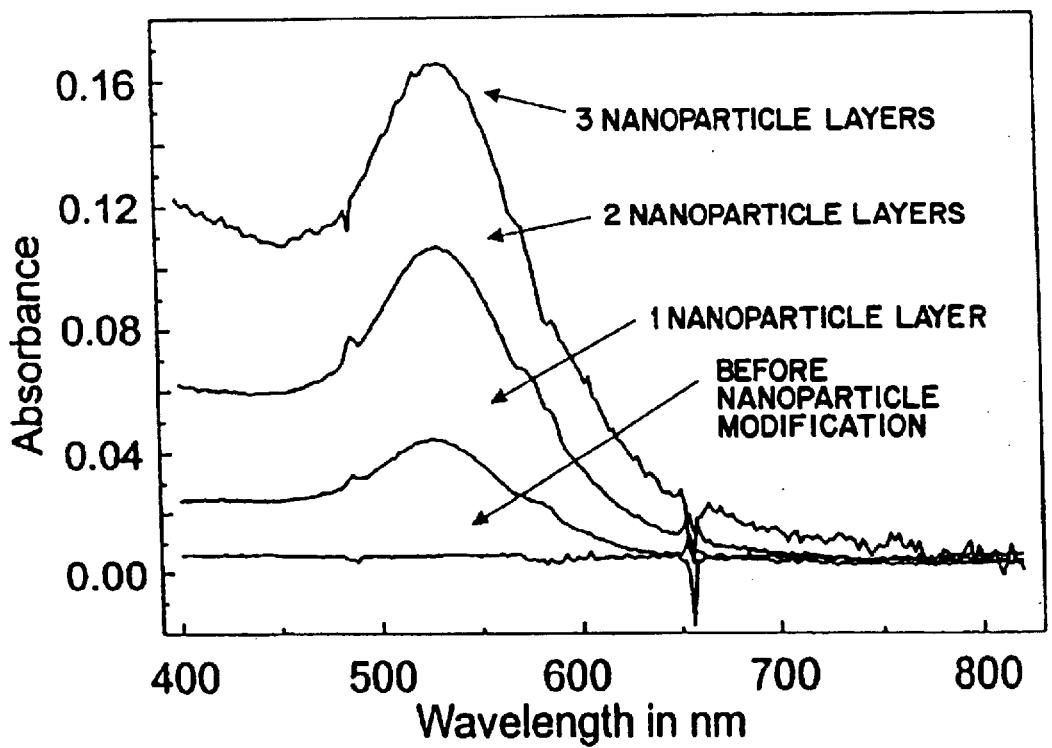
FIGS. 19A–B.

To demonstrate the ability of an analyte DNA strand to bind nanoparticles to the modified substrate, a linking oligonucleotide was prepared. The linking oligonucleotide was 24 bp long (5' TACGAGTTGAGAATCCTGAATGCG [SEQ ID NO:34]) with a sequence containing a 12 bp end that was complementary to the DNA already adsorbed onto the substrate surface. The substrate was then soaked in a hybridization buffer (0.5 M NaCl, 10 mM phosphate buffer pH 7) solution containing the linking oligonucleotide (0.4 OD, 1.7 μM) for 12 hours. After removal and rinsing with similar buffer, the substrate was soaked in a solution containing 13 nm diameter gold nanoparticles which had been modified with an oligonucleotide (TAGGACTTACGC 5' thiol [SEQ ID NO:35]) that is complementary to the unhybridized portion of the linking oligonucleotide attached to the substrate. After 12 hours of soaking, the substrate was removed and rinsed with the hybridization buffer. The glass substrate's color had changed from clear and colorless to a transparent pink color. See FIG. 19A.

Additional layers of nanoparticles were added to the slides by soaking the slides in a solution of the linking oligonucleotide as described above and then soaking in a solution containing 13 nm gold nanoparticles having oligonucleotides (3' thiol ATGCTCAACTCT [SEQ ID NO:33]) attached thereto. After soaking for 12 hours, the slides were removed from the nanoparticle solution and rinsed and soaked in hybridization buffer as described above. The color of the slide had become noticeably more red. See FIG. 19A. A final nanoparticle layer was added by repeating the linking oligonucleotide and nanoparticle soaking procedures using 13 nm gold nanoparticles which had been modified with an oligonucleotide (TAGGACTTACGC 5' thiol [SEQ ID NO:35]) as the final nanoparticle layer. Again, the color darkened, and the UV-vis absorbance at 520 nm increased. See FIG. 19A.

Figure 19B:
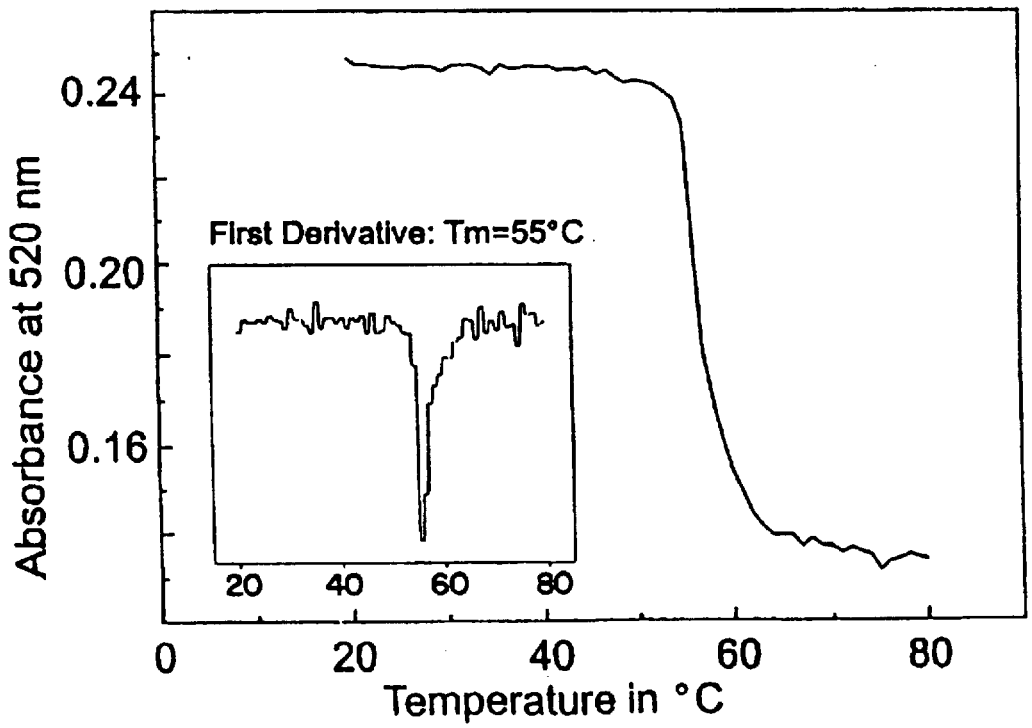

To verify that the oligonucleotide modified gold nanoparticles were attached to the oligonucleotide modified surface through DNA hybridization interactions with the linking oligonucleotide, a melting curve was performed. For the melting experiment, a slide was placed in a cuvette containing 1.5 mL of hybridization buffer, and an apparatus similar to that used in Example 2, part B, was used. The absorbance signal due to the nanoparticles (520 nm) was monitored at each degree as the temperature of the substrate was increased from 20° C. to 80° C., with a hold time of 1 minute at each integral degree. The nanoparticle signal dramatically dropped when the temperature passed 52° C. See FIG. 19B. A first derivative of the signal showed a melting temperature of 55° C., which corresponds with the temperature seen for the oligonucleotide-nanoparticle conjugates and linking oligonucleotides hybridized in solution. See FIG. 19B.

Example 11

Assay of a Polyribonucleotide Using Nanoparticle-Oligonucleotide Conjugates as Probes The previous Examples utilized oligo-deoxyribonucleotides as targets in the assays. The present example demonstrates that the nanoparticle-oligonucleotide conjugates can also be used as probes in assaying a Polyribonucleotide. The experiment was carried out by adding 1 μL of a solution of poly(rA) (0.004 $A_{260}$ Units) to 100 μL of gold nanoparticles (~10 nM in particles) conjugated to $dT_{20}$ (a 20-mer oligonucleotide containing thymidylate residues) through a mercaptoalkyl linker at the 5'-terminus. The conjugation procedure was that described in Example 3. Following freezing in a Dry Ice/isopropyl alcohol bath, thawing at room temperature, and spotting on a C18 TLC plate as described in Example 4, a blue spot characteristic of aggregation of the nanoparticles by hybridization was observed. Control experiments carried out in absence of the target gave a pink spot, rather than a blue spot.

Example 12

Assay for Protective Antigen DNA Segment of Anthrax Using Nanoparticle-Oligonucleotide Conjugates In many cases amplification of a double-stranded DNA target by PCR is needed to provided sufficient material for an assay. The present example demonstrates that the nanoparticle-oligonucleotide conjugates can be used to assay for a DNA strand in the presence of its complement (i.e., assaying for a single strand after thermal dehybridization of a double-stranded target) and can recognize and specifically bind to an amplicon obtained from a PCR reaction.

A PCR solution containing a 141 base pair duplex amplicon of the Protective Antigen segment of Anthrax was provided by the Navy (sequence given in FIG. 23). The assay for this amplicon was carried out by isolating the DNA from 100 µL of the PCR solution using a Qiaquick Nucleotide Removal Kit (Qiagen, Inc., Santa Clarita, Calif.) and the standard protocol for this kit, with the exception that elution of the DNA was effected with 10 mM phosphate buffer at pH 8.5, rather than with the buffer provided with the kit. The eluant was then evaporated to dryness on a Speed Vac (Savant). To this residue was added 5 µL of a master mix prepared by mixing equal volumes of each of two solutions of two different oligonucleotide-nanoparticle probes (see FIG. 23). Each oligonucleotide-nanoparticle probe was prepared as described in Example 3. The solutions of the probes which were combined to form the master mix were prepared by adding 10 µL of 2 M NaCl and 5 µL of oligonucleotide blocker solution (50 pmoles of each Blocker oligonucleotide (see FIG. 23 and below) in a 0.3 M NaCl, 10 mM phosphate, pH 7.0., solution) to 5 µL of full-strength (about 10 nM) nanoparticle-oligonucleotide solution. The amplicon-probe mixture was heated to 100° C. for 3 minutes, then frozen in a DRY ICE/ethanol bath and allowed to come to room temperature. A small aliquot (2 µL) was spotted on a C18 TLC plate and allowed to dry. A strong blue spot indicative of hybridization was obtained.

Control tests carried out in the same manner in absence of the amplicon target DNA, in the absence of Probe 1, in the absence of Probe 2, or in the absence of the sodium chloride, were all negative, that is, gave a pink spot. Similarly a test carried out using probes 1 and 2 with a PCR amplicon derived from the Lethal Factor segment of Anthrax in place of the Protective Antigen Segment was negative (pink spot). These controls confirmed that both probes were essential, that salt conditions appropriate for hybridization were needed, and that the test was specific for the specified target sequence.

The oligonucleotide Blockers were added to inhibit binding of the second strand of the initial duplex target (i.e., the strand complementary to the target strand) to regions of the target nucleic acid strand outside the segment that binds to the probes (see FIG. 23 for sequences), since such binding interferes with binding of the nanoparticle oligonucleotide probes to the target strand. In this example, the Blocker oligonucleotides were complementary to the single-stranded target in regions not covered by the probes. An alternative scheme is to use blocker oligonucleotides that are complementary to the PCR complementary strand (the strand complementary to the target strand) outside the region that competes with the probe oligonucleotides.

Example 13

Direct Assay of PCR Amplicons Without Isolation of the Amplicons from the PCR Solution The procedure described in Example 12 involved separation of the PCR amplicon from the PCR solution before addition of the nanoparticle-oligonucleotide probes. For many purposes it would be desirable to be able to carry out the assay directly in the PCR solution without preliminary isolation of the polynucleotide products. A protocol for such an assay has been developed and is described below. This protocol has been performed successfully with several PCR products derived under standard conditions using a Gene-Amp PCR Reagent Kit with Amplitaq DNA polymerase.

To 50 µL of the PCR sample solution, 5 µL of a mixture of two gold nanoparticle-oligonucleotide probes (0.008 $A_{520}$ Units of each) was added, followed by addition of a solution made up from 1 µL of Blocker oligonucleotides (10 pmoles each), 5 µL of 5 M NaCl, and 2 µL of 150 mM $MgCl_2$. This mixture was heated for 2 minutes at 100° C. to separate the strands of the duplex target, the tube was immersed directly in a cold bath (e.g., Dry Ice/ethanol) for 2 minutes, then removed, and the solution allowed to thaw at room temperature (the freeze-thaw cycle facilitates hybridization of the probes with the target oligonucleotide). Finally, a few µL of the solution were spotted on a plate (e.g., C18 RP TLC plate, a silica plate, a nylon membrane, etc.). As usual, blue color signifies the presence of the targeted nucleic acid in the PCR solution; a pink color is negative for this target.

Example 14

Direct Recognition of Duplex Oligonucleotides without Dehybridization, Using Assembly of Nanoparticle-Oligonucleotide Conjugates In the previous Examples, double-stranded targets were dehybridized by heating to generate single strands which interacted with single-stranded oligonucleotide probes bound to nanoparticles. The present example demonstrates that in cases where triple-stranded complexes can form, double-stranded oligonucleotide sequences can be recognized by the nanoparticle probes without prior dehybridization of the target.

Tests were carried out with two different systems—polyA:polyU and $dA_{40}$:$dT_{40}$—by adding 1 µL of a solution containing 0.8 $A_{260}$ Units of the target duplex in 100 µL of buffer (0.1 M NaCl, 10 mM phosphate, pH 7.0) to 100 µL of a colloidal solution of Au-sd$T_{20}$ nanoparticle-oligonucleotide conjugate (~10 nM in particles; see Example 11) in 0.3 M NaCl, 10 mM phosphate buffer at pH 7.0. Subsequent quick freezing by immersing the tube in a Dry Ice/isopropyl alcohol bath and thawing by removing the tube from the bath and letting it stand at room temperature (22° C.), followed by spotting 3 µL of the solution on a C18 TLC plate, afforded a blue spot characteristic of hybridization and aggregation of the nanoparticles.

The rationale for this test is that the nanoparticle probes (bearing pyrimidine oligonucleotides in this example) bind in a sequence specific manner at purine oligonucleotide/pyrimidine oligonucleotide sites along the duplex target. Since many binding sites are available on each double stranded entity, the binding leads to formation of an aggregate of nanoparticles. The results show that this assay, based on formation of triple-stranded complexes involving the nanoparticle probes, works both for oligoribo- and oligodeoxyribonucleotide double-stranded targets.

Example 15

Assay Employing Both Fluorescence and Colorimetric Detection

All hybridization experiments were performed in a 0.3 M NaCl, 10 mM phosphate, pH 7.0, buffer solution. AcetatePlus™ filtration membranes (0.45 µm) were purchased from Micron Separations Inc., Westboro, Mass. Alkylamine-functionalized latex microspheres (3.1 µm) were purchased from Bangs Laboratories, Fishers Ind. Fluorophore-labeled oligonucleotides functionalized with alklylamino groups at the 3'-terminus were synthesized using standard phosphoramidite chemistry (Eckstein, ed., in *Oligonucleotides and Analogues,* 1st ed., Oxford University, New York, N.Y. 1991) with an Amino-Modifier C7 CPG solid support (Glen Research) and a 5'-fluorescein phosphoramidite (6-FAM, Glen Research) on an Expedite 8909 synthesizer and were purified by reverse phase HPLC. They were attached to the amine-functionalized latex microspheres by means of diisothiocyanate coupling to yield a dithiourea linkage as described in Charreyre et al., Langmuir, 13, 3103–3110 (1997). Briefly, a DMF solution of a one thousand fold excess of 1,4-phenylene diisothiocyanate was added to an aqueous borate buffer solution (0.1 M, pH 9.3) of the amino-modified oligonucleotide. After several hours, the excess 1,4-phenylene diisothiocyanate was extracted with butanol and the aqueous solution lyophilized. The activated oligonucleotides were redissolved in borate buffer and reacted with the amino-functionalized latex microspheres in a carbonate buffer (0.1 M, pH 9.3, 1 M NaCl). After 12 hrs, the particles were isolated by centrifugation and washed three times with buffered saline solution (0.3 M NaCl, 10 mM phosphate pH 7.0). The 5'-oligonucleotide-modified gold nanoparticle probes were prepared as described in Example 3.

The target oligonucleotide (1–5 $\mu$l, 3 nM) was added to 3 $\mu$l of fluorophore-labeled oligonucleotide-modified latex microsphere probe solution (3.1 $\mu$m; 100 fM). After 5 minutes, 3 $\mu$l of the 5' oligonucleotide-modified gold nanoparticle probe solution (13 nm; 8 nM) were added to the solution containing the target and latex microsphere probes. Upon standing for an additional 10 minutes, the solution containing both probes and target was vacuum-filtered through the AcetatePlus membrane. The membrane retained the relatively large latex particles and allowed any non-hybridized gold nanoparticle probes to pass through. In the presence of a sufficient concentration of target, the latex microspheres and the gold nanoparticles hybridized with the target, and a red spot was observed on the membrane (positive result). A control experiment was always carried out where the aliquot of solution containing the target oligonucleotide was replaced by an equal volume of water. In this case, a white spot was left on the membrane (negative result). For a 24-base-pair model system, using the unaided eye, 3 femtomoles of target oligonucleotide could be detected calorimetrically.

A double-stranded target oligonucleotide (1–5 $\mu$l, 20 nM), 3 $\mu$l of a solution of fluorophore-labeled-oligonucleotide-latex microspheres (3.1 $\mu$m; 100 fM) and 3 $\mu$l of a solution of 5'-oligonucleotide-gold nanoparticles (13 nm; 8 nM) were combined and heated to 100° C. for 3 minutes. Then, the solution was immediately frozen by immersing the reaction vessel containing it in a liquid $N_2$ bath for 3 minutes. This solution was then thawed at room temperature and filtered as described above. For a 24-base pair model system, using the unaided eye, 20 femtomoles of duplex target oligonucleotide could be detected calorimetrically.

When monitored by fluorescence, the detection method described above proved to be difficult due to background fluorescence from the membrane. This problem was overcome by "washing" the latex microspheres by centrifugation to remove excess gold nanoparticle probes before spotting an aliquot on a reverse-phase TLC plate. The hybridization experiments were performed as described above. After hybridization was effected between the probes and target, 10 $\mu$l of buffer were added to the solution, which was subsequently centrifuged at 10,000×g for 2 minutes. The supernatant was removed, and 5 $\mu$l of buffer were added to help resuspend the precipitate. A 3 $\mu$l aliquot was then spotted on a reverse-phase TLC plate. For both single-stranded and duplex target oligonucleotides, 25 femtomoles could be detected colorimetrically by the naked eye. Fluorescent spots could be visualized by the naked eye with a hand-held UV-lamp until the target amount in the 3 $\mu$l aliquot used to form the spot was as low as 50 femtomoles. It is believed that optimization of this system will allow for detection of even lower amounts of target nucleic acid.

Example 16

Assays Employing Silver Staining

DNA hybridization tests on oligonucleotide-modified substrates are commonly used to detect the presence of specific DNA sequences in solution. The developing promise of combinatorial DNA arrays for probing genetic information illustrates the importance of these heterogeneous sequence assays to future science. In most assays, the hybridization of fluorophore-labeled targets to surface-bound probes is monitored by fluorescence microscopy or densitometry. Although fluorescence detection is very sensitive, its use is limited by the expense of the experimental equipment and by background emissions from most common substrates. In addition, the selectivity of labeled oligonucleotide targets for perfectly complementary probes over those with single-base mismatches is poor, preventing the use of surface hybridization tests for detection of single nucleotide polymorphisms. A detection scheme which improved upon the simplicity, sensitivity and selectivity of fluorescent methods could allow the full potential of combinatorial sequence analysis to be realized. The present invention provides such improved detection schemes.

For instance, oligonucleotide-modified gold nanoparticles and unmodified DNA target could be hybridized to oligonucleotide probes attached to a glass substrate in a three-component sandwich assay (see FIGS. 25A–B). Note that the nanoparticles can either be individual ones (see FIG. 25A) or "trees" of nanoparticles (see FIG. 25B). The "trees" increase signal sensitivity as compared to the individual nanoparticles, and the hybridized gold nanoparticles "trees" often can be observed with the naked eye as dark areas on the glass substrate. When "trees" are not used, or to amplify the signal produced by the "trees," the hybridized gold nanoparticles can be treated with a silver staining solution. The "trees" accelerate the staining process, making detection of target nucleic acid faster as compared to individual nanoparticles.

The following is a description of one specific system (illustrated in FIG. 25A). Capture oligonucleotides (3'-HS (CH$_2$)$_3$—A$_{10}$ATGCTCAACTCT; SEQ ID NO: 43) were immobilized on a glass substrate as described in Example 10. A target oligonucleotide (5'-TACGAGTTGAGAATCCTGAATGCG-3', SEQ ID NO: 44, concentrations given below in Table 6 for each experiment) was hybridized with the capture oligonucleotides in 0.3 M NaCl, 10 mM phosphate buffer as described in Example 10. The substrate was rinsed twice with the same buffer solution and immersed in a solution containing gold nanoparticle probes functionalized with target-complementary DNA (5'-HS(CH$_2$)$_6$A$_{10}$CGCATTCAGGAT, SEQ ID NO: 45)(preparation described in Example 3) for 12 hours. Next, the substrate was rinsed copiously with 0.3 M NaNO$_3$ to remove Cl$^-$. The substrate was then developed with silver staining solution (1:1 mixture of Silver Enhancer Solutions A and B, Sigma Chemical Co., #S-5020 and #S-5145) for 3 minutes. Greyscale measurements were made by scanning the substrate on a flatbed scanner (normally used for scanning documents into a computer) linked to a computer loaded with software capable of calculating greyscale measurements (e.g., Adobe Photoshop). The results are presented in Table 6 below.

TABLE 6

| Target DNA Concentration | Mean Greyscale | Standard Deviation |
|---|---|---|
| 10 nM | 47.27 | 2.10 |
| 5 nM | 53.45 | 0.94 |
| 2 nM | 54.56 | 1.17 |
| 1 nM | 59.98 | 1.82 |
| 500 pM | 61.61 | 2.26 |
| 200 pM | 90.06 | 3.71 |
| 100 pM | 99.04 | 2.84 |
| 50 pM | 135.20 | 7.49 |
| 20 pM | 155.39 | 3.66 |
| None (control) | 168.16 | 10.03 |

Example 17

Assemblies Containing Quantum Dots

This example describes the immobilization of synthetic single-stranded DNA on semiconductor nanoparticle quantum dots (QDs). Native CdSe/ZnS core/shell QDs (~4 nm) are soluble only in organic media, making direct reaction with alkylthiol-terminated single-stranded DNA difficult. This problem was circumvented by first capping the QDs with 3-mercaptopropionic acid. The carboxylic acid group was then deprotonated with 4-(dimethylamino)pyridine, rendering the particles water soluble, and facilitating reaction of the QDs with either 3'-propylthiol- or 5'-hexylthiol-modified oligonucleotide sequences. After DNA modification, the particles were separated from unreacted DNA by dialysis. A "linker" DNA strand was then hybridized to surface-bound sequences, generating extended assemblies of nanoparticles. The QD assemblies, which were characterized by TEM, UV/Visible spectroscopy, and fluorescence spectroscopy, could be reversibly assembled by controlling the temperature of the solution. The temperature dependent UV-Vis spectra were obtained for the novel QD assemblies and composite aggregates formed between QDs and gold nanoparticles (~13 nm).

A. General Methods

Nanopure water (18.1 MΩ) prepared using a NANOpure ultrapure water purification system was employed throughout. Fluorescence spectra were obtained using a Perkin Elmer LS 50 B Luminescence Spectrometer. Melting analyses were performed using a HP 8453 diode array spectrophotometer equipped with a HP 9090a Peltier Temperature Controller. Centrifugation was carried out using either an Eppendorf 5415C centrifuge or a Beckman Avanti 30 centrifuge. TEM images were acquired using a Hitachi HF-2000 field emission TEM operating at 200 kV.

B. Preparation of Oligonucleotide-OD Conjugates

Synthetic methodologies for semiconductor quantum dots (QDs) have improved greatly in recent years, and for some materials, most notably CdSe, monodisperse samples of pre-determined size can now be prepared with relative ease. Murray et al., *J. Am. Chem. Soc.* 1993, 115, 8706; Hines, et al., *J. Phys. Chem.* 1996, 100, 468. As a result, the unique electronic and luminescent properties of these particles have been studied extensively (see, Alivisatos, *J. Phys. Chem.* 1996, 100, 13226, and references therein; Klein et al., *Nature* 1997, 699; Kuno et al., *J. Chem. Phys.* 1997, 106, 9869; Nirmal et al., *Nature* 1996, 383, 802), potentially paving the way for QDs to be employed in diverse technologies, such as light-emitting diodes (Schlamp et al., *J. Appl. Phys.* 1997, 82, 5837; Dabbousi et al., *Appl. Phys. Lett.* 1995, 66, 1316) and as non-radioactive biological labels (Bruchez et al., *Science* 1998, 281, 2013; Chan et al., *Science* 1998, 281, 2016). However, many applications will require that the particles be arranged spatially on a surface or organized into three-dimensional materials (Vossmeyer et al., *J. Appl. Phys.* 1998, 84, 3664). Moreover, the ability to organize one or more types of nanoparticles into superlattice structures (Murray et al., *Science* 1995, 270, 1335) would allow for the construction of completely new types of hybrid materials with new and potentially interesting and useful properties.

DNA is the ideal synthon for programming the assembly of nanoscale building blocks into periodic two- and three-dimensional extended structures. The many attributes of DNA, which include ease of synthesis, extraordinary binding specificity, and virtually unlimited programmability by virtue of nucleotide sequence, can be exploited for the use of QD assembly.

The modification of QDs with DNA has proven to be more difficult than for gold nanoparticles. The common methods for preparing highly luminescent CdSe QDs yield materials that are coated with a mixture of trioctylphosphine oxide (TOPO) and trioctylphosphine (TOP). As a result, these QDs are soluble only in non-polar solvents, making them difficult to functionalize with highly charged DNA strands by direct reaction. This difficulty has been overcome by the method described below, which is the first successful modification of semiconductor nanoparticles with single-stranded DNA. It should be noted that others, in elegant studies, have looked at the interactions between QDs and duplex DNA, but these studies did not make use of the sequence specific binding properties of DNA to direct the assembly of extended QD structures. Coffer et al., *Appl. Phys. Lett,* 1996, 69, 3851; Mahtab et al., *J. Am. Chem. Soc.,* 1996, 118, 7028.

Since the surface of CdSe/ZnS core/shell QDs binds organic thiols, it was desired to modify these semiconductor particles with alkylthiol-terminated DNA strands by a substitution reaction. The lack of water solubility of these QDs, though, hindered such an approach. Two different methods recently have been reported for making QDs water soluble, allowing for the immobilization of protein structures on the QD surfaces. One involves encapsulation of the core/shell structures with a silica layer (Bruchez et al., *Science* 1998, 281, 2013), while the other utilizes mercaptoacetic acid both to stabilize the particles and provide water solubility (Chan et al., *Science* 1998, 281, 2016). The procedure described in this example, which produces remarkably stable colloid under DNA hybridization conditions, utilizes 3-mercaptopropionic acid to passivate the QD surface.

An excess of 3-mercaptopropionic acid (0.10 mL, 1.15 mmol; Aldrich) was added by syringe to a suspension of ~20 mg of TOP/TOPO stabilized CdSe/ZnS QDs (prepared as described in Hines, et al., *J. Phys. Chem.* 1996, 100, 468) in 1.0 mL of N,N,-dimethyl formamide (DMF; Aldrich) generating a clear, dark orange solution containing 3-mercaptopropionic acid functionalized QDs. The reaction occurred quickly. For subsequent reactions, excess 3-mercaptopropionic acid was not removed, and the particles were stored at room temperature in DMF.

However, to characterize the QDs, a portion of the sample was purified by removing unreacted 3-mercapto-propionic acid as follows. A 0.50 mL sample was centrifuged (4 hours at 30,000 rpm), and the supernatant was removed. The remaining solution was washed with ~0.3 mL of DMF and recentrifuged. This step was repeated two additional times before recording the FTIR spectrum. FTIR (polyethylene card, 3M):1710 cm$^{-1}$ (s), 1472 cm$^{-1}$ (m), 1278 cm$^{-1}$ (w), 1189 cm$^{-1}$ (m), 1045 cm$^{-1}$ (w), 993 cm$^{-1}$ (m), 946 cm$^{-1}$ (w), 776 cm$^{-1}$ (m), 671 cm$^{-1}$ (m). Unlike the TOP/TOPO stabilized native QDs, the 3-mercaptopropionic acid modified QDs exhibited a characteristic $\sigma_{CO}$ band at 1710 cm$^{-1}$ for the surface bound propionic acid.

Although the 3-mercaptopropionic acid modified QDs were practically insoluble in water, their solubility could be significantly enhanced by deprotonating the surface bound mercaptopropionic acid sites with 4-(dimethylamino) pyridine (DMAP; Aldrich) as described in the next paragraph. The QDs then dispersed readily in water, producing orange solutions that were stable for up to a week at room temperature.

To attach oligonucleotides to QDs, 150 µL (optical density at 530 nm=21.4) of a solution of the 3-mercaptopropionic acid functionalized particles in DMF were added to a solution of DMAP (8.0 mg, 0.065 mmol) in 0.4 mL of DMF. An orange precipitate was formed. It was separated by centrifugation (~30 seconds at 3000 rpm) and then dissolved in 1.0 mL of a solution of 3' propylthiol- or 5' hexylthiol-terminated oligonucleotides (1.0–2.0 ODs/mL; prepared as described in Example 1; sequences given below). Precipitate (dissolved in water) was characterized by IR spectroscopy (polyethylene card, 3M). IR (cm$^{-1}$): 1647 (m), 1559 (s), 1462 (m), 1214 (w), 719 (w), 478 (s). After standing for 12 hours, the oligonucleotide-containing solution was brought to 0.15 M NaCl, and the particles were aged for an additional 12 hours. The NaCl concentration was then raised to 0.3 M, and the mixture was allowed to stand for a further 24–40 hours before dialyzing against PBS (0.3 M NaCl, 10 mM phosphate buffer, pH 7, 0.01% sodium azide) using a 100 kDa membrane (Spectra/Por Cellulose Ester Membrane). The dialysis was carried out over a period of 48 hours, during which time the dialysis bath was refreshed three times.

Oligonucleotide-QD conjugates prepared in this manner displayed indefinite aqueous stability. Moreover, the colloid remained strongly fluorescent, with a sharp [fall width at half maximum (FWHM)=33 nm], symmetrical emission at 546 nm (indicative of a ~3.2 nm CdSe core; Murray et al., *J. Am. Chem. Soc.* 1993, 115, 8706).

Two different oligonucleotide-QD conjugates were prepared by this protocol and is stored in PBS. One was modified with a 22 mer, comprised of a propylthiol functionality at the 3'-end, a 12 mer capture sequence, and an intervening 10 base (all A) spacer: 5'-TCTCAACTCGTAA$_{10}$-(CH$_2$)$_3$—SH [SEQ ID NO: 46]. The other employed a 5'-hexylthiol-terminated sequence, also with a 10 base (all A) spacer, and a 12 mer capture sequence which was non-complementary with the 3'-propylthiol sequence: 5'-SH—(CH$_2$)$_6$—A$_{10}$CGCATTCAGGAT-3' [SEQ ID NO: 47].

C. Preparation of QD Assemblies

Figure 26A:
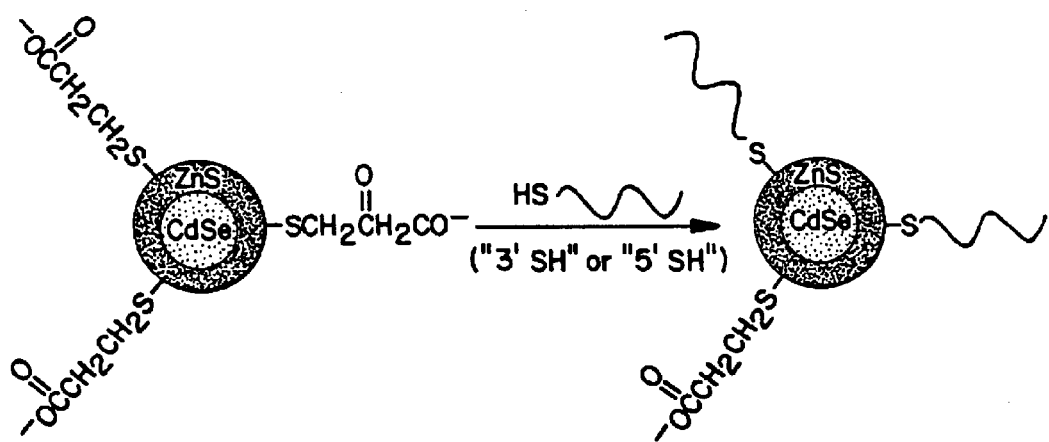
FIG. 26: Schematic diagram illustrating systems for forming assemblies of CdSe/ZnS core/shell quantum dots (QD).
Figure 26B:
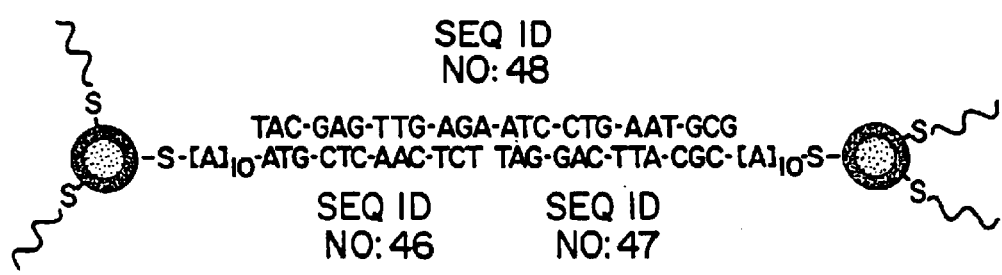

When approximately equal quantities of these two oligonucleotides (200 µL, OD$_{530}$=0.224 and 0.206, respectively) were mixed and then combined with 6 µL (60 pmol) of a solution of a complementary linking 24 mer sequence (5'-TACGAGTTGAGAATCCTGAATGCG-3', SEQ ID NO: 48), QD assemblies formed within 20–30 minutes at room temperature, FIG. 26. Faster linking took place when the mixture was frozen (−78° C.) and then allowed to warm slowly to room temperature.

The clusters generated were not large enough to settle out of solution. However, they could be separated by centrifugation at relatively low speeds (10,000 RPM for 10 min), as compared with the unlinked particles (30,000 RPM for 2–3 hours).

The decrease in fluorescence upon hybridization was determined by integration of the fluorescence signal (320 nm excitation wavelength) from 475 nm to 625 nm of 4 pairs of samples. Each pair was prepared in the following manner. A solution of 3' propylthiol-terminated DNA-modified particles (30 µL, optical density at 530 nm=0.224) was combined with a solution of 5' hexylthiol-terminated DNA-modified QDs (30 µL, optical density at 530 nm=0.206) in an Eppendorf centrifuge tube, and then diluted with 140 µL of PBS. The mixture was then split into two equal portions, and complementary "linker" DNA (3 µL, 30 pmol) was added to one, while non-complementary "linker" DNA (5'-CTACTTAGATCCGAGTGCCCACAT-3', SEQ ID NO: 49) (3 µL, 30 pmol) was added to the other. All eight of the samples were then frozen in a dry ice/acetone bath (−78° C.), after which they were removed from the bath and allowed to warm slowly to room temperature. To estimate the change in fluorescence efficiency upon hybridization, the fluorescence intensities of the "target" (complementary "linker") samples were adjusted to account for the difference in absorbance at 320 nm from the corresponding control samples, which contained non-complementary "linker".

Figure 27A:
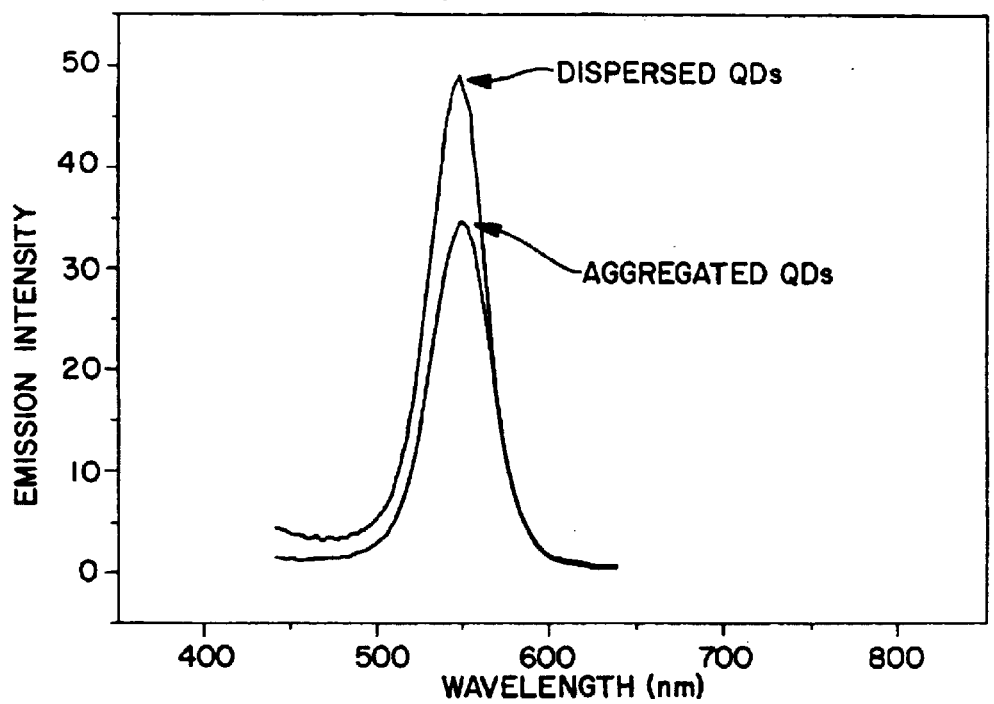
FIGS. 27A–D.

The results showed that hybridization of QD/QD assemblies was accompanied by a decrease in integrated fluorescence intensity by an average of 26.4±6.1%, and a ~2 nm red shift of the emission maximum, presumably due to cooperative effects between QDs, FIG. 27A. Interestingly, Bawendi, et al. noticed a similar, albeit slightly larger, red shift when comparing the fluorescence of close-packed QDs and widely separated dots isolated in a frozen matrix (Murray et al., *Science* 1995, 270, 1335). These changes in the fluorescence spectra may be an indication of excimer formation between QDs, but the exact nature of such a complex is still largely a matter of speculation. As expected, no aggregation was observed when the "linker" was missing or not complementary, or when either one of the two types of particles was absent.

The "melting" behavior of the DNA was monitored by observing the UV-Vis spectra of the aggregates as a function of temperature. For this "melting" analysis, the precipitate containing the QD/QD assemblies was centrifuged at 10,000 rpm for 10 minutes, washed with 7 µL of PBS, recentrifuged, and suspended in 0.7 mL of PBS. The UV/Visible spectroscopic signature of the assemblies was recorded at two degree intervals as the temperature was increased from 25° C. to 75° C., with a holding time of 1 minute prior to each measurement. The mixture was stirred at a rate of 500 rpm to ensure homogeneity throughout the experiment. Temperature vs extinction profiles were then compiled from the extinction at 600 nm. The first derivative of these profiles was used to determine the "melting" temperatures.

Figure 27B:
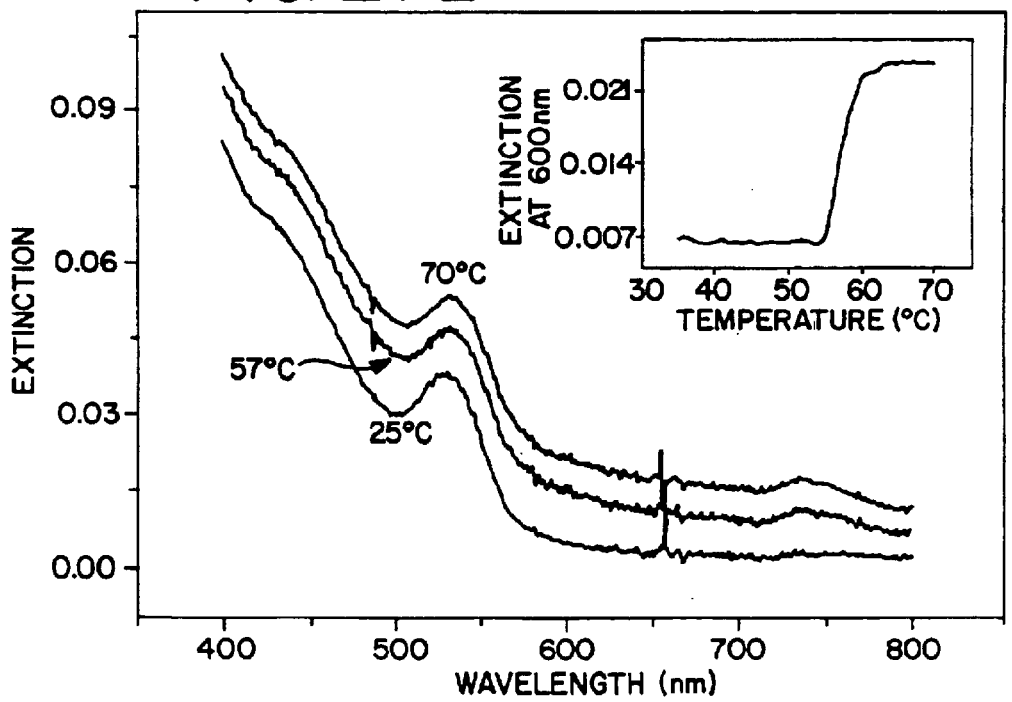

The results, FIG. 27B ($T_m$=57° C.), demonstrated conclusively that DNA had been immobilized on the QD surfaces and that hybridization was responsible for the assembly process. The transition also was extremely sharp when compared with DNA alone (FWHM of the respective first derivatives: 4° C. vs 9° C.), which is consistent with the formation of an aggregate structure with multiple DNA links per particle. An increase in extinction was observed upon denaturation, most likely because of a screening effect whereby particles in the interiors of the assemblies are prevented from absorbing light by the surrounding QDs.

D. Preparation Of QD/Gold Assemblies

With DNA-functionalized QDs in hand, the assembly of hybrid assemblies made from multiple types of nanoparticle building blocks became feasible. To prepare these hybrid assemblies, a solution of ~17 nM 3'-hexylthiol-modified 13 nm gold nanoparticles (30 µL, ~5 fmol; prepared as described in Example 3) was mixed with a solution of 5'-hexylthiol-terminated DNA-modified QDs (15 µL, optical density at 530 nm=0.206) in an Eppendorf centrifuge tube. "Linker" DNA (5 µL, 50 pmol) was added, and the mixture cooled to −78° C., and then allowed to warm slowly to room temperature, generating a reddish-purple precipitate. No aggregation behavior was observed unless both types of particles and a complementary target were present. After centrifugation (1 min at 3,000 rpm) and removal of the supernatant, the precipitate was washed with 100 µL of PBS and recentrifuged.

For "melting" analysis, the washed precipitate was suspended in 0.7 mL of PBS. UV-Vis spectroscopy was used to follow the changes in the surface plasmon resonance of the gold nanoparticles, so temperature vs. extinction profiles were compiled at 525 nm. Using the surface plasmon resonance of the gold nanoparticles provides a much more sensitive probe with which to monitor hybridization than does the UV-Vis spectroscopic signature of the QDs alone. Therefore, a "melting" experiment can be performed on a much smaller sample (~10% of the QD solution is needed), although the intensity of the plasmon band obscures the UV/Vis signal from the QDs. Similar to the pure QD system described above, a sharp (FWHM of the first derivative=4.5° C.) melting transition occurred at 58° C. (see FIG. 27D).

Figure 27C:
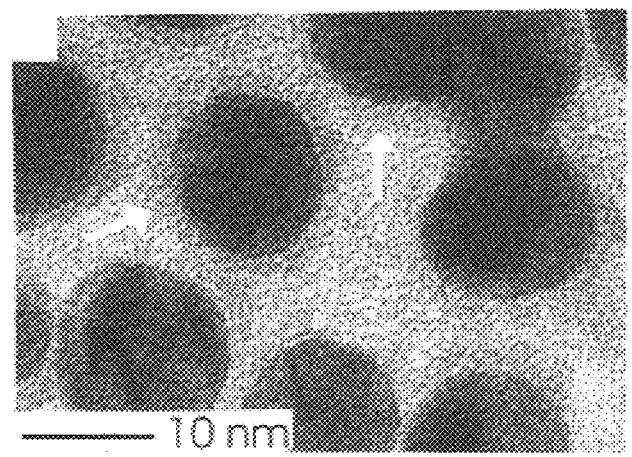
Figure 27D:
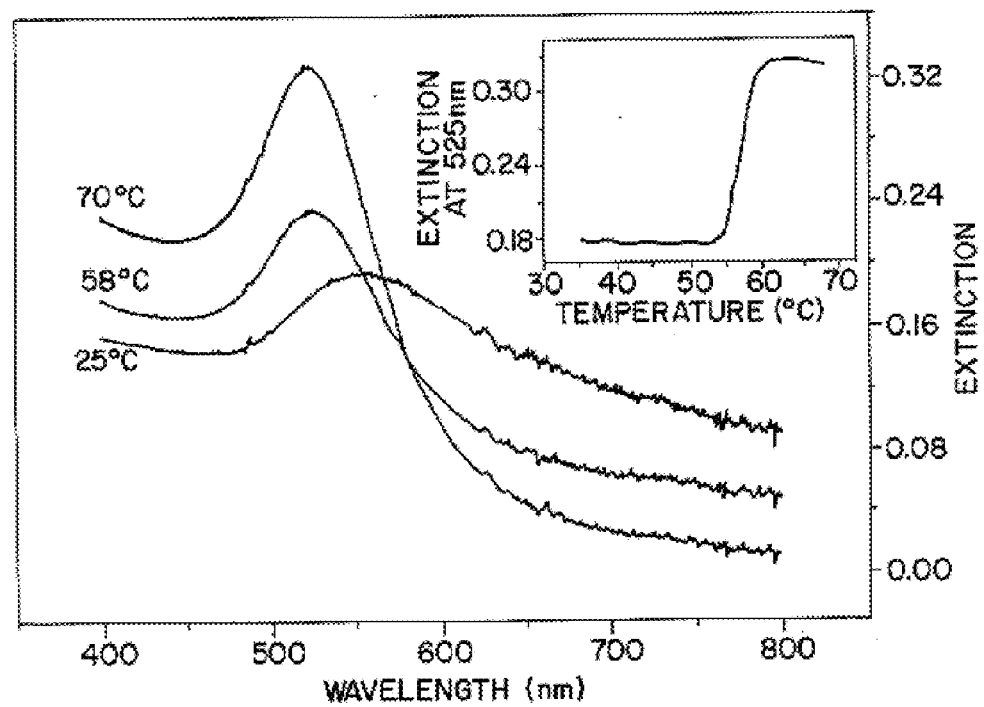

High resolution TEM images of these assemblies showed a network of gold nanoparticles interconnected by multiple QDs, FIG. 27C. The QDs, which have a much lower contrast in the TEM image than gold nanoparticles, can be identified by their lattice fringes. They are just barely resolvable with the high resolution TEM, but clearly indicate the periodic structure of these composite assemblies and the role that DNA plays in forming them.

E. Summary

The results described in this example definitively establish that the immobilization of DNA onto QD surfaces has been achieved and that these particles can now be used in combination with DNA under hybridization conditions. Using DNA-functionalized QDs, the first DNA-directed formation of QD and mixed gold/QD nanoparticle structures has been demonstrated. The successful modification of semiconductor QDs with DNA has significant implications for materials research, and the door is now open for more extensive inquiries into the luminescent, electronic, and chemical properties of these unique building blocks as they are incorporated into new and functional multi-component nanostructures and nanoscale materials.

Example 18

Methods of Synthesizing Oligonucleotide-Nanoparticle Conjugates and the Conjugates Produced by the Methods

A. General Methods $HAuCl_4 \cdot 3H_2O$ and trisodium citrate were purchased from Aldrich chemical company, Milwaukee, Wis. Gold wire, 99.999% pure, and titanium wire were purchased from Goldsmith Inc., Evanston, Ill. Silicon wafers (100) with a 1 micron thick oxide layer were purchased from Silicon Quest International, Santa Clara, Calif. 5'-thiol-modifier C6-phosphoramidite reagent, 3'-propylthiol modifier CPG, fluorescein phosphoramidite, and other reagents required for oligonucleotide synthesis were purchased from Glen Research, Sterling, Va. All oligonucleotides were prepared using an automated DNA synthesizer (Expedite) using standard phosphoramidite chemistry (Eckstein, F. *Oligonucleotides and Analogues;* 1st ed.; Oxford University Press, New York, 1991). Oligonucleotides containing only 5' hexylthiol modifications were prepared as described in Example 1. 5-(and 6)-carboxyfluorescein, succinimidyl ester was purchased from Molecular Probes, Eugene, Oreg. NAP-5 columns (Sephadex G-25 Medium, DNA grade) were purchased from Pharmacia Biotech. Nanopure $H_2O$ (>18.0 MΩ), purified using a Barnstead NANOpure ultrapure water system, was used for all experiments. An Eppendorf 5415C or a Beckman Avanti 30 centrifuge was used for centrifugation of Au nanoparticle solutions. High Performance Liquid Chromatography (HPLC) was performed using a HP series 1100 HPLC.

B. Physical Measurements

Electronic absorption spectra of the oligonucleotide and nanoparticle solutions were recorded using a Hewlett-Packard (HP) 8452a diode array spectrophotometer. Fluorescence spectroscopy was performed using a Perkin-Elmer LS50 fluorimeter. Transmission Electron Microscopy (TEM) was performed with a Hitachi 8100 Transmission Electron Microscope operating at 200 kV. A Thermo Jarrell Ash AtomScan 25 atomic emission spectrometer with an inductively coupled plasma (ICP) source was used to determine the atomic concentration of gold in the nanoparticle solutions (gold emission was monitored at 242.795 nm).

C. Synthesis and Purification of Fluorescein-Labeled Alkanethiol-Modified Oligonucleotides Thiol-modified oligonucleotide strands containing either 12 or 32 bases, with 5' hexylthiol and 3' fluorescein moieties, were prepared. The sequence of the 12 mer (S12F) was $HS(CH_2)_6$-5'-CGC-ATT-CAG-GAT-3'-$(CH_2)_6$-F [SEQ ID NO:50], and the 32 mer ($SA_{20}12F$) contained the same 12 mer sequence with the addition of a 20 dA spacer sequence to the 5' end [SEQ ID NO:51]. The thiol-modified oligonucleotides were prepared as described in Storhoff et al., *J. Am. Chem. Soc.* 120:1959–1964 (1998). An amino-modifier C7 CPG solid support was used in automated synthesis, and the 5' terminus was manually modified with hexylthiol phosphoramidite, as described previously. The 3' amino, 5' trityl-protected thiol modified oligonucleotides were purified by reverse-phase HPLC using an HP ODS Hypersil column (5 mm, 250×4 mm) with 0.03 M triethyl ammonium acetate (TEAA), pH 7 and a 1%/minute gradient of 95% $CH_3CN$/5% 0.03 M TEAA at a flow rate of 1 mL/min., while monitoring the UV signal of DNA at 254 nm. The retention times of the 5'-S-trityl, 3' amino modified 12-base and 32-base oligonucleotides were 36 and 32 minutes respectively.

The lyophilized product was redispersed in 1 ml of 0.1 M $Na_2CO_3$ and, while stirring in the dark, 100 µL of 10 mg/ml succinimidyl ester of fluorescein (5, 6 FAM-SE, Molecular Probes) in dry DMF was added over 1.5 hours according to the directions of the manufacturer (Molecular Probes literature). The solution was stirred at room temperature for an additional 15 hours, then precipitated from 100% ethanol at −20° C. The precipitate was collected by centrifugation, dissolved in H$_2$O and the coupled product separated from unreacted amino-terminated oligonucleotide by ion-exchange HPLC. A Dionex Nucleopac PA-100 column (250×4 mm) was operated with 10 mM NaOH aqueous eluent and a 1%/minute gradient of 1 M NaCl/10 mM NaOH at a flow rate of 0.8 mL/minute. Retention times of 5'-S-trityl, 3' fluorescein modified 12 mer and 32 mer were 50 and 49 minutes respectively. The oligonucleotide product was desalted by reverse-phase HPLC. Removal of the trityl protection group of the fluorescein-terminated, trityloligo-nucleotide was performed using silver nitrate and dithio-threitol (DTT) as previously described (Storhoff et al., *J. Am. Chem.Soc.* 120:1959–1964 (1998)). The yield and purity of the oligonucleotides were assessed using the techniques previously described for alkylthiol oligonucleotides (Storhoff et al., *J. Am. Chem.Soc.* 120:1959–1964 (1998)). Oligonucleotides were used immediately after detritylation of the thiol group.

Thiol-modified oligonucleotides containing 32 bases, with 3' propylthiol and 5' fluorescein moieties (HS(CH$_2$)$_3$-3'-(W)$_{20}$-TAG-GAC-TTA-CGC-5'-(CH$_2$)$_6$—F, W=A or T) [SEQ ID NO:52] were synthesized on an automated synthesizer using 3' thiol modifier CPG. The 5' terminus of each oligonucleotide was coupled manually to fluorescein phos-phoramidite (6-FAM, Glen Research). The modified oligo-nucleotides were purified by ion exchange HPLC (1%/min gradient of 1 M NaCl, 10 mM NaOH; retention time (Rt)~48 min (W=T), Rt~29 min (W=A)). After purification, the oligonucleotide solutions were desalted by reverse phase HPLC. The 3' thiol moieties were deprotected with dithio-threitol by a procedure previously described (Storhoff et al., *J. Am. Chem.Soc.* 120:1959–1964 (1998)).

D. Synthesis and Purification of Fluorescein Labeled Oligonucleotides

The fluorophore labeled complement (12' F.) consisted of 12 bases 3-GCG-TAA-GTC-CTA-5'-(CH$_2$)$_6$—F [SEQ ID NO:53] complementary to the 12 mer sequence in S12F and SA$_{20}$12F. The oligonucleotide was synthesized using standard methods, and a syringe-based procedure, similar to the procedure reported above for the 5' alkylthiol modification, was used to couple fluorescein phosphoramidite (6-FAM, Glen Research) to the 5' end of the CPG-bound oligonucle-otide. Purification was performed using reverse-phase HPLC as above. The fluorescein-labeled oligonucleotide had a retention time of 18 min. The fluorophore labeled complement, 3'12F (5'-ATC-CTG-AAT-GCG-F; [SEQ ID NO:54]) was prepared using an amino-modifier C7 CPG solid support for automated synthesis, followed by coupling of 5-(6)-carboxyfluorescein succinimidyl ester to the 3' amine using the procedure described above.

E. Preparation and Characterization of Gold Nanoparticles

Gold nanoparticles were prepared by citrate reduction of HAuCl$_4$ as described in Example 1. Transmission Electron Microscopy (TEM) performed with a Hitachi 8100 TEM was used to determine the size distribution of the resulting nanoparticles. At least 250 particles were sized from TEM negatives using graphics software (ImageTool). The average diameter of a typical particle preparation was 15.7±1.2 nm. Assuming spherical nanoparticles and density equivalent to that of bulk gold (19.30 g/cm$^2$), an average molecular weight per particle was calculated (2.4×10$^7$ g/mol). The atomic gold concentration in a solution of gold nanoparticles was determined by ICP-AES (inductively coupled plasma atomic emission spectroscopy). A gold atomic absorption standard solution (Aldrich) was used for calibration. Comparison of atomic gold concentration in the particle solution to the average particle volume obtained by TEM analysis yielded the molar concentration of gold particles in a given preparation, typically ~10 nM. By measuring the UV-vis absorbance of nanoparticle solutions at the surface plasmon frequency (520 nm), the molar extinction coefficients ($\epsilon$ at 520 nm) were calculated for the particles, typically 4.2×10$^8$ M$^{-1}$ cm$^{-1}$ for 15.7±1.2 nm diameter particles.

F. Preparation of Gold Thin Films

Silicon wafers were cut into ~10 mm×6 mm pieces and cleaned with piranha etch solution (4:1 concentrated H$_2$SO$_4$:30% H$_2$O$_2$) for 30 min at 50° C., then rinsed with copious amounts of water, followed by ethanol. (Warning: piranha etch solution reacts violently with organic materials and should be handled with extreme caution.) Metal was deposited at a rate of 0.2 nm/s using an Edwards Auto 306 evaporator (base pressure of 3×10$^{-7}$ millibar) equipped with an Edwards FTM6 quartz crystal microbalance. The oxidized sides of the silicon were coated with a Ti adhesion layer of 5 nm, followed by 200 nm of gold.

G. Preparation of 5' Alkylthiol Oligonucleotide-Modified Gold Nanoparticles

Gold nanoparticles were modified with fluorescein-alkylthiol oligonucleotides by adding freshly deprotected oligonucleotides to aqueous nanoparticle solution (particle concentration ~10 nM) to a final oligonucleotide concentration of 3 $\mu$M. After 24 hours, the solution was buffered at pH 7 (0.01 M phosphate), and NaCl solution was added (to final concentration of 0.1 M). The solution was allowed to 'age' under these conditions for an additional 40 hours. Excess reagents were then removed by centrifugation for 30 minutes at 14,000 rpm. Following removal of the supernatant, the red oily precipitate was washed twice with 0.3 M NaCl, 10 mM phosphate buffer, pH 7, solution (PBS) by successive centrifugation and redispersion, then finally redispersed in fresh buffer solution. Invariably, a small amount (~10% as determined by UV-vis spectroscopy) of nanoparticle is discarded with the supernatant during the washing procedure. Therefore, final nanoparticle concentrations were determined by TEM, ICP-AES, and UV-vis spectroscopy (see above). Extinction coefficients and particle size distributions did not change significantly as a result of the oligonucleotide modification.

H. Preparation of 5' Alkylthiol Oligonucleotide-Modified Gold Thin Films

Silicon supported gold thin films were immersed in deposition solutions of deprotected alkylthiol modified oligonucleotides for equal times and buffer conditions as for the gold nanoparticles. Following oligonucleotide deposition, the films were rinsed extensively with 0.3 M PBS and stored in buffer solution. Gold was evaporated on one side only, leaving an unpassivated silicon/silicon oxide face. However, alkylthiol modified DNA did not adsorb appreciably to bare silicon oxide surfaces that were rinsed with PBS.

I. Quantitation of Alkylthiol-Oligonucleotides Loaded on Nanoparticles

Mercaptoethanol (ME) was added (final concentration 12 mM) to fluorophore-labeled oligonucleotide modified nanoparticles or thin films in 0.3 M PBS, to displace the oligonucleotides. After 18 hours at room temperature with intermittent shaking, the solutions containing displaced oligonucleotides were separated from the gold by either centrifugation of the gold nanoparticles, or by removal of the gold thin film. Aliquots of the supernatant were diluted two-fold by addition of 0.3 M PBS, pH 7. Care was taken to keep the pH and ionic strength of the sample and calibration standard solutions the same for all measurements due to the sensitivity of the optical properties of fluorescein to these conditions (Zhao et al., *Spectrochimica Acta* 45A:1113–1116(1989)). The fluorescence maxima (measured at 520 nm) were converted to molar concentrations of the fluorescein-alkylthiol modified oligonucleotide by interpolation from a standard linear calibration curve. Standard curves were prepared with known concentrations of fluorophore-labeled oligonucleotides using identical buffer and salt concentrations. Finally, the average number of oligonucleotides per particle was obtained by dividing the measured oligonucleotide molar concentration by the original Au nanoparticle concentration. Normalized surface coverage values were then calculated by dividing by the estimated particle surface area (assuming spherical particles) in the nanoparticle solution. The assumption of roundness is based on a calculated average roundness factor of 0.93. Roundness factor is computed as: (4×pi×Area)/(perimeter× 2) taken from Baxes, Gregory, *Digital Image Processing*, p. 157 (1994).

J. Quantitation of the Hybridized Target Surface Density

To determine the activity of attached oligonucleotides for hybridization, fluorophore-labeled oligonucleotides, which were complementary to the surface-bound oligonucleotides (12'F), were reacted with oligonucleotide modified surfaces (gold nanoparticles or thin films) under hybridization conditions (3 μM complementary oligonucleotide, 0.3 M PBS, pH 7, 24 hr). Non-hybridized oligonucleotides were removed from the gold by rinsing twice with buffered saline as described above. Then, the fluorophore-labeled oligonucleotides were dehybridized by addition of NaOH (final concentration ~50 mM, pH 11–12, 4 hr). Following separation of the solution containing the 12'F from the nanoparticle solutions by centrifugation, and neutralization of the solutions by addition of 1 M HCl, the concentrations of hybridized oligonucleotide and corresponding hybridized target surface density were determined by fluorescence spectroscopy.

K. Quantitation of Surface Coverage and Hybridization

Citrate stabilized gold nanoparticles were functionalized with 12 mer fluorescein-modified alkylthiol DNA (HS—$(CH_2)_6$-5'-CGC-ATT-CAG-GAT-$(CH_2)_4$—F [SEQ ID NO:50]). Surface coverage studies were then performed by thoroughly rinsing away non-chemisorbed oligonucleotides, followed by removal of the fluorophore-labeled oligonucleotides from the gold surface, and quantitation of oligonucleotide concentration using fluorescence spectroscopy (as described above).

Removal of all the oligonucleotides from the gold surface and subsequent removal of gold nanoparticles from the solution is critical for obtaining accurate coverage data by fluorescence for several reasons. First, the fluorescence signal of labeled, surface bound DNA is efficiently quenched as a result of fluorescence resonance energy transfer (FRET) to the gold nanoparticle. Indeed, there is almost no measurable signal for fluorescein-modified oligonucleotides (12–32 nucleotide strands, sequences are given above) after they are immobilized on 15.7±1.2 nm gold nanoparticles and residual oligonucleotide in solution is washed away. Second, the gold nanoparticles absorb a significant amount of light between 200 nm and 530 nm, so their presence in solution during fluorescence measurements acts as a filter and diminishes the available excitation energy, as well as the intensity of emitted radiation. The gold surface plasmon band at 520 nm falls at the emission maximum of fluorescein.

Figure 29:
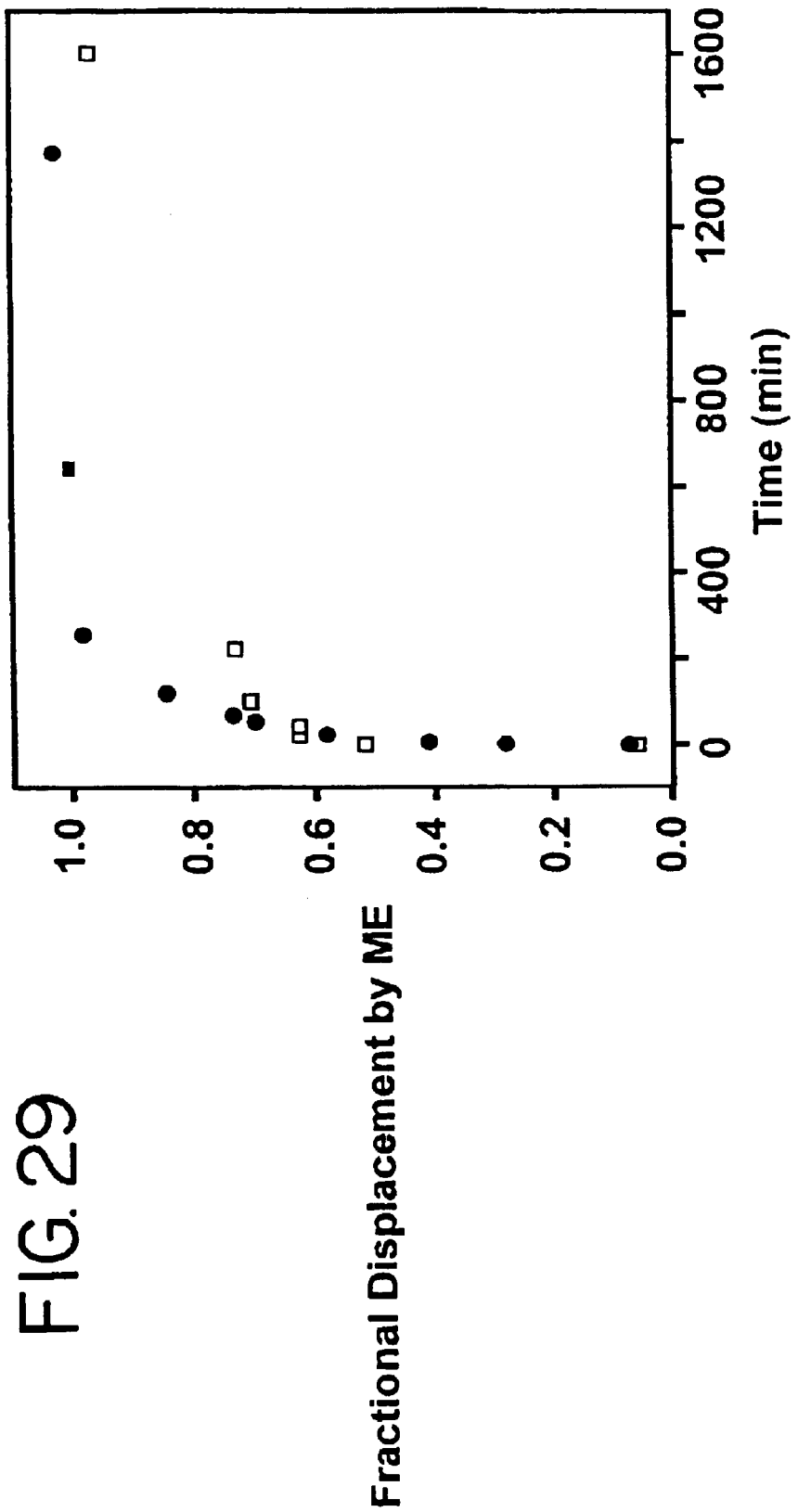
FIG. 29: Graph of fractional displacement of oligonucleotides by mercaptoethanol from nanoparticles (closed circles) or gold thin films (open squares) to which the oligonucleotides had been attached.

Mercaptoethanol (ME) was used to rapidly displace the surface bound oligonucleotides by an exchange reaction. To examine the displacement kinetics, oligonucleotide-modified nanoparticles were exposed to ME (12 mM) for increasing periods of time prior to centrifugation and fluorescence measurements. The intensity of fluorescence associated with the solution free of nanoparticles can be used to determine how much oligonucleotide was released from the nanoparticles. The amount of oligonucleotide freed in exchange with ME increased until about 10 hours of exposure (FIG. 29), which is indicative of complete oligonucleotide displacement. The displacement reaction was rapid, which is presumably due to the inability of the oligonucleotide film to block access of the ME to the gold surface (Biebuyck et al., *Langmuir* 9:1766 (1993)).

The average oligonucleotide surface coverage of alkylthiol-modified 12 mer oligonucleotide (S12F) on gold nanoparticles was 34±1 pmol/cm$^2$ (average of ten independent measurements of the sample.) For 15.7±1.2 nm diameter particles, this corresponds to roughly 159 thiol-bound 12 mer strands per gold particle. Despite slight particle diameter variation from batch to batch, the area-normalized surface coverages were similar for different nanoparticle preparations.

In order to verify that this method is useful for obtaining accurate oligonucleotide surface coverages, it was used to displace flourophore-labeled oligonucleotides from gold thin films, and the surface coverage data was compared with experiments aimed at getting similar information but with different techniques. In these experiments, gold thin films were subjected to a similar oligonucleotide modification and ME displacement procedure as the citrate stabilized gold nanoparticles (see above). The oligonucleotide displacement versus time curves for the gold thin films are very similar to those measured for gold nanoparticles. This suggests a similar rate of displacement for the thin films, even though the typical surface coverage values measured for these films were somewhat lower than the oligonucleotide coverages on gold nanoparticles. Importantly, the oligonucleotide surface coverages on gold thin films measured by our technique (18±3 pmol/cm$^2$) fall within the range of previously reported coverages on oligonucleotide thin films (10 pmol/cm$^2$ for a 25 base oligonucleotide on gold electrodes determined using electrochemistry or surface plasmon resonance spectroscopy (SPRS) (Steel et al., *Anal. Chem.* 70:4670–4677 (1998)). Differences in surface coverages are expected due to different oligonucleotide sequences and lengths, as well as film preparation methods.

The extent of hybridization of complementary fluorophore-labeled oligonucleotides (12F') to nanoparticles with surface-bound 12 mer oligonucleotides was measured as described above. Briefly, S12F modified nanoparticles were exposed to 12F' at a concentration of 3 μM for 24 hours under hybridization conditions (0.3 M PBS, pH 7) and then rinsed extensively with buffer solution. Again, it was necessary to remove the hybridized strands from the gold before measuring fluorescence. This was accomplished by denaturing the duplex DNA in a high pH solution (NaOH, pH 11) followed by centrifugation. Hybridized 12'F amounted to 1.3±0.2 pmol/cm$^2$ (approximately 6 duplexes per 15.7 nm particle; the average number of duplexes per particle was computed by multiplying the normalized hybridized surface coverage in pmol/cm$^2$by the average particle surface area as found from size distributions measured by TEM.). In order to measure the extent of non-specific adsorption, S12F modified gold nanoparticles were exposed to fluorophore-labeled non-complementary 12 base oligonucleotides (12F') in 0.3 M PBS. After extensive rinsing (successive centrifugation/redispersion steps) and subsequent high pH treatment, the coverage of non-specifically adsorbed oligonucleotides on the nanoparticles was determined to be on the order of 0.1 pmol/cm$^2$. An analogous procedure was used to measure hybridization to S12F modified gold thin films in order to compare the hybridization results to reported values on gold electrodes. The degree of hybridization, 6±2 pmol/cm$^2$, was consistent with hybridization reported for mixed base 25 mer on an gold electrode (2–6 pmol/cm$^2$) (Steel et al., Anal. Chem. 70:4670–4677 (1998)).

Surface coverages and hybridization values of the S12F/12F' system for both nanoparticles and thin films are summarized in Table 7. The most striking result is the low hybridization efficiency (~4% of surface-bound strands on nanoparticles while 33% of strands on thin films hybridize). Previous studies have shown similarly low hybridization for sufficiently densely packed oligonucleotide monolayers. This may reflect a low accessibility to incoming hybridizing strands, due to a combination of steric crowding of the bases, especially those near the gold surface, as well as electrostatic repulsive interactions.

L. Effect of Oligonucleotide Spacer on Surface Coverage and Hybridization

Although the high coverage of the S12F oligonucleotide is advantageous in terms of nanoparticle stabilization, the low hybridization efficiency prompted us to devise a means of decreasing steric congestion around the hybridizing sequence. Oligonucleotides (32 mer) were synthesized having a 20 dA spacer sequence inserted between the alkylthiol group and the original 12 base recognition sequence. This strategy was chosen based on the assumption that: 1) bases near the nanoparticle surface are sterically inaccessible because of weak interactions between the nitrogenous bases and the gold surface, as well as interstrand steric crowding, and 2) on a 15.7 nm diameter roughly spherical particle, 12 mer sequences attached to the end of 20 mer spacer units roughly perpendicular to the surface (Levicky et al., *J. Am. Chem. Soc.* 120:9787–9792 (1998)) will lead to a film with a greater free volume as compared with a film formed from the same 12 mer directly bound to the surface.

While the surface density of single-stranded SA$_{20}$12F strands (15±4 pmol/cm$^2$) was lower than that of S12F (34±1 pmol/cm$^2$), the particles modified with a 32-mer using the identical surface modification showed comparable stability compared to those modified with 12-mer. As anticipated, the hybridization efficiency of the SA$_{20}$12F/12F' system (6.6±0.2 pmol/cm$^2$, 44%) was increased to approximately 10 times that of the original S12F/12F' system, Table 7.

M. Effect of Electrolyte Concentration During Oligonucleotide Attachment

In working with the S12F sequence a salt aging step was found to be crucial in obtaining stable oligonucleotide modified nanoparticles (see Example 3). The gold nanoparticles modified with S12F in pure water fused together irreversibly to form a black precipitate upon centrifugation, while those aged in salt resisted aggregation when centrifuged, even in high ionic strength solutions. It is proposed that the increased stability is due to higher oligonucleotide surface coverages which leads to greater steric and electrostatic protection. Using the SA$_{20}$12F modified particles, the effect of electrolyte conditions on oligonucleotide surface loading was investigated. As shown in Table 8, final surface coverages for gold nanoparticles which were exposed to oligonucleotides in water for 48 hours are much lower (7.9±0.2 pmol/cm$^2$) compared to those that were 'aged' in salt, or prepared by increasing the salt concentration gradually over the course of the final 24 hours of the experiment (see above).

It is important to note that gold nanoparticles as synthesized irreversibly agglomerate even in very low ionic strength media. Indeed, they are naturally incompatible with salts and especially polyanions such as oligonucleotides. This aging treatment is essential for preparing stable oligonucleotide particles. Therefore, the particles must be initially modified with alkylthiol oligonucleotides in water prior to gradually increasing the ionic strength. It is likely that oligonucleotides initially lie flat, bound through weak interactions of the nitrogenous bases with gold. A similar mode of interaction has been proposed for oligonucleotides on thin films (Heme et al., *J. Am. Chem. Soc.* 119:8916–8920 (1997)). However, the interaction between oligonucleotides and the positively charged nanoparticle surface (Weitz et al., *Surf. Sci.* 158:147–164 (1985)) is expected to be even stronger. In the aging step, the high ionic strength medium effectively screens charge repulsion between neighboring oligonucleotides, as well as, attraction between the polyanionic oligonucleotide and the positively charged gold surface. This allows more oligonucleotides to bind to the nanoparticle surface, thereby increasing oligonucleotide surface coverage.

N. Effect of Oligonucleotide Spacer Sequence on Surface Coverage

In order to examine how the sequence of the spacer affects oligonucleotide coverage on Au nanoparticles, fluorescein-modified 32-mer strands, with 20 dA and 20 dT spacers inserted between a 3' propylthiol and the fluorescein-labeled 12-mer sequence, were prepared. The most notable result of surface coverage and hybridization studies of nanoparticles modified with S3'T$_{20}$12F and S3'A$_{20}$12F is the greater surface coverage achieved with the 20 dT spacer (35±1 pmol/cm$^2$), in comparison to the 20 dA spacer (24±1 pmol/cm$^2$). The number of hybridized strands was comparable, although the percentage of surface bound strands which hybridized was lower for ST$_{20}$12 mer nanoparticles (79%) than the SA$_{20}$12 nanoparticles (~94%). These results suggest that dT rich oligonucleotide strands interact non-specifically with the nanoparticle surface to a lesser degree than dA rich oligonucleotide strands. Consequently, 20 dT spacer segments may extend perpendicular from the gold surface, promoting higher surface coverages, while 20 dA spacer segments block gold sites by lying flat on the particle surface.

O. Effect of Coadsorbed Diluent Oligonucleotides

In addition to efficient hybridization, another important property of oligonucleotide modified nanoparticles is the possibility of adjusting the total number of hybridization events. This is most readily accomplished by adjusting the surface density of recognition strands. Other researchers have used coadsorbed diluent alkylthiols such as mercaptohexanol with modified oligonucleotides on gold electrodes to control hybridization (Steel et al., *Anal. Chem.* 70:4670–4677 (1998); Herne et al., *J. Am. Chem. Soc.* 119:8916–8920 (1997)). However, the inherent low stability of unprotected gold nanoparticles poses serious constraints on the choice of diluent molecule. A thiol modified 20 dA sequence ($SA_{20}$) [SEQ ID NO:55] proved to be suitable in terms of maintaining particle stability in the high ionic strength buffers which are needed for hybridization and protecting the surface from non-specific adsorption.

Figure 30:
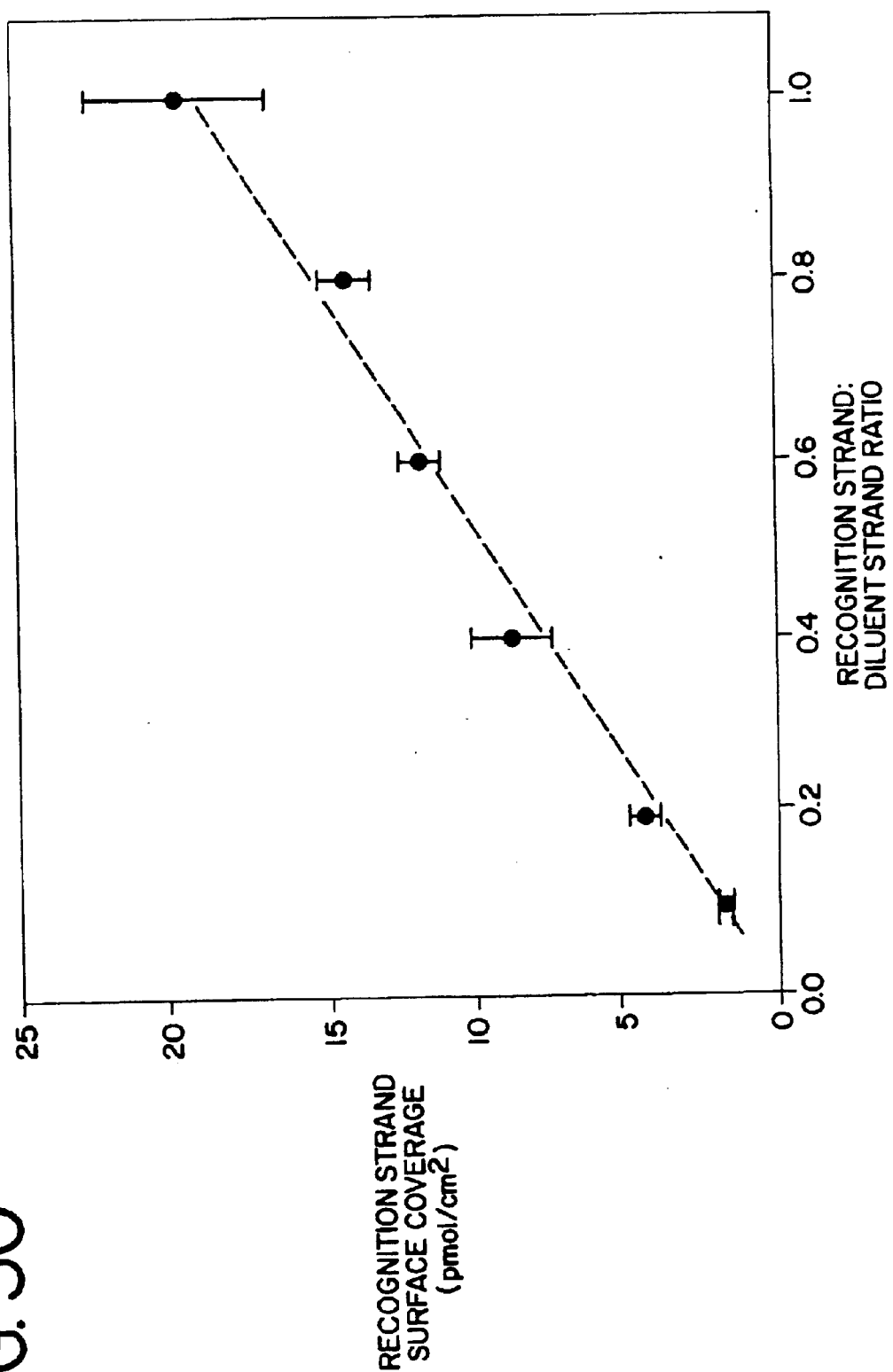
FIG. 30: Graph of surface coverages of recognition oligonucleotides on nanoparticles obtained for different ratios of recognition:diluent oligonucleotides used in the preparation of the nanoparticle-oligonucleotide conjugates.

Nanoparticles were modified using solutions containing different recognition strand ($SA_{20}12F$) to diluent ($SA_{20}$) strand molar ratios. The resulting particles were analyzed by the fluorescence method described above to determine the $SA_{20}12F$ surface density, and then tested for hybridization efficiency with 12'F The $SA_{20}12F$ surface density increased linearly with respect to the proportion of $SA_{20}12F$ to $SA_{20}$ in the deposition solution, FIG. 30. This is an interesting result because it suggests that the ratio of $SA_{20}12F$ to $SA_{20}$ attached to the nanoparticles reflects that of the solution. This result is in contrast to what is normally seen for mixtures of short chain alkyl or ω-functionalized thiols, where solubility and chain length play a crucial role in adsorption kinetics (Bain et al., *J. Am. Chem. Soc.* 111:7155–7164(1989); Bain et al., *J. Am. Chem. Soc.* 111:7164–7175 (1989)).

Figure 31:
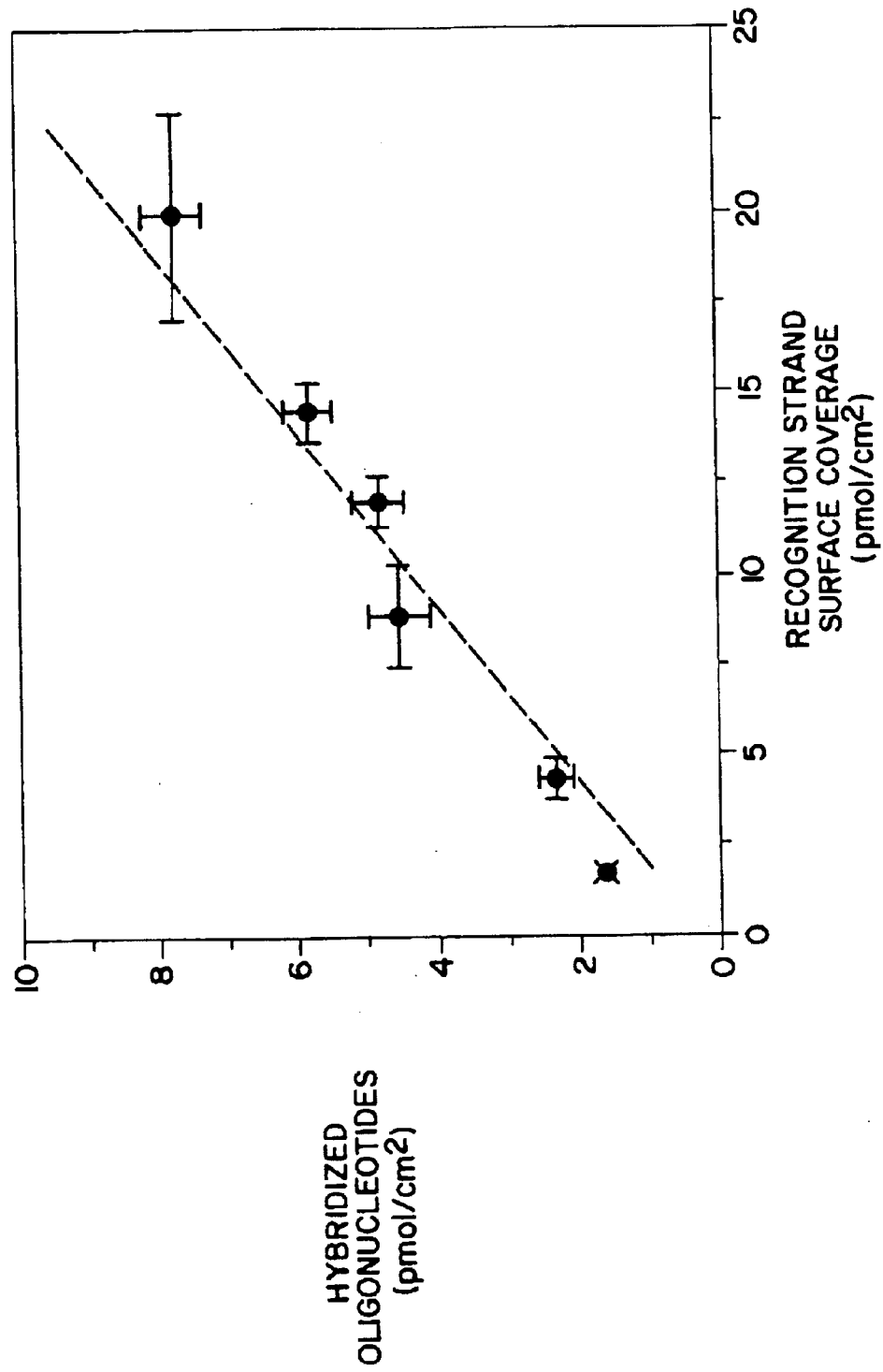
FIG. 31: Graph of surface coverages of hybridized complementary oligonucleotides versus different surface coverages of recognition oligonucleotides on nanoparticles.

The amount of complementary 12F' oligonucleotide which hybridized to each different sample also increased linearly with increasing $SA_{20}12F$ surface coverage, FIG. 31.

The fact that this relationship is well defined indicates that it is possible to predict and control the extent of hybridization of the nanoparticle-oligonucleotide conjugates. This suggests that hybridization of 12F' becomes more difficult at higher $SA_{20}12F$ coverages, which is most likely a result of steric crowding and electrostatic repulsion between oligonucleotides.

P. Summary

This study has shown that it is important to achieve a balance between oligonucleotide coverage high enough to stabilize the nanoparticles to which they are attached, yet low enough so that a high percentage of the strands are accessible for hybridization with oligonucleotides in solution. This has been achieved by adjusting salt conditions during oligonucleotide attachment to the nanoparticles to gain high oligonucleotide surface coverages, oligonucleotide spacer segments to reduce electrosteric interactions, and coadsorbed diluent strands to reproducibly control the average number of hybridization events for each nanoparticle. It has also been shown that the nature of the tether (spacer) sequence influences the number of oligonucleotide strands loaded onto gold nanoparticles. This work has important implications regarding understanding interactions between oligonucleotides and nanoparticles, as well as optimizing the sensitivity of nanoparticle-oligonucleotide detection methods.

TABLE 7

Single strand surface coverage and corresponding hybridized surface coverages for gold thin films and gold nanoparticles. Comparison between S12F and $SA_{20}12F$ surface coverage and hybridization. Thiol modified oligonucleotides were attached to the gold from 3 μM aqueous solutions and aged in 0.1 M NaCl. All hybridization studies were performed in 0.3 M PBS, pH 7.

| Oligonucleotide Pair | Surface Coverage (pmol/cm²) | Hybridization Coverage (pmol/cm²) | % Hybridization Efficiency |
|---|---|---|---|
| | Au nanoparticles | | |
| S12F/12F' | 34 ± 1 | 1.3 ± 0.2 | ~4% |
| $SA_{20}12F/12F'$ | 15 ± 4 | 6.6 ± 0.2 | ~44% |
| | Au thin films | | |
| S12F/12F' | 18 ± 3 | 6 ± 2 | ~33% |

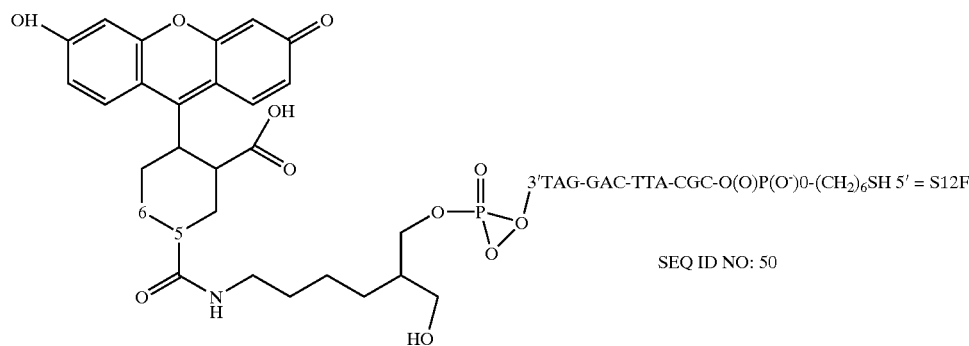

3'TAG-GAC-TTA-CGC-O(O)P(O⁻)0-(CH₂)₆SH 5' = S12F

SEQ ID NO: 50

TABLE 8

Effect of salt aging on surface coverage of $SA_{20}12F$ oligonucleotides to gold nanoparticles and hybridization to 12F'. All hybridization experiments were performed in 0.3 M PBS, pH 7.

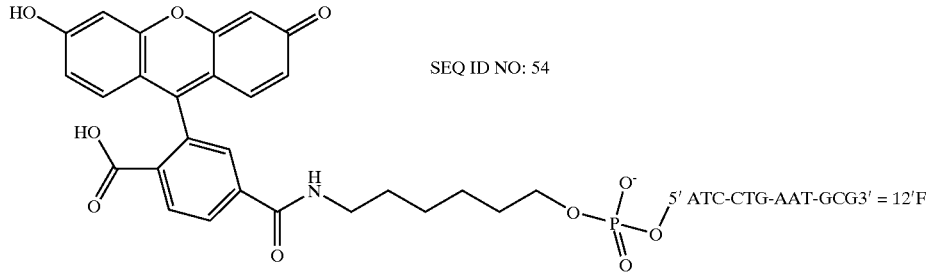

SEQ ID NO: 54

5' ATC-CTG-AAT-GCG3' = 12'F

| Buffer conditions during adsorption of alkylthiol DNA | Surface Coverage (pmol/cm²) | Hybridization Coverage (pmol/cm²) | Hybridization Efficiency (%) |
|---|---|---|---|
| H₂O | 7.9 ± 0.2 | —[a] | — |
| 0.1 M NaCl, 10 mM phosphate | 15 ± 4 | 6.6 ± 0.2 | ~44 |
| 1.0 M NaCl, 10 mM phosphate | 20 ± 2 | 6.5 ± 0.2 | ~33 |

[a]Reliable values for these experiments could not be obtained due to a small amount of particle aggregation which occurred after centrifugation.

TABLE 9

Effect of oligonucleotide spacer sequence on surface coverage and hybridization efficiency.

| Oligonucleotide Pair | Surface Coverage (pmol/cm²) | Hybridization Coverage (pmol/cm²) | Hybridization Efficiency (%) |
|---|---|---|---|
| S3'A₂₀12F/3'12F | 24 ± 1 | 9 ± 2 | ~38 |
| S3'T₂₀12F/3'12F | 35 ± 1 | 12 ± 1 | ~34 |

S3'A₂₀12F/S3'T₂₀12F = HS(CH₂)₃-3'-W₂₀-TAG-GAC-TTA-CGC-5'-(CH₂)₆-F [SEQ ID NO:52]
3'12F = 5'-ATC-CTG-AAT-GCG-F [SEQ ID NO:54]

Example 19

Gene Chip Assay

An ultraselective and ultrasensitive method for analyzing combinatorial DNA arrays using oligonucleotide-functionalized gold nanoparticles is described in this example. An unusually narrow temperature range for thermal dissociation of nanoparticle-target complexes permits the discrimination of a given oligonucleotide sequence from targets with single nucleotide mismatches with extraordinary selectivity. In addition, when coupled with signal amplification method based on nanoparticle-catalyzed reduction of silver(I), the sensitivity of this nanoparticle array detection system exceeds that of the analogous, conventional fluorophore system by two orders of magnitude.

Sequence-selective DNA detection has become increasingly important as scientists unravel the genetic basis of disease and use this new information to improve medical diagnosis and treatment. Commonly used heterogeneous DNA sequence detection systems, such as Southern blots and combinatorial DNA chips, rely on the specific hybridization of surface-bound, single-strand capture oligonucleotides complementary to target DNAs. Both the specificity and sensitivity of these assays are dependent upon the dissociation properties of capture strands hybridized to perfectly-matched and mismatched targets. As described below, it has surprisingly been discovered that a single type of nanoparticles hybridized to a substrate exhibits a melting profile that is substantially sharper than both the analogous fluorophore-based system and unlabeled DNA. Moreover, the melting temperature for the nanoparticle duplex is 11 degrees higher than for the analogous fluorophore system with identical sequences. These two observations, combined with the development of a quantitative signal amplification method based upon nanoparticle catalyzed reduction of silver(I), have allowed the development of a new chip-based detection system for DNA that has single-base mismatch selectivity and a sensitivity that is two orders of magnitude more sensitive than the conventional analogous fluorescence-based assays.

Figure 34:
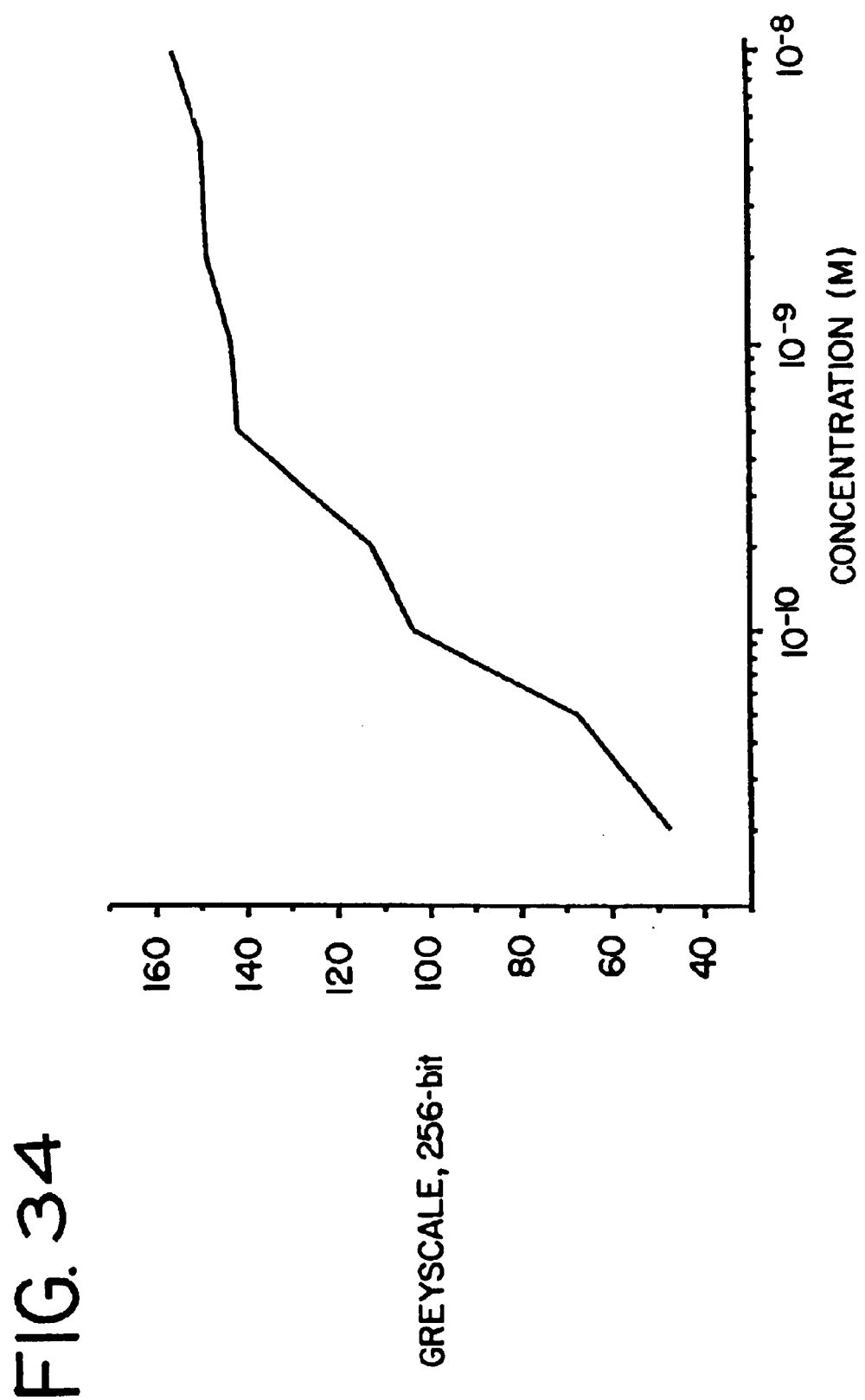
FIG. 34: Graph of greyscale (optical density) of oligonucleotide-functionalized glass surface exposed to varying concentrations of target DNA, followed by 5 nM gold of nanoparticle-oligonucleotide indicator conjugates and silver amplification for 5 minutes.

Gold nanoparticles (13 nm diameter) having oligonucleotide attached to them prepared as described in Example 3 were used to indicate the presence of a particular DNA sequence hybridized to a transparent substrate in a three-component sandwich assay format (see FIG. 32). In a typical experiment, a substrate was fabricated by functionalizing a float glass microscope slide (Fisher Scientific) with amine-modified probe oligonucleotides as described in Example 10. This method was used to generate slides functionalized with a single type of oligonucleotides over their entire surface or in arrays of multiple types of oligonucleotides spotted with a commercial microarrayer. Nanoparticles having indicator oligonucleotides attached to them and synthetic 30-mer oligonucleotide targets (based on the anthrax protective antigen sequence) were then cohybridized to these substrates (see FIG. 32). Therefore, the presence of nanoparticles at the surface indicated the detection of a particular 30-base sequence. At high target concentrations ($\geq 1$ nM), the high density of hybridized nanoparticles on the surface made the surface appear light pink (see FIG. 33). At lower target concentrations, attached nanoparticles could not be visualized with the naked eye (although they could be imaged by field-emission scanning electron microscopy). In order to facilitate the visualization of nanoparticles hybridized to the substrate surface, a signal amplification method in which silver ions are catalytically reduced by hydroquinone to form silver metal on the slide surface was employed. Although this method has been used for enlargement of protein- and antibody-conjugated gold nanoparticles in histochemical microscopy studies (Hacker, in *Colloidal Gold: Principles, Methods, and Applications*, M. A. Hayat, Ed. (Academic Press, San Diego, 1989), vol. 1, chap. 10; Zehbe et al., *Am. J. Pathol.* 150, 1553 (1997)) its use in quantitative DNA hybridization assays is novel (Tomlinson et al., *Anal. Biochem.*, 171:217 (1988)). Not only did this method allow very low surface coverages of nanoparticle probes to be visualized by a simple flatbed scanner or the naked eye (FIG. 33), it also permitted quantification of target hybridization based on the optical density of the stained area (FIG. 34). Significantly, in the absence of the target, or in the presence of noncomplementary target, no staining of the surface was observed, demonstrating that neither nonspecific binding of nanoparticles to the surface, nor nonspecific silver staining, occurs. This result is an extraordinary feature of these nanoparticle-oligonucleotide conjugates which enables ultra-sensitive and -selective detection of nucleic acids.

Figure 35A:
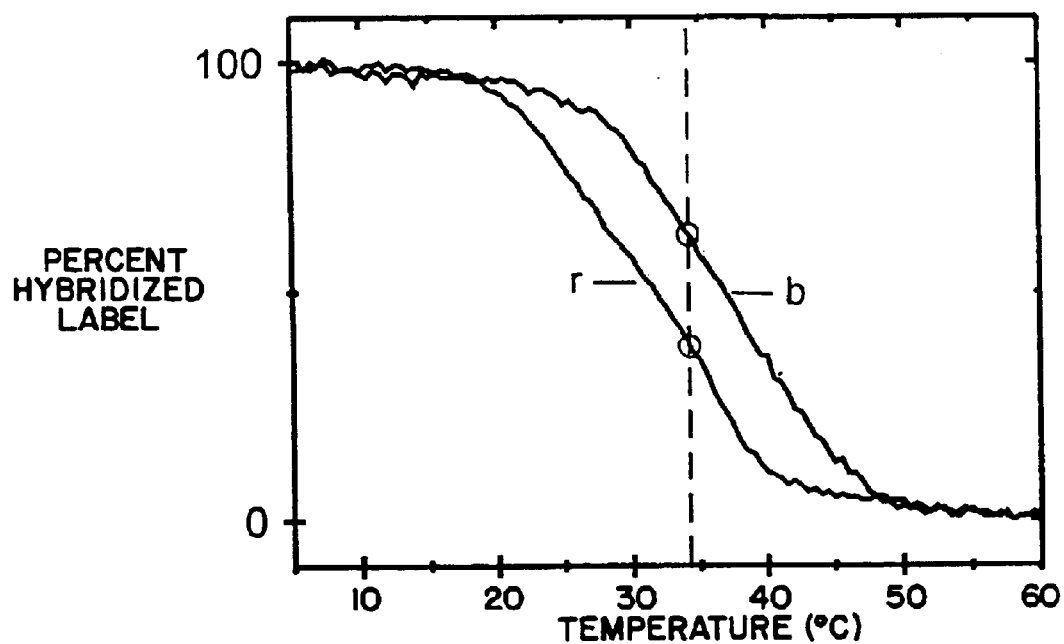
FIGS. 35A–B: Graphs of percent hybridized label versus temperature showing dissociation of fluorophore-labeled (FIG. 35A) and nanoparticle-labeled (FIG. 35B) targets from an oligonucleotide-functionalized glass surface. Measurements were made by measuring fluorescence (FIG. 35A) or absorbance (FIG. 35B) of dissociated label in the solution above the glass surface. The lines labeled "b" show the dissociation curves for perfectly matched oligonucleotides on the glass, and the lines labeled "r" show curves for mismatched oligonucleotides (a one-base mismatch) on the glass. Vertical lines in the graphs illustrate the fraction of target dissociated at a given temperature (halfway between the melting temperatures $T_m$ of each curve) for each measurement, and the expected selectivity of sequence identification for fluorophore- and nanoparticle-based gene chips. Fluorescence (FIG. 35A): complement (69%)/mismatch (38%)=1.8:1. Absorbance (FIG. 35B): complement (85%)/mismatch (14%)=6:1. The breadth of the fluorophore-labeled curves (FIG. 35A) is characteristic of the dissociation of fluorophore-labeled targets from gene chips (Forman et al., in *Molecular Modeling of Nucleic Acids,* Leontis et al., eds., (ACS Symposium Series 682, American Chemical Society, Washington D.C., 1998), pages 206–228).
Figure 35B:
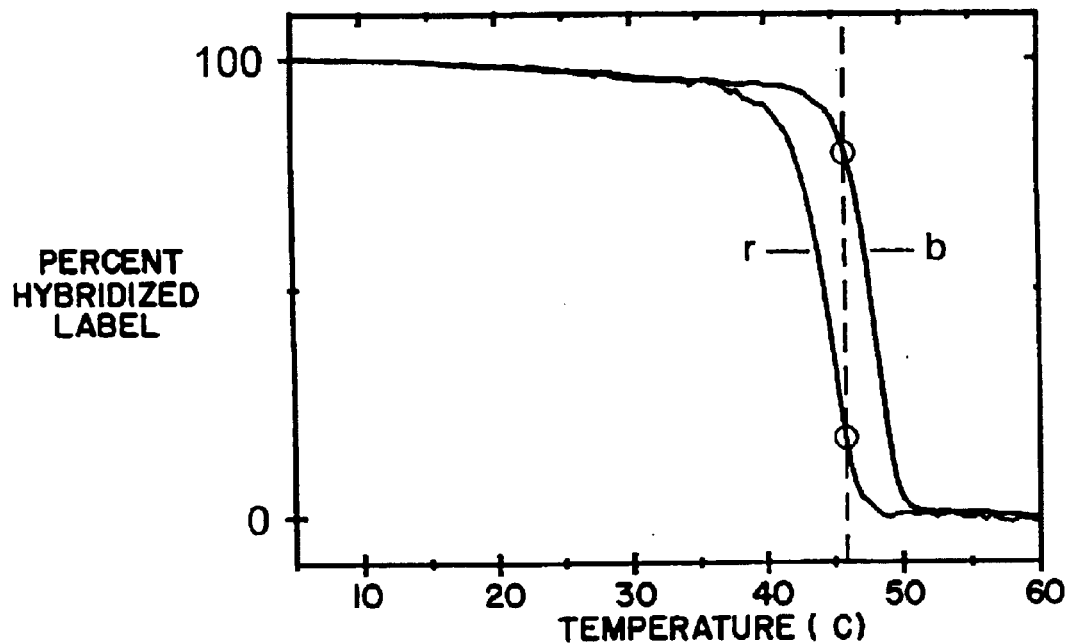

It has been determined that the unique hybridization properties of oligonucleotide-functionalized nanoparticles of the present invention can be further used to improve the selectivity of combinatorial oligonucleotide arrays (or "gene chips") (Fodor, *Science* 277, 393 (1997)). The relative ratio of target hybridized to different elements of an oligonucleotide array will determine the accuracy of the array in determining the target sequence; this ratio is dependent upon the hybridization properties of the duplex formed between different capture strands and the DNA target. Remarkably, these hybridization properties are dramatically improved by the use of nanoparticle labels instead of fluorophore labels. As shown in FIG. 35, the dehybridization of nanoparticle-labeled targets from surface-bound capture strands was much more sensitive to temperature than that of fluorophore-labeled targets with identical sequences. While the fluorophore-labeled targets dehybridized from surface capture strands over a very broad temperature range (first derivative FWHM=16° C.), identical nanoparticle-labeled targets melted much more sharply (first derivative FWHM= 3° C.). It was anticipated that these sharpened dissociation profiles would improve the stringency of chip-based sequence analysis, which is usually effected by a post-hybridization stringency wash. Indeed, the ratio of target hybridized to complementary surface probes to that hybridized to mismatched probes after a stringency wash at a specific temperature (represented by the vertical lines in FIG. 35) is much higher with nanoparticle labels than fluorophore labels. This should translate to higher selectivity in chip detection formats. In addition, nanoparticle labels should increase array sensitivity by raising the melting temperature ($T_m$) of surface duplexes, which lowers the critical concentration below which duplexes spontaneously melt at room temperature.

In order to evaluate the effectiveness of nanoparticles as calorimetric indicators for oligonucleotide arrays, test chips were probed with a synthetic target and labeled with both fluorophore and nanoparticle indicators. The test arrays and oligonucleotide target were fabricated according to published protocols (Guo et al., *Nucl. Acids Res.*, 22:5456 (1994); arrays of 175 µm diameter spots separated by 375 µm were patterned using a Genetic Microsystems 417 Microarrayer). Arrays contained four elements corresponding to the each of the four possible nucleotides (N) at position 8 of the target (see FIG. 32). The synthetic target and either fluorescent-labeled or nanoparticle-labeled probes were hybridized stepwise to arrays in hybridization buffer, and each step was followed with a stringency buffer wash at 35° C. First, 20 µL of a 1 nM solution of synthetic target in 2×PBS (0.3 M NaCl, 10 mM $NaH_2PO_4/Na_2HPO_4$ buffer, pH 7) was hybridized to the array for 4 hours at room temperature in a hybridization chamber (Grace Bio-Labs Cover Well PC20), and then washed at 35° C. with clean 2×PBS buffer. Next, 20 µL of a 100 µM solution of oligonucleotide-functionalized gold nanoparticles in 2×PBS was hybridized to the array for 4 hours at room temperature in a fresh hybridization chamber. The array was washed at 35° C. with clean 2×PBS, then twice with 2×PBN (0.3 M $NaNO_3$, 10 mM $NaH_2PO_4/Na_2HPO_4$ buffer, pH 7). Then, the nanoparticle arrays were immersed in a silver amplification solution (Sigma Chemical, Silver Enhancer Solution) for 5 min and washed with water. Silver amplification darkened the array elements considerably, and 200 µm diameter elements could be easily imaged with a flatbed scanner or even the naked eye.

Figure 36A:
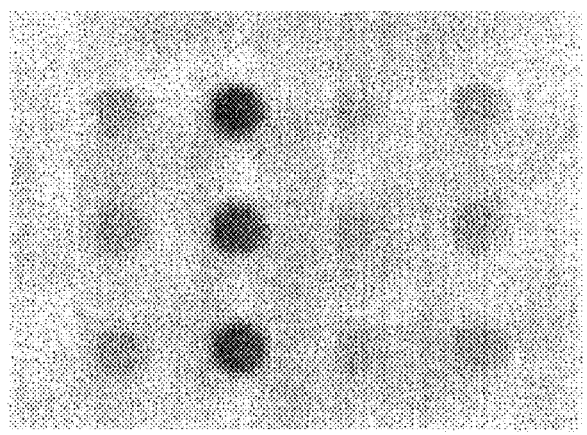
FIGS. 36A–B: Images of model oligonucleotide arrays challenged with synthetic target and fluorescent-labeled (FIG. 36A) or nanoparticle-labeled (FIG. 36B) nanoparticle-oligonucleotide conjugate probes. C, A, T, and G represent spots (elements) on the array where a single base change has been made in the oligonucleotide attached to the substrate to give a perfect match with the target (base A) or a single base mismatch (base C, T or G in place of the perfect match with base A). The greyscale ratio for elements C:A:T:G is 9:37:9:11 for FIG. 36A and 3:62:7:34 for FIG. 36B.
Figure 36B:
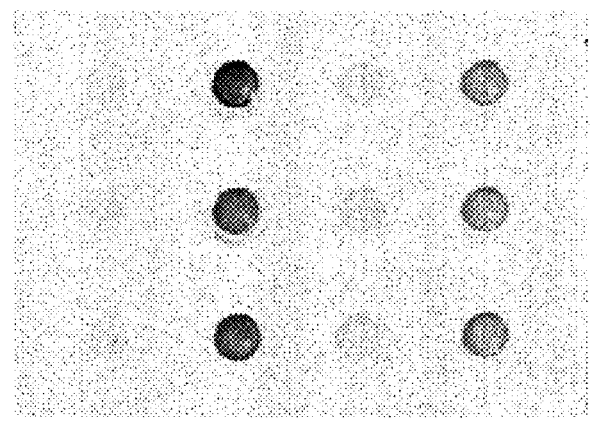

Arrays challenged with the model target and nanoparticle-labeled probes and stained with the silver solution clearly exhibited highly selective hybridization to complementary array elements (FIG. 36A). Redundant spots of the same capture sequence showed reproducible and consistent hybridization signal. No background adsorption by nanoparticles or silver stain was observed; the image greyscale value reported by the flatbed scanner is the same as that observed for a clear microscope slide. The darker spots corresponding to adenine at position 8 (N=A) indicate that oligonucleotide target hybridized preferentially to perfectly complementary capture strands over mismatched ones, by a greater than 3:1 ratio. In addition, integrated greyscale values for each set of spots follows the predicted stability of the Watson-Crick base pairs, A:T>G:T>C:T>T:T (Allawi et al., *Biochemistry* 36, 10581, (1988)). Normally, G:T mismatches are particularly difficult to discriminate from A:T complements (Saiki et al., in *Mutation Detection,* Cotton et al., eds. (Oxford University Press, Oxford, 1998), chap. 7; S. Ikuta et al., *Nucl. Acids Res.* 15, 797 (1987)), and the distinction of these two array elements demonstrates the remarkable resolving power of nanoparticle labels in single nucleotide mismatch detection. The selectivity of the nanoparticle-based arrays was higher than that of the fluorophore-indicated arrays, FIG. 36B; fluorophore labels provided only 2:1 selectivity for adenine at position 8.

The assays utilizing nanoparticle-labeled probes were significantly more sensitive than those utilizing fluorophore-labeled probes. Hybridization signal could be resolved at the N=A elements at target concentrations as low as 50 fM (or, for a hybridization chamber containing 20 µL of solution, $1 \times 10^6$ total copies); this represents a dramatic increase in sensitivity over common Cy3/Cy5 fluorophore-labeled arrays, for which ~1 pM or greater target concentrations are typically required. The higher melting temperatures observed for nanoparticle-target complexes immobilized on surfaces undoubtedly contribute to array sensitivity. The greater stability of the probe/target/surface-oligonucleotide complex in the case of the nanoparticle system as compared with the fluorophore system presumably results in less target and probe lost during washing steps.

Colorimetric, nanoparticle labeling of combinatorial oligonucleotide arrays will be useful in applications such as single nucleotide polymorphism analysis, where single mismatch resolution, sensitivity, cost and ease of use are important factors. Moreover, the sensitivity of this system, which has yet to be totally optimized, points toward a potential method for detecting oligonucleotide targets without the need for target amplification schemes such as polymerase chain reaction.

Example 2

Nanoparticle Structures

The reversible assembly of supramolecular layered gold nanoparticle structures onto glass supports, mediated by hybridized DNA linkers, is described. Layers of oligonucleotide-functionalized nanoparticles were successively attached to oligonucleotide-functionalized glass substrates in the presence of a complementary DNA linker. The unique recognition properties of DNA allow the nanoparticle structures to be assembled selectively in the presence of the complementary linker. In addition, the structures can be assembled and disassembled in response to external stimuli which mediate hybridization of the linking duplex DNA, including solution temperature, pH, and ionic strength. In addition to offering a very selective and controlled way of building nanoparticle based architectures on a solid support, this system allows one to study the factors that influence both the optical and melting properties of nanoparticle network structures linked with DNA.

Others have demonstrated how bifunctional organic molecules (Gittins et al., *Adv. Mater.* 11:737 (1999); Brust et al., *Langmuir* 14:5425 (1998); Bright et al., *Langmuir* 14:5695 (1998); Grabar et al., *J. Am. Chem. Soc.* 118:1148 (1996); Freeman et al., *Science* 267:1629 (1995); Schmid et al., *Angew. Chem. Int. Ed. Engl.* 39:181 (2000); Marinakos et al., *Chem. Mater.* 10:1214 (1998)) or polyelectrolytes (Storhoff et al., *J. Am. Chem. Soc.* 120:1959 (1998); Storhoff et al., *J. Cluster Sci.* 8:179 (1997); Elghanian et al., *Science* 277:1078 (1997); Mirkin et al., *Nature* 382:607 (1996)) can be used to controllably construct mono- and multilayered nanoparticle materials off of planar substrates. The attractive feature of using DNA as a nanoparticle interconnect is that one can synthetically program interparticle distances, particle periodicities, and particle compositions through choice of DNA sequence. Moreover, one can utilize the reversible binding properties of oligonucleotides to ensure the formation of thermodynamic rather than kinetic structures. In addition to providing a new and powerful method for controlling the growth of nanoparticle-based architectures from solid substrates, this strategy also allows one to evaluate the relationship between nanoparticle aggregate size and both melting and optical properties of aggregate DNA-interlinked structures. An understanding of these two physical parameters and their relationship to materials architecture is essential for utilizing nanoparticle network materials, especially in the area of biodetection.

The oligonucleotide-functionalized, 13-nm-diameter gold nanoparticles used to construct the multilayer assemblies were prepared as described in Examples 1 and 3. The nanoparticles had 5'-hexanethiol-capped oligonucleotide 1 (5'-HS(CH$_2$)$_6$O(PO$_2^+$)O-CGCATTCAGGAT-3' [SEQ ID NO:50]) and 3'-propanethiol-capped oligonucleotide 2 (3'-HS(CH$_2$)$_3$O(PO$_2^-$)O-ATGCTCAACTCT-5' [SEQ ID NO:59]) attached to them to yield nanoparticles a and b, respectively (see FIG. 37). Glass slides were functionalized with 12-mer oligonucleotide 2 as described in Example 10. To build nanoparticle layers, the substrates were first immersed in a 10 nM solution of 24-mer linker 3 (5'-TACGAGTTGAGAATCCTGAATGCG-3' [SEQ ID NO:60]) and allowed to hybridize with it for 4 hours at room temperature (see FIG. 37). The substrates were washed with clean buffer solution, and then hybridized with a 2 nM solution of particle a for 4 hours at room temperature to attach the first nanoparticle layer. A second nanoparticle layer could be attached to the first one by similarly exposing the surface to solutions of linker 3 and nanoparticle b. These hybridization steps could be repeated to attach multiple, alternating layers of nanoparticles a and b, each layer connected to the previous one by linker 3. In the absence of linker, or in the presence of noncomplementary oligonucleotide, no hybridization of nanoparticles to the surface was observed. In addition, multilayer assembly was only observed under conditions which promoted the hybridization of the DNA linkers: neutral pH, moderate salt concentration (>0.05 M NaCl), and a temperature below the duplex melting temperature ($T_m$).

Figure 38A:
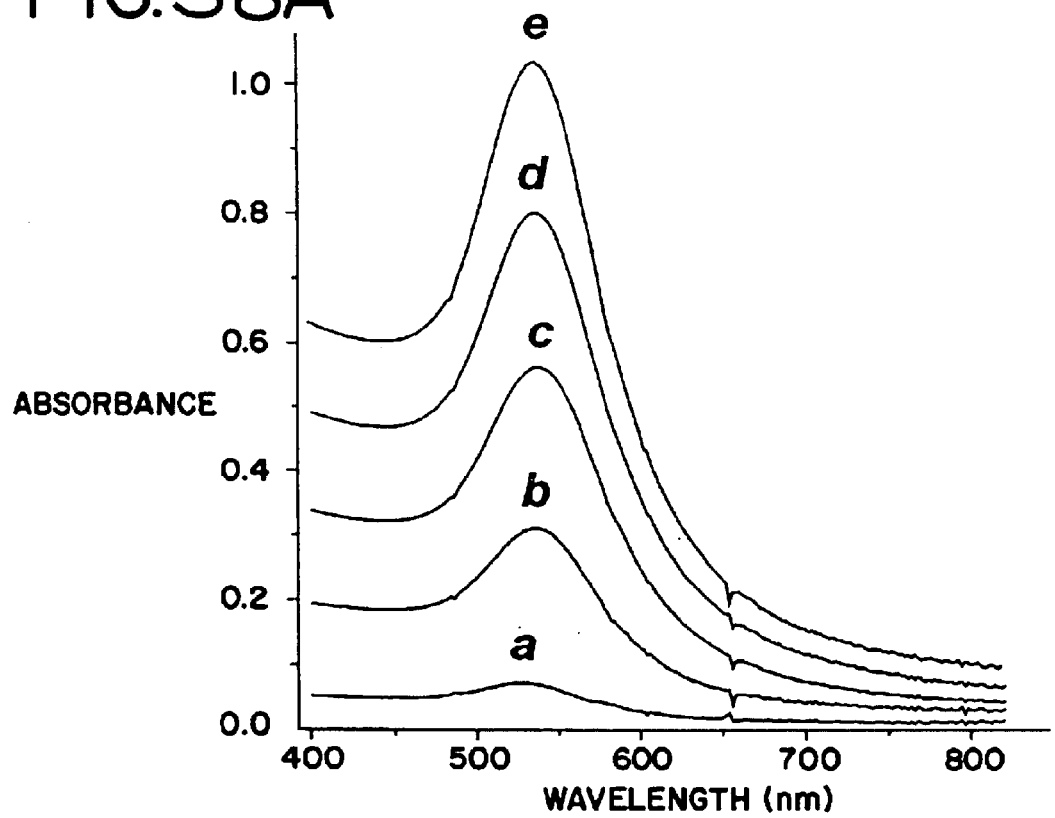
FIG. 38A: UV-visible spectra of alternating layers of gold nanoparticles a and b (see FIG. 37) hybridized to an oligonucleotide-functionalized glass microscope slide via the complementary linker 3. The spectra are for assemblies with 1 (a, $\lambda_{max}$=524 nm), 2 (b, $\lambda_{max}$=529 nm), 3 (c, $\lambda_{max}$=532 nm), 4 (d, $\lambda_{max}$=534 nm) or 5 (e, $\lambda_{max}$=534 nm) layers. These spectra were measured directly through the slide.
Figure 38B:
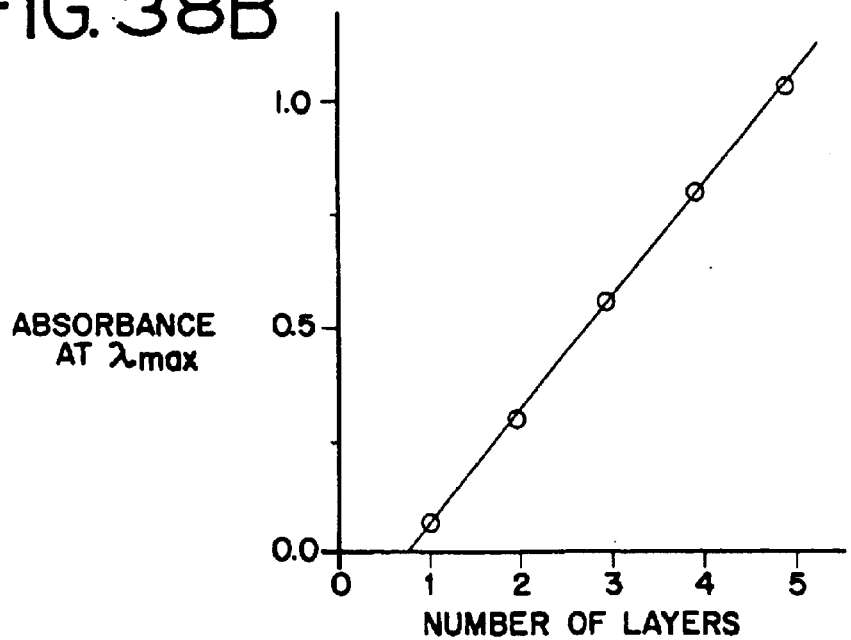
FIG. 38B: Graph of absorbance for nanoparticle assemblies (see FIG. 38A) at $\lambda_{max}$ with increasing numbers of layers.
Figure 39A:
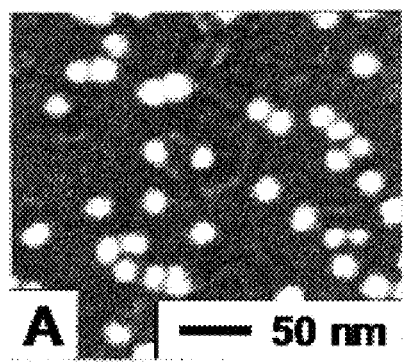
FIGS. 39A–F.
Figure 39B:
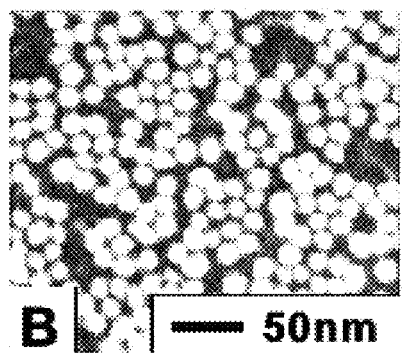

Each hybridized nanoparticle layer imparted a deeper red color to the substrate, and after ten hybridized layers, the supporting glass slide appeared reflective and gold in color. Transmission UV-vis spectroscopy of the substrate was used to monitor the successive hybridization of nanoparticle layers to the surface, FIG. 38A. The low absorbance of the initial nanoparticle layer suggests that it seeded the formation of further layers, which showed a near linear increase in the intensity of the plasmon band with each additional layer (for each successive nanoparticle layer formation, no additional absorbance was observed on exposure for longer times or to higher concentrations of either linker 3 or nanoparticle solution). The linearity of the absorbance increase after the generation of the initial nanoparticle layer indicates that the surface was saturated with hybridized nanoparticles with each successive application, FIG. 38B. This is supported by field-emission scanning electron microscope (FE-SEM) images of one (FIG. 39A) and two (FIG. 39B) nanoparticle layers on a surface, which show low nanoparticle coverage with one layer, but near complete coverage with two layers. The $\lambda_{max}$ of the plasmon band for the multilayer assemblies shifts no more than 10 nm, even after 5 layers. The direction of this shift is consistent with other experimental (Grabar et al., *J. Am. Chem. Soc.* 118:1148 (1996)) and theoretical (Quinten et al., *Surf Sci.* 172:557 (1986); Yang et al., *J. Chem. Phys.* 103:869 (1995)) treatments of gold nanoparticle aggregates. However, the magnitude of the shift is small compared to that previously observed for suspensions of oligonucleotide-linked gold nanoparticle networks, which show $\lambda_{max}$>570 nm (see previous examples). This suggests that many more linked nanoparticles—perhaps hundreds or thousands—are required to produce the dramatic color change from red to blue observed for gold nanoparticle-based oligonucleotide probes. (Storhoff et al., *J. Am. Chem. Soc.* 120:1959 (1998); Storhoff et al., *J. Cluster Sci.* 8:179 (1997); Elghanian et al., *Science* 277:1078 (1997); Mirkin et al., *Nature* 382:607 (1996).). Surface plasmon shifts for aggregated gold nanoparticles have been shown to be highly dependent on interparticle distance (Quinten et al., *Surf Sci* 172:557 (1986); Storhoff et al., *J. Am. Chem. Soc.*, in press), and the large distances provided by oligonucleotide linkers (8.2 nm for this system)) significantly reduce the progressive effect of nanoparticle aggregation on the gold surface plasmon band.

The dissociation properties of the assembled nanoparticle multilayers were highly dependent upon the number of layers. When the multilayer-coated substrates were suspended in buffer solution and the temperature raised above the $T_m$ of the linking oligonucleotides (53° C.), the nanoparticles dissociated into solution, leaving behind a colorless glass surface. Increasing or decreasing the pH (>11 or <3) or decreasing the salt concentration of the buffer suspension (below ~0.01 M NaCl) also dissociated the nanoparticles by dehybridizing the linking DNA. The multilayer assembly was fully reversible, and nanoparticles could be hybridized to, and dehybridized from, the glass substrates (e.g. three cycles were demonstrated with no detectable irreversible nanoparticle binding).

Significantly, while all of the surface bound nanoparticle assemblies dissociated above the $T_m$ of the linking oligonucleotides, the sharpness of these transitions depended on the size of the supported aggregate, FIGS.

Figure 39C:
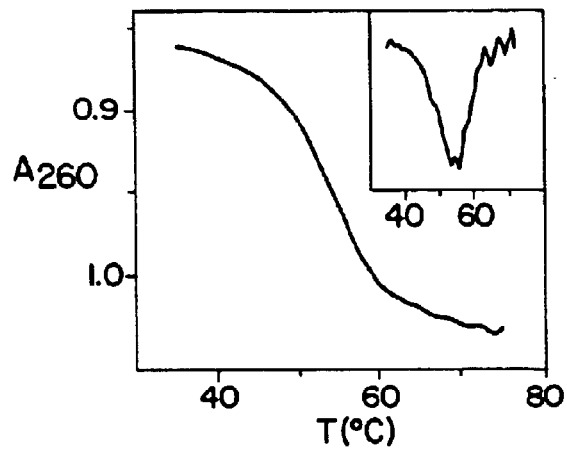
Figure 39D:
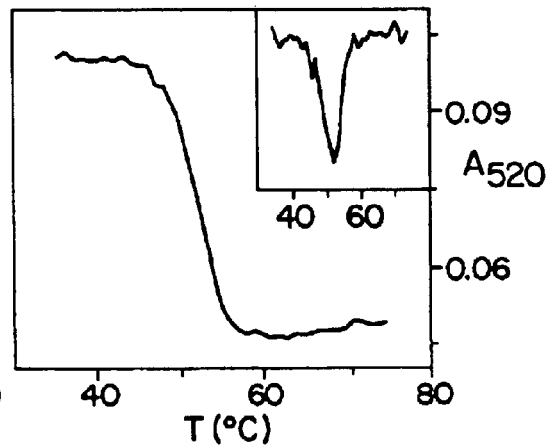
Figure 39E:
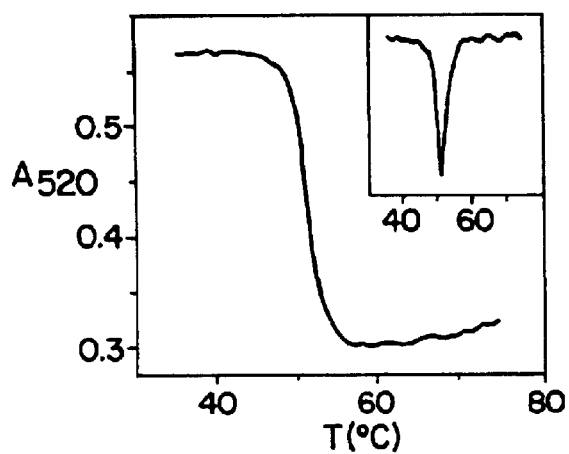
Figure 39F:
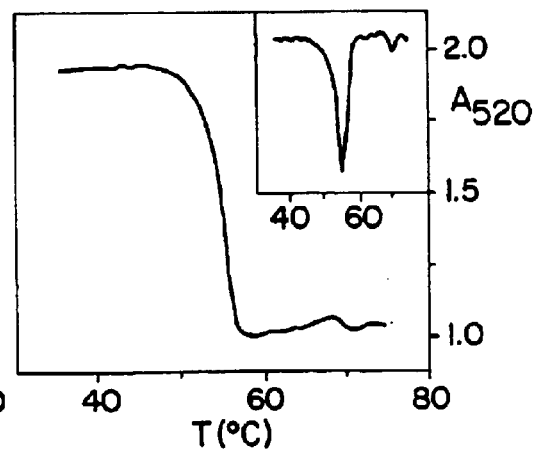

39D–F. Surprisingly, the dissociation of the first nanoparticle layer from the substrate exhibited a transition (FIG. 39D, FWHM of the first derivative=5° C.) that was sharper than that of the same oligonucleotides without nanoparticles in solution, FIG. 39C. As more nanoparticle layers were hybridized to the substrate, the melting transition of the oligonucleotide-linked nanoparticles became successively sharper (FIGS. 39E–F, FWHM of the first derivative=3° C.), until it matched that of the large nanoparticle network assemblies found in solution. (Gittins et al., *Adv. Mater.* 11:737(1999); Brust et al., *Langmuir* 14:5425 (1998)). These experiments confirm that more than two nanoparticles and multiple DNA interconnects are required to obtain the optimally sharp melting curves. They also show that the optical changes in this system are completely decoupled from the melting properties (i.e., small aggregates can give sharp transitions but still not change color).

Example 21

Electrical Properties of Gold Nanoparticle Assemblies

Electron transport through DNA has been one of the most intensely debated subjects in chemistry over the past five years. (Kelley et al., *Science* 283:375–381 (1999); Turro et al., *JBIC* 3:201–209 (1998); Lewis et al., *JBIC* 3:215–221 (1998); Ratner, M. *Nature* 397:480–481 (1999); Okahata et al., *J. Am. Chem. Soc.* 120:6165–6166 (1998)) Some claim that DNA is able to efficiently transport electrons, while others believe it to be an insulator.

In a seemingly disparate field of study, a great deal of effort has been devoted to examining the electrical properties of nanoparticle-based materials. (Terrill et al., *J. Am. Chem. Soc.* 117:12537–12548 (1995); Brust et al., *Adv. Mater.* 7:795–797 (1995); Bethell et al., *J. Electroanal. Chem.* 409:137–143 (1996); Musick et al., *Chem. Mater.* 9:1499–1501 (1997); Brust et al., *Langmuir* 14:5425–5429 (1998); Collier et al., *Science* 277:1978–1981 (1997)). Indeed, many groups have explored ways to assemble nanoparticles into two- and three-dimensional networks and have investigated the electronic properties of such structures. However, virtually nothing is known about the electrical properties of nanoparticle-based materials linked with DNA.

For the first time, in this study, the electrical properties of gold nanoparticle assemblies, formed with different length DNA interconnects have been examined. As shown below, these hybrid inorganic assemblies behave as semiconductors, regardless of oligonucleotide particle interconnect length over a 24 to 72 nucleotide range. The results reported herein indicate that DNA interconnects can be used as chemically specific scaffolding materials for metallic nanoparticles without forming insulating barriers between them and thereby destroying their electrical properties. These results point towards new ways such hybrid assemblies can be exploited as electronic materials.

At the heart of this issue is the following question: Can nanoparticles assembled by DNA still conduct electricity or will the DNA interconnects, which are heavily loaded on each particle, (Mucic, R. C. *Synthetically Programmable Nanoparticle Assembly Using DNA*, Thesis Ph. D., Northwestern University (1999)) act as insulating shells? The conductivities of these materials as a function of temperature, oligonucleotide length, and relative humidity were examined. The DNA-linked nanoparticle structures were characterized by field emission scanning electron microscopy (FE-SEM), synchrotron small angle x-ray scattering (SAXS) experiments, thermal denaturation profiles, and UV-vis spectroscopy.

Figure 40:
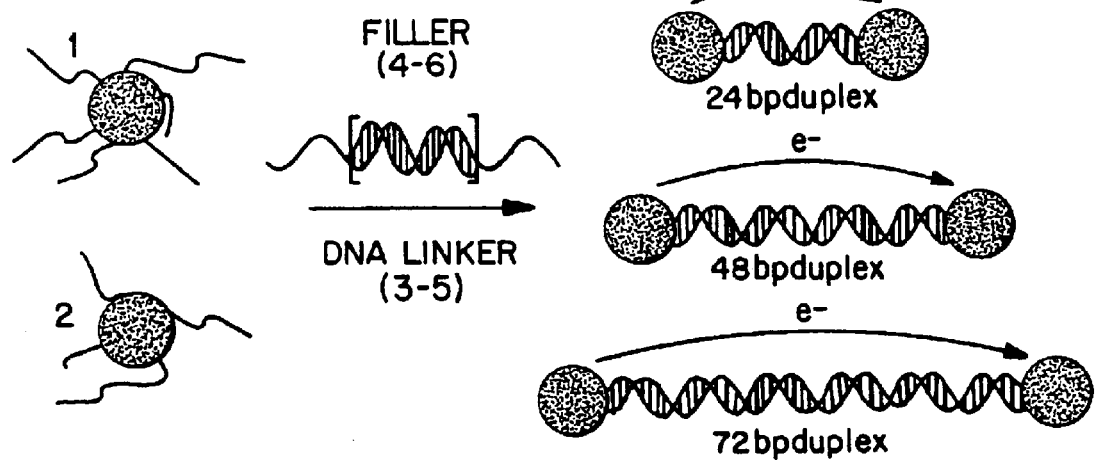
FIG. 40: Schematic diagram illustrating system used to measure the electrical properties of gold nanoparticle assemblies linked by DNA. For simplicity, only one hybridization event is drawn.

In a typical experiment (see FIG. 40), citrate-stabilized 13 nm gold nanoparticles were modified with 3' and 5' alkanethiol-capped 12-mer oligonucleotides 1 (3' SH $(CH_2)_3O(PO^{2-})O$-ATGCTCAACTCT 5' [SEQ ID NO:59]) and 2 (5' SH $(CH_2)_6O(PO^{2-})O$-CGCATTCAGGAT 3' [SEQ ID NO:50]) as described in Examples 1 and 3. DNA strands with lengths of 24, 48, or 72 bases (3 (5'TACGAGTTGAGAATCCTGAATGCG3' [SEQ ID NO:60]), 4 (5'TACGAGTTGAGACCGTTAAGACG AGGCAATCATGCAATCCTGAATGCG 3'[SEQ ID NO:61]), and 5 (5'TACGAGTT AGACCGTTAAGAC-GAGGCAATCATGCATATATTGGACGCTTT ACGGACAACATCCTGAATGCG3'[SEQ ID NO:62]) were used as linkers. Fillers 6 (3'GGCAATTCTGCTCCGTTAGTACGT5'[SEQ ID NO:63]) and 7 (3'GGCAATTCTGC TCCGTTAGTACG-TATATAACCTGCGAAATGCCTGTTG5' [SEQ ID NO:64]) were used with the 48 and 72 base linkers. The DNA-modified nanoparticles and DNA linkers and fillers were stored in 0.3 M NaCl, 10 mM phosphate (pH 7) buffer (referred as to 0.3 M PBS) prior to use. To construct nanoparticle assemblies, 1-modified gold nanoparticles (652 μl, 9.7 nM) and 2-modified gold nanoparticles (652 μl, 9.7 nM) were added to linker DNA 3, 4, or 5 (30 μl, 10 nM). After full precipitation, the aggregates were washed with 0.3 M $CH_3COONH_4$ solution to remove excess linker DNA and NaCl.

Lyophilization ($10^{-3}$~$10^{-2}$ torr) of the aggregate to dryness results in pellets and removal of the volatile salt, $CH_3COONH_4$. Unfunctionalized, citrate-stabilized particles, prepared by the Frens method, (Frens, *Nature Phys. Sci.* 241:20–22 (1973)) were dried as a film and used for comparison purposes. The resulting dried aggregates had a color resembling tarnished brass and were very brittle. FE-SEM images demonstrated that oligonucleotide-modified nanoparticles remained intact upon drying, while citrate-stabilized nanoparticles fused to one another. Significantly, the dried DNA-linked aggregates could be redispersed in 0.3 M PBS buffer (1 ml), and exhibited excellent melting properties; heating such a dispersion to 60° C. resulted in dehybridization of the DNA interconnects, yielding a red solution of dispersed nanoparticles. This combined with the FE-SEM data conclusively demonstrated that DNA-modified gold nanoparticles are not irreversibly aggregated upon drying.

The electrical conductivities of the three samples (dried aggregates linked by 3, 4, and 5, respectively) were measured using a computer-controlled, four-probe technique. Electrical contacts consisted of fine gold wires (25 and 60 μm diameter) attached to pellets with gold paste. Samples were cooled in a moderate vacuum ($10^{-3}$ to $10^{-2}$ torr), and conductivity was measured as the temperature was increased under a dry, low pressure of helium gas. The sample chamber was insulated from light in order to eliminate possible optoelectronic effects. Excitation currents were kept at or below 100 nA, and the voltage across the entire sample was limited to a maximum of 20 V. Surprisingly, the conductivities of the aggregates formed from all three linkers, ranged from $10^{-5}$ to $10^{-4}$ S/cm at room temperature, and they showed similar temperature dependent behavior. The conductivities of the DNA-linked aggregates showed Arrhenius behavior up to about 190° K, which is characteristic of a semiconducting material. This is similar to the behavior of activated electron hopping observed in discontinuous metal island films (Barwinski, *Thin Solid Films*

128:1–9 (1985)). Gold nanoparticle networks linked by alkanedithiols have shown similar temperature dependence (Brust et al., *Adv. Mater.* 7:795–797 (1995); Bethell et al., *J. Electroanal. Chem.* 409:137–143 (1996)). Activation energies of charge transport can be obtained from a plot of 1 n σ versus 1/T using equation (1).

$$\sigma = \sigma_o \exp[-E_a/(kT)] \quad (1)$$

The average activation energies calculated from three measurements were 7.4±0.2 meV, 7.5±0.3 meV, and 7.6±0.4 meV for the 24-, 48-, and 72-mer linkers, respectively. Conductivity data from 50° K to 150° K were used for these calculations.

Since the electrical properties of these types of materials should depend on the distance between particles, synchrotron SAXS experiments were used to determine interparticle distances of the dispersed and dried aggregates. The SAXS experiments were performed at the Dupont-Northwestern-Dow Collaborative Access Team (DND-CAT) Sector 5 of the Advanced Photon Source, Argonne National Laboratory. DNA-linked aggregates and dilute samples of DNA-modified colloid were irradiated with an 0.3 micron beam of 1.54 Å radiation, and scattered radiation was collected on a CCD detector. The 2D data were circularly averaged and transformed into a function, I (s), of the scattering vector magnitude, s=2 sin(θ)/λ, where 2 θ is the scattering angle and λ is the wavelength of the incident radiation. All data were corrected for background scattering and sample absorption. The first peak position, which is sensitive to interparticle distance, drastically changed from s values of 0.063 nm$^{-1}$, 0.048nm$^{-1}$, and 0.037nm$^{-1}$ for the 24-, 48-, and 72-mer linked aggregates, respectively, to an s value of 0.087 nm$^{-1}$ upon drying for all three aggregates structures. This indicates that interparticle distances decreased significantly upon drying, to the point where the particles were almost touching, and that such distances were virtually independent of linker length, while those in solution were highly dependent on linker length. This explains why similar activation energies were observed for the three different linker systems in the dried pellet conductivity experiments. Moreover, it also explains why relatively high conductivities were observed, regardless of how one views the electronic properties of DNA. Unlike the DNA-linked materials, the dried film of citrate-stabilized gold nanoparticles showed metallic behavior. This is consistent with the SEM data, which showed that such particles fuse together.

Above 190° K, the measured conductivities of the DNA-linked samples showed an anomalous dipping behavior. For all samples, the conductivity started to decrease abruptly at approximately 190° K and continued to decrease until approximately 250° K, at which point it increased again. To investigate this unusual behavior in detail, the electrical conductivity was measured as the sample was cooled and warmed repeatedly. Interestingly, the dip in conductivity only occurred in the direction of increasing temperature. Since DNA is hydrophilic and water could potentially affect the electrical properties of the hybrid structures, the effect of relative humidity on the conductivity of the gold aggregates was examined. The resistance increased by a factor of 10 with increasing humidity from 1% to 100%. It should be noted that the characteristic dip was very weak when the sample was kept in vacuum (10$^{-6}$ Torr) for 48 hours prior to the conductivity measurement. From these observations, it was concluded that the unusual dip and subsequent rise in conductivity above 190° K is associated with water melting and the hygroscopic nature of the DNA, which temporarily increased the interparticle distance (until evaporation took place). Consistent with this hypothesis, SAXS measurements on a dried aggregate that was wetted with 0.3 M PBS buffer showed a 200% increase in interparticle distance (~2 nm).

These studies are important for the following reasons. First, they show that one can use the molecular recognition properties of DNA to assemble nanoparticle-based materials without passivating them or destroying their discrete structural or electrical properties. If these DNA-functionalized particles are to be used to study electrical transport in three-dimensional macroscopic assemblies or even lithographically patterned structures (Piner et al., *Science* 283:661–663 (1999)), it is imperative that their electrical transport properties be delineated. Second, it shows that over a fairly long linker distance (8~24 nm), the conductivities of the dried assemblies are virtually independent of DNA linker length. This is likely a result of the removal of water and the use of a volatile salt in these experiments; indeed, the free volume created by removal of solvent and salt allows the DNA to be compressed on the surface and close approach of the particles within the aggregates. Third, the aggregates with the DNA-protected nanoparticles behave as semiconductors, while films formed from citrate-stabilized particles exhibit irreversible particle fusion and metallic behavior. Finally, these results point toward the use of these materials in DNA diagnostic applications where sequence specific binding events between nanoparticles functionalized with oligonucleotides and target DNA effect the closing of a circuit and a dramatic increase in conductivity (i.e. from an insulator to a semiconductor) (see next example).

Example 22

Detection of Nucleic Acid Using Gold Electrodes

Figure 41:
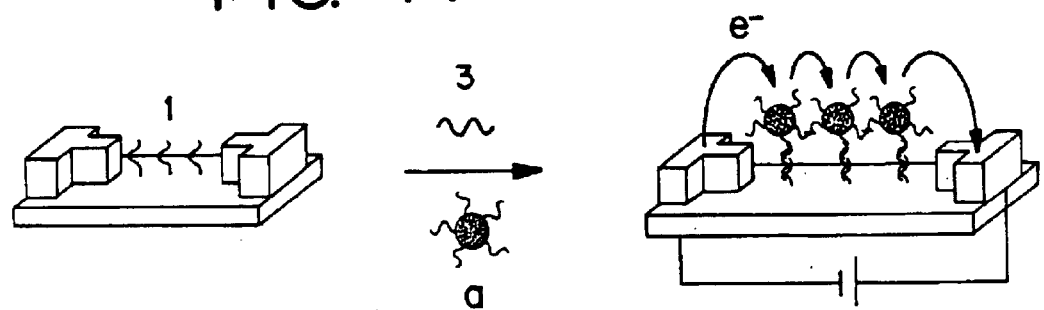
FIG. 41: Schematic diagram illustrating a method of detecting nucleic acid using gold electrodes and gold nanoparticles.

A method of detecting nucleic acid using gold electrodes is illustrated diagramatically in FIG. 41. A glass surface between two gold electrodes was modified with 12-mer oligonucleotides 1 (3' NH$_2$(CH$_2$)$_7$O(PO$^{2-}$)O-ATG-CTC-AAC-TCT [SEQ ID NO:59]) complementary to target DNA 3 (5' TAC GAG TTG AGA ATC CTG AAT GCG [SEQ ID NO:60]) by the method of Guo at al., *Nucleic Acids Res.,* 22, 5456–5465 (1994). Oligonucleotides 2 (5' SH(CH$_2$)$_6$O(PO$^{2-}$)O-CGC-ATT-CAG-GAT [SEQ ID NO:50]) were prepared and attached to 13 nm gold nanoparticles as described in Examples 1 and 18 to yield nanoparticles a. Target DNA 3 and nanoparticles a were added to the device. The color of the glass surface turned pink, indicating that target DNA-gold nanoparticle assemblies were formed on the glass substrate. Next, the device was immersed in 0.3 M NaCl, 10 mM phosphate buffer and heated at 40° C. for 1 hour to remove nonspecifically bound DNA, and then treated with a silver staining solution as described in Example 19 for 5 minutes. The resistance of the electrode was 67 kΩ.

For comparison, a control device modified by attaching oligonucleotides 4, instead of oligonucleotides 1, between the electrodes. Oligonucleotides 4 have the same sequence (5'NH$_2$(CH$_2$)$_6$O(PO$^{2-}$)O-CGC-ATT-CAG-GAT [SEQ ID NO:50]) as oligonucleotides 2 on the nanoparticles and will bind to target DNA 3 so as to prevent binding of the nanoparticles. The test was otherwise performed as described above. The resistance was higher than 40 MΩ, the detection limit of the multimeter that was used.

This experiment shows that only complementary target DNA strands form nanoparticle assemblies between the two electrodes of the device, and that the circuit can be completed by nanoparticle hybridization and subsequent silver staining. Therefore, complementary DNA and noncomplementary DNA can be differentiated by measuring conductivity. This format is extendable to substrate arrays (chips) with thousands of pairs of electrodes capable of testing for thousands of different nucleic acids simultaneously.

We claim:

1. A method of detecting a nucleic acid having at least two portions, the method comprising:
providing a type of nanoparticles having oligonucleotides attached thereto, the oligonucleotides on each nanoparticle having a sequence complementary to the sequence of at least two portions of the nucleic acid;
contacting the nucleic acid and the nanoparticles under conditions effective to allow hybridization of the oligonucleotides on the nanoparticles with the two or more portions of the nucleic acid to form a complex, the complex having a sharp melting profile and increased melting temperature relative to a melting profile and a melting temperature of an analogous complex formed with the nucleic acid and unlabeled or fluorophore-labeled oligonucleotides having a sequence identical to the oligonucleotides bound to the nanoparticles to allow for selective discrimination of any nucleotide insertion, deletion, or mismatch in the nucleic acid; and
observing a detectable change brought about by hybridization of the oligonucleotides on the nanoparticles with the nucleic acid.

2. A method of detecting nucleic acid having at least two portions, the method comprising:
contacting the nucleic acid with at least two types of nanoparticles having oligonucleotides attached thereto, the oligonucleotides on the first type of nanoparticles having a sequence complementary to a first portion of the sequence of the nucleic acid, the oligonucleotides on the second type of nanoparticles having a sequence complementary to a second portion of the sequence of the nucleic acid, the contacting taking place under conditions effective to allow hybridization of the oligonucleotides on the nanoparticles with the nucleic acid to form a complex, the complex having a sharp melting profile and increased melting temperature relative to a melting profile and a melting temperature of an analogous complex formed with the nucleic acid and at least two types of unlabeled or fluorophore-labeled oligonucleotides, a first type and a second type of unlabeled or fluorophore-labeled oligonucleotides having sequences identical to the oligonucleotides bound to the first and second types of nanoparticles respectively to allow for selective discrimination of any nucleotide insertion, deletion, or mismatch in the nucleic acid; and observing a detectable change brought about by hybridization of the oligonucleotides on the nanoparticles with the nucleic acid.

3. The method according to any one of claims 1 or 2 wherein the contacting conditions include freezing and thawing.

4. The method according to any one of claims 1 or 2 wherein the contacting conditions include heating.

5. The method according to any one of claims 1 or 2 wherein the detectable change is observed on a solid surface.

6. The method according to any one of claims 1 or 2 wherein the detectable change is a color change observable with the naked eye.

7. The method according to claim 6 wherein the color change is observed on a solid surface.

8. The method according to any one of claims 1 or 2 wherein the nanoparticles are made of gold.

9. The method according to claim 2 wherein the oligonucleotides attached to the nanoparticles are labeled on their ends not attached to the nanoparticles with molecules that produce a detectable change upon hybridization of the oligonucleotides on the nanoparticles with the nucleic acid.

10. The method according to claim 9 wherein the nanoparticles are metallic or semiconductor nanoparticles and the oligonucleotides attached to the nanoparticles are labeled with fluorescent molecules.

11. The method according to claim 2 wherein:

the nucleic acid has a third portion located between the first and second portions, and the sequences of the oligonucleotides on the nanoparticles do not include sequences complementary to this third portion of the nucleic acid; and the nucleic acid is further contacted with a filler oligonucleotide having a sequence complementary to this third portion of the nucleic acid, the contacting taking place under conditions effective to allow hybridization of the filler oligonucleotide with the nucleic acid.

12. The method according to any one of claims 1 or 2 wherein the nucleic acid is viral RNA or DNA.

13. The method according to any one of claims 1 or 2 wherein the nucleic acid is a gene associated with a disease.

14. The method according to any one of claims 1 or 2 wherein the nucleic acid is a bacterial DNA.

15. The method according to any one of claims 1 or 2 wherein the nucleic acid is a fungal DNA.

16. The method according to any one of claims 1 or 2 wherein the nucleic acid is a synthetic DNA, a synthetic RNA, a structurally-modified natural or synthetic RNA, or a structurally-modified natural or synthetic DNA.

17. The method according to any one of claims 1 or 2 wherein the nucleic acid is from a biological source.

18. The method according to any one of claims 1 or 2 wherein the nucleic acid is a product of a polymerase chain reaction amplification.

19. The method according to any one of claims 1 or 2 wherein the nucleic acid is contacted with the first and second types of nanoparticles simultaneously.

20. The method according to any one of claims 1 or 2 wherein the nucleic acid is contacted and hybridized with the oligonucleotides on the first type of nanoparticles before being contacted with the second type of nanoparticles.

21. The method according to claim 20 wherein the first type of nanoparticles is attached to a substrate.

22. The method according to any one of claims 1 or 2 wherein the nucleic acid is double-stranded and hybridization with the oligonucleotides on the nanoparticles results in the production of a triple-stranded complex.

23. The method according to any one of claims 1 or 2, wherein the oligonucleotides are attached to the nanoparticles in a stepwise ageing process comprising (i) contacting the oligonucleotides with the nanoparticles in a first aqueous solution for a period of time sufficient to allow some of the oligonucleotides to bind to the nanoparticles; (ii) adding at least one salt to the aqueous solution to create a second aqueous solution; and (iii) contacting the oligonucleotides and nanoparticles in the second aqueous solution for an additional period of time to enable additional oligonucleotides to bind to the nanoparticles.

24. The method according to claim 23, wherein the salt solution has an ionic strength sufficient to overcome at least partially the electrostatic attraction or repulsion of the oligonucleotides for the nanoparticles and the electrostatic repulsion of the oligonucleotides for each other.

25. The method according to claim 23 wherein the nanoparticles are metal nanoparticles or semiconductor nanoparticles.

26. The method according to claim 25 wherein the nanoparticles are gold nanoparticles.

27. The method according to claim 26 wherein the oligonucleotides include a moiety comprising a functional group which can bind to a nanoparticle.

28. The method according to claim 23 wherein all of the salt is added to the water in a single addition.

29. The method according to claim 23 wherein the salt is added gradually over time.

30. The method according to claim 23 wherein the salt is selected from the group consisting of sodium chloride, magnesium chloride, potassium chloride, ammonium chloride, sodium acetate, ammonium acetate, a combination of two or more of these salts, one of these salts in a phosphate buffer, and a combination of two or more these salts in a phosphate buffer.

31. The method according to claim 30 wherein the salt is sodium chloride in a phosphate buffer.

32. The method according to any one of claims 1 or 2 wherein the oligonucleotides present on surface of the nanoparticles at a surface density of at least 10 picomoles/$cm^2$.

33. The method according to claim 32 wherein the oligonucleotides are present on surface of the nanoparticles at a surface density of at least 15 picomoles/$cm^2$.

34. The method according to claim 33 wherein the oligonucleotides are present on surface of the nanoparticles at a surface density of from about 15 picomoles/$cm^2$ to about 40 picomoles/$cm^2$.

* * * * *